United States Patent
Dutruc-Rosset et al.

(10) Patent No.: US 6,949,579 B2
(45) Date of Patent: Sep. 27, 2005

(54) AMINOINDAZOLE DERIVATIVES AND INTERMEDIATES, PREPARATION THEREOF, AND PHARMACEUTICAL COMPOSITIONS THEREOF

(75) Inventors: Gilles Dutruc-Rosset, Paris (FR); Dominique Lesuisse, Montreuil (FR); Thomas Rooney, Orsay (FR); Franck Halley, Sevres (FR)

(73) Assignee: Aventis Pharma S.A., Antony (FR)

( * ) Notice: Subject to any disclaimer, the term of this patent is extended or adjusted under 35 U.S.C. 154(b) by 219 days.

(21) Appl. No.: 10/385,871

(22) Filed: Mar. 11, 2003

(65) Prior Publication Data
US 2004/0014802 A1 Jan. 22, 2004

(30) Foreign Application Priority Data
Mar. 11, 2002 (FR) .............................. 02 02997

(51) Int. Cl.⁷ .................... A61K 31/416; C07D 231/56; C07D 401/04; C07D 413/04
(52) U.S. Cl. ................ 514/403; 540/602; 544/62; 544/140; 544/371; 546/199; 546/275.7; 548/382.1; 568/647
(58) Field of Search ...................... 548/362.1; 514/403; 540/602; 544/62, 371, 140; 546/199, 275.7; 568/647

(56) References Cited

U.S. PATENT DOCUMENTS

| | | | | |
|---|---|---|---|---|
| 2,971,842 A | * | 2/1961 | Moore et al. ............... | 430/155 |
| 3,133,081 A | * | 5/1964 | Lafferty et al. .......... | 548/362.1 |
| 3,316,207 A | | 4/1967 | Hermann et al. | |
| 4,533,731 A | * | 8/1985 | Ibuki et al. ................ | 544/140 |
| 5,837,853 A | * | 11/1998 | Takashima et al. ........ | 536/24.5 |

FOREIGN PATENT DOCUMENTS

| | | |
|---|---|---|
| DE | 2458965 | 6/1976 |
| DE | 2622761 | 12/1976 |
| WO | WO 01/85726 | 11/2001 |

OTHER PUBLICATIONS

Bianchetti et al., Chemical Abstracts, 64:5633a–e, 1964.*
Buee et al., Chemical Abstracts, 134:129142, 2000.*
Lau et al., Chemical Abstracts, 137:210258, 2002.*

Nicolo Vivona et al., Mononuclear Heterocyclic Rearrangements. Part 12 (1), Rearrangement of 1,2,4–Oxadiazoles into Indazoles, J. Heterocycl. Chem., vol. 16(4), pp. 783–784, (1979).

Demetrio Raffa et al., Synthesis and Antiproliferative Activity of Novel 3–(Indazol–3–yl)–quinazolin–4(3H)–one and 3–(indazol–3–yl)–benzotriazin–4(3H)–one Derivatives, Arch. Pharm. Pharm. Med. Chem., vol. 332, pp. 317–320, (1999).

Dezso Korbonits et al., Ring Transformation of 3–(2–Aminoaryl)–1,2,4–oxadiazoles into 3–Acyl–aminoindazoles; Extension of the Boulton–Katritzky Scheme, J. Chem. Soc. Perkin Trans. 1, vol. 3, pp. 759–766, (1982).

Giuseppe Daidone et al., Synthesis, Crystallographic Studies and Biological Evaluation of some 2–Substituted 3–Indazolyl–4(3H)–Quinazolinones and 3–Indazolyl–4(3H)–Benzotriazinones. Heterocycles, vol. 43, No. 11, pp. 2385–2396, (1996).

* cited by examiner

Primary Examiner—Fiona T. Powers
(74) Attorney, Agent, or Firm—Balaram Gupta

(57) ABSTRACT

The present invention relates to the novel indazole derivatives of general formula (I):

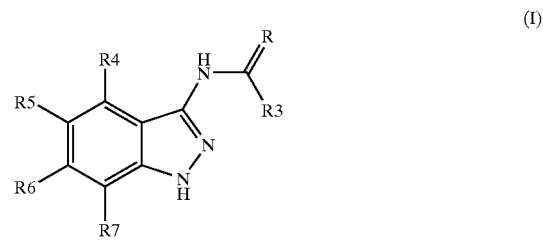

(I)

in which: R is either O, S or NH; R3 is an alkyl, aryl, arylalkyl, heteroaryl, heteroarylalkyl, aryl, heterocycle, cycloalkyl, alkenyl, etc. radical; these radicals being optionally substituted with one or more substituents; R4, R5, R6 and R7 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2R8$, $NHSO_2R8$, $SO_2NR8R9$, trifluoromethyl, trifluoromethoxy, alkyl, alkoxy, aryl, arylalkyl, heteroaryl, heteroarylalkyl, heterocycle, cycloalkyl, alkenyl, etc.; these radicals being optionally substituted with one or more substituents.

17 Claims, No Drawings

AMINOINDAZOLE DERIVATIVES AND INTERMEDIATES, PREPARATION THEREOF, AND PHARMACEUTICAL COMPOSITIONS THEREOF

The present invention relates to the use of aminoindazole derivatives of formula (I):

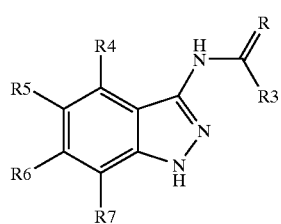

or the pharmaceutically acceptable salts thereof, as kinase inhibitors.

The invention relates to the use of the aminoindazole derivatives of formula (I) and the pharmaceutically acceptable salts thereof for the preparation of pharmaceutical compositions for preventing and treating diseases that may result from an abnormal activity of kinases, such as, for example, those involved in neurodegenerative diseases, Alzheimer's disease, Parkinson's disease, frontoparietal dementia, corticobasal degeneration, Pick's disease, stroke, cranial and spinal trauma and peripheral neuropathies, obesity, metabolic diseases, type II diabetes, essential hypertension, atherosclerotic cardiovascular diseases, polycystic ovarian syndrome, syndrome X, immunodeficiency and cancer, to the pharmaceutical compositions containing the novel aminoindazole derivatives and the pharmaceutically acceptable salts thereof, and to the novel aminoindazoles and the pharmaceutically acceptable salts thereof.

More specifically, the present invention relates to the aminoindazole derivatives of formula (I) in which:

R is either O, S or NH

R3 is a (1–6C)alkyl, aryl, aryl(1–6C)alkyl, heteroaryl, heteroaryl(1–6C)alkyl, aryl or heteroaryl fused to a cycloalkyl (1–10C), heterocycle, cycloalkyl, adamantyl, polycycloalkyls, alkenyl, alkynyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4, R5, R6 and R7 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C) alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, polycycloalkyls; these radicals being optionally substituted with one or more substituents chosen from halogen, CN, $NO_2$, $NH_2$, OH, OR10, COOH, C(O) OR10, —O—C(O)R10, NR10R11, NHC(O)R10, C(O)NR10R11, NHC(S)R10, C(S)NR10R 11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves optionally being substituted with one or more substituents chosen from halogen, (1–6C)alkyl, (1–6C) alkoxy, CN, $NO_2$, $NH_2$, OH, COOH, COOalkyl, $CONH_2$, formyl, trifluoromethyl and trifluoromethoxy;

with the exception of 3-(2-nitrobenzamido)indazole, 3-(2-aminobenzamido)indazole, 3-(2-nitrobenzamido)indazole, 3-(4-chloro-2-nitrobenzamido)indazole, 3-(5-chloro-2-nitrobenzamido)indazole, 3-(2-aminobenzamido)indazole, 3-(2-amino-4-chlorobenzamido)indazole, 3-(2-amino-5-chlorobenzamido)indazole, 3-(benzamido)-indazole, 3-(4-methylbenzamido)indazole, 3-(4-chlorobenzamido) indazole, 3-(4-nitrobenzamido)indazole, 3-acetamidoindazole, N-(1H-indazol-3-yl)butanamide, N-(1H-indazol-3-yl)phenylacetamide, N-(1H-indazol-3-yl) benzhydrylacetamide, 3-acetamidoindazole, 5-amino-3-acetamidoindazole, 3-(2-hydroxybenzamido)indazole, N-(6-chloro-1H-indazol-3-yl)-2,2,2-trifluoroacetamide, N-(6-chloro-1H-indazol-3-yl)-2-furancarboxamide, N-(6-chloro-1H-indazol-3-yl)-2,2,2-trifluoroacetamide, N-(6-chloro-1H-indazol-3-yl)-2-thiophenecarboxamide, N-(6-chloro-1H-indazol-3-yl)-2,2,2-trifluoroacetamide, N-(6-chloro-1H-indazol-3-yl)-4-(hexyloxy)benzamide, 3-chloro-N-(6-chloro-1H-indazol-3-yl)benzamide, 4-chloro-N-(6-chloro-1H-indazol-3-yl)benzamide and N-(5-nitro-1H-indazol-3-yl)acetamide;

to the isomers thereof, the mixtures thereof, the racemic mixtures, enantiomers, diastereoisomers and tautomers thereof, and also the pharmaceutically acceptable salts thereof.

More particularly, the present invention relates to the aminoindazole derivatives of formula (I) in which:

R is either O, S or NH

R3 is a (1–6C)alkyl, aryl, aryl(1–6C)alkyl, heteroaryl, heteroaryl(1–6C)alkyl, cycloalkyl, alkenyl or alkynyl radical; these radicals being optionally substituted with one or more substituents chosen from halogen, CN, $NO_2$, $NH_2$, OH, OR8, COOH, C(O)OR8, —O—C(O)R8, NR8R9, NHC (O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4 and R7 are hydrogen;

R5 and R6 are chosen, independently of each other, from the following radicals: hydrogen, halogen, CN, $NO_2$, $NH_2$, OH, COOH, C(O)OR8, —O—C(O)R8, NR8R9, NHC(O) R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, cycloalkyl, heterocycle, alkenyl, alkynyl, adamantyl, polycycloalkyl; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C) alkoxy, CN, $NO_2$, $NH_2$, OH, COOH, COOalkyl, $CONH_2$, formyl, trifluoromethyl and trifluoromethoxy;

with the exception of 3-(2-nitrobenzamido)indazole, 3-(2-aminobenzamido)indazole, 3-(2-nitrobenzamido)indazole, 3-(4-chloro-2-nitrobenzamido)indazole, 3-(5-chloro-2- nitrobenzamido)indazole, 3-(2-aminobenzamido)indazole, 3-(2-amino-4-chlorobenzamido)indazole, 3-(2-amino-5-chlorobenzamido)indazole, 3-(benzamido)-indazole, 3-(4-methylbenzamido)indazole, 3-(4-chlorobenzamido)indazole, 3-(4-nitrobenzamido)indazole, 3-acetamidoindazole, N-(1H-indazol-3-yl)butanamide, N-(1H-indazol-3-yl)phenylacetamide, N-(1H-indazol-3-yl)benzhydrylacetamide, 3-acetamidoindazole, 5-amino-3-acetamidoindazole, 3-(2-hydroxybenzamido)indazole, N-(6-chloro-1H-indazol-3-yl)-2,2,2-trifluoroacetamide, N-(6-chloro-1H-indazol-3-yl)-2-furancarboxamide, N-(6-chloro-1H-indazol-3-yl)-2,2,2-trifluoroacetamide, N-(6-chloro-1H-indazol-3-yl)-2-thiophenecarboxamide, N-(6-chloro-1H-indazol-3-yl)-2,2,2-trifluoroacetamide, N-(6-chloro-1H-indazol-3-yl)-4-(hexyloxy)benzamide, 3-chloro-N-(6-chloro-1H-indazol-3-yl)benzamide, 4-chloro-N-(6-chloro-1H-indazol-3-yl)benzamide and N-(5-nitro-1H-indazol-3-yl)acetamide;

to the isomers thereof, the mixtures thereof, the racemic mixtures, enantiomers, diastereoisomers and tautomers thereof, and also the pharmaceutically acceptable salts thereof.

Preferably, the present invention relates to the aminoindazole derivatives of formula (I) in which:

R is O

R4 and R7 are H

R3 is a (1–6C)alkyl, aryl, aryl(1–6C)alkyl, heteroaryl, heteroaryl(1–6C)alkyl, heterocycle, cycloalkyl or alkenyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R5 and R6 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C)alkoxy, CN, $NO_2$, $NH_2$, OH, COOH, COOalkyl, $CONH_2$, formyl, trifluoromethyl and trifluoromethoxy;

with the exception of 3-(2-nitrobenzamido)indazole, 3-(2-aminobenzamido)indazole, 3-(2-nitrobenzamido)indazole, 3-(4-chloro-2-nitrobenzamido)indazole, 3-(5-chloro-2-nitrobenzamido)indazole, 3-(2-aminobenzamido)indazole, 3-(2-amino-4-chlorobenzamido)indazole, 3-(2-amino-5-chlorobenzamido)indazole, 3-(benzamido)-indazole, 3-(4-methylbenzamido)indazole, 3-(4-chlorobenzamido)indazole, 3-(4-nitrobenzamido)indazole, 3-acetamidoindazole, N-(1H-indazol-3-yl)butanamide, N-(1H-indazol-3-yl)phenylacetamide, N-(1H-indazol-3-yl)benzhydrylacetamide, 3-acetamidoindazole, 5-amino-3-acetamidoindazole, 3-(2-hydroxybenzamido)indazole, N-(6-chloro-1H-indazol-3-yl)-2,2,2-trifluoroacetamide, N-(6-chloro-1H-indazol-3-yl)-2-furancarboxamide, N-(6-chloro-1H-indazol-3-yl)-2,2,2-trifluoroacetamide, N-(6-chloro-1H-indazol-3-yl)-2-thiophenecarboxamide, N-(6-chloro-1H-indazol-3-yl)-2,2,2-trifluoroacetamide, N-(6-chloro-1H-indazol-3-yl)-4-(hexyloxy)benzamide, 3-chloro-N-(6-chloro-1H-indazol-3-yl)benzamide, 4-chloro-N-(6-chloro-1H-indazol-3-yl)benzamide and N-(5-nitro-1H-indazol-3-yl)acetamide;

to the racemic mixtures, enantiomers, diastereoisomers and mixtures thereof, the tautomers thereof and also the pharmaceutically acceptable salts thereof.

The present invention relates to the aminoindazole derivatives of formula (I) in which:

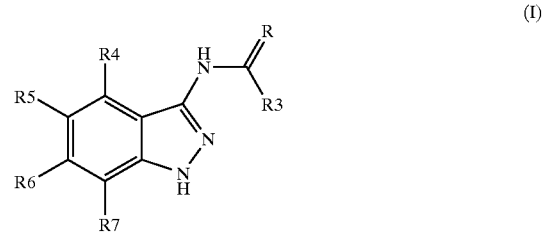

R is either O, S or NH

R3 is a (1–6C)alkyl, aryl, aryl(1–6C)alkyl, heteroaryl, heteroaryl(1–6C)alkyl, aryl or heteroaryl fused to a cycloalkyl (1–10C), heterocycle, cycloalkyl, adamantyl, polycycloalkyls, alkenyl, alkynyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4, R5, R6 and R7 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, polycycloalkyls; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C)alkoxy, CN, $NO_2$, $NH_2$, OH, COOH, COOalkyl, $CONH_2$, formyl, trifluoromethyl and trifluoromethoxy;

to the isomers thereof, the mixtures thereof, the racemic mixtures, enantiomers, diastereoisomers and tautomers thereof, and also the pharmaceutically acceptable salts thereof, for the preparation of medicinal products.

More particularly, the present invention relates to the use of the aminoindazole derivatives of formula (I) in which:

R is either O, S or NH

R3 is a (1–6C)alkyl, aryl, aryl(1–6C)alkyl, heteroaryl, heteroaryl(1–6C)alkyl, cycloalkyl, alkenyl or alkynyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4 and R7 are hydrogen;

R5, R6 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, cycloalkyl, heterocycle, alkenyl, alkynyl, adamantyl, polycycloalkyl; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C)alkoxy, CN, $NO_2$, $NH_2$, OH, COOH, COOalkyl, $CONH_2$, formyl, trifluoromethyl and trifluoromethoxy;

to the isomers thereof, the mixtures thereof, the racemic mixtures, enantiomers, diastereoisomers and tautomers thereof, and also the pharmaceutically acceptable salts thereof, for the preparation of medicinal products.

Preferably also, the present invention relates to the aminoindazole derivatives of formula (I) in which:

R is O

R4 and R7 are H

R3 is a (1–6C)alkyl, aryl, aryl(1–6C)alkyl, heteroaryl, heteroaryl(1–6C)alkyl, heterocycle, cycloalkyl or alkenyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R5 and R6 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C)alkoxy, CN, $NO_2$, $NH_2$, OH, COOH, COOalkyl, $CONH_2$, formyl, trifluoromethyl and trifluoromethoxy;

to the racemic mixtures, enantiomers, diastereoisomers and mixtures thereof, the tautomers thereof and the pharmaceutically acceptable salts thereof, for the preparation of medicinal products.

In the definitions hereinabove and hereinbelow, the alkyl (1–6C) radicals contain 1 to 6 carbon atoms in a straight or branched chain; the alkenyl radicals contain 2 to 6 carbon atoms and 1 to 3 conjugated or non-conjugated double bonds in a straight or branched chain; the alkynyl radicals contain 2 to 6 carbon atoms and 1 to 3 conjugated or non-conjugated triple bonds in a straight or branched chain; the aryl radicals are chosen from phenyl, naphthyl and indenyl and may be substituted with one or more halogens; the heteroaryl radicals are 3- to 10-membered, optionally containing one or more hetero atoms chosen from oxygen, sulphur and nitrogen, in particular thiazolyl, thienyl, pyrrolyl, pyridyl, furyl, imidazolyl, oxazolyl, pyrazinyl, tetrazolyl; the halogen radical is either chlorine, iodine, fluorine or bromine; the polycycloalkyl radicals are chosen from adamantyl, quinuclidinyl, bornanyl, norbornanyl, bornenyl and norbornenyl; the heteroaryl radicals fused to a cycloalkyl (1–10C) are chosen from indanyl, isochromanyl, chromanyl, 1,2,3,4-tetrahydroisoquinolyl and 1,2,3,4-tetrahydroquinolyl; the heterocyclic radicals contain one or two hetero atoms chosen from oxygen, sulphur and nitrogen and in particular represent piperidyl, morpholinyl, pyrrolidinyl, imidazolidinyl, pyrrazolidinyl, isothiazolidinyl, thiazolidinyl, isoxazolidinyl, oxazolidinyl and piperazinyl.

The compounds of formula (I) contain one or more asymmetric carbons and may therefore be in the form of isomers, racemic mixtures, enantiomers and diastereoisomers; these forms also form part of the invention, as do mixtures thereof.

Among the compounds of formula (I) that are useful according to the invention, mention may be made of the following compounds:

(2Z) 4-[(6-chloro-1H-indazol-3-yl)amino]-4-oxo-2-butenoic acid (2E) 4-[(6-chloro-1H-indazol-3-yl)amino]-4-oxo-2-butenoic acid ethyl (2E) 4-[(6-chloro-1H-indazol-3-yl)amino]-4-oxo-2-butenoate ethyl (2Z) 4-[(6-chloro-1H-indazol-3-yl)amino]-4-oxo-2-butenoate 4-[(6-chloro-1H-indazol-3-yl)amino]-4-oxo-2-butanoic acid (2Z) 4-[(5-bromo-1H-indazol-3-yl)amino]-4-oxo-2-butenoic acid (2E) 4-[(6-chlorom-1H-indazol-3-yl)amino]-4-oxo-2-butenoic acid (2E) 4-[(5-bromo-1H-indazol-3-yl)amino]-4-oxo-2-butenoic acid (2Z) 4-[(6-chloro-1H-indazol-3-yl)amino]-4-oxo-2-butenoic acid 4-[(5-bromo-1H-indazol-3-yl)amino]-4-oxo-2-butanoic acid (2E) N-(6-chloro-1H-indazol-3-yl)-2-butenamide (2Z) N-(6-chloro-1H-indazol-3-yl)-2-butenamide N-(6-chloro-1H-indazol-3-yl)-3-butenamide hydrochloride methyl 4-[(6-chloro-1H-indazol-3-yl)amino]-4-oxo-2-butanoate N-(6-chloro-1H-indazol-3-yl)acetamide
N-(6-chloro-1H-indazol-3-yl)butanamide
(2E) N-(6-bromo-1H-indazol-3-yl)-2-butenamide
(2E) N-(5-methyl-1H-indazol-3-yl)-2-butenamide
(2Z) N-(6-bromo-1H-indazol-3-yl)-2-butenamide
(2Z) N-(5-methyl-1H-indazol-3-yl)-2-butenamide
N-(6-chloro-1H-indazol-3-yl)-2-propanamide
(2E) N-[6-(trifluoromethyl)-1H-indazol-3-yl]-2-butenamide
(2Z) N-[6-(trifluoromethy)1–1H-indazol-3-yl]-2-butenamide
ethyl 4-[[6-(trifluoromethyl)-1H-indazol-3-yl]amino]-4-oxobutanoate
(2E) N-[5-(trifluoromethyl)-1H-indazol-3-yl]-2-butenamide
(2Z) N-[5-(trifluoromethyl)-1H-indazol-3-yl]-2-butenamide
N-[5-chloro-1H-indazol-3-yl]-2-butanamide
N-[4-chloro-1H-indazol-3-yl]butanamide
N-[6-(trifluoromethyl)-1H-indazol-3-yl]butanamide
N-[6-chloro-1H-indazol-3-yl]propenamide
N-[5-(trifluoromethyl)-1H-indazol-3-yl]butanamide
N-[5-nitro-1H-indazol-3-yl]butanamide
N-[6-bromo-1H-indazol-3-yl]butanamide
N-[6-(3-pyridyl)-1H-indazol-3-yl]butanamide
N-[4-iodo-1H-indazol-3-yl]butanamide
N-[6-phenyl-1H-indazol-3-yl]butanamide
N-[6-bromo-5,7-dinitro-1H-indazol-3-yl]butanamide
N-[6-bromo-7-nitro-1H-indazol-3-yl]butanamide
N-[6-bromo-5-nitro-1H-indazol-3-yl]butanamide
N-[6-(3-furyl)-1H-indazol-3-yl]butanamide
N-[6-[4-(phenylmethoxy)phenyl]-1H-indazol-3-yl]butanamide
N-[6-(4-hydroxyphenyl)-1H-indazol-3-yl]butanamide
N-[6-chloro-1H-indazol-3-yl]benzenamide
N-[6-(3,5-difluorophenyl)-1H-indazol-3-yl]butanamide
N-[6-(3-thiophenyl)-1H-indazol-3-yl]butanamide
N-[6-chloro-1H-indazol-3-yl]-2-thiopheneacetamide
N-[5-[[3-(fluorophenyl)sulphonyl]amino]-1H-indazol-3-yl]benzamide
N-[6-(2-chlorophenyl)-1H-indazol-3-yl]butanamide
N-[6-(2-chloro-4-hydroxyphenyl)-1H-indazol-3-yl]butanamide
N-[6-(4-ethylphenyl)-1H-indazol-3-yl]butanamide
N-[6-(4-ethenylphenyl)-1H-indazol-3-yl]butanamide
N-[6-(4pyridyl)-1H-indazol-3-yl]butanamide
N-[6-(phenylmethyl)-1H-indazol-3-yl]butanamide
N-[6-(4-aminophenyl)-1H-indazol-3-yl]butanamide
N-[6-(1-morpholino)-1H-indazol-3-yl]butanamide
N-[6-[(4-phenylethynyl)phenyl]-1H-indazol-3-yl]butanamide
N-[6-(2-propenyl)-1H-indazol-3-yl]butanamide
N-[5-amino-1H-indazol-3-yl]butanamide
N-[6-bromo-5-chloro-1H-indazol-3-yl]butanamide
N-[6-chloro-5-bromo-1H-indazol-3-yl]butanamide
N-[6-chloro-5-nitro-1H-indazol-3-yl]butanamide
N-[6-(4-hydroxyphenyl)-5-bromo-1H-indazol-3-yl]butanamide
N-[6-(4-hydroxyphenyl)-5-(phenylamino)-1H-indazol-3-yl]butanamide
N-[6-(4-hydroxyphenyl)-5-(2-phenylethenyl)-1H-indazol-3-yl]butanamide
N-[6-(4-hydroxyphenyl)-5-phenylcarbonyl-1H-indazol-3-yl]butanamide
N-[6-(4-hydroxyphenyl)-5-[3-(dimethylamino)propynyl]-1H-indazol-3-yl]butanamide
N-[6-chloro-1H-indazol-3-yl]-3-thiophenecarboxamide
N-[6-chloro-1H-indazol-3-yl]-2-pyridineacetamide
N-[6-chloro-1H-indazol-3-yl]-3-pyridinecarboxamide
N-[6-chloro-1H-indazol-3-yl]benzeneacetamide
N-[6-chloro-1H-indazol-3-yl]benzenepropanamide
N-[6-chloro-1H-indazol-3-yl]-3-pyridineacetamide
N-[6-chloro-1H-indazol-3-yl]-2-chloroacetamide
N-[6-chloro-1H-indazol-3-yl]-4-morpholineacetamide
N-[6-chloro-1H-indazol-3-yl]-1-piperazineacetamide
N-[6-chloro-1H-indazol-3-yl]-4-[(2-methoxyethyl)amino]cyclohexanecarboxamide
4-amino-N-[6-chloro-1H-indazol-3-yl]-1-piperidinecarboxamide
N-[6-chloro-1H-indazol-3-yl]-4-morpholinylcarboxamide
the isomers thereof, the mixtures thereof, the racemic mixtures, enantiomers, diastereoisomers and tautomers thereof, and also the pharmaceutically acceptable salts thereof,
and more particularly the following compounds
(2Z) 4-[(6-chloro-1H-indazol-3-yl)amino]-4-oxo-2-butenoic acid
ethyl (2E) 4-[(6-chloro-1H-indazol-3-yl)amino]-4-oxo-2-butenoate
4-[(6-chloro-1H-indazol-3-yl)amino]-4-oxo-2-butanoic acid
(2Z) 4-[(5-bromo-1H-indazol-3-yl)amino]-4-oxo-2-butenoic acid
(2E) 4-[(6-chloro-1H-indazol-3-yl)amino]-4-oxo-2-butenoic acid
4-[(5-bromo-1H-indazol-3-yl)amino]-4-oxo-2-butanoic acid
(2E) N-(6-chloro-1H-indazol-3-yl)-2-butenamide
N-(6-chloro-1H-indazol-3-yl)-3-butenamide hydrochloride
methyl 4-[(6-chloro-1H-indazol-3-yl)amino]-4-oxo-2-butanoate
N-(6-chloro-1H-indazol-3-yl)acetamide
N-(6-chloro-1H-indazol-3-yl)butanamide
(2E) N-(6-bromo-1H-indazol-3-yl)-2-butenamide
(2E) N-(5-methyl-1H-indazol-3-yl)-2-butenamide
N-(6-chloro-1H-indazol-3-yl)-2-propanamide
(2E) N-[6-(trifluoromethyl)-1H-indazol-3-yl]-2-butenamide
ethyl 4-[[6-(trifluoromethyl)-1H-indazol-3-yl]amino]-4-oxobutanoate
(2E) N-[5-(trifluoromethyl)-1H-indazol-3-yl]-2-butenamide
N-[5-chloro-1H-indazol-3-yl]-2-butanamide
N-[4-chloro-1H-indazol-3-yl]butanamide
N-[6-(trifluoromethyl)-1H-indazol-3-yl]butanamide
N-[6-chloro-1H-indazol-3-yl]propenamide
N-[5-(trifluoromethyl)-1H-indazol-3-yl]butanamide
N-[5-nitro-1H-indazol-3-yl]butanamide
N-[6-bromo-1H-indazol-3-yl]butanamide
N-[6-chloro-1-[[2-(trimethylsilyl)ethoxy]methyl]-1H-indazol-3-yl]butanamide
N-[6-(3-pyridyl)-1H-indazol-3-yl]butanamide
N-[4-iodo-1H-indazol-3-yl]butanamide
N-[6-phenyl-1H-indazol-3-yl]butanamide
N-[6-bromo-5,7-dinitro-1H-indazol-3-yl]butanamide
N-[6-bromo-7-nitro-1H-indazol-3-yl]butanamide
N-[6-bromo-5-nitro-1H-indazol-3-yl]butanamide
N-[(6-furan-3-yl)-1H-indazol-3-yl]butanamide
N-[6-[4-(phenylmethoxy)phenyl]-1H-indazol-3-yl]butanamide
N-[6-(4-hydroxy-phenyl)-1H-indazol-3-yl]butanamide
N-[6-chloro-1H-indazol-3-yl]benzenamide
N-[[6-(3,5-difluorophenyl)-1H-indazol-3-yl]]butanamide
N-[6-(3-thienyl)-1H-indazol-3-yl]butanamide
N-[6-chloro-1H-indazol-3-yl]-2-thiopheneacetamide
N-[5-[[(3-fluorophenyl)sulphonyl]amino]-1H-indazol-3-yl]benzamide
N-[6-(2-phenylethyl)-1H-indazol-3-yl]butanamide
N-(6,7-difluoro-1H-indazol-3-yl)butanamide
N-[6-(4-methoxyphenyl)-1H-indazol-3-yl]butanamide N-[6-(4-methylthiophenyl)-1H-indazol-3-yl]butanamide
N-[6-(4-trifluoromethoxyphenyl)-1H-indazol-3-yl]
butanamide
N-[(6-(1-propenyl)-1H-indazol-3-yl]butanamide
N-[6-chloro-1H-indazol-3-yl]-2-pyridinecarboxamide
N-[6-(4-fluorophenyl)-1H-indazol-3-yl]butanamide
N-[6-[4-(1,1-dimethylethyl)phenyl]-1H-indazol-3-yl]
butanamide
N-[6-bromo-7-amino-1H-indazol-3-yl]butanamide
N-[6-[4-(trifluoromethyl)phenyl]-1H-indazol-3-yl]
butanamide
N-[6-(4-methylphenyl)-1H-indazol-3-yl]butanamide
N-[6-(3,5-dichlorophenyl)-1H-indazol-3-yl]butanamide
N-[6-chloro-1H-indazol-3-yl]-3,5-dichlorobenzamide
N-[6-(4-chlorophenyl)-1H-indazol-3-yl]butanamide
N-[6-chloro-1H-indazol-3-yl]benzenepropanamide trifluoroacetate
N-[6-chloro-1H-indazol-3-yl]benzenepropanamide
N-[[6-(4-ethylphenyl)-1H-indazol-3-yl]]butanamide
N-[6-(4-pyridyl)-1H-indazol-3-yl]butanamide
N-(5-amino-1H-indazol-3-yl)butanamide
N-(5-bromo-6-chloro-1H-indazol-3-yl)butanamide
N-(6-chloro-1H-indazol-3-yl)-2-thiophenecarboxamide
N-(6-chloro-1H-indazol-3-yl)-2-methylpropylamide
4-chloro-N-(6-chloro-1H-indazol-3-yl)butanamide
N-(5-phenyl-6-chloro-1H-indazol-3-yl)butanamide
N-[5-bromo-6-[4-(phenylmethoxy)phenyl]-1H-indazol-3-yl]butanamide
N-[5-bromo-6-(4-hydroxyphenyl)-1H-indazol-3-yl]butanamide
N-[[6-(4-nitrophenyl)-1H-indazol-3-yl]]butanamide
N-[6-(2-chlorophenyl)-1H-indazol-3-yl]butanamide
N-[6-[3-(phenylmethoxy)phenyl]-1H-indazol-3-yl]butanamide
N-[6-(3-hydroxyphenyl)-1H-indazol-3-yl]butanamide
N-[6-chloro-5-(4-pyridyl)-1H-indazol-3-yl]butanamide
N-[6-chloro-5-(3-furyl)-1H-indazol-3-yl]butanamide,
N-[6-[2-chloro-4-(phenylmethoxy)phenyl]-1H-indazol-3-yl]butanamide
N-[6-(2-chloro-4-hydroxyphenyl)-1H-indazol-3-yl]butanamide
N-[5,6-dibromo-1H-indazol-3-yl]butanamide
N-[6-chloro-1H-indazol-3-yl]-2,2,3,3,4,4,4-heptafluorobutanamide
N-[6-chloro-5-(4-fluorophenyl)-1H-indazol-3-yl]butanamide
N-[[6-(4-aminophenyl)-1H-indazol-3-yl]]butanamide
N-[6-[4-(dimethylamino)phenyl]-1H-indazol-3-yl]butanamide
N-(6-chloro-1H-indazol-3-yl)-4-methyl-1-piperazineacetamide
N-(6-chloro-1H-indazol-3-yl)-1-piperidineacetamide
N-(6-chloro-1H-indazol-3-yl)-4-morpholineacetamide
N-(6-chloro-1H-indazol-3-yl)-1H-1,2,4-triazole-1-acetamide
N-(6-chloro-1H-indazol-3-yl)-2-(cyclohexylamino)acetamide
2-[(phenylmethyl)amino]-N-(6-chloro-1H-indazol-3-yl)acetamide
N-(6-chloro-1H-indazol-3-yl)-1H-azepine-1-acetamide
N-(6-chloro-1H-indazol-3-yl)-1-piperazineacetamide
N-(6-chloro-1H-indazol-3-yl)-2-[[3-(dimethylamino)propyl]amino]acetamide
N-(6-chloro-1H-indazol-3-yl)-thiomorpholine-4-acetamide
N-(6-chloro-1H-indazol-3-yl)-1pyrrolidineacetamide
N-(6-chloro-1H-indazol-3-yl)-2-[[2-(dimethylamino)ethyl]amino]acetamide
N-(6-chloro-1H-indazol-3-yl)-1-cyclopropylaminoacetamide trifluoroacetate
N-(6-chloro-1H-indazol-3-yl)-1-cyclopropylaminoacetamide
N-(6-chloro-1H-indazol-3-yl)-2-(2-diethylaminoethylamino)acetamide tris(trifluoroacetate)
N-(6-chloro-1H-indazol-3-yl)-2-(2-diethylaminoethylamino)acetamide,
N-[5,6-diphenyl-1H-indazol-3-yl]butanamide
N-[6-chloro-5-(4-methylphenyl)-1H-indazol-3-yl]butanamide
N-[5-phenyl-6-[4-(phenylmethoxy)phenyl]-1H-indazol-3-yl]butanamide
N-[5-phenyl-6-(4-hydroxyphenyl)-1H-indazol-3-yl]butanamide
N-[6-chloro-5-(4-pyridyl)-1H-indazol-3-yl]butanamide
N-[5-(4-aminophenyl)-6-chloro-1H-indazol-3-yl]butanamide
N-[6-chloro-5-(4-ethylphenyl)-1H-indazol-3-yl]butanamide
N-[6-chloro-5-[4-(phenylmethoxy)phenyl]-1H-indazol-3-yl]butanamide
N-[6-chloro-5-(4-hydroxyphenyl)-1H-indazol-3-yl]butanamide
N-[5,6-bis[4-(phenylmethoxy)phenyl]-1H-indazol-3-yl]butanamide
N-[5,6-bis(4-hydroxyphenyl)-1H-indazol-3-yl]butanamide
N-[5-(3-furyl)-6-[4-(phenylmethoxy)phenyl]-1H-indazol-3-yl]butanamide
N-[5-(3-furyl)-6-([4-hydroxyphenyl)-1H-indazol-3-yl]butanamide
N-[5-(4-ethylphenyl)-6-[4-(phenylmethoxy)phenyl]-1H-indazol-3-yl]butanamide
N-[5-(4-ethylphenyl)-6-(4-hydroxyphenyl)-1H-indazol-3-yl]butanamide
N-[5-(3-pyridyl)-6-[4-(phenylmethoxy)phenyl]-1H-indazol-3-yl]butanamide
N-[5-(3-pyridyl)-6-(4-hydroxyphenyl)-1H-indazol-3-yl]butanamide
N-[5-(2-furyl)-6-[4-(phenylmethoxy)phenyl]-1H-indazol-3-yl]butanamide
N-[5-(2-furyl)-6-(4-hydroxyphenyl)-1H-indazol-3-yl]butanamide
N-(5-bromo-6-chloro-7-nitro-1H-indazol-3-yl)butanamide
N-(5-bromo-6,7-difluoro-1H-indazol-3-yl)butanamide
N-[6-(4-cyanophenyl)-1H-indazol-3-yl]butanamide
N-(6,7-difluoro-5-nitro-1H-indazol-3-yl)butanamide
N-(6,7-difluoro-5-phenyl-1H-indazol-3-yl)butanamide
N-[6-(6-hydroxypyrid-3-yl)-1H-indazol-3-yl]butanamide
N-[6-(3,4-dihydroxyphenyl)-1H-indazol-3-yl]butanamide trifluoroacetate
N-[6-(3,4-dihydroxyphenyl)-1H-indazol-3-yl]butanamide
N-[7-fluoro-5-nitro-6-[2-(phenylethyl)amino]-1H-indazol-3-yl]butanamide
N-(7-fluoro-5-nitro-6-morpholino-1H-indazol-3-yl)butanamide
N-(7-fluoro-5-amino-6-morpholino-1H-indazol-3-yl)butanamide
N-(5-bromo-7-fluoro-6-morpholino-1H-indazol-3-yl)butanamide
N-[7-fluoro-6-(trifluoromethyl)-1H-indazol-3-yl]butanamide
N-(6-bromo-4,5,7-trifluoro-1H-indazol-3-yl)butanamide
N-[6-(6-aminopyrid-3-yl)-1H-indazol-3-yl]butanamide difluoroacetate
N-[6-(6-aminopyrid-3-yl)-1H-indazol-3-yl]butanamide
2-chloro-N-(6,7-difluoro-1H-indazol-3-yl)acetamide
N-(6,7-difluoro-1H-indazol-3-yl)-1-piperidineacetamide the isomers thereof, the mixtures thereof, the racemic mixtures, enantiomers, diastereoisomers and tautomers thereof, and also the pharmaceutically acceptable salts thereof.

The invention also relates to the pharmaceutical compositions containing, as active principle, a derivative of formula (I) for which, either R is either O, S or NH R3 is a (1–6C)alkyl, aryl, aryl(1–6C)alkyl, heteroaryl, heteroaryl(1–6C)alkyl, aryl or heteroaryl fused to a cycloalkyl (1–10C), heterocycle, cycloalkyl, adamantyl, polycycloalkyl, alkenyl or alkynyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4, R5, R6 and R7 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C) alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, polycycloalkyls; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C) alkoxy, CN, $NO_2$, $NH_2$, OH, COOH, COOalkyl, $CONH_2$, formyl, trifluoromethyl and trifluoromethoxy;

to the isomers thereof, the mixtures thereof, the racemic mixtures, enantiomers, diastereoisomers and tautomers thereof, and also the pharmaceutically acceptable salts thereof.

More particularly, the present invention relates to the use of the aminoindazole derivatives of formula (I) in which:

R is either O, S or NH

R3 is a (1–6C)alkyl, aryl, aryl(1–6C)alkyl, heteroaryl, heteroaryl(1–6C)alkyl, cycloalkyl, alkenyl or alkynyl radical; these radicals being optionally substituted with one or more substituents chosen from halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4 and R7 are hydrogen;

R5 and R6 are chosen, independently of each other, from the following radicals: hydrogen, halogen, CN, $NO_2$, $NH_2$, OH, COOH, C(O)OR8, —O—C(O)R8, NR8R9, NHC(O) R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl (1–6C)alkyl, cycloalkyl, heterocycle, alkenyl, alkynyl, adamantyl, polycycloalkyl; these radicals being optionally substituted with one or more substituents chosen from halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C) alkoxy, CN, $NO_2$, $NH_2$, OH, COOH, COOalkyl, $CONH_2$, formyl, trifluoromethyl and trifluoromethoxy;

to the isomers thereof, the mixtures thereof, the racemic mixtures, enantiomers, diastereoisomers and tautomers thereof, and also the pharmaceutically acceptable salts thereof.

Preferably, the present invention relates to the use of the aminoindazole derivatives of formula (I) in which:

R is O

R4 and R7 are H

R3 is a (1–6C)alkyl, aryl, aryl(1–6C)alkyl, heteroaryl, heteroaryl(1–6C)alkyl, heterocycle, cycloalkyl or alkenyl radical; these radicals being optionally substituted with one or more substituents chosen from halogen, CN, $NO_2$, $NH_2$, OH, OR8, COOH, C(O)OR8, —O—C(O)R8, NR8R9, NHC (O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R5 and R6 are chosen, independently of each other, from the following radicals: hydrogen, halogen, CN, $NO_2$, $NH_2$, OH, COOH, C(O)OR8, —O—C(O)R8, NR8R9, NHC(O) R8, C(O)NR8R9, NHC(S)R8, C(S)NR8R9, SR8, S(O)R8, $SO_2$R8, $NHSO_2$R8, $SO_2$NR8R9, trifluoromethyl, trifluoromethoxy, (1–6C)alkyl, (1–6C)alkoxy, aryl, aryl (1–6C)alkyl, heteroaryl, heteroaryl(1–6C)alkyl, heterocycle, cycloalkyl, alkenyl; these radicals being optionally substituted with one or more substituents chosen from halogen, CN, $NO_2$, $NH_2$, OH, OR10, COOH, C(O)OR10, —O—C (O)R10, NR10R11, NHC(O)R10, C(O)NR10R11, NHC(S) R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C) alkoxy, CN, $NO_2$, $NH_2$, OH, COOH, COOalkyl, $CONH_2$, formyl, trifluoromethyl and trifluoromethoxy;

to the racemic mixtures, mixtures, enantiomers, diastereoisomers and mixtures thereof, tautomers thereof, and the pharmaceutically acceptable salts thereof.

In the definitions hereinabove and hereinbelow, the alkyl and alkyl(1–6C) radicals contain 1 to 6 carbon atoms in a straight or branched chain; the alkenyl radicals contain 1 to 6 carbon atoms and 1 to 3 conjugated or non-conjugated double bonds in a straight or branched chain; the alkynyl radicals contain 1 to 6 carbon atoms and 1 to 3 conjugated or non-conjugated triple bonds in a straight or branched chain; the aryl radicals are chosen from phenyl, naphthyl and indenyl and may be substituted with one or more halogens; the heteroaryl radicals are 3- to 10-membered, optionally containing one or more hetero atoms chosen from oxygen, sulphur and nitrogen, in particular thiazolyl, thienyl, pyrrolyl, pyridyl, furyl, imidazolyl, oxazolyl, pyrazinyl, tetrazolyl; the halogen radical is either chlorine, iodine, fluorine or bromine; the polycycloalkyl radicals are chosen from adamantyl, quinuclidinyl, bornanyl, norbornanyl, bornenyl and norbornenyl; the heteroaryl radicals fused to a cycloalkyl (1–10C) are chosen from indanyl, isochromanyl, chromanyl, 1,2,3,4-tetrahydroisoquinolyl and 1,2,3,4-tetrahydroquinolyl; the heterocyclic radicals contain one or two hetero atoms chosen from oxygen, sulphur and nitrogen and in particular represent piperidyl, morpholinyl, pyrrolidinyl, imidazolidinyl, pyrrazolidinyl, isothiazolidinyl, thiazolidinyl, isoxazolidinyl, oxazolidinyl and piperazinyl.

The derivatives of formula (I) for which R=O may be obtained by acylation of the corresponding 3-amino derivatives, either using an acid chloride or an anhydride, or by reaction of an acid in the presence of an activating agent.

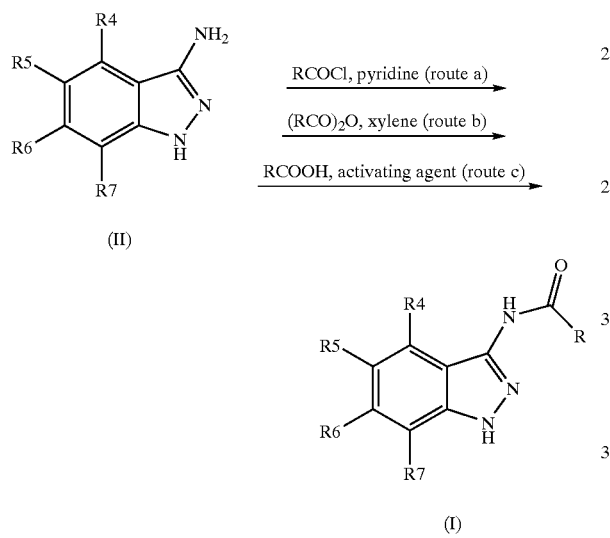

Via route (a), the reaction is performed in the presence of a base, for instance pyridine, triethylamine or diisopropylethylamine; the reaction can start at 0° C. and, when the addition of the acid chloride is complete, the mixture is left stirring at room temperature (G. Daidone, Heterocycles, 43, (11), 2385–96, (1996)) or is heated, if necessary.

Via route (b), the reaction may be performed at the reflux point of an inert solvent such as xylene or tetrahydrofuran (F. Albericio, Synth. Commun., 31, (2), 225–32, (2001)) or dichloromethane (G. Procter. Tetrahedron, 51, (47), 12837–842, (1995)) or in the anhydride itself.

Via route (c), the reaction is performed in the presence of an activating agent of the type such as carbodiimide alone (DCC, EDAC) (M. C. Desai. Tetrahedron Lett., 34, 7685, (1993)) or in the presence of hydroxybenzotriazole and dimethylaminopyridine (J. P. Gamet. Tetrahedron, 40, 1995, (1984), K. Barlos, J. Org. Chem., 50, 696, (1985)) or according to the well-known coupling methods of peptide chemistry (M. Bodanszky, Principles of Peptide Synthesis; Springer-Verlag, New York, N.Y., pages 9–58, (1984)) or the methods forming amide bonds.

When, in (I), R3 comprises an acid on the terminal carbon, this acid may be obtained by condensation of a cyclic anhydride such as maleic, succinate or phthalic anhydride, or by condensation of an ester acid chloride followed by saponification of the ester, according to the following scheme:

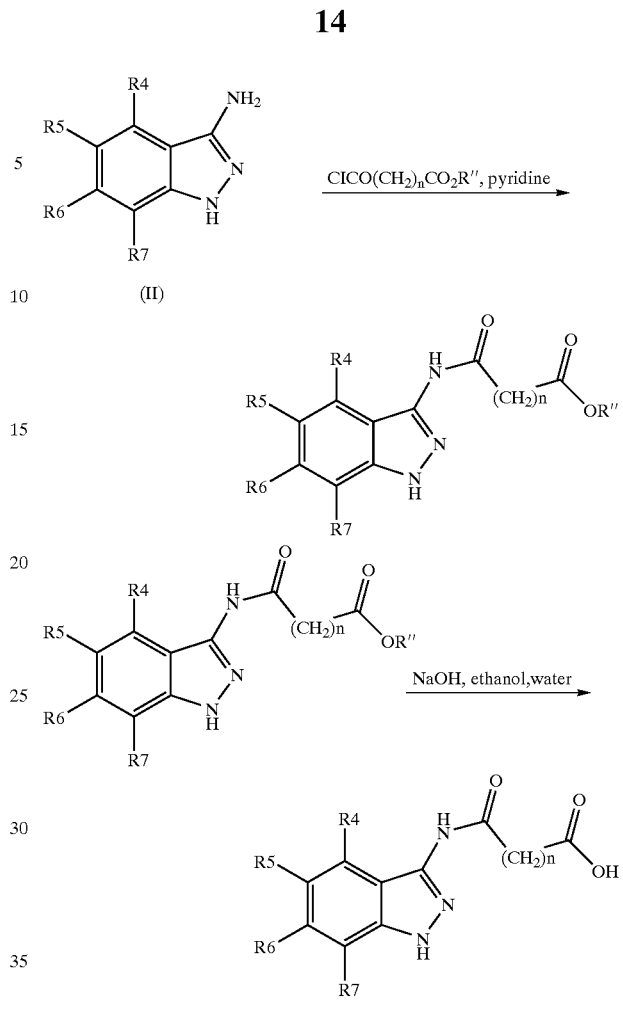

The ester function may be reduced by the methods known to those skilled in the art, such as sodium tetrahydridoborate in methanol or lithium aluminium hydride in dioxane or THF, to give the corresponding alcohol according to the following scheme:

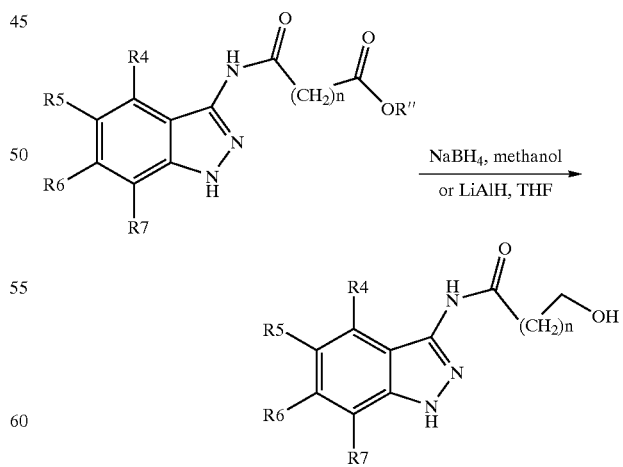

For the derivatives of formula (I) for which R=S, they are obtained by thionation of the corresponding oxo derivatives using Lawesson's reagent (R. Olsson, Tetrahedron Lett., 41,(41), 7947–50, (2000)) or by treatment with phosphorus pentasulphide in pyridine or toluene (J. Voss, Justus Liebig Ann. Chem., 716, 209, (1968); O. Tsuge, Chem. Lett., 1369, (1980)).

The derivatives of formula (I) for which R=NH may be obtained by reaction of the 3-amino-1H-indazoles with a nitrile or with a Meerwein salt (S. Patai. The Chemistry of amidines and imidates, J. Wiley and Sons, (1975), page 283).

The 3-amino-1H-indazoles of formula (II) may be obtained by reaction of a 2-fluorobenzonitrile with hydrazine, as the hydrate or the hydrochloride, at reflux for 2 to 18 hours in an alcohol such as ethanol or n-butanol, according to (R. F. Kaltenbach, Bioorg. Med. Chem. Lett., 9, (15), 2259–62, (1999)):

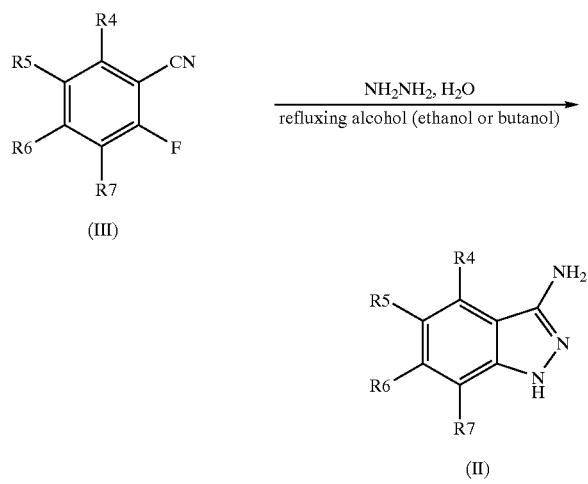

For the compounds for which R4, R5, R6 and R7 are chosen, independently of each other, from the following radicals: hydrogen, halogen, CN, NO$_2$, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C) alkoxy, aryl, aryl(1–6C)alkyl, heteroaryl, heteroaryl(1–6C) alkyl, cycloalkyl, alkenyl, alkynyl, adamantyl; these radicals being optionally substituted with one or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl and trifluoromethoxy; they may be obtained by reactions involving palladium chemistry: Suzuki, (A. Suzuki, Pure Appl. Chem. 63, 419–22, (1991), Stille (J. C. Stille, Angew. Chem. Int. Ed. 25, 508–24, (1986), Heck, (R. F. Heck, Org. React., 27, 345–90, (1982), Sonogashira, (K. Sonogashira, Synthesis 777, (1977), Buckwald (S. L. Buckwald, Acc. Chem. Res., 31, 805, (1998), starting with the corresponding halo derivatives.

For this, it is necessary to protect the reactive functions. Thus, the OH, SH, COOH and NH$_2$ functions must be protected before performing the coupling. The protecting groups are introduced according to any method known to those skilled in the art and especially those described by T. W. Greene, Protective groups in Organic Synthesis, J. Wiley-Interscience Publication (1991). It is preferable to protect the nitrogen in position 1 with groups such as tert-butoxycarbonyl or silicon derivatives. A tert-butyldimethylsilyl or triisopropylsilyl group will preferably be chosen, and may be removed with fluoride anions or with acetic acid, and more particularly a trimethylsilylethoxymethyl group, which may be cleaved off with tetrabutylammonium fluoride in refluxing solvents such is tetrahydrofuran or dioxane (J. P. Whitten, J. Org. Chem., 51, 1891, (1986); B. H. Lipshutz. Tetrahedron Lett., 4095, (1986)).

The derivatives protected in position 1 with trimethylsilylethoxymethyl are obtained by reacting the starting compounds with trimethylsilylethoxymethyl chloride in the presence of sodium hydride in a solvent such as dimethylformamide at room temperature (J. P. Whitten, J. Org. Chem., 51, 1891, (1986); M. P. Edwards. Tetrahedron, 42, 3723, (1986)).

Similarly, the 1-NH nitrogen function of the indazole will be protected with groups such as tosyl, carbamate, benzyl or silyl derivatives. For example, when it is desired to perform a palladium coupling on a derivative halogenated in position 6, the nitrogen in position 1 will have to be protected, as shown below (X=Cl, Br, I):

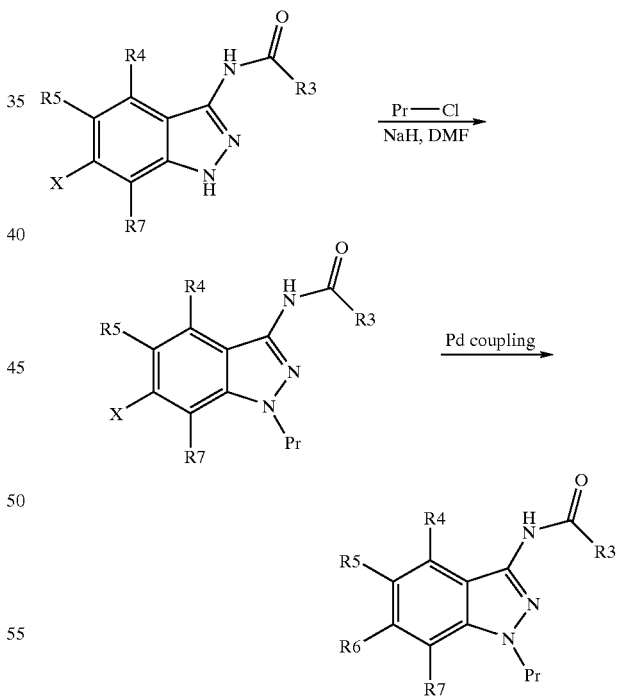

The deprotection is performed according to the methods known to those skilled in the art and described by T. W. Greene, Protective groups in Organic Synthesis, J. Wiley-Interscience Publication (1991). For example, if the protecting group in position 1 is a trimethylsilylethoxymethyl, it may be deprotected by reaction with tetrabutylammonium fluoride as shown below:

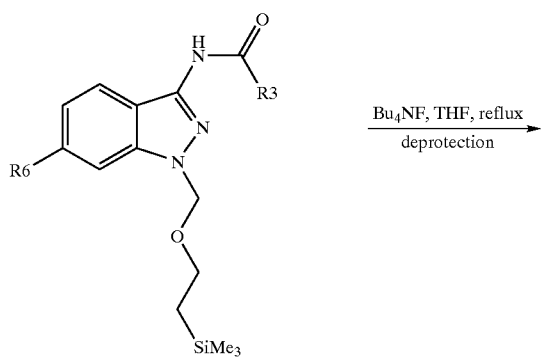

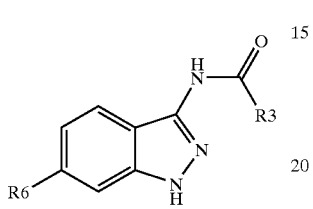

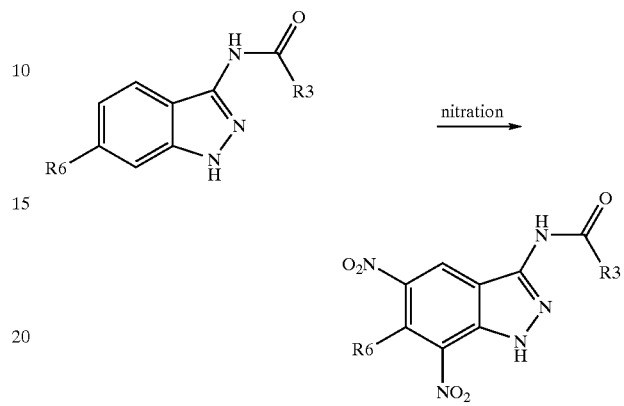

When one of the groups R4, R5, R6 or R7 employed for the coupling using palladium chemistry itself contains a reactive function such as hydroxyl, amine, thiol, acid or generally contains a hetero atom, it is necessary to protect these functions also before performing the palladium coupling. Thus, for example, a phenol function will be introduced in the protected form (for example O-benzyl) starting with the chloro derivative and the nitrogen in position 1 being protected as described previously:

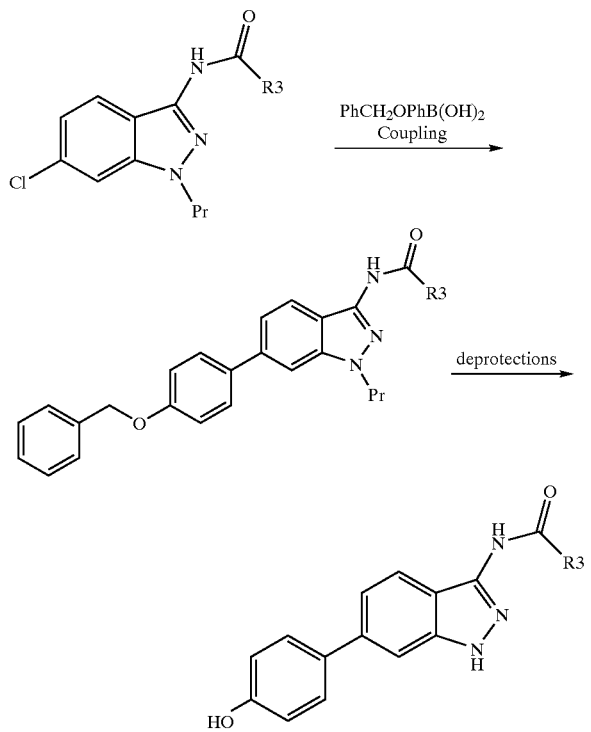

The benzyl group will then be removed, for example, by treatment with trimethylsilyl iodide in refluxing acetonitrile. The protection may also be performed with a trimethylsilylethoxymethyl group, which may be cleaved off with tetrabutylammonium fluoride in refluxing solvents such as tetrahydrofuran or dioxane (J. P. Whitten, J. Org. Chem., 51, 1891, (1986); B. H. Lipshutz. Tetrahedron Lett., 4095, (1986)).

Certain derivatives may undergo electrophilic substitution, nitrogen, halogenation or Friedel-Crafts acylation reactions.

For example, the nitration of the derivatives substituted in position 6 (as described above) may be performed by well-known methods such as nitric acid in acetic acid or nitronium tetrafluoroborate in solvents such as acetonitrile (J. L. Duffy, J. Org. Chem., 56, 3006–09, (1991)). Needless to say, the nitro function may be reduced with hydrogen in the presence of palladium (B. Baragatti, Eur. J. Med, 35, (10), 949–55, (2000)), or with stannous chloride in the presence of hydrochloric acid (R. P. Dixon, Org. Prep. Proced. Int., 32, (6), 573–77, (2000)), or with ferrous sulphate in the presence of aqueous ammonia (S. Castellano, J. Heterocycl. Chem., 37, (6), 1539–42, (2000)). The amine function thus freed may be acylated or may undergo a diazotization leading to Sandmeyer-Gatterman reactions (substitution with Cl, Br, I, CN, RS or OH,) (H. H. Hodgson, Chem. Rev., 40, 251–77, (1947); T. Sugaya, Synthesis, 73–76, (1994); the diazonium derivatives (N. Suzuki, J. Chem. Soc. Perkin Tr., 645, (1987)) or the halo derivatives obtained being able to give rise once again, as previously, to reactions involving palladium chemistry.

The compounds of formula (II) of 3-aminoindazole in which:

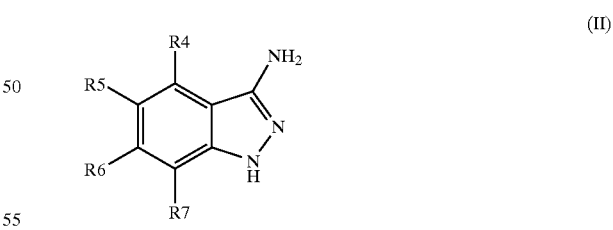

(II)

R4, R5, R6 and R7 are chosen, independently of each other, from the following radicals: hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C) alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, polycycloalkyls; these radicals being optionally substituted with one or more substituents chosen from halogen, CN, $NO_2$, $NH_2$, OH, OR10, COOH, C(O)

OR10, —O—C(O)R10, NR10R11, NHC(O)R10, C(O)NR10R11, NHC(S)R10, C(S)NR10R11, SR10, S(O)R10, SO₂R10, NHSO₂R10, SO₂NR10R11, —O—SO₂R10, —SO₂—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents chosen from halogen, (1–6C)alkyl, (1–6C) alkoxy, CN, NO₂, NH₂, OH, COOH, COOalkyl, CONH₂, formyl, trifluoromethyl and trifluoromethoxy;

the isomers thereof, the mixtures thereof and the racemic mixtures, enantiomers, diastereoisomers and tautomers thereof are useful as intermediates for preparing derivatives of general formula (I).

The compounds of general formula (II) or the pharmaceutically acceptable salts thereof may also be used to prepare a medicinal product and pharmaceutical compositions for the same indications as the compounds of formula (I).

Among the compounds of formula (II) that may be mentioned are the following products:
3-amino-5-bromo-1H-indazole
3-amino-6-bromo-1H-indazole
3-amino-5-methyl-1H-indazole
3-amino-6-(trifluoromethyl)-1H-indazole
3-amino-5-(trifluoromethyl)-1H-indazole
3-amino-4-chloro-1H-indazole
3-amino-5-nitro-1H-indazole
3-amino-6-(3-pyridyl)-1H-indazole
3-amino-4-iodo-1H-indazole
3-amino-6-phenyl-1H-indazole
3-amino-6-bromo-5,7-dinitro-1H-indazole
3-amino-6-bromo-7-nitro-1H-indazole
3-amino-6-bromo-5-nitro-1H-indazole
3-amino-6-(furan-3-yl)-1H-indazole
3-amino-6-[4-(phenylmethoxy)phenyl]-1H-indazole
3-amino-6-(4-hydroxyphenyl)-1H-indazole
3-amino-6-(3,5-difluorophenyl)-1H-indazole
3-amino-6-(3-thienyl)-1H-indazole
3-amino-5-[[(3-fluorophenyl)sulphonyl]amino]-1H-indazole
3-amino-6-(2-phenylethyl)-1H-indazole
3-amino-6,7-difluoro-1H-indazole
3-amino-6-(4-methoxyphenyl)-1H-indazole
3-amino-6-(4-methylthiophenyl)-1H-indazole
3-amino-6-(4-trifluoromethoxyphenyl)-1H-indazole
3-amino-(6-(1-propenyl)-1H-indazole
3-amino-6-(4-fluorophenyl)-1H-indazole
3-amino-6-[4-(1,1-dimethylethyl)phenyl]-1H-indazole
3-amino-6-bromo-7-amino-1H-indazole
3-amino-6-(4-methylphenyl)-1H-indazole
3-amino-6-(3,5-dichlorophenyl)-1H-indazole
3-amino-6-(4-chlorophenyl)-1H-indazole
3-amino-6-(4-ethylphenyl)-1H-indazole
3-amino-6-(4-pyridyl)-1H-indazole
3-amino-5-amino-1H-indazole
3-amino-5-bromo-6-chloro-1H-indazole
3-amino-5-phenyl-6-chloro-1H-indazole
3-amino-5-bromo-6-[4-(phenylmethoxy)phenyl]-1H-indazole
3-amino-5-bromo-6-(4-hydroxyphenyl)-1H-indazole
3-amino-6-(4-nitrophenyl)-1H-indazole
3-amino-6-(2-chlorophenyl)-1H-indazole
3-amino-6-[3-(phenylmethoxy)phenyl]-1H-indazole
3-amino-6-(3-hydroxyphenyl)-1H-indazole
3-amino-6-chloro-5-(4-pyridyl)-1H-indazole
3-amino-6-chloro-5-(3-furyl)-1H-indazole
3-amino-6-[2-chloro-4-(phenylmethoxy)-phenyl]-1H-indazole
3-amino-6-(2-chloro-4-hydroxyphenyl)-1H-indazole
3-amino-5,6-dibromo-1H-indazole
3-amino-6-chloro-5-(4-fluorophenyl)-1H-indazole
3-amino-6-(4-aminophenyl)-1H-indazole
3-amino-6-[4-(dimethylamino)phenyl]-1H-indazole
3-amino-6-chloro-1H-indazole
3-amino-5,6-diphenyl-1H-indazole
3-amino-6-chloro-5-(4-methylphenyl)-1H-indazole
3-amino-5-phenyl-6-[4-(phenylmethoxy)phenyl]-1H-indazole
3-amino-5-phenyl-6-(4-hydroxyphenyl)-1H-indazole
3-amino-5-(4-aminophenyl)-6-chloro-1H-indazole
3-amino-6-chloro-5-(4-ethylphenyl)-1H-indazole
3-amino-6-chloro-5-[4-(phenylmethoxy)phenyl]-1H-indazole
3-amino-6-chloro-5-(4-hydroxyphenyl)-1H-indazole
3-amino-5,6-bis [4-(phenylmethoxy)phenyl]-1H-indazole
3-amino-5,6-bis(4-hydroxyphenyl)-1H-indazole
3-amino-5-(3-furyl)-6-[4-(phenylmethoxy)phenyl]-1H-indazole
3-amino-5-(3-furyl)-6-([4-hydroxyphenyl)-1H-indazole
3-amino-5-(4-ethylphenyl)-6-[4-(phenylmethoxy)phenyl]-1H-indazole
3-amino-5-(4-ethylphenyl)-6-(4-hydroxyphenyl)-1H-indazole
3-amino-5-(3-pyridyl)-6-[4-(phenylmethoxy)phenyl]-1H-indazole
3-amino-5-(3-pyridyl)-6-(4-hydroxyphenyl)-1H-indazole
3-amino-5-(2-furyl)-6-[4-(phenylmethoxy)phenyl]-1H-indazole
3-amino-5-(2-furyl)-6-(4-hydroxyphenyl)-1H-indazole
3-amino-5-bromo-6-chloro-7-nitro-1H-indazole
3-amino-5-bromo-6,7-difluoro-1H-indazole
3-amino-6-(4-cyanophenyl)-1H-indazole
3-amino-6,7-difluoro-5-nitro-1H-indazole
3-amino-6,7-difluoro-5-phenyl-1H-indazole
3-amino-6-(6-hydroxypyrid-3-yl)-1H-indazole
3-amino-6-(3,4-dihydroxyphenyl)-1H-indazole
3-amino-7-fluoro-5-nitro-6-[2-(phenylethyl)amino]-1H-indazole
3-amino-7-fluoro-5-nitro-6-morpholino-1H-indazole
3-amino-7-fluoro-5-amino-6-morpholino-1H-indazole
3-amino-5-bromo-7-fluoro-6-morpholino-1H-indazole
3-amino-7-fluoro-6-(trifluoromethyl)-1H-indazole
3-amino-6-bromo-4,5,7-trifluoro-1H-indazole
3-amino-6-(6-aminopyrid-3-yl)-1H-indazole The compounds of formula (I) are isolated and may be purified by the usual known methods, for example by crystallization, chromatography or extraction.

The compounds of formula (I) may optionally be converted into addition salts with a mineral or organic acid by the action of such an acid in an organic solvent such as an alcohol, a ketone, an ether or a chlorinated solvent. These salts also form part of the invention.

Examples of pharmaceutically acceptable salts that may be mentioned include the following salts: benzenesulphonate, hydrobromide, hydrochloride, citrate, ethanesulphonate, fumarate, gluconate, iodate, maleate, isethionate, methanesulphonate, methylene-bis-β-oxynaphthoate, nitrate, oxalate, pamoate, phosphate, salicylate, succinate, sulphate, tartrate, theophyllinacetate and p-toluenesulphonate.

The compounds of formula (I) are kinase inhibitors and are thus useful for preventing and treating neurodegenerative diseases, Alzheimer's disease, Parkinson's disease, frontoparietal dementia, corticobasal degeneration, Pick's disease, strokes, cranial and spinal trauma and peripheral neuropathies, obesity, essential hypertension, atherosclerotic cardiovascular diseases, polycystic ovarian syndrome, syndrome X, immunodeficiency and cancer.

Their activities were determined by measuring the inhibition of the phosphorylation of the tau protein in sections of adult rat cortex.

The cortex sections are 300 µm thick and are prepared using 8–10-week-old male OFA rats (Iffa-Credo), sacrificed by decapitation. They are incubated in 5 ml of DMEM medium containing pyruvate and glucose 4.5 g/l at 37° C. for 40 minutes. The sections are then washed twice with the medium, distributed into microtubes (50 µl in 500 µl of medium with or without test compounds) and incubated at 37° C. with stirring. Two hours later, the experiment is stopped by centrifugation. The sections are lysed, sonicated and centrifuged at 18 300×g for 15 minutes at 4° C. The protein concentration of the supernatant is determined by means of a commercial assay (BCA Protein Assay, Pierce) based on the Lowry method.

The samples, denatured beforehand for ten minutes at 70° C., are separated on 4–12% Bis-Tris vertical gel in the presence of MOPS-SDS buffer and electrotransferred on nitrocellulose membrane. The immunolabelling is performed with the AD2 monoclonal antibody, which specifically recognizes the Ser396/404 phosphorylated epitopes of the tau protein. The immunoreactive proteins are visualized by adding a second antibody directed against mouse IgGs and coupled to peroxidase and to a chemoluminescent substrate. The autoradiograms obtained are finally quantified using the 'GeneTools' software from Syngene (GeneGnome, Ozyme) to determine an $IC_{50}$.

The compounds of formula (I) show very advantageous activity, and in particular certain compounds have an $IC_{50}$ of less than 100 µM.

The examples that follow illustrate the invention in a non-limiting manner.

EXAMPLE 1

(2Z) 4-[(6-chloro-1H-indazol-3-yl)amino]-4-oxo-2-butenoic acid 585 mg of preground maleic anhydride are added to 1 g of 6-chloro-1H-indazole-3-amine in 30 cm³ of ortho-xylene. The reaction medium is refluxed at 145° C. for ten minutes and then cooled in a water bath. The insoluble material is filtered off and washed successively with 2×25 cm³ of ethyl acetate and then with 2×25 cm³ of diisopropyl ether. The solid is then dried under reduced pressure (90 Pa; 50° C.) to give 1 g of 4-[(6-chloro-1H-indazol-3-yl)amino]-4-oxo-2-butenoic acid (Z form) in the form of yellow crystals melting at 230° C.

¹H NMR spectrum (300 MHz, $(CD_3)_2SO$-d6, δ in ppm): 6.38 (d, J=12 Hz: 1H); 6.60 (d, J=12 Hz: 1H); 7.13 (dd, J=9 and 1.5 Hz: 1H); 7.55 (d, J=1.5 Hz: 1H); 7.94 (d, J=9 Hz: 1H); 10.99 (broad s: 1H); from 12.60 to 13.40 (broad unresolved peak: 1H); 12.92 (unresolved peak: 1H).

EXAMPLE 2

Ethyl (2E) 4-[(6-chloro-1H-indazol-3-yl)amino]-4-oxo-2-butenoate 865 mg of monoethyl fumarate are added to 1 g of 6-chloro-1H-indazole-3-amine in 50 cm³ of dichloromethane. 1.4 g of 1-(3-dimethylaminopropyl)-3-ethylcarbodiimide hydrochloride are then introduced and the mixture is stirred for 30 minutes at about 20° C. The resulting mixture is washed with 50 cm³ of distilled water and then with 50 cm³ of saturated aqueous sodium chloride solution. The organic phase is dried over magnesium sulphate, filtered and then evaporated under reduced pressure (2 kPa; 40° C.). 2 g of a brick-coloured gummy mass are obtained, and are purified by chromatography under an argon pressure of 50 kPa, on a column of silica gel (particle size 40–60 µm; diameter 4.5 cm), eluting with a cyclohexane/ethyl acetate mixture (90/10 by volume) and collecting 40 cm³ fractions. The fractions containing the expected product are combined and then evaporated under reduced pressure (2 kPa) at a temperature in the region of 40° C. After drying (90 Pa; 45° C.), 900 mg of ethyl 4-[(6-chloro-1H-indazol-3-yl)amino]-4-oxo-2-butenoate, (E form), melting at 220° C., are obtained.

¹H NMR spectrum (300 MHz, $(CD_3)_2SO$-d6, δ in ppm): from 2.50 to 2.75 (mt: 4H); 7.07 (dd, J=8.5 and 1.5 Hz: 1H); 7.52 (d, J=1.5 Hz: 1H); 7.83 (d, J=8.5 Hz: 1H); 11.50 (broad s: 1H); 12.19 (broad unresolved peak: 1H); 12.75 (unresolved peak: 1H).

EXAMPLE 3

4-[(6-chloro-1H-indazol-3-yl)amino]-4-oxo-2-butanoic acid 300 mg of succinic anhydride are added to 500 mg of 6-chloro-1H-indazole-3-amine in 30 cm³ of ortho-xylene. The reaction medium is refluxed at about 145° C. for 16 hours and the heating is then stopped and the mixture is allowed to cool to room temperature of about 20° C. The reaction medium is then filtered through a sinter funnel; the solid is taken up in 20 cm³ of ethyl acetate and 30 cm³ of 10% sodium hydrogen carbonate solution. The organic phase is dried over magnesium sulphate, filtered and then evaporated according to the conditions already described. The white crystals thus obtained are stirred with 30 cm³ of 10% sodium hydrogen carbonate solution for 20 minutes. A light insoluble material is removed by filtration and the filtrate is acidified with 12N hydrochloric acid; the precipitate formed is washed with 2×10 cm³ of distilled water, with 1×5 cm³ of acetone and with 2×10 cm³ of diisopropyl ether. The solid is then dried under reduced pressure at about 40° C. and then purified by chromatography under an argon pressure of 50 kPa, on a column of silica gel (particle size 40–60 µm; diameter 2 cm), eluting with a dichloromethane/methanol mixture (99/1 by volume) and collecting 20 cm³ fractions. The fractions containing the expected product are combined and then evaporated according to the conditions described previously. The product obtained is taken up in 10 cm³ of ethyl acetate, filtered off on a sinter funnel and rinsed with 2×5 cm³ of ethyl acetate and then with 20 cm³ of diethyl ether. The product is dried under reduced pressure overnight (90 Pa; 40° C.) to give 110 mg of 4-[(6-chloro-1H-indazol-3-yl)amino]-4-oxo-2-butanoic acid in the form of a white solid melting at 200° C.

¹H NMR spectrum (300 MHz, $(CD_3)_2SO$-d6, δ in ppm): from 2.50 to 2.75 (mt: 4H); 7.07 (dd, J=8.5 and 1.5 Hz: 1H); 7.52 (d, J=1.5 Hz: 1H); 7.83 (d, J=8.5 Hz: 1H); 11.50 (broad s: 1H); 12.19 (broad unresolved peak: 1H); 12.75 (unresolved peak: 1H).

EXAMPLE 4

(2Z) 4-[(5-bromo-1H-indazol-3-yl)amino]-4-oxo-2-butenoic acid 350 mg of maleic anhydride are added to 500 mg of 5-bromo-1H-indazole-3-amine, prepared as described in U.S. Pat. No. 3,133,081, in 20 cm³ of toluene. The medium is refluxed at about 110° C. for one hour. The heating is then stopped and the mixture is stirred at about 19° C. for 12 hours. The precipitate formed is filtered off on a sinter funnel and rinsed with 20 cm³ of diisopropyl ether, 2 cm³ of ethyl acetate and 2 cm³ of dichloromethane. After drying (90 Pa; 45° C.), 448 mg of 4-[(5-bromo-1H-indazol-3-yl)amino]-4-oxo-2-butenoic acid, Z form, are obtained in the form of a yellow solid melting at 172° C.

¹H NMR spectrum (400 MHz, (CD₃)₂SO-d6, δ in ppm): 6.38 (d, J=12 Hz: 1H); 6.62 (d, J=12 Hz: 1H); 7.49 (mt: 2H); 8.15 (broad s: 1H); 10.95 (broad s: 1H); from 12.70 to 13.30 (broad unresolved peak: 1H); 12.98 (unresolved peak: 1H).

EXAMPLE 5

(2E) 4-[(6-chloro-1H-indazol-3-yl)amino]-4-oxo-2-butenoic acid 0.95 cm³ of 1N sodium hydroxide is added to 280 mg of ethyl (2E) 4-[(6-chloro-1H-indazol-3-yl)amino]-4-oxo-2-butenoate, described in Example 2, in 25 cm³ of ethanol. The reaction medium is then heated at 50° C. for two hours, followed by addition of a further 1 equivalent of 1N sodium hydroxide. The temperature is maintained at 50° C. for a further 30 minutes and the heating is then stopped. At about 20° C., the medium is neutralized with 1N hydrochloric acid and then concentrated under reduced pressure (2 kPa; 40° C.). The solid thus obtained is taken up in 25 cm³ of tetrahydrofuran, 50 cm³ of ethyl acetate and 25 cm³ of distilled water. The organic phase is washed with 30 cm³ of saturated aqueous sodium chloride solution and then dried over magnesium sulphate. The solution is filtered and evaporated under the conditions described previously. The residue is taken up in 10 cm³ of ethyl acetate and the insoluble material is then filtered off and rinsed with 5 cm³ of ethyl acetate and with 10 cm³ of diethyl ether and dried under reduced pressure (90 Pa; 50° C.). 155 mg of 4-[(6-chloro-1H-indazol-3-yl)amino]-4-oxo-2-butenoic acid (E form) are obtained in the form of a pale yellow solid melting at 260° C.

¹H NMR spectrum (300 MHz, (CD₃)₂SO-d6, δ in ppm): 6.75 (d, J=15.5 Hz: 1H); 7.11 (dd, J=9 and 2 Hz: 1H); 7.27 (d, J=15.5 Hz: 1H); 7.55 (d, J=2 Hz: 1H); 7.96 (d, J=9 Hz: 1H); 11.13 (broad s: 1H); from 12.40 to 13.10 (broad unresolved peak: 1H); 12.94 (unresolved peak: 1H).

EXAMPLE 6

4-[(5-bromo-1H-indazol-3-yl)amino]-4-oxo-2-butanoic acid 354 mg of succinic anhydride are added to 500 mg of 5-bromo-1H-indazole-3-amine, prepared as described in U.S. Pat. No. 3,133,081, in 20 cm³ of toluene. The reaction medium is refluxed at about 110° C. for 13 hours. The precipitate is filtered off and then rinsed with 10 cm³ of diisopropyl ether and 10 cm³ of dichloromethane. The product is taken up in 20 cm³ of saturated aqueous sodium hydrogen carbonate solution and acidified with 5N hydrochloric acid to pH 9/10. The precipitate formed is filtered off and rinsed with 20 cm³ of distilled water, and the solid is then taken up in 20 cm³ of acetone. The solution is then evaporated to dryness under reduced pressure (2 kPa; 40° C.) to give, after drying (90 Pa; 45° C.), 270 mg of 4-[(5-bromo-1H-indazol-3-yl)amino]-4-oxo-2-butanoic acid in the form of a white solid melting at about 173° C.

¹H NMR spectrum (300 MHz, (CD₃)₂SO-d6, δ in ppm): from 2.50 to 2.75 (mt: 4H); 7.45 (broad s: 2H); 8.02 (broad s: 1H); 16.55 (unresolved peak: 1H); 12.83 (unresolved peak: 1H).

EXAMPLE 7

(2E) N-(6-chloro-1H-indazol-3-yl)-2-butenamide 0.67 cm³ of distilled crotonyl chloride is added to 50 mg of 6-chloro-1H-indazole-3-amine dissolved in 5 cm³ of pyridine and cooled to about 6° C. The mixture is stirred for 10 minutes and the temperature is then allowed to rise to about 19° C. over 22 hours. The reaction medium is then concentrated to dryness under reduced pressure (2 kPa; 40° C.) and the residue is then taken up in 50 cm³ of tetrahydrofuran and 25 cm³ of ethyl acetate. The organic phase is washed with 2×50 cm³ of distilled water and then with 50 cm³ of saturated aqueous sodium chloride solution. The resulting solution is dried over magnesium sulphate, filtered through a sinter funnel and then evaporated under the conditions described previously. The residue obtained is purified by chromatography under an argon pressure of 50 kPa, on a column of silica gel (particle size 40–60 μm; diameter 4.5 cm), eluting with a cyclohexane/ethyl acetate mixture (80/20 by volume) and collecting 20 cm³ fractions. The fractions containing the expected product are combined and then evaporated under the conditions already described. After drying (90 Pa; 45° C.), 100 mg of N-(6-chloro-1H-indazol-3-yl)-2-butenamide, E form, are obtained in the form of a white solid melting at 226° C.

¹H NMR spectrum (300 MHz, (CD₃)₂SO-d6, δ in ppm): 1.90 (broad d, J=7 Hz: 3H); 6.27 (dd, J=15 and 1.5 Hz: 1H); 6.88 (dq, J=15 and 7 Hz: 1H); 7.08 (dd, J=9 and 2 Hz: 1H); 7.52 (d, J=2 Hz: 1H); 7.92 (d, J=9 Hz: 1H); 10.53 (unresolved peak: 1H); 12.80 (unresolved peak: 1H).

EXAMPLE 8

6-chloro-1-[(1,1-dimethylethoxy)carbonyl]-1H-indazole-3-amine 1.3 g of di-tert-butyl dicarbonate and 10 mg of dimethylaminopyridine are added to 1 g of 6-chloro-1H-indazole-3-amine in 30 cm³ of dichloromethane. The mixture is stirred for 17 hours at about 19° C. The reaction medium is evaporated to dryness according to the conditions already described, and the residue is then purified by chromatography under an argon pressure of 50 kPa, on a column of silica gel (particle size 40–60 μm; diameter 4 cm), eluting with a cyclohexane/ethyl acetate mixture (90/10 by volume). The fractions containing the expected product are combined and evaporated under reduced pressure (2 kPa; 50° C.). After drying (90 Pa; 45° C.), 1.2 g of 6-chloro-1-[(1,1-dimethylethoxy)carbonyl]-1H-indazole-3-amine are obtained in the form of a white solid.

¹H NMR spectrum (400 MHz, (CD₃)₂SO-d6, δ in ppm): 1.61 (s: 9H); 6.43 (broad s: 2H); 7.36 (dd, J=9 and 1.5 Hz: 1H); 7.89 (d, J=9 Hz: 1H); 7.97 (broad s: 1H).

N-(6-chloro-1-[(1,1-dimethylethoxy)carbonyl]-1H-indazol-3-yl)-3-butenamide 0.45 cm³ of predistilled crotonyl chloride is added to 1 g of 6-chloro-1-[(1,1-dimethylethoxy)carbonyl]-1H-indazole-3-amine described previously, in 40 cm³ of dichloromethane and 1.05 cm³ of triethylamine. The mixture is stirred at about 19° C. for 16 hours. The medium is then concentrated under reduced pressure (20 kPa; 40° C.). The residue is taken up in 100 cm³ of ethyl acetate and 50 cm³ of distilled water. The organic phase is then washed with 50 cm³ of saturated aqueous sodium chloride solution. The resulting solution is dried over magnesium sulphate, filtered through a sinter funnel and then evaporated under the conditions already described previously. The residue is purified by chromatography under an argon pressure of 50 kPa, on silica gel (particle size 40–60 μm; diameter 3 cm), eluting with a cyclohexane/ethyl acetate mixture (90/10 by volume) and collecting 15 cm³ fractions. The fractions containing the expected product are combined and then evaporated under reduced pressure (2 kPa; 40° C.). After drying (90 Pa; 45° C.), 120 mg of N-(6-chloro-1-[(1,1-dimethylethoxy)carbonyl]-1H-indazol-3-yl)-3-butenamide are obtained in the form of a yellow solid.

$^1$H NMR spectrum (300 MHz, $(CD_3)_2SO$-d6, δ in ppm): 1.66 (s: 9H); 3.28 (broad d, J=7.5 Hz: 2H); 5.20 (dd, J=10.5 and 1.5 Hz: 1H); 5.26 (dd, J=17 and 1.5 Hz: 1H); 6.02 (mt: 1H); 7.43 (dd, J=9 and 2 Hz: 1H); 8.05 (d, J=9 Hz: 1H); 8.12 (d, J=2 Hz: 1H); 11.09 (unresolved peak: 1H).

N-(6-chloro-1H-indazol-3-yl)-3-butenamide hydrochloride 10 cm³ of 4N hydrochloric dioxane are added to 240 mg of N-(6-chloro-1-[(1,1-dimethylethoxy)carbonyl]-1H-indazol-3-yl)-3-butenamide described previously. The mixture is stirred at about 19° C. for 17 hours. The crystalline product is filtered off on a sinter funnel, rinsed with 2×5 cm³ of ethyl acetate and with 2×5 cm³ of diethyl ether and then dried under reduced pressure (90 Pa; 40° C.). 125 mg of N-(6-chloro-1H-indazol-3-yl)-3-butenamide, in the form of the hydrochloride and melting at 150° C., are thus obtained.

$^1$H NMR spectrum (300 MHz, $(CD_3)_2SO$-d6, δ in ppm): 3.22 (d, J=7 Hz: 2H); 5.17 (broad d, J=10.5 Hz: 1H); 5.23 (broad d, J=18 Hz: 1H); from 5.30 to 6.80 (broad unresolved peak: 2H); 6.02 (mt: 1H); 7.07 (dd, J=9 and 2 Hz: 1H); 7.52 (d, J=2 Hz: 1H); 7.82 (d, J=9 Hz: 1H); 10.50 (broad s: 1H).

EXAMPLE 9 methyl 4-[(6-chloro-1H-indazol-3-yl)amino]-4-oxo-2-butanoate 4 g of 6-chloro-1H-indazole-3-amine in 40 cm³ of pyridine at 5° C. are added to 3.5 g of methyl 4-chloro-4-oxobutanoate in 10 cm³ of dichloromethane. The mixture is allowed to return to 19° C. over 19 hours. The reaction medium is evaporated under the conditions described previously. The residue is taken up in 75 cm³ of tetrahydrofuran and 75 cm³ of ethyl acetate. The mixture is washed with 3×50 cm³ of distilled water. The resulting solution is dried over magnesium sulphate, filtered through a sinter funnel and evaporated under reduced pressure (2 kPa; 40° C.). The product is purified by chromatography under an argon pressure of 50 kPa, on a column of silica gel (particle size 40–60 μm; diameter 6 cm), eluting with a cyclohexane/ethyl acetate mixture (70/30 by volume) and collecting 50 cm³ fractions. The fractions containing the expected product are combined and then evaporated under reduced pressure (2 kPa; 40° C.). After drying (90 Pa; 45° C.), 3 g of methyl 4-[(6-chloro-1H-indazol-3-yl)amino]-4-oxo-2-butanoate are obtained in the form of a white solid melting at 170° C.

$^1$H NMR spectrum (300 MHz, $(CD_3)_2SO$-d6, δ in ppm): from 2.60 to 2.80 (mt: 4H); 3.63 (s: 3H); 7.08 (dd, J=9 and 2 Hz: 1H); 7.52 (d, J=2 Hz: 1H); 7.82 (d, J=9 Hz: 1H); 10.52 (unresolved peak: 1H); 12.77 (broad unresolved peak: 1H).

EXAMPLE 10

N-(6-chloro-1H-indazol-3-yl)acetamide 0.32 cm³ of predistilled acetyl chloride is added to 750 mg of 6-chloro-1H-indazole-3-amine in 10 cm³ of pyridine, after the reaction medium has been cooled to about 3° C. The medium is then allowed to return to 19° C. over 48 hours. The reaction medium is evaporated to dryness under reduced pressure (2 kPa; 40° C.). The residue is taken up in 75 cm³ of ethyl acetate and 50 cm³ of distilled water. The organic phase is washed again with 50 cm³ of distilled water and then dried over magnesium sulphate, filtered through a sinter funnel and evaporated under reduced pressure. The residue obtained is purified by chromatography under an argon pressure of 50 kPa, on a column of silica gel (particle size 40–60 μm; diameter 4 cm), eluting with a cyclohexane/ethyl acetate mixture (60/40 by volume) and collecting 35 cm³ fractions. The fractions containing the expected product are combined and evaporated under reduced pressure (2 kPa; 40° C.). After drying (90 Pa; 45° C.), 700 mg of N-(6-chloro-1H-indazol-3-yl)-acetamide, melting at 240° C., are obtained.

$^1$H NMR spectrum (300 MHz, $(CD_3)_2SO$-d6, δ in ppm): 2.13 (s: 3H); 7.08 (dd, J=9 and 2 Hz: 1H); 7.52 (d, J=2 Hz: 1H); 7.86 (d, J=9 Hz: 1H); 10.45 (unresolved peak: 1H); from 12.50 to 13.10 (broad unresolved peak: 1H).

EXAMPLE 11

N-(6-chloro-1H-indazol-3-yl)butanamide 0.47 cm³ of butyryl chloride is added to 750 mg of 6-chloro-1H-indazole-3-amine in 10 cm³ of pyridine, after the reaction medium has been cooled to about 3° C. The medium is then allowed to return to 19° C. over 14 hours. The reaction medium is evaporated to dryness under reduced pressure (2 kPa; 40° C.). The residue is taken up in 50 cm³ of ethyl acetate, 50 cm³ of tetrahydrofuran and 50 cm³ of distilled water. The organic phase is washed again with 50 cm³ of distilled water and with 50 cm³ of saturated aqueous sodium chloride solution, and then dried over magnesium sulphate, filtered through a sinter funnel and evaporated under reduced pressure. The residue obtained is purified by chromatography under an argon pressure of 50 kPa, on a column of silica gel (particle size 40–60 μm; diameter 2.5 cm), eluting with cyclohexane/ethyl acetate (70/30 by volume) and collecting 25 cm³ fractions. The fractions containing the expected product are combined and then evaporated under reduced pressure (2 kPa; 40° C.). After drying (90 Pa; 45° C.), 200 mg of N-(6-chloro-1H-indazol-3-yl)-butanamide are obtained in the form of a white solid melting at 230° C.

$^1$H NMR spectrum (300 MHz, $(CD_3)_2SO$-d6, δ in ppm): 0.98 (t, J=7 Hz: 3H); 1.67 (mt: 2H); 2.40 (t, J=7 Hz: 2H); 7.08 (dd, J=9 and 2 Hz: 1H); 7.52 (d, J=2 Hz: 1H); 7.84 (d, J=9 Hz: 1H); 10.39 (unresolved peak: 1H); from 12.50 to 13.00 (broad unresolved peak: 1H).

EXAMPLE 12

6-bromo-1H-indazole-3-amine 7.3 cm³ of hydrazine monohydrate are added to 10 g of 4-bromo-2-fluorobenzonitrile in 100 cm³ of ethanol. The medium is refluxed at about 78° C. for 12 hours. The precipitate formed is then filtered off on a sinter funnel. After drying (90 Pa; 45° C.), 9.7 g of 6-bromo-1H-indazole-3-amine are obtained in the form of a white solid.

$^1$H NMR spectrum (300 MHz, $(CD_3)_2SO$-d6, δ in ppm): 5.45 (broad s: 2H); 7.03 (dd, J=9 and 2 Hz: 1H); 7.43 (d, J=2 Hz: 1H); 7.65 (d, J=9 Hz: 1H); 11.50 (unresolved peak: 1H).

(2E) N-(6-bromo-1H-indazol-3-yl)-2-butenamide 1.07 cm³ of crotonyl chloride are added to 2 g of 6-bromo-1H-indazole-3-amine, prepared previously, in 30 cm³ of pyridine, cooled to about 3° C. The medium is allowed to return to about 19° C. over 12 hours. The reaction medium is evaporated under reduced pressure (2 kPa; 50° C.) and the residue is taken up in 20 cm³ of ethyl acetate and 20 cm³ of distilled water. The aqueous phase is re-extracted with 20 cm³ of ethyl acetate. The aqueous phases are combined and then evaporated under the conditions described previously. The residue is purified by chromatography under an argon pressure of 50 kPa, on a column of silica gel (particle size 40–60 µm; diameter 2.5 cm), eluting with a cyclohexane/ethyl acetate mixture (50/50 by volume) and collecting 15 cm³ fractions. The fractions containing the expected product are combined and evaporated under reduced pressure (2 kPa; 50° C.). After drying (90 Pa; 45° C.), 130 mg of N-(6-bromo-1H-indazol-3-yl)-2-butenamide (E form) are obtained in the form of a beige-coloured solid melting at 232° C.

$^1$H NMR spectrum (300 MHz, $(CD_3)_2$SO-d6, δ in ppm): 1.91 (dd, J=7 and 1.5 Hz: 3H); 6.27 (dd, J=15 and 1.5 Hz: 1H); 6.89 (dq, J=15 and 7 Hz: 1H); 7.20 (dd, J=9 and 2 Hz: 1H); 7.68 (d, J=2 Hz: 1H); 7.87 (d, J=9 Hz: 1H); 10.54 (unresolved peak: 1H); 12.80 (broad unresolved peak: 1H).

EXAMPLE 13

(2E) N-(5-methyl-1H-indazol-3-yl)-2-butenamide 0.33 cm³ of crotonyl chloride is added to 560 mg of 5-methyl-1H-indazole-3-amine, prepared as described in patent EP 909 720, in 30 cm³ of pyridine. The medium is allowed to return to about 19° C. over 12 hours. The reaction medium is evaporated under reduced pressure (2 kPa; 50° C.) and the residue is taken up in 25 cm³ of tetrahydrofuran, 25 cm³ of ethyl acetate and 25 cm³ of distilled water. The organic phase is washed with 2×25 cm³ of distilled water. The resulting solution is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 2.5 cm), eluting with a cyclohexane/ethyl acetate mixture (50/50 by volume) and collecting 20 cm³ fractions. The fractions containing the expected product are combined and evaporated under reduced pressure (2 kPa; 50° C.). After drying (90 Pa; 45° C.), 50 mg of N-(5-methyl-1H-indazol-3-yl)-2-butenamide (E form) are obtained in the form of a white solid melting at about 218° C.

$^1$H NMR spectrum (300 MHz, $(CD_3)_2$SO-d6, δ in ppm): 1.90 (broad d, J=7 Hz: 3H); 2.38 (s: 3H); 6.25 (dd, J=15 and 1.5 Hz: 1H); 6.86 (dq, J=15 and 7 Hz: 1H); 7.17 (dd, J=9 and 2 Hz: 1H); 7.34 (d, J=9 Hz: 1H); 7.56 (broad s: 1H); 10.31 (unresolved peak: 1H); 12.52 (unresolved peak: 1H).

EXAMPLE 14

N-(6-chloro-1H-indazol-3-yl)-2-propanamide 0.39 cm³ of propionyl chloride is added to 750 mg of 6-chloro-1H-indazole-3-amine in 10 cm³ of pyridine, cooled to about 3° C. The reaction medium is allowed to return to about 19° C. over 12 hours and is evaporated under reduced pressure (2 kPa; 50° C.). The residue is taken up in 40 cm³ of tetrahydrofuran, 40 cm³ of ethyl acetate and 40 cm³ of distilled water. The organic phase is washed with 40 cm³ of distilled water and 40 cm³ of saturated aqueous sodium chloride solution. The resulting solution is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 4 cm), eluting with a cyclohexane/ethyl acetate mixture (70/30 by volume) and collecting 35 cm³ fractions. The fractions containing the expected product are combined and evaporated under reduced pressure (2 kPa; 50° C.). The product obtained is taken up in 50 cm³ of diethyl ether, filtered off on a sinter funnel and then washed with 2×10 cm³ of diethyl ether. The product is filtered off by suction and, after drying (90 Pa; 45° C.), 440 mg of N-(6-chloro-1H-indazol-3-yl)-2-propanamide are obtained in the form of a white solid melting at 210° C.

$^1$H NMR spectrum (300 MHz, $(CD_3)_2$SO-d6, δ in ppm): 5.66 (s: 2H); 7.42 (d, J=9 Hz: 1H); 7.50 (broad d, J=9 Hz: 1H); 8.22 (broad s: 1H); 10.86 (unresolved peak: 1H).

EXAMPLE 15

(2E) N-[6-(trifluoromethyl)-1H-indazol-3-yl]-2-butenamide 0.23 cm³ of crotonyl chloride is added to 500 mg of 6-trifluoro methyl-1H-indazole-3-amine, prepared as described in patent U.S. Pat. No. 3,133,081, in 10 cm³ of pyridine, cooled to about 10° C. The temperature is allowed to return to about 19° C. over 17 hours. The reaction medium is evaporated under reduced pressure (2 kPa; 50° C.) and the residue is taken up in 25 cm³ of tetrahydrofuran, 25 cm³ of ethyl acetate and 25 cm³ of distilled water. The organic phase is washed with 25 cm³ of distilled water. The combined organic phases are dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 2 cm), eluting with a cyclohexane/ethyl acetate mixture (70/30 by volume) and collecting 30 cm³ fractions. The fractions containing the expected product are combined and evaporated under reduced pressure (2 kPa; 50° C.). The residue is taken up in 30 cm³ of diisopropyl ether and then filtered off on a sinter funnel. After drying (90 Pa; 45° C.), 41 mg of N-[6-(trifluoromethyl)-1H-indazol-3-yl]-2-butenamide (E form) are obtained in the form of a white solid melting at 208° C.

$^1$H NMR spectrum (300 MHz, $(CD_3)_2$SO-d6, δ in ppm): 1.91 (dd, J=7 and 1.5 Hz: 3H); 6.29 (dd, J=15 and 1.5 Hz: 1H); 6.91 (dq, J=15 and 7 Hz: 1H); 7.35 (broad d, J=9 Hz: 1H); 7.83 (broad s: 1H); 8.11 (d, J=9 Hz: 1H); 10.65 (unresolved peak: 1H); from 12.60 to 13.50 (broad unresolved peak: 1H).

EXAMPLE 16

Ethyl 4-[[6-(trifluoromethyl)-1H-indazol-3-yl]amino]-4-oxobutanoate 0.23 cm³ of crotonyl chloride is added to 249 mg of 6-(trifluoromethyl)-1H-indazole-3-amine, prepared as described in patent U.S. Pat. No. 3,133,081, in 10 cm³ of pyridine, cooled to about 10° C. The temperature is allowed to return to about 19° C. over 17 hours. The reaction medium is evaporated under reduced pressure (2 kPa; 50° C.). The residue is taken up in 25 cm³ of tetrahydrofuran, 25 cm³ of ethyl acetate and 25 cm³ of distilled water. The organic phase is washed with 2×25 cm³ of distilled water. The combined organic phases are dried over magnesium sulphate and filtered through a sinter funnel, and then evaporated under reduced pressure (2 kPa; 50° C.). The residue is purified by chromatography under an argon pressure of 50 kPa, on a column of silica gel (particle size 40–60 µm; diameter 2 cm), eluting with a dichloromethane/methanol mixture (98/2 by volume) and collecting 30 cm³ fractions. The fractions containing the expected product are combined and evaporated under reduced pressure (2 kPa; 50° C.). After drying (90 Pa; 45° C.), 210 mg of ethyl 4-[[6-(trifluoromethyl)-1H-indazol-3-yl]amino]-4-oxobutanoate are obtained in the form of a white solid melting at 248° C.

$^1$H NMR spectrum (300 MHz, $(CD_3)_2$SO-d6, δ in ppm): 1.21 (t, J=7 Hz: 3H); from 2.60 to 2.80 (mt: 4H); 4.10 (q, J=7 Hz: 2H); 7.35 (broad d, J=9 Hz: 1H); 7.84 (broad s: 1H); 8.02 (d, J=9 Hz: 1H); 10.61 (unresolved peak: 1H); from 12.60 to 13.60 (broad unresolved peak: 1H).

EXAMPLE 17

(2E) N-[5-(trifluoromethyl)-1H-indazol-3-yl]-2-butenamide 0.24 cm³ of crotonyl chloride is added to 500 mg of 5-(trifluoromethyl)-1H-indazole-3-amine, prepared according to patent U.S. Pat. No. 3,133,081, in 15 cm³ of pyridine. The reaction medium is stirred at about 19° C. for 12 hours and then evaporated under reduced pressure (2 kPa; 50° C.). The residue is taken up in 25 cm³ of tetrahydrofuran, 25 cm³ of ethyl acetate and 25 cm³ of distilled water. The organic phase is washed again with 25 cm³ of distilled water. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 2.5 cm), eluting with a cyclohexane/ethyl acetate mixture (40/60 by volume) and collecting 25 cm³ fractions. The fractions containing the expected product are combined and evaporated under reduced pressure (2 kPa; 50° C.). After drying (90 Pa; 45° C.), 63 mg of N-[5-(trifluoromethyl)-1H-indazol-3-yl]-2-butenamide (E form) are obtained in the form of an off-white solid melting at about 242° C.

$^1$H NMR spectrum (300 MHz, $(CD_3)_2$SO-d6, δ in ppm): 1.91 (dd, J=7 and 1.5 Hz: 3H); 6.30 (dd, J=15 and 1.5 Hz: 1H); 6.93 (dq, J=15 and 7 Hz: 1H); 7.60 (dd, J=9 and 2 Hz: 1H); 7.66 (d, J=9 Hz: 1H); 8.42 (broad s: 1H); 10.73 (unresolved peak: 1H); from 12.90 to 13.40 (broad unresolved peak: 1H).

EXAMPLE 18

N-[5-chloro-1H-indazol-3-yl]-2-butanamide 0.31 cm³ of butyryl chloride is added to 500 mg of 5-chloro-1H-indazole-3-amine, prepared according to patent EP 90 972, in 25 cm³ of pyridine, cooled to about 5° C. The temperature is allowed to return to about 19° C. over 17 hours and the reaction medium is evaporated under reduced pressure (2 kPa; 50° C.). The residue is taken up in 25 cm³ of tetrahydrofuran, 25 cm³ of ethyl acetate and 25 cm³ of distilled water. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 2.5 cm), eluting with a cyclohexane/ethyl acetate mixture (60/40 by volume) and collecting 30 cm³ fractions. The fractions containing the expected product are combined and evaporated under reduced pressure (2 kPa; 50° C.). After drying (90 Pa; 45° C.), 100 mg of N-[5-chloro-1H-indazol-3-yl]-2-butanamide are obtained in the form of a white solid melting at 216° C.

$^1$H NMR spectrum (300 MHz, $(CD_3)_2$SO d6, δ in ppm): 0.97 (t, J=7.5 Hz: 3H); 1.68 (mt: 2H); 2.40 (t, J=7.5 Hz: 2H); 7.35 (dd, J=9 and 2 Hz: 1H); 7.49 (dd, J=9 and 0.5 Hz: 1H); 7.86 (dd, J=2 and 0.5 Hz: 1H); 10.41 (unresolved peak: 1H); 12.82 (unresolved peak: 1H).

EXAMPLE 19

N-[4-chloro-1H-indazol-3-yl]butanamide 0.23 cm³ of butyryl chloride is added to 1 g of 4-chloro-1H-indazole-3-amine, prepared as described in patent EP 90 972, in 10 cm³ of pyridine, cooled to about 10° C. The temperature is allowed to return to about 19° C. over 17 hours. The reaction medium is evaporated under reduced pressure (2 kPa; 50° C.). The residue is taken up in 25 cm³ of ethyl acetate and 25 cm³ of distilled water. The organic phase is washed with 2×25 cm³ of distilled water and with 25 cm³ of saturated aqueous sodium chloride solution. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 4 cm), eluting with a dichloromethane/methanol mixture (99/1 by volume) and collecting 30 cm³ fractions. The fractions containing the expected product are combined and evaporated under reduced pressure (2 kPa; 50° C.). 80 mg of N-[4-chloro-1H-indazol-3-yl]butanamide are thus obtained in the form of a white solid melting at 198° C.

$^1$H NMR spectrum (300 MHz, $(CD_3)_2$SO-d6, δ in ppm): 0.98 (broad t, J=7 Hz: 3H); 1.66 (mt: 2H); 2.35 (very broad t, J=7 Hz: 2H); 7.15 (broad d, J=8 Hz: 1H); 7.34 (t, J=8 Hz: 1H); 7.49 (d, J=8 Hz: 1H); 9.80 (unresolved peak: 1H).

EXAMPLE 20

N-[6-(trifluoromethyl)-1H-indazol-3-yl]butanamide 0.26 cm³ of butyryl chloride is added to 500 mg of 6-(trifluoromethyl)-1H-indazole-3-amine, prepared as described in patent U.S. Pat. No. 3,133,081, in 5 cm³ of pyridine, cooled to about 10° C. The temperature is allowed to return to about 19° C. over 19 hours. The reaction medium is evaporated under reduced pressure (2 kPa; 50° C.). The residue is taken up in 15 cm³ of ethyl acetate and 15 cm³ of distilled water. The organic phase is washed with 15 cm³ of distilled water and with 15 cm³ of saturated aqueous sodium chloride solution. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 2 cm), eluting with a cyclohexane/ethyl acetate mixture (70/30 by volume) and collecting 20 cm³ fractions. The fractions containing the expected product are combined and evaporated under reduced pressure (2 kPa; 50° C.). After drying (90 Pa; 45° C.), 49 mg of N-[6-(trifluoromethyl)-1H-indazol-3-yl]butanamide are thus obtained in the form of a white solid melting at 200° C.

$^1$H NMR spectrum (300 MHz, $(CD_3)_2$SO-d6, δ in ppm): 0.98 (t, J=7, 5 Hz: 3H); 1.69 (mt: 2H); 2.42 (t, J=7.5 Hz: 2H); 7.34 (broad d, J=9 Hz: 1H); 7.82 (broad s: 1H); 8.04 (d, J=9 Hz: 1H); 10.49 (unresolved peak: 1H); 13.10 (broad unresolved peak: 1H).

EXAMPLE 21

6-chloro-1-[[2-(trimethylsilyl)ethoxy]methyl]-1H-indazole-3-amine

A solution of 2 g of 6-chloro-1H-indazole-3-amine in 20 cm³ of dimethylformamide is added to 478 mg of sodium hydride in 50 cm³ of anhydrous dimethylformamide. The resulting solution is then cooled to about 3° C. and 2.12 cm³ of [2-(trimethylsilyl)ethoxy]methyl chloride in 10 cm³ of dimethylformamide are added. The resulting mixture is allowed to return to about 19° C. over 45 minutes and is then taken up in 250 cm³ of ethyl acetate. This mixture is washed with 3×100 cm³ of distilled water and 100 cm³ of saturated aqueous sodium chloride solution. The organic phase is dried over magnesium sulphate, filtered through a sinter funnel and then evaporated under reduced pressure (2 kPa; 40° C.). The residue is purified by chromatography under an argon pressure of 50 kPa, on a column of silica gel (particle size 40–60 µm; diameter 4 cm), eluting with a cyclohexane/ethyl acetate mixture (90/10 by volume) and collecting 100 cm³ fractions. The fractions containing the expected product are combined and evaporated under reduced pressure (2 kPa; 50° C.). 2 g of 6-chloro-1-[[(2-trimethylsilyl)ethoxy]methyl]-1H-indazole-3-amine are obtained in the form of a yellow oil.

¹H NMR spectrum (300 MHz, (CD₃)₂SO-d6, δ in ppm): −0.09 (s: 9H); 0.80 (t, J=8 Hz: 2H); 3.48 (t, J=8 Hz: 2H); 5.43 (s: 2H); 5.68 (broad s: 2H); 7.01 (dd, J=9 and 2 Hz: 1H); 7.61 (d, J=2 Hz: 1H); 7.74 (d, J=9 Hz: 1H).

N-[6-chloro-1-[(2-trimethylsilylethoxy)methyl]-1H-indazol-3-yl]propenamide 0.33 cm³ of acryloyl chloride is added to 1 g of 6-chloro-1-[[(2-trimethylsilyl)ethoxy]methyl]-1H-indazole-3-amine, described previously, in 25 cm³ of dichloromethane and 0.57 cm³ of triethylamine. The reaction medium is stirred for 30 minutes and then evaporated under reduced pressure (2 kPa; 40° C.). The residue is taken up in 100 cm³ of ethyl acetate and this mixture is washed with 2×50 cm³ of distilled water and with 50 cm³ of saturated aqueous sodium chloride solution. The organic phase is dried over magnesium sulphate, filtered through a sinter funnel and then evaporated under reduced pressure (2 kPa; 40° C.). The residue is purified by chromatography under an argon pressure of 50 kPa, on a column of silica gel (particle size 40–60 µm; diameter 2.5 cm), eluting with a cyclohexane/ethyl acetate mixture (90/10 by volume) and collecting 35 cm³ fractions. The fractions containing the expected product are combined and evaporated under reduced pressure (2 kPa; 50° C.). After drying (90 Pa; 45° C.), 160 mg of N-[6-chloro-1-[[2-(trimethylsilyl)ethoxy]methyl]-1H-indazol-3-yl]propenamide are thus obtained in the form of a white solid.

¹H NMR spectrum (300 MHz, (CD₃)₂SO-d6, δ in ppm): −0.08 (s: 9H); 0.83 (t, J=8 Hz: 2H); 3.54 (t, J=8 Hz: 2H); 5.68 (s: 2H); 5.84 (dd, J=10.5 and 2 Hz: 1H); 6.35 (dd, J=16.5 and 2 Hz: 1H); 6.60 (dd, J=16.5 and 10.5 Hz: 1H); 7.18 (dd, J=9 and 2 Hz: 1H); 7.88 (d, J=2 Hz: 1H); 8.00 (d, J=9 Hz: 1H); 10.40 (unresolved peak: 1H).

N-[6-chloro-1H-indazol-3-yl]propenamide 5 cm³ of 5N hydrochloric acid are added to 160 mg of N-[6-chloro-1-[[2-(trimethylsilyl)ethoxy]methyl]-1H-indazol-3-yl]]propenamide described previously, in 10 cm³ of ethanol. The medium is heated at about 78° C. for 30 minutes. The mixture is then allowed to return to about 19° C. and 6 cm³ of 5N sodium hydroxide are added. The reaction medium is evaporated under reduced pressure (2 kPa; 40° C.) and the residue is taken up in 50 cm³ of ethyl acetate, 25 cm³ of tetrahydrofuran and 20 cm³ of distilled water. The organic phase is washed with 50 cm³ of saturated aqueous sodium chloride solution. The resulting solution is then dried over magnesium sulphate, filtered through a sinter funnel and then evaporated under reduced pressure (2 kPa; 40° C.). The residue is purified by chromatography under an argon pressure of 50 kPa, on a column of silica gel (particle size 40–60 µm; diameter 1.5 cm), eluting with a cyclohexane/ethyl acetate mixture (50/50 by volume) and collecting 7 cm³ fractions. The fractions containing the expected product are combined and evaporated under reduced pressure (2 kPa; 50° C.). The residue is taken up in 10 cm³ of dichloromethane, the insoluble material is filtered off on a sinter funnel and this mixture is washed with 2×5 cm³ of dichloromethane. After drying (90 Pa; 45° C.), 10 mg of N-[6-chloro-1H-indazol-3-yl]propenamide are thus obtained in the form of a white solid melting at 205° C.

¹H NMR spectrum (300 MHz, (CD₃)₂SO-d6, δ in ppm): 5.82 (dd, J=10.5 and 2 Hz: 1H); 6.34 (dd, J=17 and 2 Hz: 1H); 6.60 (dd, J=17 and 10.5 Hz: 1H); 7.10 (dd, J=9 and 2 Hz: 1H); 7.54 (d, J=2 Hz: 1H); 7.95 (d, J=9 Hz: 1H); 10.78 (broad unresolved peak: 1H); 12.86 (broad unresolved peak: 1H).

EXAMPLE 22

N-[5-(trifluoromethyl)-1H-indazol-3-yl]butanamide 0.26 cm³ of butyryl chloride is added to 500 mg of 5-(trifluoromethyl)-1H-indazole-3-amine, prepared according to patent U.S. Pat. No. 3,133,081, in 15 cm³ of pyridine, and cooled to about 5° C. The reaction medium is allowed to return to about 19° C. over 12 hours. The reaction medium is evaporated under reduced pressure (2 kPa; 50° C.). The residue is taken up in 15 cm³ of ethyl acetate and 15 cm³ of distilled water. The organic phase is dried over magnesium sulphate, filtered through a sinter funnel and then evaporated under reduced pressure (2 kPa; 50° C.). The residue is taken up in 15 cm³ of dichloromethane, filtered and dried under reduced pressure (90 Pa; 50° C.) to give 390 mg of N-[5-(trifluoromethyl)-1H-indazol-3-yl]butanamide in the form of an off-white solid melting at 230° C.

¹H NMR spectrum (300 MHz, (CD₃)₂SO-d6, δ in ppm): 0.97 (t, J=7.5 Hz: 3H); 1.68 (mt: 2H); 2.43 (t, J=7 Hz: 2H); 7.60 (dd, J=9 and 1.5 Hz: 1H); 7.65 (d, J=9 Hz: 1H); 8.34 (broad s: 1H); 10.60 (broad s: 1H); 13.06 (broad s: 1H).

EXAMPLE 23

N-[5-nitro-1H-indazol-3-yl]butanamide 0.58 cm³ of butyryl chloride is added to 1 g of 5-nitro-1H-indazole-3-amine, prepared as described in, SU 742430 (CA: 94 :65676) in 25 cm³ of pyridine, and cooled to about 5° C. The reaction medium is allowed to return to about 19° C. over 12 hours. The insoluble material present is filtered off and the filtrate is then evaporated under reduced pressure (2 kPa; 50° C.). The residue is taken up in 15 cm³ of ethyl acetate and 15 cm³ of distilled water. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 µm; diameter 3.5 cm), eluting with a cyclohexane/ethyl acetate mixture (70/30 by volume) and collecting 20 cm³ fractions. The fractions containing the expected product are combined and evaporated under reduced pressure (2 kPa; 50° C.). After drying (90 Pa; 50° C.), 480 mg of N-[5-nitro-1H-indazol-3-yl]butanamide are thus obtained in the form of a white solid.

¹H NMR spectrum (300 MHz, (CD₃)₂SO-d6, δ in ppm): 0.98 (t, J=7.5 Hz: 3H); 1.70 (mt: 2H); 2.46 (t, J=7 Hz: 2H);

7.63 (d, J=9 Hz: 1H); 8.18 (dd, J=9 and 2 Hz: 1H); 9.05 (d, J=2 Hz: 1H); 10.77 (unresolved peak: 1H); from 13.00 to 13.70 (broad unresolved peak: 1H).

EXAMPLE 24

N-[6-bromo-1H-indazol-3-yl]butanamide 0.24 cm$^3$ of butyryl chloride is added to 500 mg of 6-bromo-1H-indazole-3-amine described previously in Example 12, in 15 cm$^3$ of pyridine, and cooled to about 5° C. The reaction medium is allowed to return to about 19° C. over 50 hours. The reaction medium is evaporated under reduced pressure (2 kPa; 50° C.). The residue is taken up in 15 cm$^3$ of ethyl acetate and 15 cm$^3$ of distilled water. The organic phase is dried over magnesium sulphate, filtered through a sinter funnel and then evaporated under reduced pressure (2 kPa; 50° C.). The residue is taken up in 15 cm$^3$ of dichloromethane and filtered to give after drying (90 Pa; 50° C.), 356 mg of N-[6-bromo-1H-indazol-3-yl]butanamide in the form of an off-white solid melting at 202° C.

$^1$H NMR spectrum (300 MHz, (CD$_3$)$_2$SO-d6, δ in ppm): 0.98 (broad t, J=7.5 Hz: 3H); 1.67 (mt: 2H); 2.39 (broad t, J=7 Hz: 2H); 7.20 (broad d, J=9 Hz: 1H); 7.68 (broad s: 1H); 7.78 (broad d, J=9 Hz: 1H); 10.40 (unresolved peak: 1H); 12.75 (unresolved peak: 1H).

EXAMPLE 25

N-[6-chloro-1-[[2-(trimethylsilyl)ethoxy]methyl]-1H-indazol-3-yl]]butanamide 3 g of N-(6-chloro-1H-indazol-3-yl)butanamide, described previously in Example 11, dissolved in 40 cm$^3$ of dimethylformamide are added to 606 mg of 60% sodium hydride in 20 cm$^3$ of dimethylformamide. After cooling to about 5° C., 2.68 cm$^3$ of [[2-(trimethylsilyl)ethoxy]methyl] chloride in 10 cm$^3$ of dimethylformamide are added. The temperature is allowed to return to about 21° C. and the mixture is stirred for 2 hours. The reaction medium is then evaporated under reduced pressure (2 kPa; 45° C.). The residue is taken up in 200 cm$^3$ of ethyl acetate and 100 cm$^3$ of distilled water. This mixture is washed again with 2×100 cm$^3$ of distilled water and with 100 cm$^3$ of saturated aqueous sodium chloride solution. The organic phase is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 μm; diameter 4.5 cm), eluting with a cyclohexane/ethyl acetate mixture (80/20 by volume) and collecting 100 cm$^3$ fractions. The fractions containing the expected product are combined and evaporated under reduced pressure (2 kPa; 50° C.). After drying (90 Pa; 50° C.), 3 g of N-[6-chloro-1-[[2-(trimethylsilyl)ethoxy]methyl]-1H-indazol-3-yl]] butanamide are thus obtained in the form of a yellow oil.

$^1$H NMR spectrum (300 MHz, (CD$_3$)$_2$SO-d6, δ in ppm): −0.08 (s: 9H); 0.83 (broad t, J=8 Hz: 2H); 0.96 (t, J=7.5 Hz: 3H); 1.67 (mt: 2H); 2.40 (t, J=7.5 Hz: 2H); 3.53 (t, J=8 Hz: 2H); 5.66 (s: 2H); 7.16 (dd, J=9 and 2 Hz: 1H); 7.86 (d, J=2 Hz: 1H); 7.88 (d, J=9 Hz: 1H); 10.53 (unresolved peak: 1H).

N-[6-(3-pyridyl)-1-[[2-(trimethylsilyl)ethoxy]methyl]-1H-indazol-3-yl]butanamide 900 mg of diethyl-3-pyridylborane, 1.86 g of caesium fluoride, 18.4 mg of palladium acetate and finally 48 mg of 2-dicyclohexylphosphine-2-(N,N-dimethylamino)biphenyl are added to 1.5 g of N-[6-chloro-1-[[2(trimethylsilyl) ethoxy]methyl]-1H-indazol-3-yl]butanamide, described previously, in 40 cm$^3$ of dioxane. The mixture is then heated at about 100° C. for 17 hours and then filtered through a sinter funnel and evaporated under reduced pressure (2 kPa; 50° C.). The residue is taken up in 75 cm$^3$ of ethyl acetate and 50 cm$^3$ of distilled water. The organic phase is washed again with 50 cm$^3$ of distilled water and with 50 cm$^3$ of saturated aqueous sodium chloride solution. The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 2.5 cm), eluting with a cyclohexane/ethyl acetate mixture (50/50 by volume) and collecting 25 cm$^3$ fractions. The fractions containing the expected product are combined and evaporated under reduced pressure (2 kPa; 50° C.). After drying (90 Pa; 50° C.), 900 mg of N-[6-(3-pyridyl)-1-[[2-(trimethylsilyl)ethoxy]methyl]-1H-indazol-3-yl]butanamide are thus obtained in the form of a yellow oil.

$^1$H NMR spectrum (300 MHz, (CD$_3$)$_2$SO-d6, δ in ppm): −0.09 (s: 9H); 0.84 (broad t, J=8 Hz: 2H); 0.98 (t, J=7.5 Hz: 3H); 1.70 (mt: 2H); 2.43 (t, J=7.5 Hz: 2H); 3.59 (t, J=8 Hz: 2H); 5.76 (s: 2H); 7.52 (dd, J=9 and 2 Hz: 1H); 7.55 (broad dd, J=8.5 and 4.5 Hz: 1H); 7.97 (d, J=9 Hz: 1H); 8.09 (broad s: 1H); 8.20 (ddd, J=8.5–2.5 and 2 Hz: 1H); 8.63 (dd, J=4.5 and 2 Hz: 1H); 9.02 (broad d, J=2.5 Hz: 1H); 10.51 (unresolved peak: 1H).

N-[6-(3-pyridyl)-1H-indazol-3-yl]butanamide 13.3 cm$^3$ of tetrabutylammonium fluoride as a 1M solution in tetrahydrofuran are added to 900 mg of N-[6-(3-pyridyl)-1-[[2-(trimethylsilyl)ethoxy]methyl]-1H-indazol-3-yl]butanamide, described previously, in 20 cm$^3$ of tetrahydrofuran. The reaction medium is heated at about 66° C. for 21 hours. The heating is then stopped and 100 cm$^3$ of ethyl acetate are added. This mixture is washed with 50 cm$^3$ of saturated aqueous sodium hydrogen carbonate solution and then with 2×50 cm$^3$ of distilled water and 50 cm$^3$ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 2 cm), eluting with ethyl acetate and collecting 25 cm$^3$ fractions. The fractions containing the expected product are combined and evaporated under reduced pressure (2 kPa; 50° C.). After drying (90 Pa; 50° C.), 380 mg of N-[6-(3-pyridyl)-1H-indazol-3-yl] butanamide are thus obtained in the form of a white product melting at 205° C.

$^1$H NMR spectrum (300 MHz, (CD$_3$)$_2$SO-d6, δ in ppm): 0.98 (t, J=7.5 Hz: 3H); 1.70 (mt: 2H); 2.41 (t, J=7 Hz: 2H); 7.42 (dd, J=9 and 1.5 Hz: 1H); 7.53 (ddd, J=8–5 and 0.5 Hz: 1H); 7.73 (broad s: 1H); 7.92 (broad d, J=9 Hz: 1H); 8.18 (ddd, J=8–2 and 1.5 Hz: 1H); 8.62 (dd, J=5 and 2 Hz: 1H); 8.98 (broad d, J=1.5 Hz: 1H); 10.37 (unresolved peak: 1H); 12.80 (unresolved peak: 1H).

EXAMPLE 26

4-iodo-1H-indazole-3-amine 1.2 cm$^3$ of hydrazine monohydrate are added to 2 g of 2-fluoro-6-iodobenzonitrile in 25 cm$^3$ of ethanol. The reaction medium is then refluxed at about 78° C. for 12 hours.

The medium is allowed to return to about 20° C. and 20 cm$^3$ of distilled water are then added in order to precipitate the product. The insoluble material is filtered on a sinter funnel, rinsed with 20 cm$^3$ of distilled water and then taken up in 20 cm$^3$ of dichloromethane. The organic phase is then dried over magnesium sulphate and evaporated under reduced pressure (2 kPa; 45° C.). After drying (90 Pa; 50° C.), 1.65 g of 4-iodo-1H-indazole-3-amine are obtained in the form of a yellow solid melting at 157° C.

$^1$H NMR spectrum (300 MHz, (CD$_3$)$_2$SO-d6, δ in ppm): 5.05 (broad s: 2H); 6.95 (dd, J=7.5 and 8.5 Hz: 1H); 7.30 (dd, J=8.5 and 1 Hz: 1H); 7.37 (broad d, J=7.5 Hz: 1H); 11.80 (unresolved peak: 1H).

N-[4-iodo-1H-indazol-3-yl]butanamide 0.20 cm$^3$ of butyryl chloride is added to 500 mg of 4-iodo-1H-indazole-3-amine, described previously, in 15 cm$^3$ of pyridine, and cooled to about 5° C. The reaction medium is allowed to return to about 19° C. over 50 hours. The reaction medium is evaporated under reduced pressure (2 kPa; 50° C.). The residue is taken up in 15 cm$^3$ of ethyl acetate, 15 cm$^3$ of tetrahydrofuran and 15 cm$^3$ of distilled water. The organic phase is dried over magnesium sulphate and then filtered through a sinter funnel and evaporated under reduced pressure (2 kPa; 50° C.). The residue is taken up in 15 cm$^3$ of dichloromethane and filtered. The insoluble material is taken up in 10 cm$^3$ of methanol and filtered off and the filtrate is evaporated under reduced pressure, to give after drying (90 Pa; 50° C.), 70 mg of N-[4-iodo-1H-indazol-3-yl]butanamide in the form of an off-white solid.

$^1$H NMR spectrum (300 MHz, (CD$_3$)$_2$SO-d6, δ in ppm): 0.98 (broad t, J=7.5 Hz: 3H); 1.68 (mt: 2H); 2.39 (broad t, J=7 Hz: 2H); 7.09 (t, J=8 Hz: 1H); 7.54 (d, J=8 Hz: 1H); 7.58 (broad d, J=8 Hz: 1H); 9.68 (broad s: 1H); 13.08 (unresolved peak: 1H).

EXAMPLE 27

N-[6-phenyl)-1-[[2-(trimethylsilyl)ethoxy]methyl]-1H-indazol-3-yl]butanamide 497 mg of phenylboronic acid, 1.24 g of caesium fluoride, 12.35 mg of palladium acetate and finally 48 mg of 2-dicyclohexylphosphine-2-(N,N-dimethylamino)biphenyl are added to 1.5 g of N-[6-chloro-1-[[2-(trimethylsilyl)-ethoxy]methyl]-1H-indazol-3-yl]butanamide, described above in Example 25, in 30 cm$^3$ of dioxane. The mixture is then heated at about 100° C. for 18 hours and then filtered through a sinter funnel and evaporated under reduced pressure (2 kPa; 50° C.). The residue is rinsed with 50 cm$^3$ of tetrahydrofuran and 50 cm$^3$ of distilled water. The resulting residue is taken up in 75 cm$^3$ of ethyl acetate and 50 cm$^3$ of distilled water. The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 2.5 cm), eluting with a cyclohexane/ethyl acetate mixture (75/25 by volume) and collecting 25 cm$^3$ fractions. The fractions containing the expected product are combined and evaporated under reduced pressure (2 kPa; 50° C.). After drying (90 Pa; 50° C.), 1 g of N-[6-phenyl)-1-[[2-(trimethylsilyl)ethoxy]methyl]-1H-indazol-3-yl]butanamide is thus obtained in the form of a yellow oil.

$^1$H NMR spectrum (300 MHz, (CD$_3$)$_2$SO-d6, δ in ppm): −0.08 (s: 9H); 0.84 (t, J=8 Hz: 2H); 0.98 (t, J=7.5 Hz: 3H); 1.69 (mt: 2H); 2.42 (t, J=7 Hz: 2H); 3.59 (t, J=8 Hz: 2H); 5.74 (s: 2H); 7.42 (broad t, J=7.5 Hz: 1H); 7.47 (dd, J=9 and 1.5 Hz: 1H); 7.53 (broad t, J=7.5 Hz: 2H); 7.79 (broad d, J=7.5 Hz: 2H); 7.93 (d, J=9 Hz: 1H); 7.96 (broad s: 1H); 10.48 (unresolved peak: 1H).

N-[6-phenyl-1H-indazol-3-yl]butanamide 14.65 cm$^3$ of tetrabutylammonium fluoride as a 1M solution in tetrahydrofuran are added to 900 mg of N-[6-phenyl)-1-[[2-(trimethylsilyl)ethoxy]methyl]-1H-indazol-3-yl]butanamide, described previously, in 30 cm$^3$ of tetrahydrofuran. The reaction medium is heated at about 66° C. for 16 hours. The heating is then stopped and 75 cm$^3$ of ethyl acetate are added. This mixture is washed with 75 cm$^3$ of saturated aqueous sodium hydrogen carbonate solution and then with 2×75 cm$^3$ of distilled water and 50 cm$^3$ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 3.5 cm), eluting with ethyl acetate and collecting 35 cm$^3$ fractions. The fractions containing the expected product are combined and evaporated under reduced pressure (2 kPa; 50° C.). The residue is taken up in 10 cm$^3$ of ethyl acetate and then filtered on a sinter funnel, and this mixture is washed with 2×5 cm$^3$ of ethyl acetate and with 20 cm$^3$ of diisopropyl ether. After drying (90 Pa; 50° C.), 420 mg of N-[6-phenyl-1H-indazol-3-yl]butanamide are thus obtained in the form of a white product melting at 220° C.

$^1$H NMR spectrum (300 MHz, (CD$_3$)$_2$SO-d6, δ in ppm): 0.99 (broad t, J=7 Hz: 3H); 1.70 (mt: 2H); 2.41 (t, J=7 Hz: 2H); 7.37 (dd, J=9 and 1.5 Hz: 1H); 7.40 (broad t, J=7.5 Hz: 1H); 7.51 (broad t, J=7.5 Hz: 2H); 7.63 (broad s: 1H); 7.74 (broad d, J=7.5 Hz: 2H); 7.98 (d, J=9 Hz: 1H); 10.34 (unresolved peak: 1H); 12.70 (unresolved peak: 1H).

EXAMPLE 28

N-[6-bromo-5,7-dinitro-1H-indazol-3-yl]butanamide 470 mg of nitronium tetrafluoroborate are added in a single portion to 500 mg of N-[6-bromo-1H-indazol-3-yl]butanamide, described previously in Example 24, in 20 cm$^3$ of acetonitrile, cooled to about 3° C. The resulting mixture is allowed to return to about 19° C. over 14 hours. 15 cm$^3$ of ethyl acetate and 15 cm$^3$ of distilled water are added to the reaction medium. The medium is then evaporated under reduced pressure (2 kPa; 40° C.) and the residue is taken up in 20 cm$^3$ of dichloromethane. The insoluble material is filtered off and washed with 20 cm$^3$ of diisopropyl ether. After drying (90 Pa; 45° C.), 200 mg of N-[6-bromo-5,7-dinitro-1H-indazol-3-yl]butanamide are thus obtained in the form of an ochre-coloured solid melting at 260° C.

$^1$H NMR spectrum (300 MHz, (CD$_3$)$_2$SO-d6, δ in ppm): 0.98 (t, J=7.5 Hz: 3H); 1.69 (mt: 2H); 2.45 (t, J=7.5 Hz: 2H); 9.05 (s: 1H); 11.06 (unresolved peak: 1H); 14.04 (unresolved peak: 1H).

EXAMPLE 29

N-[6-bromo-7-nitro-1H-indazol-3-yl]butanamide 235 mg of nitronium tetrafluoroborate are added in a single portion to 500 mg of N-[6-bromo-1H-indazol-3-yl]butanamide, described previously in Example 24, in 25 cm$^3$ of acetonitrile, cooled to about 3° C. The mixture is maintained at about 3° C. for 1 hour and the resulting mixture is then allowed to return to about 19° C. over 14 hours. 15 cm³ of ethyl acetate and 15 cm³ of distilled water are added to the reaction medium. The medium is then evaporated under reduced pressure (2 kPa; 40° C.) and the residue is taken up in 20 cm³ of dichloromethane. The insoluble material is filtered off and washed with 20 cm³ of diisopropyl ether. The residue is purified by chromatography under an argon pressure of 50 kPa, on a column of silica gel (particle size 40–60 μm; diameter 3.5 cm), eluting with ethyl acetate/cyclohexane (30/70 by volume) and collecting 35 cm³ fractions. The fractions containing the expected product are combined and evaporated under reduced pressure (2 kPa; 50° C.). After drying (90 Pa; 50° C.), 30 mg of N-[6-bromo-7-nitro-1H-indazol-3-yl]butanamide are thus obtained in the form of a white product melting at 248° C.

$^1$H NMR spectrum (300 z, $(CD_3)_2SO$-d6, δ in ppm): 0.98 (t, J=7.5 Hz: 3H); 1.69 (mt: 2H); 2.43 (t, J=7.5 Hz: 2H); 7.54 (broad d, J=9 Hz: 1H); 8.13 (d, J=9 Hz: 1H); 10.68 (unresolved peak: 1H); 13.44 (broad unresolved peak: 1H).

EXAMPLE 30

N-[6-bromo-5-nitro-1H-indazol-3-yl]butanamide

During the purification by chromatography of Example 29 under an argon pressure of 50 kPa, on a column of silica gel (particle size 40–60 μm; diameter 3.5 cm), eluting with ethyl acetate/cyclohexane (30/70 by volume); 35 cm³ fractions are collected. The fractions containing the expected product are combined and evaporated under reduced pressure (2 kPa; 50° C.). After drying (90 Pa; 50° C.), 10 mg of N-[6-bromo-5-nitro-1H-indazol-3-yl]butanamide are thus obtained in the form of a white product melting at 259° C.

$^1$H NMR spectrum (300 MHz, $(CD_3)_2SO$-d6, δ in ppm): 0.96 (t, J=7.5 Hz: 3H); 1.69 (mt: 2H); 2.43 (t, J=7.5 Hz: 2H); 7.95 (s: 1H); 8.81 (s: 1H); 10.80 (unresolved peak: 1H); from 12.70 to 13.70 (broad unresolved peak: 1H).

EXAMPLE 31

N-[6-(furan-3-yl)-1-[[2-(trimethylsilyl)ethoxy]methyl]-1H-indazol-3-yl]butanamide 457 mg of furan-3-boronic acid, 1.24 g of caesium fluoride, 13 mg of palladium acetate and finally 31 mg of 2-dicyclohexylphosphine-2-(N,N-dimethylamino)biphenyl are added to 1 g of N-[6-chloro-1-[[2-(trimethylsilyl)ethoxy]methyl]-1H-indazol-3-yl]butanamide, described previously in Example 25, in 30 cm³ of dioxane. The mixture is then heated at about 100° C. for 23 hours. A further 457 mg of furan-3-boronic acid, 1.24 g of caesium fluoride, 13 mg of palladium acetate and finally 31 mg of 2-dicyclohexylphosphine-2-(N,N-dimethylamino)biphenyl are added and refluxing is continued for 7 hours. The mixture is then allowed to return to about 19° C. over 16 hours and then filtered through a sinter funnel and evaporated under reduced pressure (2 kPa; 50° C.). The residue is rinsed with 50 cm³ of tetrahydrofuran and 50 cm³ of distilled water. The resulting residue is taken up in 75 cm³ of ethyl acetate and 50 cm³ of distilled water. The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 3.5 cm), eluting with a cyclohexane/ethyl acetate mixture (80/20 by volume) and collecting 35 cm³ fractions. The fractions containing the expected product are combined and evaporated under reduced pressure (2 kPa; 50° C.). 130 mg of N-[6-(furan-3-yl)-1-[[2-(trimethylsilyl)ethoxy]methyl]-1H-indazol-3-yl]butanamide are thus obtained in the form of an orange-coloured oil.

The mass spectrum was performed by electron impact (70 eV) EI m/z=399 M$^+$; m/z=282 $C_{16}H_{13}N_3O_2^+$; m/z=271 $C_{15}H_{13}N_3O_2^+$, m/z=212 $C_{12}H_{10}N_3O^+$; m/z=73 $C_3H_9Si^+$ N-[6-(furan-3-yl)-1H-indazol-3-yl]butanamide 1.95 cm³ of tetrabutylammonium fluoride as a 1M solution in tetrahydrofuran are added to 120 mg of N-[6-(furan-3-yl)-1-[[2-(trimethylsilyl)ethoxy]methyl]-1H-indazol-3-yl]butanamide, described previously, in 5 cm³ of tetrahydrofuran. The reaction medium is heated at about 66° C. for 17 hours. The heating is then stopped and 50 cm³ of ethyl acetate are added. This mixture is washed with 50 cm³ of saturated aqueous sodium hydrogen carbonate solution and then with 50 cm³ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 2 cm), eluting with ethyl acetate/cyclohexane (30/70 by volume) and collecting 15 cm³ fractions. The fractions containing the expected product are combined and evaporated under reduced pressure (2 kPa; 50° C.). The residue is taken up in 10 cm³ of diisopropyl ether. This solution is filtered through a sinter funnel to give, after drying (90 Pa; 50° C.), 35 mg of N-[6-(furan-3-yl)-1H-indazol-3-yl]butanamide in the form of a white solid melting at 195° C.

$^1$H NMR spectrum (300 MHz, $(CD_3)_2SO$-d6, δ in ppm): 0.98 (broad t, J=7.5 Hz: 3H); 1.68 (mt: 2H); 2.39 (t, J=7 Hz: 2H); 7.06 (broad s: 1H); 7.34 (broad d, J=9 Hz: 1H); 7.60 (broad s: 1H); from 7.70 to 7.85 (mt: 2H); 8.27 (broad s: 1H); 10.29 (unresolved peak: 1H); 12.62 (unresolved peak: 1H).

EXAMPLE 32

N-[6-[4-(phenylmethoxy)phenyl]-1-[[2-(trimethylsilyl)ethoxy]methyl]-1H-indazol-3-yl]butanamide 930 mg of 4-benzyloxyphenylboronic acid, 1.24 g of caesium fluoride, 13 mg of palladium acetate and finally 31 mg of 2-dicyclohexylphosphine-2-(N,N-dimethylamino) biphenyl are added to 1 g of N-[6-chloro-1-[[2-(trimethylsilyl)ethoxy]methyl]-1H-indazol-3-yl]butanamide, described previously in Example 25, in 30 cm³ of dioxane. The mixture is then heated at about 100° C. for 5 hours. The mixture is then allowed to return to about 19° C. and is then filtered through a sinter funnel and evaporated under reduced pressure (2 kPa; 50° C.). The residue is rinsed with 50 cm³ of tetrahydrofuran and 50 cm³ of distilled water. The resulting residue is taken up in 150 cm³ of ethyl acetate, 50 cm³ of distilled water and 50 cm³ of saturated aqueous sodium chloride solution. The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 3.5 cm), eluting with a cyclohexane/ethyl acetate mixture (80/20 by volume) and collecting 35 cm³ fractions. The fractions containing the expected product are combined and evaporated under reduced pressure (2 kPa; 50° C.). 1.2 g of N-[6-[4-(phenylmethoxy)phenyl]-1-[[2-(trimethylsilyl)ethoxy]methyl]-1H-indazol-3-yl]butanamide are thus obtained in the form of an orange-coloured oil.

$^1$H NMR spectrum (300 MHz, (CD$_3$)$_2$SO-d6, δ in ppm): −0.08 (s: 9H); 0.83 (broad t, J=8 Hz: 2H); 0.99 (t, J=7.5 Hz: 3H); 1.68 (mt: 2H); 2.42 (broad t, J=7 Hz: 2H); 3.57 (broad t, J=8 Hz: 2H); 5.21 (s: 2H); 5.73 (s: 2H); 7.16 (d, J=8.5 Hz: 2H); from 7.30 to 7.50 (mt: 4H); 7.51 (broad d, J=7.5 Hz: 2H); 7.73 (d, J=8.5 Hz: 2H); from 7.85 to 7.95 (mt: 2H); 10.46 (unresolved peak: 1H).

N-[6-[4-(phenylmethoxy)phenyl]-1H-indazol-3-yl]butanamide 14 cm$^3$ of tetrabutylammonium fluoride as a 1M solution in tetrahydrofuran are added to 1.2 g of N-[6-[4-(phenylmethoxy)phenyl]-1-[[2-(trimethylsilyl)ethoxy]methyl]-1H-indazol-3-yl]butanamide, described previously, in 30 cm$^3$ of tetrahydrofuran. The reaction medium is heated at about 66° C. for 17 hours. The heating is then stopped and 75 cm$^3$ of ethyl acetate are added. This mixture is washed with 50 cm$^3$ of saturated aqueous sodium hydrogen carbonate solution and then with 50 cm$^3$ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 3.5 cm), eluting with cyclohexane/ethyl acetate (80/20 by volume) and collecting 30 cm$^3$ fractions. The fractions containing the expected product are combined and evaporated under reduced pressure (2 kPa; 50° C.). The residue is taken up in 2×2 cm$^3$ of diisopropyl ether. This mixture is filtered through a sinter funnel to give, after drying (90 Pa; 50° C.), 220 mg of N-[6-[4-(phenylmethoxy)phenyl]-1H-indazol-3-yl]butanamide in the form of a white solid melting at 220° C.

$^1$H NMR spectrum (300 MHz, (CD$_3$)$_2$SO-d6, δ in ppm): 1.00 (broad t, J=7.5 Hz: 3H); 1.69 (mt: 2H); 2.41 (t, J=7 Hz: 2H); 5.20 (s: 2H); 7.15 (d, J=8.5 Hz: 2H); from 7.30 to 7.50 (mt: 3H); 7.33 (broad d, J=9 Hz: 1H); 7.51 (broad d, J=7.5 Hz: 2H); 7.57 (broad s: 1H); 7.68 (d, J=8.5 Hz: 2H); 7.83 (d, J=9 Hz: 1H); 10.31 (unresolved peak: 1H); 12.64 (unresolved peak: 1H).

EXAMPLE 33

N-[6-(4-hydroxyphenyl)-1H-indazol-3-yl]butanamide 0.15 cm$^3$ of iodotrimethylsilane and then 5 cm$^3$ of tetrahydrofuran are added to 200 mg of N-[6-[4-(phenylmethoxy)phenyl]-1H-indazol-3-yl]butanamide, described previously, in 7.5 cm$^3$ of acetonitrile, and the medium is heated at about 82° C. for 2 hours. 0.15 cm$^3$ of iodotrimethylsilane is added and heating is continued for 17 hours. The reaction medium is then evaporated to dryness under reduced pressure (2 kPa; 40° C.). The residue is taken up in 75 cm$^3$ of ethyl acetate, and this mixture is then washed with 2×50 cm$^3$ of saturated aqueous sulphate solution and with 50 cm$^3$ of saturated sodium chloride solution. The organic phase is dried over magnesium sulphate, filtered and then evaporated under reduced pressure (2 kPa; 45° C.). The residue is purified by chromatography under an argon pressure of 50 kPa, on a column of silica gel (particle size 40–60 μm; diameter 1.5 cm), eluting with ethyl acetate and collecting 30 cm$^3$ fractions. The fractions containing the expected product are combined and evaporated under reduced pressure (2 kPa; 50° C.). The residue is washed with 3×5 cm$^3$ of diisopropyl ether. It is filtered off on a sinter funnel and, after drying (90 Pa; 40° C.), 100 mg of N-[6-(4-hydroxyphenyl)]-1H-indazol-3-yl]butanamide are thus obtained in the form of a white solid melting at about 235° C.

$^1$H NMR spectrum (300 MHz, (CD$_3$)$_2$SO-d6, δ in ppm): 0.98 (broad t, J=7.5 Hz: 3H); 1.68 (mt: 2H); 2.40 (t, J=7.5 Hz: 2H); 6.88 (d, J=8.5 Hz: 2H); 7.29 (broad d, J=9 Hz: 1H); 7.51 (broad s: 1H); 7.55 (d, J=8.5 Hz: 2H); 7.80 (d, J=9 Hz: 1H); 9.56 (broad s: 1H); 12.29 (unresolved peak: 1H).

EXAMPLE 34

N-[6-chloro-1H-indazol-3-yl]benzenamide 0.69 cm$^3$ of benzoyl chloride is added to 1 g of 6-chloro-1H-indazole-3-amine in 15 cm$^3$ of pyridine, cooled to about 3° C. The reaction medium is allowed to return to about 19° C. over 12 hours and is then evaporated under reduced pressure (2 kPa; 50° C.). The residue is taken up in 25 cm$^3$ of ethyl acetate and 25 cm$^3$ of distilled water. The organic phase is washed with 25 cm$^3$ of distilled water and 25 cm$^3$ of saturated aqueous sodium chloride solution. The resulting solution is dried over magnesium sulphate, filtered through a sinter funnel and then evaporated under reduced pressure (2 kPa; 50° C.). The residue is purified by chromatography under an argon pressure of 50 kPa, on a column of silica gel (particle size 40–60 μm; diameter 4 cm), eluting with a dichloromethane/methanol mixture (99/1 by volume) and collecting 15 cm$^3$ fractions. The fractions containing the expected product are combined and evaporated under reduced pressure (2 kPa; 50° C.). After drying (90 Pa; 45° C.), 990 mg of N-[6-chloro-1H-indazol-3-yl]benzenamide are obtained in the form of a white solid melting at 188° C.

$^1$H NMR spectrum (300 MHz, (CD$_3$)$_2$SO-d6, δ in ppm): 7.13 (dd, J=9 and 1.5 Hz: 1H); from 7.50 to 7.70 (mt: 3H); 7.59 (broad s: 1H); 7.82 (d, J=9 Hz: 1H); 8.10 (broad d, J=7.5 Hz: 2H); 10.88 (unresolved peak: 1H); 12.95 (unresolved peak: 1H).

EXAMPLE 35

N-[6-(3,5-difluorophenyl)-1-[[2-(trimethylsilyl)ethoxy]methyl]-1H-indazol-3-yl]butanamide 645 mg of 3,4-difluorophenylboronic acid, 1.24 g of caesium fluoride, 13 mg of palladium acetate and finally 31 mg of 2-dicyclohexylphosphine-2-(N,N-dimethylamino)biphenyl are added to 1 g of N-[6-chloro-1-[[2-(trimethylsilyl)ethoxy]methyl]-1H-indazol-3-yl]butanamide, described previously in Example 25, in 30 cm$^3$ of dioxane. The mixture is then heated at about 100° C. for 17 hours. The mixture is allowed to return to about 19° C. and then filtered through a sinter funnel and evaporated under reduced pressure (2 kPa; 50° C.). The residue is taken up in 75 cm$^3$ of ethyl acetate and 50 cm$^3$ of distilled water. The insoluble material is filtered off on a sinter funnel The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 3.5 cm), eluting with a cyclohexane/ethyl acetate mixture (80/20 by volume) and collecting 35 cm$^3$ fractions. The fractions containing the expected product are combined and evaporated under reduced pressure (2 kPa;

50° C.). 1.1 g of N-[6-(3,5-difluorophenyl)-1-[[2-(trimethylsilyl)ethoxy]methyl]-1H-indazol-3-yl]butanamide are obtained in the form of an orange-coloured oil.

$^1$H NMR spectrum (400 MHz, (CD$_3$)$_2$SO-d6, δ in ppm): −0.08 (s: 9H); 0.85 (t, J=8 Hz: 2H); 0.98 (t, J=7.5 Hz: 3H); 1.70 (mt: 2H); 2.43 (t, J=7.5 Hz: 2H); 3.59 (t, J=8 Hz: 2H); 5.77 (s: 2H); 7.28 (tt, J=9 and 2 Hz: 1H); 7.55 (dd, J=9 and 2 Hz: 1H); 7.59 (mt: 2H); 7.95 (d, J=9 Hz: 1H); 8.12 (broad s: 1H); 10.53 (unresolved peak: 1H).

N-[6-(3,5-difluorophenyl)-1H-indazol-3-yl]butanamide 14 cm$^3$ of tetrabutylammonium fluoride as a 1M solution in tetrahydrofuran are added to 1.1 g of N-[6-(3,5-difluorophenyl)-1-[[2-(trimethylsilyl)ethoxy]methyl]-1H-indazol-3-yl]butanamide, described previously, in 30 cm$^3$ of tetrahydrofuran. The reaction medium is heated at about 66° C. for 18 hours. The heating is then stopped and 100 cm$^3$ of ethyl acetate are added. This mixture is washed with 2×50 cm$^3$ of saturated aqueous sodium hydrogen carbonate solution and then with 50 cm$^3$ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 3.5 cm), eluting with cyclohexane/ethyl acetate (60/40 by volume) and collecting 35 cm$^3$ fractions. The fractions containing the expected product are combined and evaporated under reduced pressure (2 kPa; 50° C.). The residue is taken up in 2×5 cm$^3$ of diisopropyl ether. This mixture is filtered through a sinter funnel and dried under reduced pressure (90 Pa; 50° C.) to give 340 mg of N-[6-(3,5-difluorophenyl)-1H-indazol-3-yl]butanamide in the form of a white solid melting at 260° C.

$^1$H NMR spectrum (300 MHz, (CD$_3$)$_2$SO-d6, δ in ppm): 1.00 (t, J=7 Hz: 3H); 1.70 (mt: 2H); 2.42 (t, J=7 Hz: 2H); 7.27 (tt, J=9 and 2 Hz: 1H); 7.43 (dd, J=9 and 2 Hz: 1H); 7.52 (mt: 2H); 7.76 (broad s: 1H); 7.90 (d, J=9 Hz: 1H); 10.37 (unresolved peak: 1H); 12.83 (broad unresolved peak: 1H).

EXAMPLE 36

N-[6-(3-thiophenyl)-1-[[2-(trimethylsilyl)ethoxy]methyl]-1H-indazol-3-yl]butanamide 522 mg of 3-thienylboronic acid, 1.24 g of caesium fluoride, 13 mg of palladium acetate and finally 31 mg of 2-dicyclohexylphosphine-2-(N,N-dimethylamino)biphenyl are added to 1 g of N-[6-chloro-1-[[2-(trimethylsilyl)ethoxy]methyl]-1H-indazol-3-yl]butanamide, described previously in Example 25, in 30 cm$^3$ of dioxane. The mixture is then heated at about 100° C. for 2 hours. 31 mg of 2-dicyclohexylphosphine-2-(N,N-dimethylamino)biphenyl and 13 mg of palladium acetate are added and the mixture is refluxed for 17 hours. The mixture is then allowed to return to about 19° C. and then filtered through a sinter funnel, and 75 cm$^3$ of ethyl acetate and 50 cm$^3$ of distilled water are added. The insoluble material is filtered off on a sinter funnel. The organic phase is dried over magnesium sulphate, filtered through a sinter funnel and then evaporated under reduced pressure under the conditions described previously. The residue is purified by chromatography under an argon pressure of 50 kPa, on a column of silica gel (particle size 40–60 μm; diameter 4.5 cm), eluting with a cyclohexane/ethyl acetate mixture (90/10 by volume) and collecting 50 cm$^3$ fractions. The fractions containing the expected product are combined and evaporated under reduced pressure (2 kPa; 50° C.). 570 mg of N-[6-(3-thiophenyl)-1-[[2-(trimethylsilyl)ethoxy]methyl]-1H-indazol-3-yl]butanamide are obtained in the form of a yellow oil.

$^1$H NMR spectrum (300 MHz, (CD$_3$)$_2$SO-d6, δ in ppm): −0.08 (s: 9H); 0.85 (t, J=8 Hz: 2H); 0.99 (t, J=7.5 Hz: 3H); 1.69 (mt: 2H); 2.42 (t, J=7.5 Hz: 2H); 3.58 (t, J=8 Hz: 2H); 5.72 (s: 2H); 7.55 (dd, J=8.5 and 1.5 Hz: 1H); 7.71 (d, J=2 Hz: 2H); 7.88 (d, J=8.5 Hz: 1H); 8.00 (t, J=2 Hz: 1H); 8.02 (broad s: 1H); 10.45 (unresolved peak: 1H).

N-[6-(3-thiophenyl)-1H-indazol-3-yl]butanamide 8.2 cm$^3$ of tetrabutylammonium fluoride as a 1M solution in tetrahydrofuran are added to 570 mg of N-[6-(3-thiophenyl)-1-[[2-(trimethylsilyl)ethoxy]methyl]-1H-indazol-3-yl]butanamide, described previously, in 20 cm$^3$ of tetrahydrofuran. The reaction medium is heated at about 66° C. for 18 hours. The heating is then stopped and 75 cm$^3$ of ethyl acetate are added. This mixture is washed with 2×50 cm$^3$ of saturated aqueous sodium hydrogen carbonate solution and then with 50 cm$^3$ of saturated aqueous sodium chloride solution. The organic phase is dried over magnesium sulphate, filtered through a sinter funnel and evaporated under reduced pressure (2 kPa; 50° C.). The residue is purified by chromatography under an argon pressure of 50 kPa, on a column of silica gel (particle size 40–60 μm; diameter 2.5 cm), eluting with cyclohexane/ethyl acetate (60/40 by volume) and collecting 20 cm$^3$ fractions. The fractions containing the expected product are combined and evaporated under reduced pressure (2 kPa; 50° C.). The residue is taken up in 2×5 cm$^3$ of diisopropyl ether. This mixture is filtered through a sinter funnel and evaporated under reduced pressure (2 kPa; 40° C.) to give, after drying (90 Pa; 50° C.), 260 mg of N-[6-(3-thiophenyl)-1H-indazol-3-yl] butanamide in the form of a white solid melting at about 198° C.

$^1$H NMR spectrum (300 MHz, (CD$_3$)$_2$SO-d6, δ in ppm): 0.98 (t, J=7,5 Hz: 3H); 1.69 (mt: 2H); 2.40 (t, J=7 Hz: 2H); 7.45 (broad d, J=9 Hz: 1H); from 7.60 to 7.75 (mt: 2H); 7.70 (broad s: 1H); 7.82 (d, J=9 Hz: 1H); 7.95 (dd, J=3 and 1.5 Hz: 1H); 10.32 (unresolved peak: 1H); 12.66 (broad unresolved peak: 1H).

EXAMPLE 37

N-[6-chloro-1H-indazol-3-yl]-2-thiophenacetamide 0.73 cm$^3$ of 2-thiopheneacetyl chloride is added to 1 g of 6-chloro-1H-indazole-3-amine in 15 cm$^3$ of pyridine, cooled to about 3° C. The reaction medium is allowed to return to about 19° C. over 21 hours and is then evaporated under reduced pressure (2 kPa; 50° C.). The residue is taken up in 25 cm$^3$ of ethyl acetate, 10 cm$^3$ of tetrahydrofuran and 25 cm$^3$ of distilled water. The organic phase is washed with 25 cm$^3$ of distilled water and 25 cm$^3$ of saturated aqueous sodium chloride solution. The resulting solution is dried over magnesium sulphate, filtered on a sinter funnel, rinsed with 5 cm$^3$ of dimethylformamide and then evaporated under reduced pressure (2 kPa; 50° C.). The residue is purified by chromatography under an argon pressure of 50 kPa, on a column of silica gel (particle size 40–60 μm; diameter 4 cm), eluting with a dichloromethane/methanol mixture (99/1 by volume) and collecting 15 cm$^3$ fractions. The fractions containing the expected product are combined and evaporated under reduced pressure (2 kPa; 50° C.). After drying (90 Pa; 45° C.), 210 mg of N-[6-chloro-1H-indazol-3-yl]-2-thiophenacetamide are obtained in the form of a white solid melting at 210° C.

$^1$H NMR spectrum (300 MHz, (CD$_3$)$_2$SO-d6, δ in ppm): 3.99 (s: 2H); from 6.95 to 7.10 (mt: 2H); 7.09 (dd, J=9 and 2 Hz: 1H); 7.43 (dd, J=5 and 1.5 Hz: 1H); 7.53 (d, J=2 Hz: 1H); 7.82 (d, J=9 Hz: 1H); 10.76 (unresolved peak: 1H); from 12.50 to 13.20 (broad unresolved peak: 1H).

EXAMPLE 38

N-[5-[[(3-fluorophenyl)sulphonyl]amino]-1H-indazol-3-yl]benzamide

N-[5-[[(3-Fluorophenyl)sulphonyl]amino]-1H-indazol-3-yl]benzamide may be obtained from 0.45 g of N-(5-amino-1H-indazol-3-yl)benzamide, 10 cm$^3$ of pyridine and 0.35 g of (3-fluorophenyl)sulphonyl chloride. 0.6 g of N-[5-[((3-fluorophenyl)sulphonyl]amino]-1H-indazol-3-yl]benzamide is thus obtained in the form of a white solid melting at 225° C. (Analysis C20 H15 F N4 O3 S, % calculated C, 58.53; H, 3.68; F, 4.63; N, 13.65; O, 11.69; S, 7.81. % found C, 58.38; H, 3.42; N, 13.56; S, 7.44).

$^1$H NMR (300 MHz, (CD3)$_2$SO-d6, δ in ppm): 7.10 (dd, J=9 and 2 Hz: 1H); 7.39 (d, J=9 Hz: 1H); from 7.40 to 7.70 (mt: 7H); 7.42 ((broad s: 1H); 8.07 (broad d, J=7.5 Hz: 2H); 10.20 (broad unresolved peak: 1H); 10.72 (broad s: 1H); 12.77 (broad s: 1H).

N-(5-Amino-1H-indazol-3-yl)benzamide may be obtained from 0.6 g of N-(5-nitro-1H-indazol-3-yl)benzamide, 21 cm$^3$ of ethanol, 4.2 g of ferrous sulphate, 6.6 cm$^3$ of water and 5.1 cm$^3$ of 32% aqueous ammonia. 0.4 g of N-(5-amino-1H-indazol-3-yl)benzamide is thus obtained in the form of a yellow powder melting at 116° C.

N-(5-Nitro-1H-indazol-3-yl)benzamide may be obtained in the following manner: 0.39 cm$^3$ of benzoyl chloride is added dropwise to a solution of 0.6 g of 5-nitro-1H-indazole-3-amine and 5 cm$^3$ of pyridine, cooled to 0° C. The medium is returned to a temperature in the region of 20° C. and stirred for 18 hours. After addition of 20 cm$^3$ of distilled water, the medium is extracted with 20 cm$^3$ and 10 cm$^3$ of ethyl acetate. The organic phases are combined, dried over magnesium sulphate, filtered and concentrated by evaporation under reduced pressure. The residue thus obtained is purified by chromatography on a column of silica with a dichloromethane/methanol mixture (99/1 by volume) as eluent. 0.9 g of N-(5-nitro-1H-indazol-3-yl)benzamide is thus obtained in the form of an orange-coloured solid melting at 231° C.

EXAMPLE 39

N-[6-(2-phenylethyl)-1-[[2-(trimethylsilyl)ethoxy]methyl]-1H-indazol-3-yl]-butanamide 27.2 cm$^3$ of 9-borabicyclo[3.3.1]nonane are added by syringe to a solution of 0.8 cm$^3$ of styrene in 35 cm$^3$ of dioxane and the mixture is heated at 75° C. for 1 hour. 5.5 cm$^3$ of 5N sodium hydroxide are added to the cooled solution, followed by successive addition of 1 g of N-[6-chloro-1-[[2-(trimethylsilyl)ethoxy]methyl]-1H-indazol-3-yl]butanamide prepared in Example 25, 1.2 g of caesium fluoride, 32.2 mg of 2-dicyclohexylphosphino-2'-(N,N-dimethylamino)biphenyl and 12.3 mg of palladium acetate, and the mixture is heated at reflux for 3 hours. After cooling, 50 cm$^3$ of water and 75 cm$^3$ of ethyl acetate are added; the organic phase is separated out after settling of the phases has taken place, dried over magnesium sulphate, filtered and concentrated under reduced pressure (2 kPa; 40° C.) to give 4.5 g of crude product, which is chromatographed under an argon pressure of 50 kPa, on a column of silica gel (particle size 40–60 μm; diameter 3.5 cm), eluting with a cyclohexane/ethyl acetate mixture (75/25 by volume). The fractions containing the expected product are combined and then evaporated under reduced pressure (2 kPa; 40° C.) to give 1.4 g of N-[6-(2-phenylethyl)-1-[[2-(trimethylsilyl)ethoxy]methyl]-1H-indazol-3-yl]butanamide in the form of a yellow oil.

$^1$H NMR spectrum (300 MHz, (CD$_3$)$_2$SO-d6, δ in ppm): −0.06 (s: 9H); 0.83 (t, J=8 Hz: 2H); 0.97 (t, J=7.5 Hz: 3H); 1.67 (mt: 2H); 2.39 (t, J=7 Hz: 2H); 3.00 (mt: 4H); 3.53 (t, J=8 Hz: 2H); 5.62 (s: 2H); 7.04 (broad d, J=8.5 Hz: 1H); from 7.15 to 7.40 (mt: 5H); 7.50 (broad s: 1H); 7.74 (d, J=8.5 Hz: 1H); 10.38 (unresolved peak: 1H).

| EI | m/z = 437 | M$^{+\cdot}$ |
|---|---|---|
|  | m/z = 320 | [M—OCH$_2$CH$_2$Si(CH$_3$)$_3$]$^+$ |
|  | m/z = 309 | [M—C$_6$H$_{12}$OSi]$^{+\cdot}$ |

N-[6-(2-phenylethyl)-1H-indazol-3-yl]butanamide 19.2 cm$^3$ of tetrabutylammonium fluoride as a 1M solution in tetrahydrofuran are added to a solution of 1.4 g of N-[6-(2-phenylethyl)-1-[[2-(trimethylsilyl)ethoxy]methyl]-1H-indazol-3-yl]butanamide, described previously, in 40 cm$^3$ of tetrahydrofuran, and the mixture is refluxed for 18 hours. 100 cm$^3$ of ethyl acetate are added to the reaction medium and the organic phase is washed successively with 100 cm$^3$ of saturated sodium hydrogen carbonate solution, 100 cm$^3$ of water and 50 cm$^3$ of saturated sodium chloride solution. The organic phase is separated out after settling of the phases has taken place, dried over magnesium sulphate, filtered and concentrated under reduced pressure (2 kPa; 50° C.) to give 1.4 g of crude product in the form of an orange-coloured oil, which is purified by chromatography under an argon pressure of 50 kPa, on a column of silica gel (particle size 40–60 μm; diameter 3.5 cm), eluting with a cyclohexane/ethyl acetate mixture (30/70 by volume). The fractions containing the expected product are concentrated to dryness to give 0.43 g of a yellow oil which, after trituration in 20 cm$^3$ of diisopropyl ether and filtration, gives 0.34 g of a white solid in a purity of 70%. After purification by HPLC-MS, 0.11 g of product is obtained, which is triturated with 10 cm$^3$ of diisopropyl ether, filtered and washed with 5 cm$^3$ of diisopropyl ether, and then dried under reduced pressure (90 Pa; 40° C.) to give 0.10 g of N-[6-(2-phenylethyl)-1H-indazol-3-yl]butanamide in the form of a white solid melting at 175° C.

$^1$H NMR spectrum (300 MHz, (CD$_3$)$_2$SO-d6, δ in ppm): 0.97 (t, J=7.5 Hz: 3H); 1.67 (mt: 2H); 2.38 (t, J=7 Hz: 2H); 2.99 (mt: 4H); 6.97 (broad d, J=9 Hz: 1H); from 7.15 to 7,35 (mt: 5H); 7.20 (broad s: 1H); 7.77 (d, J=9 Hz: 1H); 10.22 (broad s: 1H); 12.44 (broad s: 1H).

EXAMPLE 40

6,7-difluoro-1H-indazole-3-amine 0.32 cm$^3$ of hydrazine monohydrate is added to 0.46 cm$^3$ of 2,3,4-trifluorobenzonitrile in 10 cm$^3$ of absolute ethanol. The medium is heated at about 75° C. for 17 hours and then 10 cm$^3$ of ethyl acetate, 5 cm$^3$ of tetrahydrofuran and 5 cm$^3$ of distilled water are added. The organic phase is separated out after settling of the phases has taken place, and is washed again with 10 cm³ of distilled water and then with 10 cm³ of saturated aqueous sodium chloride solution. The organic phase is separated out after settling of the phases has taken place, dried over magnesium sulphate, filtered and concentrated to dryness under reduced pressure (2 kPa; 50° C.). The residue obtained is purified by chromatography under an argon pressure of 50 kPa, on a column of silica gel (particle size 40–60 μm; diameter 1.5 cm), eluting with a cyclohexane/ethyl acetate mixture (50/50 by volume). The fractions containing the expected product are combined and then evaporated under reduced pressure (2 kPa; 40° C.); after drying (90 Pa; 40° C.), 100 mg of 6,7-difluoro-1H-indazole-3-amine are obtained in the form of a white solid melting at 183° C.

$^1$H NMR spectrum (300 MHz, (CD$_3$)$_2$SO-d6, δ in ppm): 5.57 (unresolved peak: 2H); 6.93 (mt: 1H); 7.52 (ddd, J=8.5–4.5 and 1 Hz: 1H); 12.01 (unresolved peak: 1H).

N-(6,7-difluoro-1H-indazol-3-yl)butanamide 0.61 cm³ of butyryl chloride is added to 1 g of 6,7-difluoro-1H-indazole-3-amine, described previously, in 15 cm³ of pyridine, after cooling to about 3° C., and the mixture is then left at room temperature for 76 hours. The reaction medium is concentrated under reduced pressure (2 kPa; 40° C.) and the residue is taken up in 25 cm³ of ethyl acetate and 25 cm³ of water. The organic phase is washed with 25 cm³ of distilled water and then with 25 cm³ of saturated aqueous sodium chloride solution. After drying over magnesium sulphate, filtration and concentration under reduced pressure (2 kPa; 40° C.), the residue obtained is purified by chromatography under an argon pressure of 50 kPa, on a column of silica gel (particle size 40–60 μm; diameter 3 cm), eluting with a dichloromethane/methanol mixture (98/2 by volume). The fractions containing the expected product are combined and then evaporated under reduced pressure (2 kPa; 40° C.); after drying (90 Pa; 40° C.), 596 mg of N-(6,7-difluoro-1H-indazol-3-yl)butanamide are obtained in the form of a white solid melting at 191° C.

$^1$H NMR spectrum (300 MHz, (CD$_3$)$_2$SO-d6, δ in ppm): 0.97 (t, J=7.5 Hz: 3H); 1.67 (mt: 2H); 2.40 (t, J=7 Hz: 2H); 7.10 (mt: 1H); 7.63 (broad dd, J=9 and 4.5 Hz: 1H); 10.47 (broad unresolved peak: 1H); 13.35 (broad unresolved peak: 1H).

EXAMPLE 41

N-[6-(4-methoxyphenyl)-1-[[2-(trimethylsilyl)ethoxy]methyl]-1H-indazol-3-yl]butanamide 900 mg of 4-methoxyphenylboronic acid, 1.24 g of caesium fluoride, 13.5 mg of palladium acetate and finally 31 mg of 2-dicyclohexylphosphine-2'-(N,N-dimethylamino)biphenyl are added to 1 g of N-[6-chloro-1-[[2-(trimethylsilyl)-ethoxy] methyl]-1H-indazol-3-yl]butanamide, described previously in Example 25, in 30 cm³ of dioxane. The mixture is then heated at about 100° C. for 20 hours, the temperature is allowed to return to about 19° C. over 72 hours and the reaction medium is then filtered on a sinter funnel and evaporated under reduced pressure (2 kPa; 50° C.). The residue is taken up in 50 cm³ of ethyl acetate and 50 cm³ of distilled water. The organic phase is washed again with 50 cm³ of distilled water and with 50 cm³ of saturated aqueous sodium chloride solution. The aqueous phase is dried over magnesium sulphate, filtered and then evaporated under reduced pressure under the conditions described previously. The residue is purified by chromatography under an argon pressure of 50 kPa, on a column of silica gel (particle size 40–60 μm; diameter 3.5 cm), eluting with a cyclohexane/ethyl acetate mixture (80/20 by volume). The fractions containing the expected product are combined and evaporated under reduced pressure (2 kPa; 50° C.); after drying (90 Pa; 50° C.), 1 g of N-[6-(4-methoxyphenyl)-1-[[2-(trimethylsilyl)ethoxy]methyl]-1H-indazol-3-yl]butanamide is obtained in the form of a yellow oil.

$^1$H NMR spectrum (300 MHz, (CD$_3$)$_2$SO-d6, δ in ppm): −0.09 (s: 9H); 0.83 (t, J=8 Hz: 2H); 0.97 (t, J=7.5 Hz: 3H); 1.68 (mt: 2H); 2.41 (t, J=7 Hz: 2H); 3.56 (t, J=8 Hz: 2H); 3.83 (s: 3H); 5.72 (broad s: 2H); 7.08 (broad d, J=8.5 Hz: 2H); 7.42 (broad d, J=8.5 Hz: 1H); 7.72 (d, J=8.5 Hz: 2H); from 7.85 to 7.95 (mt: 2H); 10.45 (unresolved peak: 1H).

| EI | m/z = 437 | M$^{+\cdot}$ |
|---|---|---|
|  | m/z = 320 | [M—OCH$_2$CH$_2$Si(CH$_3$)$_3$]$^+$ |
|  | m/z = 309 | [M—C$_6$H$_{12}$OSi]$^{+\cdot}$ |

N-[6-(4-methoxyphenyl)-1H-indazol-3-yl]butanamide 13.6 cm³ of tetrabutylammonium fluoride as a 1M solution in tetrahydrofuran are added to 1 g of N-[6-(4-methoxyphenyl)-1-[[2-(trimethylsilyl)ethoxy]methyl]-1H-indazol-3-yl]butanamide, described previously, in 30 cm³ of tetrahydrofuran, and the reaction medium is then heated at about 66° C. for 19 hours. The heating is then stopped and 75 cm³ of ethyl acetate are added. This mixture is washed with 2×50 cm³ of saturated aqueous sodium hydrogen carbonate solution and then with 50 cm³ of saturated aqueous sodium chloride solution. The organic phase is dried over magnesium sulphate, filtered and concentrated to dryness under reduced pressure (2 kPa; 50° C.). The residue is purified by chromatography under an argon pressure of 50 kPa, on a column of silica gel (particle size 40–60 μm; diameter 2.5 cm), eluting with an ethyl acetate/cyclohexane mixture (60/40 by volume). The fractions containing the expected product are combined and evaporated under reduced pressure (2 kPa; 50° C.). The residue is taken up in 10 cm³ of diisopropyl ether, filtered and washed with 2×5 cm³ of diisopropyl ether and then with 2×5 cm³ of ethyl acetate; after drying (90 Pa; 50° C.), 500 mg of N-[6-(4-methoxyphenyl)-1H-indazol-3-yl]butanamide are obtained in the form of a white product melting at 210° C.

$^1$H NMR spectrum (300 MHz, (CD$_3$)$_2$SO-d6, δ in ppm): 0.99 (t, J=7.5 Hz: 3H); 1.69 (mt: 2H); 2.41 (t, J=7 Hz: 2H); 3.83 (s: 3H); 7.06 (d mt, J=8.5 Hz: 2H); 7.33 (dd, J=9 and 1.5 Hz: 1H); 7.56 (broad s: 1H); 7.78 (d mt, J=8.5 Hz: 2H); 7.83 (d, J=9 Hz: 1H); 10.31 (unresolved peak: 1H); 12.62 (unresolved peak: 1H).

EXAMPLE 42

N-[6-[4-(methylthio)phenyl]-1-[[2-(trimethylsilyl)ethoxy]methyl]-1H-indazol-3-yl]butanamide 0.81 g of 86% 4-methylthiophenylboronic acid, 1.24 g of caesium fluoride, 13.5 mg of palladium acetate and finally 31 mg of 2-dicyclohexylphosphine-2-(N,N-dimethylamino)biphenyl are added to 1 g of N-[6-chloro-1-[[2-(trimethylsilyl)-ethoxy]methyl]-1H-indazol-3-yl]butanamide, described previously in Example 25, in 30 cm³ of dioxane. The mixture is then heated at about 100° C. for 20 hours, the temperature is allowed to return to room temperature over 72 hours and the reaction medium is then filtered on a sinter funnel and evaporated under reduced pressure (2 kPa; 50° C.). The work-up and the purification are performed by analogy with Example 41 above; 0.60 g of N-[6-(4-methylthiophenyl)-1-[[2-(trimethylsilyl)-ethoxy]methyl]-1H-indazol-3-yl]butanamide is thus obtained in the form of a yellow oil.

$^1$H NMR spectrum (300 MHz, (CD$_3$)$_2$SO-d6, δ in ppm): −0.09 (s: 9H); 0.83 (t, J=8 Hz: 2H); 0.97 (t, J=7.5 Hz: 3H); 1.68 (mt: 2H); 2.41 (t, J=7 Hz: 2H); 2.55 (s: 3H); 3,57 (t, J=8 Hz: 2H); 5.73 (s: 2H); 7.40 (broad d, J=8.5 Hz: 2H); 7.45 (dd, J=8.5 and 1.5 Hz: 1H); 7.75 (d, J=8.5 Hz: 2H); 7.91 (d, J=8.5 Hz: 1H); 7.94 (s: 1H); 10.47 (unresolved peak: 1H).

| EI | m/z = 455 | M$^{+\cdot}$ |
|---|---|---|
| | m/z = 338 | [M—OCH$_2$CH$_2$Si(CH$_3$)$_3$]$^+$ |
| | m/z = 327 | [M—C$_6$H$_{12}$OSi]$^{+\cdot}$ |

N-[6-(4-methylthiophenyl)-1H-indazol-3-yl]butanamide 7.9 cm$^3$ of tetrabutylammonium fluoride as a 1M solution in tetrahydrofuran are added to 600 mg of N-[6-[4-(methylthio)phenyl]-1-[[2-(trimethylsilyl]ethoxy])-methyl]-1H-indazol-3-yl]butanamide, described previously, in 30 cm$^3$ of tetrahydrofuran. The reaction medium is heated at about 66° C. for 18 hours and the heating is then stopped and 75 cm$^3$ of ethyl acetate are added. This mixture is washed with 2×50 cm$^3$ of saturated aqueous sodium hydrogen carbonate solution and then with 50 cm$^3$ of saturated aqueous sodium chloride solution. The organic phase is separated out after settling of the phases has taken place, dried over magnesium sulphate, filtered and concentrated under reduced pressure (2 kPa; 50° C.). The residue is purified by chromatography under an argon pressure of 50 kPa, on a column of silica gel (particle size 40–60 μm; diameter 2.5 cm), eluting with an ethyl acetate/cyclohexane mixture (60/40 by volume). The fractions containing the expected product are combined and evaporated under reduced pressure (2 kPa; 50° C.). The residue is taken up in 10 cm$^3$ of diisopropyl ether, filtered and washed with 2×5 cm$^3$ of diisopropyl ether and then with 2×3 cm$^3$ of ethyl acetate; after drying (90 Pa; 50° C.), 320 mg of N-[6-[4-(methylthio)phenyl]-1H-indazol-3-yl]butanamide are obtained in the form of a white product melting at 225° C.

$^1$H NMR spectrum (300 MHz, (CD$_3$)$_2$SO-d6, δ in ppm): 0.99 (t, J=7.5 Hz: 3H); 1.69 (mt: 2H); 2.40 (t, J=7 Hz: 2H); 2.54 (s: 3H); 7.36 (dd, J=9 and 1.5 Hz: 1H); 7.39 (d, J=8.5 Hz: 2H); 7.62 (broad s: 1H); 7.70 (d, J=8.5 Hz: 2H); 7.86 (d, J=9 Hz: 1H); 10.33 (unresolved peak: 1H); 12.69 (unresolved peak: 1H).

EXAMPLE 43

N-[6-[4-(trifluoromethoxy)phenyl]-1-[[2-(trimethylsilyl)ethoxy]methyl]-1H-indazol-3-yl]butanamide 840 mg of 4-trifluoromethoxyphenylboronic acid, 1.24 g of caesium fluoride, 13.5 mg of palladium acetate and finally 31 mg of 2-dicyclohexylphosphine-2-(N,N-dimethylamino) biphenyl are added to 1 g of N-[6-chloro-1-[[2-(trimethylsilyl)ethoxy]methyl]-1H-indazol-3-yl] butanamide, described previously in Example 25, in 30 cm$^3$ of dioxane. The reaction medium is then heated at about 102° C. for 20 hours and allowed to return to room temperature, and is diluted with 75 cm$^3$ of ethyl acetate, filtered through a sinter funnel packed with Celite and concentrated to dryness under reduced pressure (2 kPa; 50° C.). The work-up and the purification are performed by analogy with Example 41 described previously. 1 g of N-[6-[4-(trifluoromethoxy)phenyl]-1-[[2-(trimethylsilyl)ethoxy]methyl]-1H-indazol-3-yl]butanamide is thus obtained in the form of a yellow oil.

$^1$H NMR spectrum (300 MHz, (CD$_3$)$_2$SO-d6, δ in ppm): −0.09 (s: 9H); 0.83 (t, J=8 Hz: 2H); 0.98 (t, J=7.5 Hz: 3H); 1.68 (mt: 2H); 2.42 (t, J=7 Hz: 2H); 3.57 (t, J=8 Hz: 2H); 5.74 (broad s: 2H); 7.46 (dd, J=8.5 and 1.5 Hz: 1H); 7.50 (broad d, J=8.5 Hz: 2H); 7.90 (d, J=8.5 Hz: 2H); 7.94 (d, J=8.5 Hz: 1H); 7.99 (broad s: 1H); 10.49 (unresolved peak: 1H).

| EI | m/z = 493 | M$^{+\cdot}$ |
|---|---|---|
| | m/z = 376 | [M—OCH$_2$CH$_2$Si(CH$_3$)$_3$]$^+$ |
| | m/z = 365 | [M—C$_6$H$_{12}$OSi]$^{+\cdot}$ |

N-[6-(4-trifluoromethoxyphenyl)-1H-indazol-3-yl]butanamide 12.1 cm$^3$ of tetrabutylammonium fluoride as a 1M solution in tetrahydrofuran are added to 1 g of N-[6-[4-(trifluoromethoxy)phenyl]-1-[[2-(trimethylsilyl)ethoxy]-methyl]-1H-indazol-3-yl]butanamide, described previously, in 30 cm$^3$ of tetrahydrofuran. The reaction medium is heated at about 66° C. for 18 hours, the heating is then stopped and 75 cm$^3$ of ethyl acetate are added. This mixture is washed with 2×50 cm$^3$ of saturated aqueous sodium hydrogen carbonate solution and then with 50 cm$^3$ of saturated aqueous sodium chloride solution. The organic phase is separated out after settling of the phases has taken place, dried over magnesium sulphate, filtered and then concentrated under reduced pressure (2 kPa; 50° C.). The residue is purified by chromatography under an argon pressure of 50 kPa, on a column of silica gel (particle size 40–60 μm; diameter 2.5 cm), eluting with an ethyl acetate/cyclohexane mixture (60/40 by volume). The fractions containing the expected product are combined and evaporated under reduced pressure (2 kPa; 50° C.); the residue is taken up in 10 cm$^3$ of diisopropyl ether, filtered on a sinter funnel and then washed successively with 10 cm$^3$ of diisopropyl ether and then with 2×2 cm$^3$ of ethyl acetate. After drying (90 Pa; 50° C.), 520 mg of N-[6-[4-(trifluoromethoxy)phenyl]-1H-indazol-3-yl] butanamide are obtained in the form of a white product melting at 234° C.

$^1$H NMR spectrum (300 MHz, (CD$_3$)$_2$SO-d6, δ in ppm): 0.99 (t, J=7.5 Hz: 3H); 1.69 (mt: 2H); 2.41 (t, J=7 Hz: 2H); 7.38 (broad d, J=9 Hz: 1H); 7.52 (d, J=8.5 Hz: 2H); 7.67 (broad s: 1H); 7.86 (d, J=8.5 Hz: 2H); 7.89 (d, J=9 Hz: 1H); 10.36 (unresolved peak: 1H); 12.75 (unresolved peak: 1H).

EXAMPLE 44

N-[(6-(2-propenyl)-1-[[2-(trimethylsilyl)ethoxy] methyl]-1H-indazol-3-yl]butanamide 1.24 g of caesium fluoride, 0.77 cm$^3$ of 2-allyl-4,4,5,5-tetramethyl-1,3,2-dioxaborolane, 31.5 mg of 2-dicyclohexylphosphino-2'-(N,N-dimethylamino)-biphenyl and 13.5 mg of palladium acetate are successively added to a solution of 1 g of N-[6-chloro-1-[[2-(trimethylsilyl)ethoxy]methyl]-1H-indazol-3-yl) butanamide, prepared in Example 25, in 30 cm$^3$ of dioxane, and the mixture is refluxed for 18 hours. The reaction medium is filtered and taken up in 2×50 cm$^3$ of ethyl acetate, and the organic phase is washed successively with 50 cm³ of water and 50 cm³ of saturated sodium chloride solution. After separating out the organic phase by settling, drying over sodium sulphate, filtration and concentration to dryness under reduced pressure (2 kPa; 50° C.) 1.3 g of brown oil are obtained, which is purified by chromatography under an argon pressure of 50 kPa, on a column of silica gel (particle size 40–60 µm; diameter 4.5 cm), eluting with a cyclohexane/ethyl acetate mixture (90/10 by volume). After concentration and drying (90 Pa; 45° C.), 0.72 g of N-[(6-(2-propenyl-1-[[2-(trimethylsilyl)ethoxy]methyl]-1H-indazol-3-yl]butanamide is obtained in the form of a yellow oil in a purity of 75%.

¹H NMR spectrum (300 MHz, (CD₃)₂SO-d6, δ in ppm): −0.08 (s: 9H); 0.82 (t, J=8 Hz: 2H); 0.96 (t, J=7.5 Hz: 3H); 1.66 (mt: 2H); 2.39 (t, J=7 Hz: 2H); from 3.45 to 3.60 (mt: 4H); from 5.05 to 5.20 (mt: 2H); 5.62 (s: 2H); 6.02 (mt: 1H); 6.98 (broad d, J=8.5 Hz: 1H); 7.45 (broad s: 1H); 7.75 (d, J=8.5 Hz: 1H); 10.38 (unresolved peak: 1H).

| EI | m/z = 373 | M⁺· |
| | m/z = 256 | [M—OCH₂CH₂Si(CH₃)₃]⁺ |
| | m/z = 245 | [M—C₆H₁₂OSi]⁺· |

N-[(6-(1-propenyl)-1H-indazol-3-yl]butanamide 11.2 cm³ of tetrabutylammonium fluoride as a 1M solution in tetrahydrofuran are added to a solution of 0.70 g of N-[6-(1-propenyl)-1-[(2-(trimethylsilyl)ethoxy]methyl]-1H-indazol-3-yl]butanamide in 25 cm³ of tetrahydrofuran and the mixture is heated at reflux for 18 hours. 75 cm³ of ethyl acetate are added to the reaction medium and the organic phase is washed successively with 2×50 cm³ of saturated sodium hydrogen carbonate solution and 2×50 cm³ of saturated sodium chloride solution. The organic phase is separated out after settling of the phases has taken place, dried over magnesium sulphate, filtered and concentrated to dryness under reduced pressure (2 kPa; 50° C.) to give 0.70 g of a brown solid. The crude product is purified by chromatography under an argon pressure of 50 kPa, on a column of silica gel (particle size 40–60 µm; diameter 2.5 cm), eluting with a cyclohexane/ethyl acetate mixture (70/30 by volume). After concentration of the fractions, 0.30 g of a mixture containing 50% of the expected product is obtained. By means of a final HPLC (Hypurity; C₁₈, 5 µm column; length 100 mm, diameter 30 mm, eluent: methanol-acetonitrile-water (38/38/24 by volume) containing 0.05% trifluoroacetic acid; flow rate 20 cm³/min) and concentration to dryness of the fractions, taken up in 5 cm³ of ethyl acetate, filtration and drying (90 Pa; 45° C.), 12 mg of N-[6-(1-propenyl)-1H-indazol-3-yl]butanamide are obtained in the form of white crystals melting at 195° C.

¹H NMR spectrum (300 MHz, (CD₃)₂SO-d6, δ in ppm): 0.97 (broad t, J=7.5 Hz: 3H); 1.66 (mt: 2H); 1.89 (broad d, J=6 Hz: 3H); 2.37 (t, J=7 Hz: 2H); 6.38 (mt: 1H); 6.55 (broad d, J=16 Hz: 1H); 7.17 (broad d, J=8.5 Hz: 1H); 7.29 (broad s: 1H); 7.69 (d, J=9 Hz: 1H); 10.24 (unresolved peak: 1H); 12.52 (unresolved peak: 1H).

EXAMPLE 45

N-[6-chloro-1H-indazol-3-yl]-2-pyridinecarboxamide 4.2 cm³ of diisopropylethylamine are added to 1 g of 6-chloro-1H-indazole-3-amine in 15 cm³ of pyridine. The reaction medium is cooled to about 8° C. to add 1.08 g of picolinoyl chloride hydrochloride, and the temperature is allowed to return to room temperature over 18 hours. The reaction medium is concentrated to dryness under reduced pressure (2 kPa; 40° C.) and the residue is then taken up in 25 cm³ of ethyl acetate and 25 cm³ of distilled water. The organic phase is washed with 25 cm³ of water and then with 25 cm³ of saturated aqueous sodium chloride solution. After drying over magnesium sulphate, filtration and concentration under reduced pressure (2 kPa; 40° C.), the residue is purified by chromatography under an argon pressure of 50 kPa, on a column of silica gel (particle size 40–60 µm; diameter 3 cm), eluting with a dichloromethane/methanol mixture (99/1 by volume). The fractions containing the expected product are combined and evaporated under reduced pressure (2 kPa; 50° C.) and the residue is taken up in 2×15 cm of diisopropyl ether. After filtration on a sinter funnel and drying under reduced pressure (90 Pa; 50° C.), 572 mg of N-[6-chloro-1H-indazol-3-yl]-2-pyridinecarboxamide are obtained in the form of a white solid melting at 177° C.

¹H NMR spectrum (300 MHz, (CD₃)₂SO-d6, δ in ppm): 7.14 (dd, J=9 and 2 Hz: 1H); 7.60 (d, J=2 Hz: 1H); 7.73 (ddd, J=6.5–5 and 1.5 Hz: 1H); 7.95 (d, J=9 Hz: 1H); 8.12 (split t, J=7.5 and 2 Hz: 1H); 8.21 (broad d, J=7.5 Hz: 1H); 8.79 (broad d, J=5 Hz: 1H); from 10.50 to 11.40 (broad unresolved peak: 1H); from 12.30 to 13.40 (very broad unresolved peak: 1H).

EXAMPLE 46

N-[6-(4-fluorophenyl)-1-[[2-(trimethylsilyl)ethoxy] methyl]-1H-indazol-3-yl]butanamide 840 mg of 4-fluorophenylboronic acid, 1.24 g of caesium fluoride, 13.5 mg of palladium acetate and finally 31 mg of 2-dicyclohexylphosphine-2-(N,N-dimethylamino)biphenyl are added to 1 g of N-[6-chloro-1-[[2-(trimethylsilyl)-ethoxy]methyl]-1H-indazol-3-yl]butanamide, described in Example 25, in 30 cm³ of dioxane. The mixture is then heated at about 102° C. for 22 hours and is then allowed to return to room temperature. The reaction medium is taken up in 75 cm³ of ethyl acetate, filtered on a sinter funnel packed with Celite and then concentrated to dryness under reduced pressure (2 kPa; 50° C.). The work-up and the purification are performed by analogy with Example 41. 580 mg of N-[6-(4-fluorophenyl)-1-[[2-(trimethylsilyl)ethoxy] methyl]-1H-indazol-3-yl]butanamide are thus obtained in the form of a yellow oil.

¹H NMR spectrum (300 MHz, (CD₃)₂SO-d6, δ in ppm): −0.09 (s: 9H); 0.83 (t, J=8 Hz: 2H); 0.97 (t, J=7.5 Hz: 3H); 1.68 (mt: 2H); 2.41 (t, J=7 Hz: 2H); 3.56 (t, J=8 Hz: 2H); 5.73 (s: 2H); 7.35 (t, J=9 Hz: 2H); 7.44 (broad dd, J=9 and 1.5 Hz: 1H); 7.82 (dd, J=9 and 5.5 Hz: 2H); 7.92 (d, J=9 Hz: 1H); 7.94 (broad s: 1H); 10.48 (unresolved peak: 1H).

| EI | m/z = 427 | M⁺· |
| | m/z = 310 | [M—OCH₂CH₂Si(CH₃)₃]⁺ |
| | m/z = 299 | [M—C₆H₁₂OSi]⁺· |

N-[6-(4-fluorophenyl)-1H-indazol-3-yl]butanamide 8.1 cm³ of tetrabutylammonium fluoride as a 1M solution in tetrahydrofuran are added to 580 mg of N-[6-(4-fluorophenyl)-1-[[2-(trimethylsilyl)ethoxy]methyl]-1H-indazol-3-yl]butanamide, described previously, in 30 cm³ of tetrahydrofuran, and the reaction medium is heated at about 66° C. for 22 hours. The heating is then stopped, 75 cm³ of ethyl acetate are added and the resulting mixture is washed with 50 cm³ of saturated aqueous sodium hydrogen carbonate solution and then with 50 cm³ of saturated aqueous sodium chloride solution. The organic phase is separated out after settling of the phases has taken place, dried over magnesium sulphate, filtered and concentrated to dryness under reduced pressure (2 kPa; 50° C.). The residue is purified by chromatography under an argon pressure of 50 kPa, on a column of silica gel (particle size 40–60 μm; diameter 2.5 cm), eluting with a cyclohexane/ethyl acetate mixture (40/60 by volume). The fractions containing the expected product are combined and evaporated under reduced pressure (2 kPa; 50° C.). The residue is taken up in 10 cm³ of diisopropyl ether, filtered and washed successively with 5 cm³ of diisopropyl ether and 2×3 cm³ of ethyl acetate; after drying (90 Pa; 50° C.), 250 mg of N-[6-(4-fluorophenyl)-1H-indazol-3-yl]butanamide are thus obtained in the form of a white product melting at 232° C.

$^1$H NM spectrum (300 MHz, $(CD_3)_2SO$-d6, δ in ppm): 0.98 (t, J=7.5 Hz: 3H); 1.69 (mt: 2H); 2.39 (t, J=7 Hz: 2H); 7.30 (d, J=9 Hz: 1H); 7.32 (t, J=9 Hz: 2H); 7.61 (broad s: 1H); 7.78 (dd, J=9 and 6 Hz: 2H); 7.87 (d, J=9 Hz: 1H); 10.33 (unresolved peak: 1H); 12.70 (unresolved peak: 1H).

EXAMPLE 47

N-[6-[(1,1-dimethylethyl)phenyl]-1-[[2-(trimethylsilyl)ethoxy]methyl]-1H-indazol-3-yl]butanamide:

840 mg of 4-tert-butylphenylboronic acid, 1.24 g of caesium fluoride, 13.5 mg of palladium acetate and finally 31 mg of 2-dicyclohexylphosphine-2-(N,N-dimethylamino) biphenyl are added to 1 g of N-[6-chloro-1-[[2-(trimethylsilyl)-ethoxy]methyl]-1H-indazol-3-yl] butanamide, described in Example 25, in 30 cm³ of dioxane. The mixture is heated at about 102° C. for 21 hours and the temperature is then allowed to return to room temperature and the reaction medium is diluted with 75 cm³ of ethyl acetate, filtered through a sinter funnel packed with Celite and concentrated to dryness under reduced pressure (2 kPa; 50° C.). The work-up and the purification are performed by analogy with Example 41. 1.13 g of N-[6-[4-(1,1-dimethylethyl)phenyl]-1-[[2-(trimethylsilyl)ethoxy]methyl]-1H-indazol-3-yl]butanamide are thus obtained in the form of a yellow oil.

$^1$H NMR spectrum (300 MHz, $(CD_3)_2SO$-d6, δ in ppm): −0.08 (s: 9H); 0.83 (t, J=8 Hz: 2H); 0.98 (t, J=7.5 Hz: 3H); 1.35 (s: 9H); 1.68 (mt: 2H); 2.41 (t, J=7 Hz: 2H); 3.57 (t, J=8 Hz: 2H); 5.72 (broad s: 2H); 7.44 (broad d, J=9 Hz: 1H); 7.53 (broad d, J=8 Hz: 2H); 7.70 (broad d, J=8 Hz: 2H); 7.89 (d, J=9 Hz: 1H); 7.91 (broad s: 1H); 10.46 (unresolved peak: 1H).

| EI | m/z = 465 | M$^{+\cdot}$ |
|---|---|---|
|  | m/z = 348 | [M—OCH$_2$CH$_2$Si(CH$_3$)$_3$]$^+$ |
|  | m/z = 337 | [M—C$_6$H$_{12}$OSi]$^{+\cdot}$ |

N-[6-[4-(1,1-dimethylethyl)phenyl]-1H-indazol-3-yl]butanamide 14.6 cm³ of tetrabutylammonium fluoride as a 1M solution in tetrahydrofuran are added to 1.13 g of N-[6-[4-(1,1-dimethylethyl)phenyl]-1-[[2-(trimethylsilyl)ethoxy]-methyl]-1H-indazol-3-yl]butanamide, described previously, in 30 cm³ of tetrahydrofuran. The reaction medium is heated at about 66° C. for 22 hours, the heating is then stopped and 75 cm³ of ethyl acetate are added, and the organic phase is washed with 75 cm³ of saturated aqueous sodium hydrogen carbonate solution and then with 50 cm³ of saturated aqueous sodium chloride solution. The organic phase is dried over magnesium sulphate, filtered and concentrated to dryness under reduced pressure (2 kPa; 50° C.). The residue is purified by chromatography under an argon pressure of 50 kPa, on a column of silica gel (particle size 40–60 μm; diameter 2.5 cm), eluting with a cyclohexane/ethyl acetate mixture (70/30 by volume). The fractions containing the expected product are combined and evaporated under reduced pressure (2 kPa; 50° C.); the residue is taken up in 10 cm³ of diisopropyl ether, filtered off on a sinter funnel and washed successively with 10 cm³ of diisopropyl ether and then with 2×5 cm³ of ethyl acetate. After drying (90 Pa; 50° C.), 320 mg of N-[6-[4-(1,1-dimethylethyl)phenyl]-1H-indazol-3-yl]butanamide are thus obtained in the form of a white product melting at 246° C.

$^1$H NMR spectrum (300 MHz, $(CD_3)_2SO$-d6, δ in ppm): 0.99 (t, J=7.5 Hz: 3H); 1.36 (s: 9H); 1.70 (mt: 2H); 2.41 (t, J=7 Hz: 2H); 7.36 (broad d, J=9 Hz: 1H); 7.52 (d, J=8.5 Hz: 2H); 7.61 (broad s: 1H); 7.66 (broad d, J=8.5 Hz: 2H); 7.85 (d, J=9 Hz: 1H); 10.32 (unresolved peak: 1H); 12.66 (unresolved peak: 1H).

EXAMPLE 48

N-[6-bromo-7-amino-1H-indazol-3-yl]butanamide 4.25 g of ferrous sulphate heptahydrate dissolved in 25 cm³ of water are added dropwise to 510 mg of N-[6-bromo-7-nitro-1H-indazol-3-yl]butanamide, described in Example 29, in 20 cm³ of ethanol cooled to about 5° C. The temperature rises to about 28° C., the mixture is left stirring for 30 minutes, 5.2 cm³ of 28% aqueous ammonia are then added, the mixture is refluxed for 2 hours, a further 2×1.5 cm³ of 28% aqueous ammonia are then added and the mixture is left stirring for a further 10 minutes and filtered while hot through a sinter funnel packed with Celite. The precipitate is rinsed with 20 cm³ of methanol and the filtrate is concentrated to dryness under reduced pressure (2 kPa; 40° C.). The residue is taken up in 50 cm³ of ethyl acetate and washed with 25 cm³ of saturated sodium hydrogen carbonate solution and then with 25 cm³ of saturated sodium chloride solution. The organic phase is separated out after settling of the phases has taken place, dried over magnesium sulphate and concentrated under reduced pressure (2 kPa; 40° C.). After drying (90 Pa; 50° C.), 55 mg of N-[6-bromo-7-amino-1H-indazol-3-yl]butanamide are thus obtained in the form of a mauve-coloured solid.

$^1$H NMR spectrum (300 MHz, $(CD_3)_2SO$-d6, δ in ppm): 0.95 (t, J=7.5 Hz: 3H); 1.65 (mt: 2H); 2.35 (t, J=7 Hz: 2H); 5.47 (broad s: 2H); 6.901 (d, J=8.5 Hz: 1H); 7.00 (d, J=8.5 Hz: 1H); 10.18 (broad s: 1H); 12.38 (unresolved peak: 1H).

| EI | m/z = 296 | M$^{+\cdot}$ |
|---|---|---|
|  | m/z = 226 | [M—C$_4$H$_6$O]$^{+\cdot}$ |

EXAMPLE 49

N-[6-[4-(trifluoromethyl)phenyl]-1-[[2-(trimethylsilyl)ethoxy]methyl]-1H-indazol-3-yl]butanamide:

775 mg of 4-trifluoromethylphenylboronic acid, 1.24 g of caesium fluoride, 13.5 mg of palladium acetate and finally 31 mg of 2-dicyclohexylphosphine-2-(N,N-dimethylamino) biphenyl are added to 1 g of N-[6-chloro-1-[[2-(trimethylsilyl)-ethoxy]methyl]-1H-indazol-3-yl] butanamide, described in Example 25, in 30 cm$^3$ of dioxane. The mixture is then refluxed for 18 hours, the temperature is then allowed to return to room temperature and the reaction medium is diluted with 75 cm$^3$ of ethyl acetate, filtered through a sinter funnel packed with Celite and concentrated to dryness under reduced pressure (2 kPa; 50° C.). The work-up and the purification are performed by analogy with Example 41. 1 g of N-[6-[4-(trifluoromethyl)phenyl]-1-[[2-(trimethylsilyl)ethoxy]methyl]-1H-indazol-3-yl]butanamide is thus obtained in the form of a yellow oil in a purity of 95%.

$^1$H NMR spectrum (300 MHz, (CD$_3$)$_2$SO-d6, δ in ppm): −0.09 (s: 9H); 0.83 (t, J=8 Hz: 2H); 0.98 (t, J=7.5 Hz: 3H); 1.69 (mt: 2H); 2.42 (t, J=7 Hz: 2H); 3.56 (t, J=8 Hz: 2H); 5.75 (s: 2H); 7.52 (broad d, J=8.5 Hz: 1H); 7.88 (broad d, J=8.5 Hz: 2H); 7.97 (d, J=8.5 Hz: 1H); 8.01 (broad d, J=8.5 Hz: 2H); 8.07 (broad s: 1H); 10.51 (unresolved peak: 1H).

are added to 1 g of N-[6-chloro-1-[[2-(trimethylsilyl)-ethoxy]methyl]-1H-indazol-3-yl]butanamide, described in Example 25, in 30 cm$^3$ of dioxane, the mixture is then heated at about 104° C. for 5 hours 30 minutes and the temperature is then allowed to return to room temperature over 16 hours. The reaction medium is diluted with 75 cm$^3$ of ethyl acetate and filtered through a sinter funnel packed with Celite, and the filtrate is concentrated to dryness under reduced pressure (2 kPa; 50° C.). The work-up and the purification are performed by analogy with Example 41. 1.1 g of N-[6-(4-methylphenyl)-1-[[2-(trimethylsilyl)ethoxy]methyl]-1H-indazol-3-yl]butanamide are obtained in the form of a yellow oil.

$^1$H NMR spectrum (300 MHz, (CD$_3$)$_2$SO-d6, δ in ppm): −0.09 (s: 9H); 0.83 (t, J=8 Hz: 2H); 0.97(t, J=7.5 Hz: 3H); 1.68 (mt: 2H); 2.38 (s: 3H); 2.41 (t, J=7 Hz: 2H); 3.56 (t, J=8 Hz: 2H); 5.73 (s: 2H); 7.32 (broad d, J=8 Hz: 2H); 7.44 (broad d, J=9 Hz: 1H); 7.68 (broad d, J=8 Hz: 2H); 7.90 (d, J=9 Hz: 1H); 7.92 (broad s: 1H); 10.46 (unresolved peak: 1H).

| EI | m/z = 477 | M$^{+\cdot}$ |
| --- | --- | --- |
|    | m/z = 360 | [M—OCH$_2$CH$_2$Si(CH$_3$)$_3$]$^+$ |
|    | m/z = 349 | [M—C$_6$H$_{12}$OSi]$^{+\cdot}$ |

| EI | m/z = 423 | M$^{+\cdot}$ |
| --- | --- | --- |
|    | m/z = 306 | [M—OCH$_2$CH$_2$Si(CH$_3$)$_3$]$^+$ |
|    | m/z = 295 | [M—C$_6$H$_{12}$OSi]$^+$ |

N-[6-[4-(trifluoromethyl)phenyl]-1H-indazol-3-yl] butanamide 12.6 cm$^3$ of tetrabutylammonium fluoride as a 1M solution in tetrahydrofuran are added to a solution of 1 g of N-[6-[4-(trifluoromethyl)phenyl]-1-[(2-(trimethylsilyl) ethoxy]methyl]-1H-indazol-3-yl]butanamide in 30 cm$^3$ of tetrahydrofuran, and the mixture is heated at reflux for 18 hours. The reaction medium is diluted with 75 cm$^3$ of ethyl acetate and the organic phase is washed successively with 2×50 cm$^3$ of saturated sodium hydrogen carbonate solution and 2×50 cm$^3$ of saturated sodium chloride solution. The organic phase is separated out after settling of the phases has taken place, dried over magnesium sulphate, filtered and concentrated to dryness under reduced pressure (2 kPa; 50° C.) to give 0.95 g of a brown solid. The crude product is purified by chromatography under an argon pressure of 50 kPa, on a column of silica gel (particle size 40–60 μm; diameter 2.5 cm), eluting with a cyclohexane/ethyl acetate mixture (60/40 by volume). The fractions containing the expected product are combined and evaporated under reduced pressure (2 kPa; 50° C.) to give 0.60 g of cream-coloured crystals, which are taken up in 10 cm$^3$ of diisopropyl ether, filtered off and dried under reduced pressure (90 Pa; 50° C.) to give 0.47 g of N-[6-[4-(trifluoromethyl) phenyl]-1H-indazol-3-yl]butanamide in the form of white crystals melting above 260° C.

$^1$H NMR spectrum (300 MHz, (CD$_3$)$_2$SO-d6, δ in ppm): 0.98 (t, J=7.5 Hz: 3H); 1.69 (mt: 2H); 2.41 (t, J=7 Hz: 2H); 7.42 (dd, J=9 and 1.5 Hz: 1H); 7.73 (broad s: 1H); 7.85 (d, J=8.5 Hz: 2H); 7.92 (d, J=9 Hz: 1H); 7.97 (d, J=8.5 Hz: 2H); 10.37 (unresolved peak: 1H).

EXAMPLE 50

N-[6-(4-methylphenyl)-1-[[2-(trimethylsilyl)ethoxy] methyl]-1H-indazol-3-yl]butanamide 555 mg of 4-methylphenylboronic acid, 1.24 g of caesium fluoride, 13.5 mg of palladium acetate and finally 31 mg of 2-dicyclohexylphosphine-2-(N,N-dimethylamino)biphenyl N-[6-(4-meth-lphenyl)-1H-indazol-3-yl]butanamide 14.6 cm$^3$ of tetrabutylammonium fluoride as a 1M solution in tetrahydrofuran are added to 1.1 g of N-[6-(4-methylphenyl)-1-[[2-(trimethylsilyl)ethoxy]methyl]-1H-indazol-3-yl]butanamide, described previously, in 30 cm$^3$ of tetrahydrofuran. The reaction medium is heated at about 66° C. for 18 hours and the heating is then stopped. 75 cm$^3$ of ethyl acetate are added to the reaction medium and the organic phase is washed with 2×50 cm$^3$ of saturated aqueous sodium hydrogen carbonate solution and then with 50 cm$^3$ of saturated aqueous sodium chloride solution. The organic phase is dried over magnesium sulphate, filtered and concentrated to dryness under reduced pressure (2 kPa; 50° C.). The residue is purified by chromatography under an argon pressure of 50 kPa, on a column of silica gel (particle size 40–60 μm; diameter 2.5 cm), eluting with an ethyl acetate/cyclohexane mixture (70/30 by volume). The fractions containing the expected product are combined and evaporated under reduced pressure (2 kPa; 50° C.). The residue is taken up in 10 cm$^3$ of diisopropyl ether, filtered off and washed successively with 10 cm$^3$ of diisopropyl ether and then with 3×3 cm$^3$ of ethyl acetate. After drying (90 Pa; 50° C.), 500 mg of N-[6-(4-methylphenyl)-1H-indazol-3-yl]butanamide are obtained in the form of a white product melting at 210° C.

$^1$H NMR spectrum (300 MHz, (CD$_3$)$_2$SO-d6, δ in ppm): 0.98 (t, J=7.5 Hz: 3H); 1.69 (mt: 2H); 2.37 (s: 3H); 2.40 (t, J=7 Hz: 2H); 7.31 (d, J=8 Hz: 2H); 7.35 (mt: 1H); 7.59 (broad s: 1H); 7.63 (d, J=8 Hz: 2H); 7.85 (d, J=9 Hz: 1H); 10.32 (broad s: 1H); 12.65 (unresolved peak: 1H).

EXAMPLE 51

N-[6-bromo-1-[[2-(trimethylsilyl)ethoxy]methyl]-1H-indazol-3-yl]butanamide

A solution of 6 g of N-(6-bromo-1H-indazol-3-yl) butanamide, prepared in Example 24, in 50 cm$^3$ of dimethylformamide, is added dropwise to a suspension of 1.1 g of sodium hydride at 60% in oil in 20 cm$^3$ of dimethylformamide and cooled to 0° C., followed by addition of 4.5 cm³ of a solution of 2-(trimethylsilyl) ethoxymethyl chloride in 10 cm³ of dimethylformamide at 10° C., and the reaction medium is allowed to return to room temperature. 100 cm³ of ethyl acetate are added to the reaction medium, followed by washing with 2×50 cm³ of water; the organic phase is separated out after settling of the phases has taken place, dried over magnesium sulphate and concentrated to dryness under reduced pressure (2 kPa; 45° C.) to give 6.9 g of solid. The crude product is purified by chromatography under an argon pressure of 50 kPa, on a column of silica gel (particle size 40–60 μm; diameter 3.5 cm), eluting with a cyclohexane/ethyl acetate gradient (100/0 to 90/10 by volume). The fractions containing the expected product are concentrated to dryness to give 2.9 g of N-[6-bromo-1-[[2-(trimethylsilyl)ethoxy]methyl]-1H-indazol-3-yl]butanamide in the form of an off-white solid.

¹H NMR spectrum (300 MHz, (CD₃)₂SO-d6, δ in ppm): −0.07 (s: 9H); 0.83 (t, J=8 Hz: 2H); 0.97 (t, J=7.5 Hz: 3H); 1.67 (mt: 2H); 2.40 (t, J=7 Hz: 2H); 3.53 (t, J=8 Hz: 2H); 5.67 (s: 2H); 7.29 (dd, J=9 and 1.5 Hz: 1H); 7.82 (d, J=9 Hz: 1H); 8.01 (d, J=1.5 Hz: 1H); 10.54 (unresolved peak: 1H).

| EI | m/z = 411 | M⁺· |
|---|---|---|
|  | m/z = 294 | [M—OCH₂CH₂Si(CH₃)₃]⁺ |
|  | m/z = 283 | [M—C₆H₁₂OSi]⁺· |

N-[6-(3,5-dichlorophenyl)-1-[[2-(trimethylsilyl) ethoxy]methyl]-1H-indazol-3-yl]butanamide 0.44 g of 3,5-dichlorophenylboronic acid, 0.64 g of sodium carbonate dissolved in 18 cm³ of water and 0.186 g of tetrakis(triphenylphosphine)palladium are added to 1 g of N-[6-bromo-1-[[2-(trimethylsilyl)ethoxy]methyl]-1H-indazol-3-yl]butanamide, described previously, in 30 cm³ of dioxane, and the mixture is refluxed for 18 hours. The reaction medium is diluted with 75 cm³ of ethyl acetate and 50 cm³ of water and the medium is then filtered through a sinter funnel packed with Celite and is concentrated to dryness under reduced pressure (2 kPa; 50° C.). The work-up and the purification are performed by analogy with Example 41. 0.90 g of N-[6-(3,5-dichlorophenyl)-1-[(2-(trimethylsilyl)ethoxy]methyl]-1H-indazol-3-yl]butanamide is thus obtained in the form of a yellow wax.

¹H NMR spectrum (300 MHz, (CD₃)₂SO-d6, δ in ppm): −0.09 (s: 9H); 0.85 (t, J=8 Hz: 2H); 0.99 (t, J=7.5 Hz: 3H); 1.69 (mt: 2H); 2.42 (t, J=7 Hz: 2H); 3.58 (t, J=8 Hz: 2H); 5.77 (s: 2H); 7.53 (dd, J=8.5 and 1.5 Hz: 1H); 7.66 (t, J=2 Hz: 1H); 7.87 (d, J=2 Hz: 2H); 7.95 (d, J=8.5 Hz: 1H); 8.14 (broad s: 1H); 10.51 (unresolved peak: 1H).

| EI | m/z = 477 | M⁺· |
|---|---|---|
|  | m/z = 360 | [M—OCH₂CH₂Si(CH₃)₃]⁺ |
|  | m/z = 349 | [M—C₆H₁₂OSi]⁺· |

N-[6-(3,5-dichlorophenyl)-1H-indazol-3-yl] butanamide 11.2 cm³ of tetrabutylammonium fluoride as a 1M solution in tetrahydrofuran are added to 1 g of N-[6-(3,5-dichlorophenyl)-1-[[2-(trimethylsilyl)ethoxy]methyl]-1H-indazol-3-yl]butanamide, described previously, in 20 cm³ of tetrahydrofuran, the reaction medium is then heated at about 65° C. for 18 hours and the heating is stopped to add 75 cm³ of ethyl acetate. The organic phase is washed with 2×50 cm³ of saturated aqueous sodium hydrogen carbonate solution and then with 50 cm³ of saturated aqueous sodium chloride solution. The organic phase is dried over magnesium sulphate, filtered and evaporated under reduced pressure (2 kPa; 50° C.). After drying (90 Pa; 50° C.), 290 mg of N-[6-(3,5-dichlorophenyl)-1H-indazol-3-yl]butanamide are obtained in the form of a white product.

¹H NMR spectrum (300 MHz, (CD₃)₂SO-d6, δ in ppm): 0.98 (broad t, J=7.5 Hz: 3H); 1.69 (mt: 2H); 2.40 (t, J=7 Hz: 2H); 7.40 (broad d, J=8.5 Hz: 1H); 7.63 (t, J=2 Hz: 1H); 7.75 (broad s: 1H); 7.81 (d, J=2 Hz: 2H); 7.89 (d, J=8.5 Hz: 1H); 10.37 (unresolved peak: 1H); from 12.70 to 12.95 (broad unresolved peak: 1H).

| EI | m/z = 347 | M⁺· |
|---|---|---|
|  | m/z = 277 | [M—C₄CH₆O]⁺· |

EXAMPLE 52

N-[6-chloro-1H-indazol-3-yl]-3,5-dichlorobenzamide 0.83 cm³ of 3,5-dichlorobenzoyl chloride is added to 1 g of 6-chloro-1H-indazole-3-amine in 15 cm³ of pyridine, after cooling in an ice bath to about 3° C., and the mixture is then stirred for 10 minutes at this temperature and is allowed to return to room temperature over 18 hours. The reaction medium is then concentrated to dryness under reduced pressure (2 kPa; 50° C.) and the residue is taken up in 25 cm³ of ethyl acetate and 25 cm³ of water. The precipitate formed is filtered off and, after drying (90 Pa; 50° C.), 700 mg of N-[6-chloro-1H-indazol-3-yl]-3,5-dichlorobenzamide are obtained in the form of a white solid melting at about 240° C.

¹H NMR spectrum (300 MHz, (CD₃)₂SO-d6, δ in ppm): 7.15 (dd, J=8.5 and 2 Hz: 1H); from 7.50 to 7.65 (mt: 2H); 7.72 (d, J=8.5 Hz: 1H); 7.79 (broad s: 1H); 7.90 (d, J=8.5 Hz: 1H); 11.06 (broad s: 1H).

EXAMPLE 53

N-[6-(4-chlorophenyl)-1-[[2-(trimethylsilyl)ethoxy] methyl]-1H-indazol-3-yl]butanamide 512 mg of 4-chlorophenylboronic acid, 578 mg of potassium carbonate, and 167 mg of tetrakis(triphenyl)palladium are added to 900 mg of N-[6-bromo-1-[[2-(trimethylsilyl) ethoxy]methyl]-1H-indazol-3-yl]butanamide, described in Example 51, in 40 cm³ of dioxane. The mixture is then heated at about 104° C. for 2 hours and the temperature is allowed to return to about 19° C. over 16 hours. The reaction medium is diluted with 75 cm³ of ethyl acetate, filtered through a sinter funnel packed with Celite and concentrated to dryness under reduced pressure (2 kPa; 50° C.). The residue is taken up in 100 cm³ of ethyl acetate and 50 cm³ of water. The organic phase is washed again with 25 cm³ of saturated aqueous sodium chloride solution and then separated out after settling of the phases has taken place, dried over magnesium sulphate, filtered and evaporated under reduced pressure (2 kPa; 50° C.). The residue is purified by chromatography under an argon pressure of 50 kPa, on a column of silica gel (particle size 40–60 μm; diameter 2.5 cm), eluting with a cyclohexane/ethyl acetate mixture (80/20 by volume). The fractions containing the expected product are combined and evaporated under reduced pressure (2 kPa; 50° C.); 600 mg of N-[6-(4-chlorophenyl)-1-[[2-(trimethylsilyl)ethoxy]methyl]-1H-indazol-3-yl]butanamide are obtained in the form of a yellow wax.

$^1$H NMR spectrum (300 MHz, $(CD_3)_2SO$-d6, δ in ppm): −0.09 (s: 9H); 0.83 (t, J=8 Hz: 2H); 0.97 (t, J=7.5 Hz: 3H); 1.68 (mt: 2H); 2.41 (t, J=7 Hz: 2H); 3.56 (t, J=8 Hz: 2H); 5.73 (s: 2H); 7.46 (broad d, J=9 Hz: 1H); 7.58 (d, J=8.5 Hz: 2H); 7.81 (d, J=8.5 Hz: 2H); 7.93 (d, J=9 Hz: 1H); 7.98 (broad s: 1H); 10.49 (unresolved peak: 1H).

| EI | m/z = 443 | $M^{+\cdot}$ |
|---|---|---|
| | m/z = 326 | $[M—OCH_2CH_2Si(CH_3)_3]^+$ |
| | m/z = 315 | $[M—C_6H_{12}OSi]^{+\cdot}$ |

N-[6-(4-chlorophenyl)-1H-indazol-3-yl]butanamide 9.5 cm$^3$ of tetrabutylammonium fluoride as a 1M solution in tetrahydrofuran are added to a solution of 600 mg of N-[6-(4-chlorophenyl)-1-[[2-(trimethylsilyl)ethoxy]-methyl]-1H-indazol-3-yl]butanamide, prepared previously, in 20 cm$^3$ of tetrahydrofuran, the reaction medium is then heated at about 65° C. for 18 hours and the heating is stopped to add 40 cm$^3$ of ethyl acetate. The organic phase is washed with 2×30 cm$^3$ of saturated aqueous sodium hydrogen carbonate solution and then with 30 cm$^3$ of saturated aqueous sodium chloride solution. The organic phase is dried over magnesium sulphate, filtered and evaporated under reduced pressure (2 kPa; 50° C.). After drying (90 Pa; 50° C.), 238 mg of N-[6-(4-chlorophenyl)-1H-indazol-3-yl]butanamide are obtained in the form of a beige-coloured powder.

$^1$H NMR spectrum (300 MHz, $(CD_3)_2SO$-d6, δ in ppm): 0.98 (broad t, J=7.5 Hz: 3H); 1.68 (mt: 2H); 2.40 (t, J=7 Hz: 2H); 7.35 (broad d, J=8.5 Hz: 1H); 7.55 (d, J= 8.5 Hz: 2H); 7.64 (broad s: 1H); 7.77 (d, J=8.5 Hz: 2H); 7.88 (d, J=8.5 Hz: 1H); 10.34 (unresolved peak: 1H).

| EI | m/z = 313 | $M^{+\cdot}$ |
|---|---|---|
| | m/z = 243 | $[M—C_4CH_6O]^{+\cdot}$ |

EXAMPLE 54

N-[6-chloro-1H-indazol-3-yl]benzenepropanamide trifluoroacetate 0.88 cm$^3$ of hydrocinnamoyl chloride is added to 1 g of 6-chloro-1H-indazole-3-amine in 15 cm$^3$ of pyridine, after cooling to about 5° C., and the mixture is then allowed to return to room temperature over 18 hours. The reaction medium is then concentrated to dryness under reduced pressure (2 kPa; 45° C.) and then taken up in 25 cm$^3$ of ethyl acetate, 25 cm$^3$ of water and 10 cm$^3$ of tetrahydrofuran. The organic phase separated out after settling of the phases has taken place is washed with 25 cm$^3$ of water and then with 25 cm$^3$ of saturated aqueous sodium chloride solution; after drying over magnesium sulphate, filtering and concentrating to dryness under reduced pressure (2 kPa; 50° C.), the residue is purified by chromatography under an argon pressure of 50 kPa, on a column of silica gel (particle size 15–40 μm; diameter 4 cm), eluting with a dichloromethane/methanol mixture (97/3 by volume). The fractions containing the expected product are combined and evaporated under reduced pressure (2 kPa; 50° C.). The impure product obtained is repurified by HPLC (Hypurity; $C_{18}$, 5 μm column; length 50 mm, diameter 21 mm, eluent: acetonitrile/water gradient (5/95 to 95/5 by volume) containing 0.05% trifluoroacetic acid; flow rate 10 cm$^3$/min). After concentrating the fractions containing the expected product, and after drying (90 Pa; 50° C.), 200 mg of N-[6-chloro-1H-indazol-3-yl]benzenepropanamide trifluoroacetate are obtained in the form of a white solid melting at 224° C.

$^1$H NMR spectrum (300 MHz, $(CD_3)_2SO$-d6, δ in ppm): 2.73 (t, J=7.5 Hz: 2H); 2.97 (t, J=7.5 Hz: 2H); 7.06 (dd, J=9 and 1.5 Hz: 1H); from 7.15 to 7.40 (mt: 5H); 7.51 (d, J=1.5 Hz: 1H); 7.77 (d, J=9 Hz: 1H); 10.44 (broad s: 1H).

EXAMPLE 55

N-[6-(4-ethylphenyl)-1-[[2-(trimethylsilyl)ethoxy]methyl]-1H-indazol-3-yl]butanamide 612 mg of 4-ethylphenylboronic acid, 1.24 g of caesium fluoride, 13.5 mg of palladium acetate and finally 31 mg of 2-dicyclohexylphosphine-2-(N,N-dimethylamino)biphenyl are added to 1 g of N-[6-chloro-1-[[2-(trimethylsilyl)-ethoxy]methyl]-1H-indazol-3-yl]butanamide, described in Example 25, in 30 cm$^3$ of dioxane, and the mixture is then refluxed for 16 hours. The reaction medium is diluted with 50 cm$^3$ of ethyl acetate and 50 cm$^3$ of water, filtered through a sinter funnel packed with Celite and the filtrate is concentrated to dryness under reduced pressure (2 kPa; 50° C.). The work-up and the purification are performed by analogy with Example 41. The product, which is still impure, is repurified by HPLC (Hypurity; $C_{18}$, 5 μm column; length 50 mm, diameter 21 mm, eluent: acetonitrile/water containing 0.05% trifluoroacetic acid; flow rate 10 cm$^3$/min). After concentrating the fractions containing the expected product and drying (90 Pa; 45° C.), 240 mg of N-[6-(4-ethylphenyl)-1-[[2-(trimethylsilyl)ethoxy]methyl]-1H-indazol-3-yl]butanamide are obtained in the form of a yellow oil. The product is used directly in the next step.

N-[[6-(4-ethylphenyl)-1H-indazol-3-yl]]butanamide 3.3 cm$^3$ of tetrabutylammonium fluoride as a 1M solution in tetrahydrofuran are added to a solution of 240 mg of N-[6-(4-ethylphenyl)-1-[[2-(trimethylsilyl)ethoxy]-methyl]-1H-indazol-3-yl]butanamide, described previously, in 20 cm$^3$ of tetrahydrofuran. The medium is then maintained at 67° C. for 17 hours, and the resulting mixture is then allowed to return to room temperature and 50 cm$^3$ of ethyl acetate are added. The organic phase is washed with 2×50 cm$^3$ of saturated aqueous sodium hydrogen carbonate solution and with 2×50 cm$^3$ of water, separated out after settling of the phases has taken place, dried over magnesium sulphate, filtered and concentrated to dryness under reduced pressure (2 kPa; 45° C.). The residue is purified by chromatography under an argon pressure of 50 kPa, on a column of silica gel (particle size 40–60 μm; diameter 2.5 cm), eluting with a cyclohexane/ethyl acetate mixture (60/40 by volume). The fractions containing the expected product are combined and evaporated under reduced pressure (2 kPa; 50° C.). The residue is taken up in 10 cm$^3$ of diisopropyl ether, filtered off on a sinter funnel and washed successively with 2 cm$^3$ of ethyl acetate and then with 10 cm$^3$ of diisopropyl ether. After drying (90 Pa; 50° C.), 80 mg of N-[6-(4-ethylphenyl)-1H-indazol-3-yl]butanamide are obtained in the form of a white solid melting at 210° C.

$^1$H NMR spectrum (300 MHz, $(CD_3)_2SO$-d6, δ in ppm): 0.98 (broad t, J=7.5 Hz: 3H); 1.24 (t, J=7.5 Hz: 3H); 1.68

(mt: 2H); 2.39 (t, J=7 Hz: 2H); 2.67 (q, J=7.5 Hz: 2H); from 7.30 to 7.40 (mt: 3H); 7.59 (broad s: 1H); 7.65 (broad d, J=8 Hz: 2H); 7.84 (d, J=9 Hz: 1H); 10.31 (unresolved peak: 1H); 12.65 (unresolved peak: 1H).

EXAMPLE 56

N-[6-(4,4,5,5-tetramethyl[1,3,2]dioxaborolan-2-yl)-1-[[2-(trimethylsilyl)ethoxy]methyl]-1H-indazol-3-yl]butanamide 766 mg of bis(pinacolato)diborane, 917 mg of caesium fluoride, then 9.9 mg of palladium acetate and finally 23.6 mg of 2-dicyclohexylphosphine-2-(N,N-dimethylamino)diphenyl are added to 740 mg of N-[6-chloro-1-[[2-(trimethylsilyl)ethoxy]methyl]-1H-indazol-3-yl]butanamide, described in Example 25, in 25 cm³ of dioxane. The medium is refluxed for 20 hours and is then allowed to return to room temperature and 50 cm³ of ethyl acetate and 50 cm³ of water are added. After filtering the reaction medium through a sinter funnel packed with Celite, it is washed with 2×50 cm³ of water. The organic phase is dried over magnesium sulphate, filtered and then concentrated to dryness under reduced pressure (2 kPa; 45° C.). The residue is purified by chromatography under an argon pressure of 50 kPa, on a column of silica gel (particle size 40–60 μm; diameter 3 cm), eluting with a cyclohexane/ethyl acetate mixture (80/20 by volume). The fractions containing the expected product are combined and evaporated under reduced pressure (2 kPa; 50° C.) to give 630 mg of N-[6-(4,4,5,5-tetramethyl[1,3,2]dioxaborolan-2-yl)-1-[[2-(trimethylsilyl)ethoxy]methyl]-1H-indazol-3-yl]butanamide in the form of a yellow oil.

$^1$H NMR spectrum (300 MHz, (CD$_3$)$_2$SO-d6, δ in ppm): −0.09 (s: 9H); 0.82 (t, J=8 Hz: 2H); 0.96 (t, J=7.5 Hz: 3H); 1.34 (s: 12H); 1.67 (mt: 2H); 2.40 (t, J=7 Hz: 2H); 3.50 (t, J=8 Hz: 2H); 5.71 (s: 2H); 7.39 (d, J=8.5 Hz: 1H); 7.83 (d, J=8.5 Hz: 1H); 7.97 (s: 1H); 10.45 (unresolved peak: 1H).

| EI | m/z = 459 | M$^{+\cdot}$ |
|---|---|---|
|  | m/z = 342 | [M—OCH$_2$CH$_2$Si(CH$_3$)$_3$]$^+$ |
|  | m/z = 331 | [M—C$_6$H$_{12}$OSi]$^{+\cdot}$ |
|  | m/z = 272 | [342 - C$_4$H$_6$O]$^+$ |

N-[6-(4-pyridyl)-1-[[2-(trimethylsilyl)ethoxy]methyl]-1H-indazol-3-yl]butanamide 246 mg of 4-iodopyridine, 10 cm³ of water, 201 mg of sodium carbonate and 69 mg of tetrakis(triphenylphosphine)palladium are added to 320 mg of N-[6-(4,4,5,5-tetramethyl[1,3,2]dioxaborolan-2-yl)-1-[[2-(trimethylsilyl)ethoxy]methyl]-1H-indazol-3-yl]butanamide, described previously, in 20 cm³ of dioxane. The medium is refluxed for 20 hours, the mixture is then allowed to return to room temperature and 50 cm³ of ethyl acetate and 50 cm³ of water are added. The combined organic phases are washed with 50 cm³ of distilled water and then with 50 cm³ of saturated aqueous sodium chloride solution, and then dried over magnesium sulphate, filtered and concentrated to dryness under reduced pressure (2 kPa; 45° C.). The residue is purified by chromatography under an argon pressure of 50 kPa, on a column of silica gel (particle size 40–60 μm; diameter 2.5 cm), eluting with a cyclohexane/ethyl acetate mixture (70/30 by volume). The fractions containing the expected product are combined and evaporated under reduced pressure (2 kPa; 50° C.). 280 mg of N-[6-(4-pyridyl)-1-[[2-(trimethylsilyl)ethoxy]methyl]-1H-indazol-3-yl]butanamide are obtained in the form of a yellow oil.

$^1$H NMR spectrum (300 MHz, (CD$_3$)$_2$SO-d6, δ in ppm): −0.10 (s: 9H); 0.83 (t, J=8 Hz: 2H); 0.98 (t, J=7.5 Hz: 3H); 1.69 (mt: 2H); 2.42 (t, J=7 Hz: 2H); 3.57 (t, J=8 Hz: 2H); 5.76 (s: 2H); 7.57 (broad dd, J=8.5 and 1 Hz: 1H); 7.82 (broad d, J=6 Hz: 2H); 7.98 (d, J=8.5 Hz: 1H); 8.16 (broad s: 1H); 8.70 (broad d, J=6 Hz: 2H); 10.52 (unresolved peak: 1H).

| EI | m/z = 410 | M$^{+\cdot}$ |
|---|---|---|
|  | m/z = 293 | [M—OCH$_2$CH$_2$Si(CH$_3$)$_3$]$^+$ |
|  | m/z = 282 | [M—C$_6$H$_{12}$OSi]$^{+\cdot}$ |

N-[6-(4-pyridyl)-1H-indazol-3-yl]butanamide 4.1 cm³ of tetrabutylammonium fluoride as a 1M solution in tetrahydrofuran are added to 280 mg of N-[6-(4-pyridyl)-1-[[2-(trimethylsilyl)ethoxy]methyl]-1H-indazol-3-yl]butanamide, described previously, in 20 cm³ of tetrahydrofuran, the medium is maintained at 67° C. for 17 hours and is then allowed to return to room temperature to add 50 cm³ of ethyl acetate and 50 cm³ of saturated aqueous sodium hydrogen carbonate solution. The organic phase is washed with 50 cm³ of saturated aqueous sodium chloride solution and then with 50 cm³ of water, dried over magnesium sulphate, filtered and concentrated to dryness under reduced pressure (2 kPa; 45° C.). The residue is purified by chromatography under an argon pressure of 50 kPa, on a column of silica gel (particle size 40–60 μm; diameter 2 cm), eluting with ethyl acetate. The fractions containing the expected product are combined and concentrated to dryness under reduced pressure (2 kPa; 50° C.). The residue is taken up in 10 cm³ of diisopropyl ether, filtered off on a sinter funnel and then washed successively with 5 cm³ of ethyl acetate and with 10 cm³ of diisopropyl ether. After drying (90 Pa; 50° C.), 60 mg of N-[6-(4-pyridyl)-1H-indazol-3-yl]butanamide are obtained in the form of a white solid melting at 200° C.

$^1$H NMR spectrum (300 MHz, (CD$_3$)$_2$SO-d6, δ in ppm): 0.99 (t, J=7.5 Hz: 3H); 1.69 (mt: 2H); 2.41 (t, J=7 Hz: 2H); 7.47 (broad dd, J=9 and 1 Hz: 1H); 7.78 (broad d, J=6 Hz: 2H); 7.81 (broad s: 1H); 7.93 (d, J=9 Hz: 1H); 8.67 (broad d, J=6 Hz: 2H); 10.38 (unresolved peak: 1H); 12.84 (broad s: 1H).

EXAMPLE 57

N-(5-amino-1H-indazol-3-yl)butanamide 20 g of iron sulphate heptahydrate dissolved in 50 cm³ of hot water are added to a solution of 2.05 g of N-[5-nitro-1H-indazol-3-yl]butanamide, described in Example 23, in 80 cm³ of ethanol; the mixture is stirred for 30 minutes at room temperature, 24 cm³ of 28% aqueous ammonia are added and the mixture is then refluxed for 2 hours, 10 cm³ of 28% aqueous ammonia are added and the mixture is stirred for a further 10 minutes. The precipitate is filtered off while hot, on a sinter funnel packed with Celite, rinsed with methanol until the filtrate is colourless, and concentrated to dryness under reduced pressure (2 kPa; 50° C.). The residue is taken up in 100 cm³ of ethyl acetate and is washed with 50 cm³ of saturated aqueous sodium chloride solution. The organic phase is separated out after settling of the phases has taken place, dried over magnesium sulphate, filtered and concentrated to dryness under reduced pressure. After drying (90 Pa; 50° C.) 870 mg of N-(5-amino-1H-indazol-3-yl)butanamide are obtained in the form of a purple powder.

$^1$H NMR spectrum (300 MHz, $(CD_3)_2SO$-d6, δ in ppm): 0.98 (t, J=7.5 Hz: 3H); 1.66 (mt: 2H); 2.34 (broad t, J=7 Hz: 2H); 4.82 (unresolved peak: 2H); 6.70 (broad s: 1H); 6.77 (dd, J=9 and 2 Hz: 1H); 7.15 (d, J=9 Hz: 1H); 9.92 (unresolved peak: 1H); 12.13 (unresolved peak: 1H).

| EI | m/z = 218 | $M^{+\cdot}$ |
|----|-----------|--------------|
|    | m/z = 148 | $[M-C_4CH_6O]^{+\cdot}$ |
|    | m/z = 43  | $[C_3H_7]^+$ |

EXAMPLE 58

N-[5-bromo-6-chloro-1-[[2-(trimethylsilyl)ethoxy]methyl]-1H-indazol-3-yl]butanamide 0.22 cm$^3$ of pyridine is added to 1 g of N-[6-chloro-1-[[2-(trimethylsilyl)ethoxy]methyl]-1H-indazol-3-yl]butanamide, described in Example 25, in 15 cm$^3$ of chloroform, followed by addition of 0.14 cm$^3$ of bromine. The mixture is stirred for 24 hours at 20° C., followed by addition of 50 cm$^3$ of dichloromethane and 50 cm$^3$ of saturated aqueous sodium sulphate solution. After stirring for 10 minutes, the insoluble material is removed by filtration on a sinter funnel and the organic phase is washed with 50 cm$^3$ of saturated aqueous sodium chloride solution. The organic phase is separated out after settling of the phases has taken place, dried over magnesium sulphate, filtered and concentrated to dryness under reduced pressure (2 kPa; 45° C.). The residue is purified by chromatography under an argon pressure of 50 kPa, on a column of silica gel (particle size 40–60/m; diameter 3.5 cm), eluting with a cyclohexane/ethyl acetate mixture (80/20 by volume). The fractions containing the expected product are combined and evaporated under reduced pressure (2 kPa; 50° C.). After drying (90 Pa; 45° C.), 940 mg of N-[5-bromo-6-chloro-1-[[2-(trimethylsilyl)ethoxy]methyl]-1H-indazol-3-yl]butanamide are obtained in the form of a white solid melting at 130° C.

$^1$H NMR spectrum (300 MHz, $(CD_3)_2SO$-d6, δ in ppm): −0.08 (s: 9H); 0.82 (t, J=8 Hz: 2H); 0.95 (t, J=7.5 Hz: 3H); 1.66 (mt: 2H); 2.40 (t, J=7.5 Hz: 2H); 3.52 (t, J=8 Hz: 2H); 5.66 (s: 2H); 8.13 (s: 1H); 8.34 (s: 1H); 10.67 (broad s: 1H).

N-(5-bromo-6-chloro-1H-indazol-3-yl)butanamide 12.6 cm$^3$ of tetrabutylammonium fluoride as a 1M solution in tetrahydrofuran are added to 940 mg of N-[5-bromo-6-chloro-1-[[2-(trimethylsilyl)ethoxy]methyl]-1H-indazol-3-yl]butanamide, described previously, in 30 cm$^3$ of tetrahydrofuran. The medium is then maintained at 67° C. for 19 hours and is then allowed to return to room temperature and 50 cm$^3$ of ethyl acetate are added. The organic phase is washed with 2×50 cm$^3$ of saturated aqueous sodium hydrogen carbonate solution and then with 50 cm$^3$ of saturated aqueous sodium chloride solution, dried over magnesium sulphate, filtered and then concentrated to dryness under reduced pressure (2 kPa; 45° C.). The residue is purified by chromatography under an argon pressure of 50-kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) and the residue is taken up in 15 cm$^3$ of diisopropyl ether, filtered off on a sinter funnel and washed successively with 5 cm$^3$ of ethyl acetate and then with 2×10 cm$^3$ of diisopropyl ether. After drying (90 Pa; 50° C.), 460 mg of N-(5-bromo-6-chloro-1H-indazol-3-yl)butanamide are obtained in the form of a white solid melting at 250° C.

$^1$H NMR spectrum (300 MHz, $(CD_3)_2SO$-d6, δ in ppm): 0.96 (t, J=7.5 Hz: 3H); 1.66 (mt: 2H); 2.40 (t, J=7 Hz: 2H); 7.77 (s: 1H); 8.29 (s: 1H); 10.53 (unresolved peak: 1H); from 12.50 to 13.20 (broad unresolved peak: 1H).

EXAMPLE 59

N-(6-chloro-1H-indazol-3-yl)-2-thiophenecarboxamide 0.64 cm$^3$ of 2-thiophenecarbonyl chloride is added to 1 g of 6-chloro-1H-indazole-3-amine in 15 cm$^3$ of pyridine, after cooling to about 6° C. with an ice bath, the reaction medium is then allowed to return to room temperature over 17 hours and concentrated to dryness under reduced pressure (2 kPa; 45° C.), and the residue is then taken up in 20 cm$^3$ of ethyl acetate, 20 cm$^3$ of water and 20 cm$^3$ of saturated aqueous sodium chloride solution. The organic phase is separated out after settling of the phases has taken place, dried over magnesium sulphate, filtered and concentrated to dryness under reduced pressure (2 kPa; 45° C.), and the residue is then purified by chromatography under an argon pressure of 50 kPa, on a column of silica gel (particle size 15–40 μm; diameter 3 cm), eluting with a dichloromethane/methanol mixture (99/1 by volume). The fractions containing the expected product are combined and evaporated under reduced pressure (2 kPa; 50° C.); after drying (90 Pa; 50° C.), 660 mg of N-(6-chloro-1H-indazol-3-yl)-2-thiophenecarboxamide are obtained in the form of a pale yellow solid melting at 215° C.

$^1$H NMR spectrum (300 MHz, $(CD_3)_2SO$-d6, δ in ppm): 7.11 (dd, J=9 and 2 Hz: 1H); 7.25 (dd, J=5 and 3.5 Hz: 1H); 7.58 (dd, J=2 and 0.5 Hz: 1H); 7.81 (dd, J=9 and 0.5 Hz: 1H); 7.90 (dd, J=5 and 1.5 Hz: 1H); 8.14 (dd, J=3.5 and 1.5 Hz: 1H); 10.98 (unresolved peak: 1H); 12.96 (unresolved peak: 1H).

EXAMPLE 60

N-(6-chloro-1H-indazol-3-yl)-2-methylpropylamide 0.63 cm$^3$ of isobutyryl chloride is added to 1 g of 6-chloro-1H-indazole-3-amine in 15 cm$^3$ of pyridine, after cooling the medium to about 6° C., and the mixture is then allowed to return to room temperature over 19 hours and evaporated to dryness under reduced pressure (2 kPa; 45° C.). The residue is taken up in 25 cm$^3$ of ethyl acetate and 25 cm$^3$ of water; the precipitate formed is filtered off on a sinter funnel and then rinsed with ethyl acetate. After drying (90 Pa; 50° C.), 384 mg of N-(6-chloro-1H-indazol-3-yl)-2-methylpropylamide are obtained in the form of a white product melting at 238° C.

$^1$H NMR spectrum (300 MHz, $(CD_3)_2SO$-d6, δ in ppm): 1.17 (d, J=7 Hz: 6H); 2.75 (mt: 1H); 7.08 (dd, J=9 and 1.5 Hz: 1H); 7.52 (broad s: 1H); 7.82 (d, J=9 Hz: 1H); 10.35 (broad s: 1H); 12.76 (broad s: 1H).

EXAMPLE 61

4-Chloro-N-(6-chloro-1H-indazol-3-yl)butanamide 0.67 cm$^3$ of 4-chlorobutyryl chloride is added to 1 g of 6-chloro-1H-indazole-3-amine in 15 cm$^3$ of pyridine, after cooling to about 6° C. in an ice bath, and the mixture is then allowed to return to room temperature over 19 hours. The reaction medium is concentrated to dryness under reduced pressure (2 kPa; 45° C.) and the residue is taken up in 25 cm³ of ethyl acetate and 25 cm³ of water. The precipitate is filtered off and rinsed with 15 cm³ of ethyl acetate and 5 cm³ of dichloromethane. The organic phase is dried over magnesium sulphate, filtered and then concentrated to dryness under reduced pressure (2 kPa; 45° C.); after drying (90 Pa; 50° C.), 343 mg of 4-chloro-N-(6-chloro-1H-indazol-3-yl) butanamide are obtained in the form of a pale yellow solid melting at 220° C.

$^1$H NMR spectrum (300 MHz, $(CD_3)_2SO$-d6, δ in ppm): 2.09 (mt: 2H); 2.58 (t, J=7 Hz: 2H); 3.74 (t, J=7 Hz: 2H); 7.08 (broad dd, J=9 and 1.5 Hz: 1H); 7.52 (broad d, J=1.5 Hz: 1H); 7.84 (d, J=9 Hz: 1H); 10.51 (broad s: 1H); from 12.60 to 13.10 (broad unresolved peak: 1H).

EXAMPLE 62

N-[5-phenyl-6-chloro-1-[[2-(trimethylsilyl)ethoxy]methyl]-1H-indazol-3-yl]butanamide 821 mg of phenylboronic acid, 1.14 g of sodium carbonate in 30 cm³ of distilled water and finally 347 mg of tetrakis(triphenylphosphine)palladium are added to 2 g of N-[5-bromo-6-chloro-1-[[2-(trimethylsilyl)ethoxy]methyl]-1H-indazol-3-yl]butanamide, described in Example 58, in 180 cm³ of dioxane. The mixture is refluxed for 90 minutes and is then allowed to return to 20° C. to add 100 cm³ of ethyl acetate and 100 cm³ of distilled water. The organic phase is washed with 100 cm³ of saturated aqueous sodium chloride solution and then separated out after settling of the phases has taken place and dried over magnesium sulphate. After filtration, the filtrate is concentrated to dryness under reduced pressure (2 kPa; 50° C.) and the residue is purified by chromatography under an argon pressure of 50 kPa, on a column of silica gel (particle size 40–60 μm; diameter 4.5 cm), eluting with a cyclohexane/ethyl acetate mixture (80/20 by volume). The fractions containing the expected product are combined and evaporated under reduced pressure (2 kPa; 50° C.). After drying (90 Pa; 45° C.), 2 g of N-[5-phenyl-6-chloro-1-[[2-(trimethylsilyl)ethoxy]methyl]-1H-indazol-3-yl]butanamide are thus obtained in the form of a yellow oil.

$^1$H NMR spectrum (300 MHz, $(CD_3)_2SO$-d6, δ in ppm): −0.05 (s: 9H); 0.85 (t, J=8 Hz: 2H); 0.92 (t, J=7.5 Hz: 3H); 1.63 (mt: 2H); 2.38 (t, J=7.5 Hz: 2H); 3.56 (t, J=8 Hz: 2H); 5.70 (s: 2H); from 7.30 to 7.55 (mt: 5H); 7.91 (s: 1H); 7.99 (s: 1H); 10.59 (broad s: 1H).

| EI | m/z = 443 | M⁺· |
| --- | --- | --- |
|  | m/z = 326 | [M—OCH₂CH₂Si(CH₃)₃]⁺ |
|  | m/z = 315 | [M—C₆H₁₂OSi]⁺· |

N-(5-phenyl-6-chloro-1H-indazol-3-yl)butanamide 8.8 cm³ of tetrabutylammonium fluoride as a 1M solution in tetrahydrofuran are added to 650 mg of N-[5-phenyl-6-chloro-1-[[2-(trimethylsilyl)ethoxy]methyl]-1H-indazol-3-yl]butanamide, described previously, in 25 cm³ of tetrahydrofuran. The medium is maintained at 67° C. for 20 hours and is then allowed to return to room temperature and 75 cm³ of ethyl acetate are added; the organic phase is washed with 75 cm³ of saturated aqueous sodium hydrogen carbonate solution and then with 2×75 cm³ of saturated aqueous sodium chloride solution. The organic phase is dried over magnesium sulphate, filtered and evaporated to dryness under reduced pressure (2 kPa; 45° C.). The residue is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) and the residue is taken up in 15 cm³ of diisopropyl ether, filtered off on a sinter funnel and washed successively with 10 cm³ of diisopropyl ether and with 5 cm³ of ethyl acetate. After drying under reduced pressure (90 Pa; 50° C.), 240 mg of N-(5-phenyl-6-chloro-1H-indazol-3-yl)butanamide are obtained in the form of a white solid melting at 235° C.

$^1$H NMR spectrum (300 MHz, $(CD_3)_2SO$-d6, δ in ppm): 0.92 (t, J=7.5 Hz: 3H); 1.63 (mt: 2H); 2.37 (t, J=7 Hz: 2H); from 7.35 to 7.55 (mt: 5H); 7.66 (s: 1H); 7.85 (s: 1H); 10.47 (broad s: 1H); 12.80 (unresolved peak: 1H).

EXAMPLE 63

N-[5-bromo-6-[4-(phenylmethoxy)phenyl]-1-[[2-(trimethylsilyl)ethoxy]methyl]-1H-indazol-3-yl]butanamide 0,84 cm³ of pyridine are added to 2.64 g of N-[6-[4-(phenylmethoxy)phenyl]-1-[[2-(trimethylsilyl)ethoxy]methyl]-1H-indazol-3-yl]butanamide, prepared in Example 32, in 50 cm³ of chloroform, followed by dropwise addition of 0.52 cm³ of bromine, followed by addition of a further 0.42 cm³ of pyridine and 0.26 cm³ of bromine. 50 cm³ of methylene chloride and 100 cm³ of 10% sodium thiosulphate solution are added to the reaction medium; the organic phase is separated out after settling of the phases has taken place, washed successively with 50 cm³ of 10% sodium thiosulphate solution and with 50 cm³ of saturated sodium chloride solution, dried over magnesium sulphate, filtered and concentrated under reduced pressure (2 kPa; 50° C.) to give 3.4 g of an oil, which is purified by chromatography under an argon pressure of 50 kPa, on a column of silica gel (particle size 40–60 μm; diameter 3.5 cm), eluting with a cyclohexane/ethyl acetate mixture (90/10 by volume). The fractions containing the expected product are combined and evaporated under reduced pressure (2 kPa; 50° C.) to give 2.1 g of N-[5-bromo-6-[4-(phenylmethoxy)phenyl]-1-[[2-(trimethylsilyl)ethoxy]methyl]-1H-indazol-3-yl]butanamide in the form of a white powder melting at 140° C.

$^1$H NMR spectrum (300 MHz, $(CD_3)_2SO$-d6, δ in ppm): −0.09 (s: 9H); 0.81 (t, J=8 Hz: 2H); 0.96 (t, J=7.5 Hz: 3H); 1.67 (mt: 2H); 2.42 (broad t, J=7 Hz: 2H); 3.53 (t, J=8 Hz: 2H); 5.19 (s: 2H); 5.67 (s: 2H); 7.13 (d, J=8.5 Hz: 2H); 7.37 (d, J=8.5 Hz: 2H); 7.37 (mt: 1H); 7.43 (broad t, J=7.5 Hz: 2H); 7.51 (broad d, J=7.5 Hz: 2H); 7.70 (s: 1H); 8.26 (s: 1H); 10.61 (unresolved peak: 1H).

N-[5-bromo-6-[4-(phenylmethoxy)phenyl]-1H-indazol-3-yl]butanamide 20 cm³ of tetrabutylammonium fluoride as a 1M solution in tetrahydrofuran are added to 2 g of N-[5-bromo-6-[4-(phenylmethoxy)phenyl]-1-[[2-(trimethylsilyl)ethoxy]-methyl]-1H-indazol-3-yl]butanamide, described previously, in 60 μm³ of tetrahydrofuran, and the mixture is refluxed for 18 hours; after cooling, 75 cm³ of ethyl acetate are added and the organic phase is washed successively with 75 cm³ of saturated sodium hydrogen carbonate solution and with 75 cm³ of saturated sodium chloride solution. The organic phase is separated out after settling of the phases has taken place, dried over magnesium sulphate, filtered and concentrated to dryness under reduced pressure (2.7 kPa; 50° C.) to give 2 g of crude product, which is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) and the residue is taken up in 50 cm³ of diisopropyl ether, filtered off, washed with 2×10 cm³ of diisopropyl ether and dried (90 Pa; 45° C.) to give 500 mg of N-[5-bromo-6-[4-(phenylmethoxy)phenyl]-1H-indazol-3-yl]butanamide in the form of a solid melting at 20° C.

¹H NMR spectrum (300 MHz, (CD₃)₂SO-d6, δ in ppm): 0.98 (t, J=7.5 Hz: 3H); 1.69 (mt: 2H); 2.42 (t, J=7 Hz: 2H); 5.19 (s: 2H); 7.12 (d, J=8.5 Hz: 2H); from 7.30 to 7.50 (mt: 6H); 7.53 (broad d, J=7.5 Hz: 2H); 8.22 (s: 1H); 10.50 (unresolved peak: 1H); 12.83 (unresolved peak: 1H).

N-[5-bromo-6-(4-hydroxyphenyl)-1H-indazol-3-yl]butanamide 10 cm³ of trimethylsilyl iodide are added to 500 mg of N-[5-bromo-6-[4-(phenylmethoxy)phenyl]-1H-indazol-3-yl]butanamide, prepared previously, and the mixture is refluxed for 4 hours. 25 cm³ of methanol are added and the reaction medium is refluxed for 15 minutes and then concentrated to dryness under reduced pressure (2 kPa; 50° C.). The residue is taken up in 50 cm³ of ethyl acetate and is washed with 2×50 cm³ of 10% sodium thiosulphate solution and then with 50 cm³ of water and 50 cm³ of saturated sodium chloride solution. The organic phase is separated out after settling of the phases has taken place, dried over magnesium sulphate, filtered and then concentrated to dryness under reduced pressure to give 1 g of crude product, which is purified by chromatography under an argon pressure of 50 kPa, on a column of silica gel (particle size 40–60 μm; diameter 3.5 cm), eluting with a cyclohexane/ethyl acetate mixture (60/40 by volume). The fractions containing the expected product are combined and evaporated under reduced pressure (2 kPa; 50° C.) and the residue is taken up in 10 cm³ of ethyl acetate, filtered off, washed with 2×5 cm³ of ethyl acetate and dried (90 Pa; 45° C.) to give 130 mg of N-[5-bromo-6-(4-hydroxyphenyl)-1H-indazol-3-yl]butanamide melting above 260° C.

¹H NMR spectrum (300 MHz, (CD₃)₂SO-d6, δ in ppm): 0.98 (t, J=7.5 Hz: 3H); 1.68 (mt: 2H); 2.40 (t, J=7 Hz: 2H); 6.85 (d, J=8.5 Hz: 2H); 7.25 (d, J=8.5 Hz: 2H); 7.34 (s: 1H); 8.20 (s: 1H); 9.61 (unresolved peak: 1H); 10.48 (broad s: 1H); 12.79 (unresolved peak: 1H).

EXAMPLE 64

N-[6-(4-nitrophenyl)-1-[[2-(trimethylsilyl)ethoxy]methyl]-1H-indazol-3-yl]butanamide 790 mg of 4-bromonitrobenzene, 10 cm³ of water, 646 mg of sodium carbonate and 190 mg of tetrakis(triphenylphosphine)palladium are added to 1 g of N-[6-(4,4,5,5-tetramethyl[1,3,2]dioxaborolan-2-yl)-1-[[2-(trimethylsilyl)ethoxy]methyl]-1H-indazol-3-yl]butanamide, prepared as described in Example 56, in 50 cm³ of dioxane. The reaction medium is then refluxed for 18 hours and is allowed to return to room temperature, 75 cm³ of ethyl acetate are then added and the organic phase is washed with 2×50 cm³ of distilled water and then with 50 cm³ of saturated aqueous sodium chloride solution. After drying over magnesium sulphate, filtering and concentrating to dryness under reduced pressure (2 kPa; 45° C.), the residue is purified by chromatography under an argon pressure of 50 kPa, on a column of silica gel (particle size 40–60 μm; diameter 2.5 cm), eluting with a cyclohexane/ethyl acetate mixture (80/20 by volume). The fractions containing the expected product are combined and evaporated under reduced pressure (2 kPa; 50° C.). 650 mg of N-[6-(4-nitrophenyl)-1-[[2-(trimethylsilyl)ethoxy]methyl]-1H-indazol-3-yl]butanamide are obtained in the form of a yellow oil.

¹H NMR spectrum (300 MHz, (CD₃)₂SO-d6, δ in ppm): −0.10 (s: 9H); 0.83 (t, J=8 Hz: 2H); 0.97 (t, J=7.5 Hz: 3H); 1.68 (mt: 2H); 2.42 (t, J=7 Hz: 2H); 3.57 (t, J=8 Hz: 2H); 5.77 (s: 2H); 7.56 (broad dd, J=9 and 1.5 Hz: 1H); 7.99 (d, J=9 Hz: 1H); 8.09 (d, J=9 Hz: 2H); 8.15 (broad s: 1H); 8.37 (d, J=9 Hz: 2H); 10.56 (unresolved peak: 1H).

| EI | m/z = 454 | M⁺· |
| | m/z = 337 | [M—OCH₂CH₂Si(CH₃)₃]⁺ |
| | m/z = 326 | [M—C₆H₁₂OSi]⁺· |
| | m/z = 73 | [Si(CH₃)₃]⁺ |

N-[[6-(4-nitrophenyl)-1H-indazol-3-yl]]butanamide 8.6 cm³ of tetrabutylammonium fluoride as a 1M solution in tetrahydrofuran are added to 650 mg of N-[6-(4-nitrophenyl)-1-[[2-(trimethylsilyl)ethoxy]methyl]-1H-indazol-3-yl]butanamide, described previously, in 30 cm³ of tetrahydrofuran. The medium is maintained at 67° C. for 18 hours and is then allowed to return to room temperature to add 75 cm³ of ethyl acetate and 75 cm³ of saturated aqueous sodium hydrogen carbonate solution. The organic phase is washed with 50 cm³ of saturated aqueous sodium chloride solution and then with 50 cm³ of water, separated out after settling of the phases has taken place, dried over magnesium sulphate, filtered and concentrated to dryness under reduced pressure (2 kPa; 45° C.). The residue is purified by chromatography under an argon pressure of 50 kPa, on a column of silica gel (particle size 40–60 μm; diameter 2 cm), eluting with a cyclohexane/ethyl acetate mixture (50/50 by volume). The fractions containing the expected product are combined and concentrated to dryness under reduced pressure (2 kPa; 50° C.); the residue is taken up in 10 cm³ of ethyl acetate, filtered off on a sinter funnel and then washed successively with 5 cm³ of ethyl acetate and with 10 cm³ of diisopropyl ether. After drying (90 Pa; 50° C.), 280 mg of N-[6-(4-nitrophenyl)-1H-indazol-3-yl]butanamide are obtained in the form of yellow crystals melting at 250° C.

¹H NMR spectrum (300 MHz, (CD₃)₂SO-d6, δ in ppm): 0.98 (t, J=7.5 Hz: 3H); 1.68 (mt: 2H); 2.41 (t, J=7 Hz: 2H); 7.46 (dd, J=8.5 and 1.5 Hz: 1H); 7.79 (broad s: 1H); 7.94 (d, J=8.5 Hz: 1H); 8.05 (broad d, J=9 Hz: 2H); 8.34 (broad d, J=9 Hz: 2H); 10.42 (unresolved peak: 1H); 12.87 (broad s: 1H).

EXAMPLE 65

N-[6-(2-chlorophenyl)-1-[(2-(trimethylsilyl)ethoxy]methyl]-1H-indazol-3-yl]butanamide 853 mg of 2-chlorophenylboronic acid, 30 cm³ of water, 964 mg of sodium carbonate and 252 mg of tetrakis(triphenylphosphine)palladium are added to 1 g of N-[6-bromo-1-[[2-(trimethylsilyl)ethoxy]methyl]-1H-indazol-3-yl]butanamide, prepared as described in Example 51, in 60 μm³ of dioxane. The reaction medium is then refluxed for 18 hours and filtered through a sinter funnel packed with Celite, and then concentrated to dryness under reduced pressure (2 kPa; 50° C.). The residue is taken up in 70 cm³ of ethyl acetate and the organic phase is washed with 2×30 cm³ of distilled water and then with 30 cm³ of saturated aqueous sodium chloride solution. The organic phase is separated out after settling of the phases has taken place, dried over magnesium sulphate, filtered and concentrated to dryness under reduced pressure (2 kPa; 45° C.). The residue obtained is purified by chromatography under an argon pressure of 50 kPa, on a column of silica gel (particle size 40–60 μm; diameter 2.5 cm), eluting with a cyclohexane/ethyl acetate mixture (90/10 by volume). The fractions containing the expected product are combined and evaporated under reduced pressure (2 kPa; 50° C.); 1 g of N-[6-(2-chlorophenyl)-1-[[2-(trimethylsilyl)ethoxy]methyl]-1H-indazol-3-yl]butanamide are obtained in the form of a yellow wax.

$^1$H NMR spectrum (300 MHz, $(CD_3)_2SO$-d6, δ in ppm): −0.08 (s: 9H); 0.84 (t, J=8 Hz: 2H); 0.99 (t, J=7.5 Hz: 3H); 1.69 (mt: 2H); 2.43 (t, J=7 Hz: 2H); 3.57 (t, J=8 Hz: 2H); 5.71 (s: 2H); 7.19 (dd, J=8.5 and 2 Hz: 1H); from 7.40 to 7.70 (mt: 4H); 7.74 (broad s: 1H); 7.90 (d, J=8.5 Hz: 1H); 10.51 (unresolved peak: 1H).

| EI | m/z = 443 | M$^{+\cdot}$ |
|---|---|---|
|  | m/z = 326 | [M—OCH$_2$CH$_2$Si(CH$_3$)$_3$]$^+$ |
|  | m/z = 315 | [M—C$_6$H$_{12}$OSi]$^{+\cdot}$ |

N-[6-(2-chlorophenyl)-1H-indazol-3-yl]butanamide 2.9 cm³ of tetrabutylammonium fluoride as a 1M solution in tetrahydrofuran are added to 900 mg of N-[6-(2-chlorophenyl)-1-[[2-(trimethylsilyl)ethoxy]methyl]-1H-indazol-3-yl]butanamide, described previously, in 40 cm³ of tetrahydrofuran, and the mixture is refluxed for 18 hours. The reaction medium is diluted with 50 cm³ of ethyl acetate and the organic phase is washed successively with 2×30 cm³ of saturated sodium hydrogen carbonate solution, with 30 cm³ of water and with 30 cm³ of saturated sodium chloride solution. The organic phase is separated out after settling of the phases has taken place, dried over magnesium sulphate, filtered and then concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate mixture (90/10 by volume). The fractions containing the expected product are combined and evaporated under reduced pressure (2 kPa; 50° C.); 120 mg of N-[6-(2-chlorophenyl)-1H-indazol-3-yl]butanamide are obtained in the form of a beige-coloured foam.

$^1$H NMR spectrum (300 MHz, $(CD_3)_2SO$-d6, δ in ppm): 0.98 (t, J=7.5 Hz: 3H); 1.69 (mt: 2H); 2.40 (t, J=7 Hz: 2H); 7.09 (broad d, J=8.5 Hz: 1H); from 7.40 to 7.65 (mt: 5H); 7.83 (d, J=8.5 Hz: 1H); 10.36 (broad s: 1H); 12.74 (broad s: 1H).

| EI | m/z = 313 | M$^{+\cdot}$ |
|---|---|---|
|  | m/z = 243 | [M—C$_4$CH$_6$O]$^{+\cdot}$ |

EXAMPLE 66

N-[6-[3-(phenylmethoxy)phenyl]-1-[[2-(trimethylsilyl)ethoxy)methyl]-1H-indazol-3-yl]butanamide 930 mg of 3-benzyloxyphenylboronic acid, 1.24 g of caesium fluoride, 31.5 mg of 2-dicyclohexylphosphino-2'-(N,N-dimethylamino)diphenyl and 13.5 mg of palladium acetate are successively added to 1 g of N-[6-chloro-1-[[2-(trimethylsilyl)ethoxy)methyl]-1H-indazol-3-yl)butanamide, prepared in Example 25, and the mixture is refluxed for 18 hours. The reaction medium is filtered through a sinter funnel packed with Celite and 75 cm³ of ethyl acetate are added to the filtrate. The organic phase is washed with 25 cm³ of saturated sodium chloride solution, separated out after settling of the phases has taken place, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate gradient (90/10 to 75/25 by volume). The fractions containing the expected product are combined and evaporated under reduced pressure (2 kPa; 50° C.); 1.1 g of N-[6-[3-(phenylmethoxy)phenyl]-1-[[2-(trimethylsilyl)ethoxy)methyl]-1H-indazol-3-yl]butanamide are obtained in the form of an oil in a purity of 80%.

$^1$H NMR spectrum (300 MHz, $(CD_3)_2SO$-d6, δ in ppm): −0.08 (s: 9H); 0.85 (t, J=8 Hz: 2H); 0.99 (t, J=7.5 Hz: 3H); 1.69 (mt: 2H); 2.42 (t, J=7 Hz: 2H); 3.58 (t, J=8 Hz: 2H); 5.23 (s: 2H); 5.75 (s: 2H); 7.08 (broad dd, J=8.5 and 2 Hz: 1H); from 7.30 to 7.50 (mt: 7H); 7.53 (broad d, J=7.5 Hz: 2H); 7.92 (d, J=9 Hz: 1H); 7.96 (broad s: 1H); 10.48 (unresolved peak: 1H).

| DCI | m/z = 516 | [M + H]$^+$ |
|---|---|---|

N-[6-[3-(phenylmethoxy)phenyl]-1H-indazol-3-yl]butanamide 2.9 cm³ of tetrabutylammonium fluoride as a 1M solution in tetrahydrofuran are added to 1 g of N-[6-[3-(phenylmethoxy)phenyl]-1-[[2-(trimethylsilyl)ethoxy]-methyl]-1H-indazol-3-yl]butanamide, described previously, in 20 cm³ of tetrahydrofuran, and the mixture is refluxed for 18 hours. The reaction medium is diluted with 100 cm³ of ethyl acetate and the organic phase is washed successively with 50 cm³ of saturated sodium hydrogen carbonate solution, with 2×50 cm³ of water and with 50 cm³ of saturated sodium chloride solution. The organic phase is separated out after settling of the phases has taken place, dried over magnesium sulphate, filtered and concentrated under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate gradient (70/30 to 40/60 by volume). The fractions containing the expected product are combined and evaporated under reduced pressure (2 kPa; 50° C.); 0.43 g of N-[6-[3-(phenylmethoxy)phenyl]-1H-indazol-3-yl]butanamide is obtained in the form of a white powder.

$^1$H NMR spectrum (300 MHz, $(CD_3)_2SO$-d6, δ in ppm): 0.98 (t, J=7.5 Hz: 3H); 1.68 (mt: 2H); 2.40 (t, J=7 Hz: 2H); 5.22 (s: 2H); 7.05 (broad dd, J=8.5 and 2 Hz: 1H); from 7.25 to 7.50 (mt: 7H); 7.52 (broad d, J=7.5 Hz: 2H); 7.63 (broad s: 1H); 7.35 (d, J=9 Hz: 1H); 10.33 (unresolved peak: 1H); 12.68 (unresolved peak: 1H).

| EI | m/z = 385 | M$^{+\cdot}$ |
|---|---|---|
|  | m/z = 315 | [M—C$_4$CH$_6$O]$^{+\cdot}$ |

N-[6-(3-hydroxyphenyl)-1H-indazol-3-yl]butanamide 10 cm³ of trimethylsilyl iodide are added to 0.4 g of N-[6-[3-(phenylmethoxy)phenyl]-1H-indazol-3-yl]butanamide, described previously, and the mixture is refluxed for 3 hours. 50 cm³ of methanol are then added and refluxing is continued for 15 minutes. The reaction medium is concentrated to dryness under reduced pressure (2 kPa; 50° C.), 50 cm³ of ethyl acetate are added and the organic phase is washed with 3×50 cm³ of 10% sodium thiosulphate solution. The organic phase is separated out after settling of the phases has taken place, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate mixture (50/50 by volume). The fractions containing the expected product are combined and evaporated under reduced pressure (2 kPa; 50° C.); 0.18 g of N-[6-(3-hydroxyphenyl)-1H-indazol-3-yl]butanamide is obtained in the form of a grey powder melting at 188° C.

¹H NMR spectrum (300 MHz, (CD$_3$)$_2$SO-d6, δ in ppm): 0.98 (broad t, J=7.5 Hz: 3H); 1.68 (mt: 2H); 2.40 (t, J=7 Hz: 2H); 6.80 (broad dd, J=8 and 2 Hz: 1H); 7.08 (mt: 1H); 7.13 (broad d, J=8 Hz: 1H); from 7.25 to 7.35 (mt: 2H); 7.55 (broad s: 1H); 7.84 (d, J=8.5 Hz: 1H); 9.55 (broad s: 1H); 10.34 (unresolved peak: 1H); 12.67 (unresolved peak: 1H).

EXAMPLE 67

N-[6-chloro-5-(4-pyridyl)-1-[[2-(trimethylsilyl)ethoxy]methyl]-1H-indazol-3-yl]butanamide 415 mg of 4-pyridylboronic acid are added to 1 g of N-[[5-bromo-6-chloro-1-[[2-(trimethylsilyl)ethoxy]methyl]-1H-indazol-3-yl]]butanamide, described previously, in Example 58, in 90 cm³ of dioxane, followed by addition of a solution of 570 mg of sodium carbonate in 18 cm³ of water and finally 173 mg of tetrakis-(triphenylphosphine)palladium, and the mixture is refluxed for 18 hours. The reaction medium is diluted with 75 cm³ of ethyl acetate and 50 cm³ of water. The organic phase is separated out after settling of the phases has taken place, washed with 50 cm³ of water and 50 cm³ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate mixture (60/40 by volume). The fractions containing the expected product are combined and evaporated under reduced pressure (2 kPa; 50° C.); 770 mg of N-[6-chloro-5-(4-pyridyl)-1-[[2-(trimethylsilyl)ethoxy]methyl]-1H-indazol-3-yl]butanamide are obtained in the form of white crystals.

¹H NMR spectrum (300 MHz, (CD$_3$)$_2$SO-d6, δ in ppm): −0.05 (s: 9H); 0.85 (t, J=8 Hz: 2H); 0.93 (t, J=7.5 Hz: 3H); 1.63 (mt: 2H); 2.39 (t, J=7 Hz: 2H); 3.55 (t, J=8 Hz: 2H); 5.71 (s: 2H); 7.48 (broad d, J=6 Hz: 2H); 7.98 (s: 1H); 8.08 (s: 1H); 8.69 (broad d, J=6 Hz: 2H); 10.67 (unresolved peak: 1H).

| ES | m/z = 445 | [M + H]$^+$ |
|---|---|---|

N-[6-chloro-5-(4-pyridyl)-1H-indazol-3-yl]butanamide 10.4 cm³ of tetrabutylammonium fluoride as a 1M solution in tetrahydrofuran are added to 770 mg of N-[6-chloro-5-(4-pyridyl)-1-[[2-(trimethylsilyl)ethoxy]methyl]-1H-indazol-3-yl]butanamide, described previously, in 30 cm³ of tetrahydrofuran, and the mixture is refluxed for 18 hours. The reaction medium is diluted with 75 cm³ of ethyl acetate and 75 cm³ of saturated sodium hydrogen carbonate solution. The organic phase is separated out after settling of the phases has taken place, washed with 50 cm³ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with ethyl acetate. The fractions containing the expected product are combined and evaporated under reduced pressure (2 kPa; 50° C.); the residue is taken up in 20 cm³ of ethyl acetate, filtered off, washed with 5 cm³ of ethyl acetate and 20 cm³ diethyl ether, and dried under reduced pressure (90 Pa; 45° C.) to give 320 mg of N-[6-chloro-5-(4-pyridyl)-1H-indazol-3-yl]butanamide in the form of white crystals melting above 260° C.

¹H NMR spectrum (300 MHz, (CD$_3$)$_2$SO-d6, δ in ppm): 0.93 (t, J=7.5 Hz: 3H); 1.63 (mt: 2H); 2.38 (t, J=7 Hz: 2H); 7.47 (dd, J=5 and 1.5 Hz: 2H); 7.71 (s: 1H); 7.94 (s: 1H); 8.67 (dd, J=5 and 1.5 Hz: 2H); 10.53 (unresolved peak: 1H); 12.90 (broad s: 1H).

EXAMPLE 68

N-[6-chloro-5-(3-furyl)-1-[[2-(trimethylsilyl)ethoxy]methyl]-1H-indazol-3-yl]butanamide 377 mg of 3-furylboronic acid are added to 1 g of N-[5-bromo-6-chloro-1-[[2-(trimethylsilyl)ethoxy]methyl]-1H-indazol-3-yl]butanamide, described previously, in Example 58, in 90 cm³ of dioxane, followed by addition of 570 mg of sodium carbonate in 18 cm³ of water and finally 173 mg of tetrakis(triphenylphosphine)palladium, and the mixture is refluxed for 18 hours. The reaction medium is diluted with 75 cm³ of ethyl acetate and 50 cm³ of water. The organic phase is separated out after settling of the phases has taken place, washed with 50 cm³ of water and 50 cm³ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 2.5 cm), eluting with a cyclohexane/ethyl acetate mixture (85/15 by volume). The fractions containing the expected product are combined and evaporated under reduced pressure (2 kPa; 50° C.); 800 mg of N-[6-chloro-5-(3-furyl)-1-[[2-(trimethylsilyl)ethoxy]methyl]-1H-indazol-3-yl]butanamide are obtained in the form of a colourless oil.

¹H NMR spectrum (300 MHz, (CD$_3$)$_2$SO-d6, δ in ppm): −0.06 (s: 9H); 0.84 (t, J=8 Hz: 2H); 0.96 (t, J=7.5 Hz: 3H);

1.66 (mt: 2H); 2.41 (broad t, J=7 Hz: 2H); 3.55 (t, J=8 Hz: 2H); 5.69 (s: 2H); 6.79 (mt: 1H); 7.80 (t, J=2 Hz: 1H); from 7.95 to 8.05 (mt: 3H); 10.59 (unresolved peak: 1H).

| ES | m/z = 456 | [M + Na]$^+$ |
| --- | --- | --- |
|  | m/z = 434 | [M + H]$^+$ |
|  | m/z = 316 | [M—OCH$_2$CH$_2$Si(CH$_3$)$_3$]$^+$ |

N-[6-chloro-5-(3-furyl)-1H-indazol-3-yl]butanamide 11 cm$^3$ of tetrabutylammonium fluoride as a 1M solution in tetrahydrofuran are added to 800 mg of N-[6-chloro-5-(3-furyl)-1-[[2-(trimethylsilyl)ethoxy]methyl]-1H-indazol-3-yl]butanamide, described previously, in 30 cm$^3$ of tetrahydrofuran, and the mixture is refluxed for 18 hours. The reaction medium is diluted with 75 cm$^3$ of ethyl acetate and 50 cm$^3$ of saturated sodium hydrogen carbonate solution. The organic phase is separated out after settling of the phases has taken place, washed with 50 cm$^3$ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 µm; diameter 2.5 cm), eluting with a cyclohexane/ethyl acetate mixture (50/50 by volume). The fractions containing the expected product are combined and evaporated under reduced pressure (2 kPa; 50° C.); the residue is taken up in 25 cm$^3$ of diethyl ether, filtered off, washed with 2×10 cm$^3$ of diethyl ether and dried under reduced pressure (90 Pa; 45° C.) to give 220 mg of N-[6-chloro-5-(3-furyl)-1H-indazol-3-yl]butanamide in the form of white crystals melting at 250° C.

$^1$H NMR spectrum (300 MHz, (CD$_3$)$_2$SO-d6, δ in ppm): 0.95 (t, J=7.5 Hz: 3H); 1.65 (mt: 2H); 2.39 (broad t, J=7 Hz: 2H); 6.76 (broad s: 1H); 7.64 (s: 1H); 7.78 (t, J=1.5 Hz: 1H); 7.95 (mt: 2H); 10.94 (unresolved peak: 1H); from 12.50 to 13.00 (broad unresolved peak: 1H).

EXAMPLE 69

1-bromo-2-chloro-4-(phenylmethoxy)benzene 2 g of 4-bromo-3-chlorophenol dissolved in 20 cm$^3$ of dimethylformamide are added to 480 mg of sodium hydride at 60% in oil, in 10 cm$^3$ of dimethylformamide, followed by addition of a solution of 1.38 cm$^3$ of benzyl chloride dissolved in 5 cm$^3$ of dimethylformamide. The reaction medium is concentrated under reduced pressure and taken up in 100 cm$^3$ of ethyl acetate. The organic phase is washed successively with 2×50 cm$^3$ of water and with 50 cm$^3$ of saturated sodium chloride solution, separated out after settling of the phases has taken place, dried over magnesium sulphate, filtered and concentrated to dryness under reduced pressure (2 kPa; 50° C.) to give 3 g of crude product, which is purified by chromatography under an argon pressure of 50 kPa, on a column of silica gel (particle size 40–60 µm; diameter 2.5 cm), eluting with a cyclohexane/ethyl acetate mixture (90/10 by volume). The fractions containing the expected product are combined and evaporated under reduced pressure (2 kPa; 50° C.). 2.63 g of 1-bromo-2-chloro-4-(phenylmethoxy)benzene are obtained in the form of an orange-coloured oil which crystallizes.

$^1$H NMR spectrum (300 MHz, (CD$_3$)$_2$SO-d6, δ in ppm): 5.16 (s: 2H); 6.99 (dd, J=9 and 3 Hz: 1H); 7.34 (d, J=3 Hz: 1H); from 7.35 to 7.55 (mt: 5H); 7.65 (d, J=9 Hz: 1H).

| EI | m/z = 296 | M$^{+\cdot}$ |
| --- | --- | --- |

N-[6-[2-chloro-4-(phenylmethoxy)phenyl]-1-[[2-(trimethylsilyl)ethoxy]methyl]-1H-indazol-3-yl]butanamide 1.95 g of 1-bromo-2-chloro-4-(phenylmethoxy)benzene, described previously, 1.11 g of sodium carbonate in 36 cm$^3$ of water and 347 mg of tetrakis(triphenylphosphine) palladium are added to 2 g of N-[6-(4,4,5,5-tetramethyl[1,3,2]dioxaborolan-2-yl)-1-[[2-(trimethylsilyl)ethoxy]methyl]-1H-indazol-3-yl]butanamide, described previously in Example 56, in 180 cm$^3$ of dioxane. The medium is then refluxed for 2 hours and the mixture is allowed to return to room temperature, 200 cm$^3$ of ethyl acetate and 100 cm$^3$ of water are added and the resulting mixture is filtered through a sinter funnel packed with Celite. The combined organic phases are washed with 100 cm$^3$ of distilled water and then with 100 cm$^3$ of saturated aqueous sodium chloride solution, dried over magnesium sulphate, filtered and concentrated to dryness under reduced pressure (2 kPa; 45° C.). The residue is purified by chromatography under an argon pressure of 50 kPa, on a column of silica gel (particle size 40–60 µm; diameter 2.5 cm), eluting with a cyclohexane/ethyl acetate mixture (85/15 by volume). The fractions containing the expected product are combined and evaporated under reduced pressure (2 kPa; 50° C.). 1.34 g of N-[6-[2-chloro-4-(phenylmethoxy)phenyl]-1-[[2-(trimethylsilyl)ethoxy]methyl]-1H-indazol-3-yl]butanamide are obtained in the form of a yellow oil.

$^1$H NMR spectrum (300 MHz, (CD$_3$)$_2$SO-d6, δ in ppm): –0.08 (s: 9H); 0.83 (t, J=8 Hz: 2H); 0.98 (t, J=7.5 Hz: 3H); 1.69 (mt: 2H); 2.42 (t, J=7 Hz: 2H); 3.55 (t, J=8 Hz: 2H); 5.23 (s: 2H); 5.70 (s: 2H); 7.13 (dd, J=8.5 and 2.5 Hz: 1H); 7.15 (broad d, J=8.5 Hz: 1H); 7.30 (d, J=2.5 Hz: 1H); from 7.35 to 7.55 (mt: 6H); 7.69 (broad s: 1H); 7.86 (d, J=8.5 Hz: 1H); 10.51 (unresolved peak: 1H).

| EI | m/z = 549 | M$^{+\cdot}$ |
| --- | --- | --- |
|  | m/z = 432 | [M—OCH$_2$CH$_2$Si(CH$_3$)$_3$]$^+$ |
|  | m/z = 421 | [M—C$_6$H$_{12}$OSi]$^{+\cdot}$ |

N-[6-[2-chloro-4-(phenylmethoxy)phenyl]-1H-indazol-3-yl]butanamide 14.2 cm$^3$ of tetrabutylammonium fluoride as a 1M solution in tetrahydrofuran are added to 1.3 g of N-[6-[2-chloro-4-(phenylmethoxy)phenyl]-1-[[2-(trimethylsilyl)ethoxy]methyl]-1H-indazol-3-yl]butanamide, described previously, in 60 cm$^3$ of tetrahydrofuran, and the mixture is refluxed for 18 hours; after cooling, 75 cm$^3$ of ethyl acetate are added and the organic phase is washed successively with 50 cm$^3$ of saturated sodium hydrogen carbonate solution and with 50 cm$^3$ of saturated sodium chloride solution. The organic phase is separated out after settling of the phases has taken place, dried over magnesium sulphate, filtered and concentrated to dryness under reduced pressure (2 kPa; 50° C.) to give 1.8 g of crude product, which is purified by chromatography under an argon pressure of 50 kPa, on a column of silica gel (particle size 40–60 µm; diameter 3.5 cm), eluting with a cyclohexane/ethyl acetate mixture (60/40 by volume).

The fractions containing the expected product are combined and evaporated under reduced pressure (2 kPa; 50° C.) and the residue is taken up in 10 cm³ of diisopropyl ether, filtered off, washed with 2×10 cm³ of diisopropyl ether and dried under reduced pressure (90 Pa; 45° C.) to give 600 mg of N-[6-[2-chloro-4-(phenylmethoxy)phenyl]-1H-indazol-3-yl]butanamide in the form of white crystals.

¹H NMR spectrum (400 MHz, (CD₃)₂SO-d6, δ in ppm): 0.98 (t, J=7.5 Hz: 3H); 1.68 (mt: 2H); 2.40 (t, J=7 Hz: 2H); 5.22 (s: 2H); 7.06 (broad d, J=8.5 Hz: 1H); 7.11 (dd, J=8.5 and 2.5 Hz: 1H); 7.27 (d, J=2.5 Hz: 1H); from 7.35 to 7.55 (mt: 7H); 7.79 (d, J=8.5 Hz: 1H); 10.35 (unresolved peak: 1H); 12.69 (unresolved peak: 1H).

| EI | m/z = 419 | M⁺· |
|----|-----------|-----|
|    | m/z = 349 | [M—C₄CH₆O]⁺· |

N-[6-(2-chloro-4-hydroxyphenyl)-1H-indazol-3-yl]butanamide 15 cm³ of trimethylsilyl iodide are added to 0.6 g of N-[6-[2-chloro-4-(phenylmethoxy)phenyl]-1H-indazol-3-yl]butanamide, described previously, and the mixture is refluxed for 4 hours, followed by addition of 50 cm³ of methanol, and refluxing is continued for 15 minutes. The reaction medium is concentrated to dryness under reduced pressure (2 kPa; 50° C.), 100 cm³ of ethyl acetate are added and the organic phase is washed with 2×50 cm³ of 10% sodium thiosulphate solution and then with 50 cm³ of saturated sodium chloride solution. The organic phase is separated out after settling of the phases has taken place, dried over magnesium sulphate, filtered and concentrated to dryness. The crude product obtained is purified by chromatography under an argon pressure of 50 kPa, on a column of silica gel (particle size 40–60 μm; diameter 2.5 cm), eluting with a cyclohexane/ethyl acetate mixture (60/40 by volume). The fractions containing the expected product are combined and evaporated under reduced pressure (2 kPa; 50° C.); 0.24 g of N-[6-(2-chloro-4-hydroxyphenyl)-1H-indazol-3-yl]butanamide is obtained in the form of a white foam.

¹H NMR spectrum (400 MHz, (CD₃)₂SO-d6, δ in ppm): 0.90 (t, J=7.5 Hz: 3H); 1.68 (mt: 2H); 2.40 (t, J=7 Hz: 2H); 6.86 (dd, J=8.5 and 2 Hz: 1H); 6.97 (d, J=2 Hz: 1H); 7.05 (broad d, J=9 Hz: 1H); 7.30 (d, J=8.5 Hz: 1H); 7.37 (s: 1H); 7.78 (d, J=9 Hz: 1H); 10.02 (unresolved peak: 1H); 10.33 (broad s: 1H); 12.65 (broad s: 1H).

| EI | m/z = 329 | M⁺· |
|----|-----------|-----|
|    | m/z = 259 | [M—C₄CH₆O]⁺· |

EXAMPLE 70

N-[5,6-dibromo-1-[[2-(trimethylsilyl)ethoxy]methyl]-1H-indazol-3-yl]butanamide 3.3 cm³ of pyridine are added to 4 g of N-[6-bromo-1-[[2-(trimethylsilyl)ethoxy]methyl]-1H-indazol-3-yl]butanamide, described previously in Example 51, in 80 cm³ of chloroform, followed by dropwise addition of 2 cm³ of bromine, and the mixture is then left stirring for 18 hours. The reaction medium is diluted with 100 cm³ of methylene chloride and the organic phase is washed with 2×100 cm³ of 10% sodium thiosulphate solution and then with 75 cm³ of saturated sodium chloride solution. The organic phase is separated out after settling of the phases has taken place, dried over magnesium sulphate, filtered and concentrated to dryness under reduced pressure (2 kPa; 50° C.). The crude product is purified by chromatography under an argon pressure of 50 kPa, on a column of silica gel (particle size 40–60 μm; diameter 2.5 cm), eluting with a cyclohexane/ethyl acetate mixture (70/30 by volume). The fractions containing the expected product are combined and evaporated under reduced pressure (2 kPa; 50° C.), then dried (90 Pa; 45° C.) to give 4.24 g of N-[5,6-dibromo-1-[[2-(trimethylsilyl)ethoxy]methyl]-1H-indazol-3-yl]butanamide in the form of a yellow solid melting at 134° C.

¹H NMR spectrum (300 MHz, (CD₃)₂SO-d6, δ in ppm): −0.08 (s: 9H); 0.81 (t, J=8 Hz: 2H); 0.95 (t, J=7.5 Hz: 3H); 1.66 (mt: 2H); 2.40 (t, J=7 Hz: 2H); 3.52 (t, J=8 Hz: 2H); 5.66 (s: 2H); 8.26 (s: 1H); 8.33 (s: 1H); 10.66 (unresolved peak: 1H).

N-[5,6-dibromo-1H-indazol-3-yl]butanamide 12.2 cm³ of tetrabutylammonium fluoride as a 1M solution in tetrahydrofuran are added to 1 g of N-[5,6-dibromo-1-[[2-(trimethylsilyl)ethoxy]methyl]-1H-indazol-3-yl]butanamide, described previously, in 60 cm³ of tetrahydrofuran, and the mixture is refluxed for 18 hours; after cooling, 75 cm³ of ethyl acetate are added and the organic phase is washed successively with 100 cm³ of saturated sodium hydrogen carbonate solution and then with 75 cm³ of saturated sodium chloride solution. The organic phase is separated out after settling of the phases has taken place, dried over magnesium sulphate, filtered and concentrated to dryness under reduced pressure (2 kPa; 50° C.) to give 1.6 g of crude product, which is purified by chromatography under an argon pressure of 50 kPa, on a column of silica gel (particle size 40–60 μm; diameter 3.5 cm), eluting with a cyclohexane/ethyl acetate mixture (50/50 by volume). The fractions containing the expected product are combined and evaporated under reduced pressure (2 kPa; 50° C.) and the residue is taken up in 20 cm³ of diisopropyl ether, filtered off, washed with 2×10 cm³ of diisopropyl ether and dried (90 Pa; 45° C.) to give 460 mg of N-[5,6-dibromo-1H-indazol-3-yl]butanamide in the form of bluish crystals melting at 250° C.

¹H NMR spectrum (300 MHz, (CD₃)₂SO-d6, δ in ppm): 0.95 (t, J=7.5 Hz: 3H); 1.66 (mt: 2H); 2.39 (t, J=7 Hz: 2H); 7.91 (s: 1H); 8.28 (s: 1H); 10.55 (unresolved peak: 1H); from 12.70 to 13.20 (broad unresolved peak: 1H).

EXAMPLE 71

N-[6-chloro-1H-indazol-3-yl]-2,2,3,3,4,4,4-heptafluorobutanamide 0.60 cm³ of heptafluorobutyryl chloride is added to 1 g of 6-chloro-1H-indazole-3-amine in 10 cm³ of pyridine, after cooling the medium to about 6° C., the mixture is then allowed to return to room temperature over 19 hours and is evaporated to dryness under reduced pressure (2 kPa; 45° C.). The residue is taken up in 40 cm³ of ethyl acetate and 20 cm³ of water; the precipitate formed is filtered off on a sinter funnel and then rinsed with 2×10 cm³ of methylene chloride and purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) to give 0.77 g of N-[6-chloro-1H-indazol-3-yl]-2,2,3,3,4,4,4-heptafluorobutanamide in cottony form.

¹H NMR spectrum (300 MHz, (CD₃)₂SO-d6, δ in ppm): 7.19 (broad dd, J=9 and 1.5 Hz: 1H); 7.62 (d, J=9 Hz: 1H); 7.64 (broad s: 1H); 12.09 (unresolved peak: 1H); 13.25 (unresolved peak: 1H).

| EI | m/z = 363 | M⁺· |
| --- | --- | --- |
| | m/z = 194 | [M—CF₂CF₂CF₃]⁺ |
| | m/z = 166 | [M—COCF₂CF₂CF₃]⁺ |

EXAMPLE 72

N-[5-(4-fluorophenyl)-6-chloro-1-[[2-(trimethylsilyl)ethoxy]methyl]-1H-indazol-3-yl]butanamide 470 mg of 4-fluorophenylboronic acid, 593 mg of sodium carbonate in 40 cm³ of water and 155 mg of tetrakis(triphenylphosphine)palladium are added to 1 g of N-[5-bromo-6-chloro-1-[[2-(trimethylsilyl)ethoxy]methyl]-1H-indazol-3-yl]butanamide, described in Example 58, in 40 cm³ of dioxane. The mixture is refluxed for 18 hours and the reaction medium is filtered through a sinter funnel packed with Celite. 60 cm³ of ethyl acetate and 50 cm³ of distilled water are added to the filtrate. The organic phase is washed with 2×20 cm³ of saturated aqueous sodium chloride solution and then separated out after settling of the phases has taken place and dried over magnesium sulphate. After filtration, the filtrate is concentrated to dryness under reduced pressure (2 kPa; 50° C.) and the residue is purified by chromatography under an argon pressure of 50 kPa, on a column of silica gel (particle size 40–60 μm; diameter 4.5 cm), eluting with a cyclohexane/ethyl acetate mixture (90/10 by volume). The fractions containing the expected product are combined and evaporated under reduced pressure (2 kPa; 50° C.). After drying (90 Pa; 45° C.), 0.75 g of N-[5-(4-fluorophenyl)-6-chloro-1-[(2-(trimethylsilyl)ethoxy]methyl]-1H-indazol-3-yl]butanamide is thus obtained in the form of a yellow wax.

¹H NMR spectrum (300 MHz, (CD₃)₂SO-d6, δ in ppm): −0.05 (s: 9H); 0.85 (t, J=8 Hz: 2H); 0.93 (t, J=7.5 Hz: 3H); 1.63 (mt: 2H); 2.38 (t, J=7 Hz: 2H); 3.55 (t, J=8 Hz: 2H); 5.70 (s: 2H); 7.31 (broad t, J=9 Hz: 2H); 7.46 (dd, J=9 and 6 Hz: 2H); 7.91 (s: 1H); 8.00 (s: 1H); 10.60 (unresolved peak: 1H).

| EI | m/z = 461 | M⁺· |
| --- | --- | --- |
| | m/z = 344 | [M—OCH₂CH₂Si(CH₃)₃]⁺ |
| | m/z = 333 | [M—C₆H₁₂OSi]⁺· |

N-[6-chloro-5-(4-fluorophenyl)-1H-indazol-3-yl]butanamide 9.5 cm of tetrabutylammonium fluoride as a 1M solution in tetrahydrofuran are added to 0.73 g of N-[6-chloro-5-(4-fluorophenyl)-1-[[2-(trimethylsilyl)ethoxy]-methyl]-1H-indazol-3-yl]butanamide, described previously, in 20 cm³ of tetrahydrofuran, and the mixture is refluxed for 18 hours; after cooling, 30 cm³ of ethyl acetate are added and the organic phase is washed successively with 2×20 cm³ of saturated sodium hydrogen carbonate solution and with 20 cm³ of saturated sodium chloride solution. The organic phase is separated out after settling of the phases has taken place, dried over magnesium sulphate, filtered and concentrated to dryness under reduced pressure (2 kPa; 50° C.); the crude product obtained is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) and dried (90 Pa; 45° C.) to give 200 mg of N-[6-chloro-(4-fluorophenyl)-1H-indazol-3-yl]butanamide in the form of a cream-coloured powder.

¹H NMR spectrum (300 MHz, (CD₃)₂SO-d6, δ in ppm): 0.93 (t, J=7.5 Hz: 3H); 1.63 (mt: 2H); 2.38 (t, J=7 Hz: 2H); 7.30 (broad t, J=9 Hz: 2H); 7.45 (broad dd, J=9 and 6 Hz: 2H); 7.66 (s: 1H); 7.85 (s: 1H); 10.46 (unresolved peak: 1H); 12.80 (unresolved peak: 1H).

| EI | m/z = 331 | M⁺· |
| --- | --- | --- |
| | m/z = 261 | [M—C₄CH₆O]⁺· |

EXAMPLE 73

N-[[6-(4-aminophenyl)-1H-indazol-3-yl]]butanamide 856 mg of zinc powder are added to 0.85 g of N-[6-(4-nitrophenyl)-1H-indazol-3-yl]butanamide, described in Example 64, in 50 cm³ of acetic acid, followed, one hour later, by addition of a further 856 mg of zinc, and the mixture is stirred for 1 hour at room temperature. The reaction medium is filtered through a sinter funnel packed with Celite and the filtrate is concentrated to dryness under reduced pressure (2 kPa; 50° C.). The residue is taken up in 100 cm³ of tetrahydrofuran and 100 cm³ of ethyl acetate and the organic phase is washed successively with 100 cm³ of saturated sodium hydrogen carbonate solution and with 100 cm³ of saturated sodium chloride solution, then dried over magnesium sulphate, filtered and concentrated to dryness to give 500 mg of crude product, which is purified by chromatography under an argon pressure of 50 kPa, on a column of silica gel (particle size 40–60 μm; diameter 4.5 cm), eluting with ethyl acetate. The fractions containing the expected product are combined and the solid is triturated in 20 cm³ of diethyl ether, filtered off, washed with 2×5 cm³ of diethyl ether and then dried (90 Pa; 45° C.) to give 200 mg of N-[6-(4-aminophenyl)-1H-indazol-3-yl]butanamide in the form of yellow crystals melting at 230° C.

¹H NMR spectrum (300 MHz, (CD₃)₂SO-d6, δ in ppm): 0.98 (broad t, J=7.5 Hz: 3H); 1.68 (mt: 2H); 2.39 (t, J=7 Hz: 2H); 5.24 (broad s: 2H); 6.68 (broad d, J=8 Hz: 2H); 7.27 (broad d, J=8.5 Hz: 1H); 7.42 (broad d, J=8 Hz: 2H); 7.45 (broad s: 1H); 7.76 (d, J=8.5 Hz: 1H); 10.26 (unresolved peak: 1H); 12.49 (broad s: 1H).

EXAMPLE 74

N-[6-[4-(dimethylamino)phenyl]-1-[[2-(trimethylsilyl)ethoxy]methyl]-1H-indazol-3-yl]butanamide 785 mg of 4-bromo-N,N-dimethylaniline, 646 mg of sodium carbonate, 10 cm³ of water and 196 mg of tetrakis(triphenylphosphine)palladium are added to 1 g of N-[6-(4,4,5,5-tetramethyl [1,3,2]dioxaborolan-2-yl)-1-[[2-(trimethylsilyl)ethoxy]methyl]-1H-indazol-3-yl]

butanamide, described in Example 56, in 50 cm³ of dioxane. The medium is then refluxed for 18 hours, the resulting mixture is then allowed to return to room temperature and 75 cm³ of ethyl acetate and 75 cm³ of water are added. The organic phase is dried over magnesium sulphate, filtered and concentrated to dryness under reduced pressure (2 kPa; 45° C.) to give 1.6 g of crude product, which is purified by chromatography under an argon pressure of 50 kPa, on a column of silica gel (particle size 40–60 μm; diameter 2.5 cm), eluting with a cyclohexane/ethyl acetate mixture (80/20 by volume). The fractions containing the expected product are combined and evaporated under reduced pressure (2 kPa; 50° C.). 170 mg of N-[6-[4-(dimethylamino)phenyl]-1-[[2-(trimethylsilyl)ethoxy]methyl]-1H-indazol-3-yl]butanamide are obtained in the form of a yellow oil.

¹H NMR spectrum (400 MHz, (CD₃)₂SO-d6, δ in ppm): −0.08 (s: 9H); 0.84 (t, J=8 Hz: 2H); 0.98 (t, J=7.5 Hz: 3H); 1.68 (mt: 2H); 2.40 (t, J=7 Hz: 2H); 2.98 (s: 6H); 3.57 (t, J=8 Hz: 2H); 5.71 (s: 2H); 6.85 (d, J=9 Hz: 2H); 7.41 (broad d, J=8.5 Hz: 1H); 7.64 (d, J=9 Hz: 2H); 7.82 (broad s: 1H); 7.85 (d, J=8.5 Hz: 1H); 10.43 (unresolved peak: 1H).

| EI | m/z = 452 | M⁺· |
|---|---|---|
| | m/z = 335 | [M—OCH₂CH₂Si(CH₃)₃]⁺ |
| | m/z = 324 | [M—C₆H₁₂OSi]⁺· |

N-[6-[4-(dimethylamino)phenyl]-1H-indazol-3-yl]butanamide 2.3 cm³ of tetrabutylammonium fluoride as a 1M solution in tetrahydrofuran are added to 170 mg of N-[6-[4-(dimethylamino)phenyl]-1-[[2-(trimethylsilyl)ethoxy]-methyl]-1H-indazol-3-yl]butanamide, described previously, in 10 cm³ of tetrahydrofuran, and the mixture is refluxed for 18 hours; after cooling, 50 cm³ of ethyl acetate are added and the organic phase is washed successively with 50 cm³ of saturated sodium hydrogen carbonate solution and with 50 cm³ of saturated sodium chloride solution. The organic phase is separated out after settling of the phases has taken place, dried over magnesium sulphate, filtered and concentrated to dryness under reduced pressure (2 kPa; 50° C.) to give 160 mg of crude product, which is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.); the residue is taken up in 10 cm³ of diethyl ether, filtered off and dried under reduced pressure (90 Pa; 45° C.) to give 40 mg of N-[6-chloro-5-(4-dimethylamino)phenyl)-1H-indazol-3-yl]butanamide in the form of yellow crystals melting at 260° C.

¹H NMR spectrum (300 MHz, (CD₃)₂SO-d6, δ in ppm): 0.98 (broad t, J=7.5 Hz: 3H); 1.68 (mt: 2H); 2.39 (t, J=7 Hz: 2H); 2.97 (s: 6H); 6.84 (broad d, J=8.5 Hz: 2H); 7.31 (broad d, J=9 Hz: 1H); 7.51 (broad s: 1H); 7.58 (broad d, J=8.5 Hz: 2H); 7.78 (d, J=9 Hz: 1H); 10.27 (broad s: 1H); 12.52 (broad s: 1H).

EXAMPLE 75

2-chloro-N-(6-chloro-1H-indazol-3-yl)acetamide 5.1 g of chloracetic anhydride are added to 5 g of 6-chloro-1H-indazole-3-amine in 300 cm³ of toluene and the mixture is refluxed for 18 hours. The precipitate formed is filtered off, washed with 20 cm³ of toluene and then with 20 cm³ of methylene chloride and dried under reduced pressure (90 Pa; 45° C.) to give 5.1 g of 2-chloro-N-(6-chloro-1H-indazol-3-yl)acetamide in the form of a grey powder melting at 223° C.

¹H NMR spectrum (300 MNLz, (CD₃)₂SO-d6, δ in ppm): 4.38 (s: 2H); 7.11 (dd, J=9 and 1.5 Hz: 1H); 7.56 (broad s: 1H); 7.84 (d, J=9 Hz: 1H); 10.87 (unresolved peak: 1H); 12.96 (unresolved peak: 1H).

N-(6-chloro-1H-indazol-3-yl)-4-methyl-1-piperazineacetamide 0.7 cm³ of N-methylpiperazine is added to 500 mg of 2-chloro-N-(6-chloro-1H-indazol-3-yl)acetaride, described previously, in 15 cm³ of dimethylformamide, the reaction medium is heated at 140° C. for 2 hours and then concentrated to dryness under reduced pressure (2 kPa; 50° C.). 50 cm³ of ethyl acetate and 50 cm³ of water are then added and the organic phase is washed with 50 cm³ of saturated sodium chloride solution, dried over magnesium sulphate, filtered and concentrated to dryness to give 0.53 g of crude product, which is purified by chromatography under an argon pressure of 50 kPa, on a column of silica gel (particle size 40–60 μm; diameter 2.5 cm), eluting with a methylene chloride/methanol/aqueous ammonia mixture (93/7/1 by volume). The fractions containing the expected product are combined and evaporated under reduced pressure (2 kPa; 50° C.); the residue is taken up in 5 cm³ of diethyl ether, filtered off and dried (90 Pa; 45° C.) to give 192 mg of N-(6-chloro-1H-indazol-3-yl)-4-methyl-1-piperazineacetamide in the form of a beige-coloured powder melting at 165° C.

¹H NMR spectrum (300 MHz, (CD₃)₂SO-d6, δ in ppm): 2.18 (s: 3H); 2.40 (unresolved peak: 4H); 2.58 (unresolved peak: 4H); 3.22 (s: 2H); 7.09 (broad d, J=9 Hz: 1H); 7.53 (broad s: 1H); 7.86 (d, J=9 Hz: 1H); 10.11 (broad s: 1H); 12.83 (broads: 1H).

EXAMPLE 76

N-(6-chloro-1H-indazol-3-yl)-1-piperidineacetamide

The process is performed as in Example 75, starting with 500 mg of 2-chloro-N-(6-chloro-1H-indazol-3-yl)acetamide, 15 cm³ of acetonitrile and 0.61 cm³ of piperidine. The reaction medium is refluxed for 2 hours, the precipitate formed is then filtered off on a sinter funnel and the crystals, after taking up in methanol, are purified by chromatography under an argon pressure of 50 kPa, on a column of silica gel (particle size 40–60 μm; diameter 2.5 cm), eluting with a methylene chloride/methanol mixture (93/7 by volume). The fractions containing the expected product are combined and evaporated under reduced pressure (2 kPa; 50° C.); the residue is taken up in 5 cm³ of diethyl ether, filtered off and dried (90 Pa; 45° C.) to give 447 mg of N-(6-chloro-1H-indazol-3-yl)-1-piperidineacetamide in the form of a white powder melting at 153° C.

¹H NMR spectrum (300 MHz, (CD₃)₂SO-d6, δ in ppm): 1.42 (mt, 2H); 1.57 (mt: 4H); from 2.45 to 2.60 (mt: 4H); 3.17 (s: 2H); 7.08 (dd, J=9 and 2 Hz: 1H); 7.52 (d, J=2 Hz: 1H); 7.86 (d, J=9 Hz: 1H); 10.05 (broad s: 1H); 12.82 (unresolved peak: 1H).

EXAMPLE 77

N-(6-chloro-1H-indazol-3-yl)-4-morpholineacetamide

Working as in Example 75, starting with 500 mg of 2-chloro-N-(6-chloro-1H-indazol-3-yl)acetamide, 15 cm³ of acetonitrile and 0.54 cm³ of morpholine. The reaction medium is refluxed for 2 hours and then concentrated to dryness under reduced pressure (2.7 kPa; 50° C.) and the crude product obtained is purified by chromatography under an argon pressure of 50 kPa, on a column of silica gel (particle size 40–60 µm; diameter 2.5 cm), eluting with ethyl acetate. The fractions containing the expected product are combined and evaporated under reduced pressure (2 kPa; 50° C.), then dried (90 Pa; 45° C.) to give 470 mg of N-(6-chloro-1H-indazol-3-yl)-4-morpholineacetamide in the form of a white powder melting at about 82–90° C.

$^1$H NMR spectrum (300 MHz, $(CD_3)_2SO$-d6, δ in ppm): 2.58 (broad t, J=4 Hz: 4H); 3.24 (s: 2H); 3.66 (broad t, J=4 Hz: 4H); 7.09 (dd, J=9 and 2 Hz: 1H); 7.53 (d, J=21 Hz: 1H); 7.84 (d, J=9 Hz: 1H); 10.18 (unresolved peak: 1H); 12.83 (broad unresolved peak: 1H).

EXAMPLE 78

N-(6-chloro-1H-indazol-3-yl)-1H-1,2,4-triazole-1-acetamide

The process is performed as in Example 75, starting with 500 mg of 2-chloro-N-(6-chloro-1H-indazol-3-yl) acetamide, 15 cm³ of acetonitrile, 423 mg of 1,2,4-triazole and 283 mg of potassium carbonate. The reaction medium is refluxed for 4 hours and then concentrated to dryness under reduced pressure (2 kPa; 50° C.); the crude product obtained is purified by chromatography under an argon pressure of 50 kPa, on a column of silica gel (particle size 40–60 µm; diameter 2.5 cm), eluting with ethyl acetate. The fractions containing the expected product are combined, evaporated under reduced pressure (2 kPa; 50° C.) and dried (90 Pa; 45° C.) to give 120 mg of N-(6-chloro-1H-indazol-3-yl)-1H-1,2,4-triazole-1-acetamide in the form of a white powder melting above 260° C.

$^1$H NMR spectrum (300 MHz, $(CD_3)_2SO$-d6, δ in ppm): 5.27 (s: 2H); 7.10 (dd, J=9 and 2 Hz: 1H); 7.55 (d, J=2 Hz: 1H); 7.84 (d, J=9 Hz: 1H); 8.03 (s: 1H); 8.60 (s: 1H); 11.00 (unresolved peak: 1H); 12.90 (unresolved peak: 1H).

| DCI | m/z = 294 | $[M + NH_4]^+$ |
|-----|-----------|----------------|
|     | m/z = 277 | $[M + H]^+$    |

EXAMPLE 79

N-(6-chloro-1H-indazol-3-yl)-2-(cyclohexylamino) acetamide

The process is performed as in Example 75, starting with 500 mg of 2-chloro-N-(6-chloro-1H-indazol-3-yl) acetamide, 15 cm³ of acetonitrile and 0.7 cm³ of cyclohexylamine. The reaction medium is refluxed for 2 hours and then concentrated to dryness under reduced pressure (2 kPa; 50° C.); the crude product obtained is purified by chromatography under an argon pressure of 50 kPa, on a column of silica gel (particle size 40–60 µm; diameter 2.5 cm), eluting with a methylene chloride/methanol/aqueous ammonia mixture (97/2.5/0.25 by volume). The fractions containing the expected product are combined and the residue is taken up in 20 cm³ of diisopropyl ether, filtered off and dried under reduced pressure (90 Pa; 45° C.) to give 492 mg of N-(6-chloro-1H-indazol-3-yl)-2-(cyclohexylamino)acetamide in the form of a white powder melting at 170° C.

$^1$H NMR spectrum (300 MHz, $(CD_3)_2SO$-d6, δ in ppm): from 1.00 to 1.35 (mt: 5H); 1.56 (mt: 1H); 1.70 (mt: 2H); 1.84 (very broad d, J=12 Hz: 2H); 2.43 (mt: 1H); 3.39 (s: 2H); 7.09 (dd, J=9 and 1.5 Hz: 1H); 7.52 (d, J=1, 5 Hz: 1H); 7.93 (d, J=9 Hz: 1H); 12.82 (unresolved peak: 1H).

EXAMPLE 80

2-[(phenylmethyl)amino]-N-(6-chloro-1H-indazol-3-yl)acetamide

The process is performed as in Example 75, starting with 500 mg of 2-chloro-N-(6-chloro-1H-indazol-3-yl) acetamide, 15 cm³ of acetonitrile and 0.67 cm³ of benzylamine. The reaction medium is refluxed for 1 hour and the precipitate formed is filtered off, washed with 5 cm³ of acetonitrile and 5 cm³ of methylene chloride, then purified by chromatography under an argon pressure of 50 kPa, on a column of silica gel (particle size 40–60 µm; diameter 2.5 cm), eluting with a methylene chloride/methanol/aqueous ammonia mixture (97/2.5/0.25 by volume). The fractions containing the expected product are combined and the residue is taken up in 20 cm³ of diisopropyl ether, filtered off and dried under reduced pressure (90 Pa; 45° C.) to give 305 mg of 2-[(phenylmethyl)amino]-N-(6-chloro-1H-indazol-3-yl)acetamide in the form of a white powder melting at 156° C.

$^1$H NMR spectrum (300 MHz, $(CD_3)_2SO$-d6, δ in ppm): 3.39 (s: 2H); 3.79 (s: 2H); 7.09 (dd, J=9 and 2 Hz: 1H); 7.26 (broad t, J=7 Hz: 1H); from 7.30 to 7.45 (mt: 4H); 7.53 (d, J=2 Hz: 1H); 7.89 (d, J=9 Hz: 1H); from 10.00 to 10.60 (very broad unresolved peak: 1H); 12.82 (unresolved peak: 1H).

EXAMPLE 81

N-(6-chloro-1H-indazol-3-yl)-1H-azepine-1-acetamide

The process is performed as in Example 75, starting with 500 mg of 2-chloro-N-(6-chloro-1H-indazol-3-yl) acetamide, 15 cm³ of acetonitrile and 0.69 cm³ of hexamethyleneimine. The reaction medium is refluxed for 2 hours and then concentrated to dryness under reduced pressure (2 kPa; 50° C.); the crude product is purified by chromatography under an argon pressure of 50 kPa, on a column of silica gel (particle size 40–60 µm; diameter 2.5 cm), eluting with ethyl acetate. The fractions containing the expected product are combined and the residue is taken up in 10 cm³ of diisopropyl ether, filtered off and dried under reduced pressure (90 Pa; 45° C.) to give 670 mg of N-(6-chloro-1H-indazol-3-yl)-1H-azepine-1-acetamide in the form of a yellow foam.

$^1$H NMR spectrum (300 MHz, $(CD_3)_2SO$-d6, δ in ppm): from 1.50 to 1.75 (mt: 8H); 2.77 (t, J=5 Hz: 4H); 3.36 (s: 2H); 7.09 (dd, J=9 and 2 Hz: 1H); 7.54 (d, J=2 Hz: 1H); 7.90 (d, J=9 Hz: 1H); 10.06 (unresolved peak: 1H); from 12.50 to 13.20 (broad unresolved peak: 1H).

| EI | m/z = 306 | M$^{+\cdot}$ |
|----|-----------|--------------|

EXAMPLE 82

N-(6-chloro-1H-indazol-3-yl)-1-piperazineacetamide

The process is performed as in Example 75, starting with 500 mg of 2-chloro-N-(6-chloro-1H-indazol-3-yl) acetamide, 15 cm³ of acetonitrile and 528 mg of piperazine.

The reaction medium is refluxed for 1 hour and then concentrated to dryness under reduced pressure (2 kPa; 50° C.); the crude product is purified by chromatography under an argon pressure of 50 kPa, on a column of silica gel (particle size 40–60 µm; diameter 2.5 cm), eluting with a methylene chloride/methanol/aqueous ammonia mixture (90/10/1 by volume). The fractions containing the expected product are combined, concentrated under reduced pressure and then dried (90 Pa; 45° C.) to give 380 mg of N-(6-chloro-1H-indazol-3-yl)-1-piperazineacetamide in the form of a white foam.

$^1$H NMR spectrum (300 MHz, $(CD_3)_2SO$-d6, δ in ppm): 2.49 (mt: 4H); 2.77 (mt: 4H); 3.19 (s: 2H); 7.10 (dd, J=9 and 2 Hz: 1H); 7.55 (d, J=2 Hz: 1H); 7.86 (d, J=9 Hz: 1H); 10.10 (unresolved peak: 1H).

| EI | m/z = 293 | M$^{+\cdot}$ |
|---|---|---|
| | m/z = 99 | $[C_5H_{11}N_2]^+$ |

EXAMPLE 83

N-(6-chloro-1H-indazol-3-yl)-2-[[3-(dimethylamino)propyl]amino]acetamide

The process is performed as in Example 75, starting with 500 mg of 2-chloro-N-(6-chloro-1H-indazol-3-yl)acetamide, 15 cm³ of acetonitrile and 0.77 cm³ of 3-(dimethylamino)propylamine. The reaction medium is refluxed for 3 hours and then concentrated to dryness under reduced pressure (2 kPa; 50° C.); the crude product is purified by chromatography under an argon pressure of 50 kPa, on a column of silica gel (particle size 40–60 µm; diameter 2.5 cm), eluting with a methylene chloride/methanol/aqueous ammonia mixture (90/10/1 by volume). The fractions containing the expected product are combined, concentrated under reduced pressure and then dried (90 Pa; 45° C.) to give 300 mg of N-(6-chloro-1H-indazol-3-yl)-2-[[3-(dimethylamino)propyl]amino]acetamide in the form of light-brown foam.

$^1$H NMR spectrum (300 MHz, $(CD_3)_2SO$-d6, δ in ppm): 1.69 (mt: 2H); 2.11 (s: 6H); 2.28 (t, J=7 Hz: 2H); 2.60 (broad t, J=7 Hz: 2H); 3.35 (s: 2H); 7.08 (dd, J=9 and 2 Hz: 1H); 7.53 (d, J=2 Hz: 1H); 7.89 (d, J=9 Hz: 1H); from 12.00 to 13.00 (very broad unresolved peak: 1H).

| EI: | m/z = 309 | M$^{+\cdot}$ |
|---|---|---|

EXAMPLE 84

N-(6-chloro-1H-indazol-3-yl)thiomorpholine-4-acetamide

The process is performed as in Example 75, starting with 500 mg of 2-chloro-N-(6-chloro-1H-indazol-3-yl)acetamide, 15 cm³ of acetonitrile and 0.62 cm³ of thiomorpholine. The reaction medium is refluxed for 2 hours, the precipitate formed is filtered off and the filtrate is concentrated to dryness under reduced pressure (2 kPa; 50° C.); the crude product obtained is purified by chromatography under an argon pressure of 50 kPa, on a column of silica gel (particle size 40–60 µm; diameter 2.5 cm), eluting with a cyclohexane/ethyl acetate mixture (50/50 by volume). The fractions containing the expected product are combined, evaporated under reduced pressure (2 kPa; 50° C.) and dried (90 Pa; 45° C.) to give 560 mg of N-(6-chloro-1H-indazol-3-yl)thiomorpholine-4-acetamide in the form of a pale yellow foam.

$^1$H NMR spectrum (300 MHz, $(CD_3)_2SO$-d6, δ in ppm): 2.70 (mt: 4H); 2.83 (mt: 4H); 3.27 (s: 2H); 7.10 (dd, J=9 and 2 Hz: 1H); 7.54 (d, J=2 Hz: 1H); 7.82 (d, J=9 Hz: 1H); 10.16 (unresolved peak: 1H); from 12.60 to 13.10 (broad unresolved peak: 1H).

| EI | m/z = 310 | M$^{+\cdot}$ |
|---|---|---|
| | m/z = 116 | $[C_5CH_{10}NS]^+$ |

EXAMPLE 85

N-(6-chloro-1H-indazol-3-yl)-1-pyrrolidineacetamide

The process is performed as in Example 75, starting with 500 mg of 2-chloro-N-(6-chloro-1H-indazol-3-yl)acetamide, 15 cm³ of acetonitrile and 0.51 cm³ of pyrrolidine. The reaction medium is refluxed for 2 hours and then concentrated to dryness under reduced pressure (2 kPa; 50° C.); the crude product obtained is purified by chromatography under an argon pressure of 50 kPa, on a column of silica gel (particle size 40–60 µm; diameter 2 cm), eluting with a methylene chloride/methanol/aqueous ammonia mixture (95/5/1 by volume). The fractions containing the expected product are combined, evaporated under reduced pressure (2 kPa; 50° C.) and dried (90 Pa; 45° C.) to give 440 mg of N-(6-chloro-1H-indazol-3-yl)-1-pyrrolidineacetamide in the form of an off-white powder melting at 168° C.

$^1$H NMR spectrum (300 MHz, $(CD_3)_2SO$-d6, δ in ppm): 1.76 (mt: 4H); 2.64 (mt: 4H); 3.35 (s: 2H); 7.09 (dd, J=9 and 2 Hz: 1H); 7.53 (d, J=2 Hz: 1H); 7.84 (d, J=9 Hz: 1H); 10.13 (unresolved peak: 1H); from 12.50 to 13.10 (very broad unresolved peak: 1H).

EXAMPLE 86

N-(6-chloro-1H-indazol-3-yl)-2-[[2-(dimethylamino)ethyl]amino]acetamide

The process is performed as in Example 75, starting with 500 mg of 2-chloro-N-(6-chloro-1H-indazol-3-yl)acetamide, 15 cm³ of acetonitrile and 0.68 cm³ of N,N-dimethylethylenediamine. The reaction medium is refluxed for 2 hours and then concentrated to dryness under reduced pressure (2 kPa; 50° C.); the crude product is purified by chromatography under an argon pressure of 50 kPa, on a column of silica gel (particle size 40–60 µm; diameter 2.5 cm), eluting with a methylene chloride/methanol/aqueous ammonia mixture (95/5/1 by volume). The fractions containing the expected product are combined, concentrated under reduced pressure and then dried (90 Pa; 45° C.) to give 113 mg of N-(6-chloro-1H-indazol-3-yl)-2-[[2-(dimethylamino)ethyl]amino]acetamide in the form of a white solid melting at 104° C.

$^1$H NMR spectrum (300 MHz, $(CD_3)_2SO$-d6, δ in ppm): 2.15 (s: 6H); 2.34 (t, J=6 Hz: 2H); 2.66 (t, J=6 Hz: 2H); 3.40 (s: 2H); 7.08 (broad dd, J=9 and 2 Hz: 1H); 7.52 (broad s: 1H); 7.90 (d, J=9 Hz: 1H); from 9.50 to 10.30 (very broad unresolved peak: 1H); 12.81 (unresolved peak: 1H).

EXAMPLE 87

N-(6-chloro-1H-indazol-3-yl)-1-cyclopropylaminoacetamide trifluoroacetate

The process is performed as in Example 75, starting with 500 mg of 2-chloro-N-(6-chloro-1H-indazol-3-yl)

acetamide, 15 cm³ of acetonitrile and 0.45 cm³ of cyclopropylamine. The reaction medium is refluxed for 2 hours and then concentrated to dryness under reduced pressure (2 kPa; 50° C.); the crude product is purified by chromatography under an argon pressure of 50 kPa, on a column of silica gel (particle size 40–60 μm; diameter 2 cm), eluting with ethyl acetate. The fractions containing the expected product are combined and concentrated under reduced pressure to give 300 mg of product which is still impure, which is purified by HPLC. After concentrating the fractions containing the expected product and drying under reduced pressure (90 Pa; 45° C.), 140 mg of N-(6-chloro-1H-indazol-3-yl)-1-cyclopropylaminoacetamide trifluoroacetate are obtained in the form of a white powder melting at 218° C.

$^1$H NMR spectrum (300 MHz, $(CD_3)_2SO$-d6, δ in ppm): from 0.70 to 0.95 (mt: 4H); 2.82 (mt: 1H); 4.15 (s: 2H); 7.14 (broad dd, J=9 and 2 Hz: 1H); 7.58 (broad s: 1H); 7.86 (d, J=9 Hz: 1H); 9.14 (unresolved peak: 2H); 11.08 (unresolved peak: 1H); 12.98 (broad s: 1H).

EXAMPLE 88

N-(6-chloro-1H-indazol-3-yl)-2-(2-diethylaminoethylamino)acetamide tris-(trifluoroacetate)

The process is performed as in Example 75, starting with 500 mg of 2-chloro-N-(6-chloro-1H-indazol-3-yl) acetamide, 15 cm³ of acetonitrile and 0.86 cm³ of N,N-diethylethylenediamine. The reaction medium is refluxed for 2 hours and then concentrated to dryness under reduced pressure (2 kPa; 50° C.); the crude product is purified by HPLC (Kromasil column; $C_8$, 7 μm; length 350 mm, diameter 60 μm, eluent: acetonitrile/water (20/80 by volume) containing 0.1% trifluoroacetic acid; flow rate 125 cm³/min). The fractions containing the expected product are combined, concentrated under reduced pressure (2 kPa; 50° C.) and then dried (90 Pa; 45° C.) to give 870 mg of N-(6-chloro-1H-indazol-3-yl)-2-(2-diethylaminoethylamino)acetamide tris(trifluoroacetate) in the form of a white solid melting at 160° C.

$^1$H NMR spectrum (400 MHz, $(CD_3)_2SO$-d6 with addition of a few drops of $CD_3COOD$-d4, at a temperature of 363 K, δ in ppm); 1.24 (t, J=7.5 Hz: 6H); 3.23 (q, J=7.5 Hz: 4H); 3.47 (mt: 4H); 4.16 (s: 2H); 7.12 (broad d, J=8.5 Hz: 1H); 7.58 (broad s: 1H); 7.87 (d, J=8.5 Hz: 1H).

EXAMPLE 89

N-[5,6-diphenyl-1-[[2-(trimethylsilyl)ethoxy] methyl]-1H-indazol-3-yl]butanamide 1.12 g of phenylboronic acid, 1.55 g of sodium carbonate in 40 cm³ of water and 463 mg of tetrakis(triphenylphosphine)palladium are added to 1 g of N-[5,6-dibromo-1-[[2-(trimethylsilyl)ethoxy]methyl]-1H-indazol-3-yl]butanamide, described in Example 70, in 150 cm³ of dioxane, and the mixture is refluxed for 18 hours. The reaction medium is diluted with 100 cm³ of ethyl acetate and with 100 cm³ of water and is then filtered through a sinter funnel packed with Celite. The organic phase is separated out after settling of the phases has taken place and washed with 75 cm³ of saturated sodium chloride solution, separated out after settling of the phases has taken place, dried over magnesium sulphate, filtered and concentrated under reduced pressure (2 kPa; 50° C.) to give 2.6 g of crude product, which is purified by chromatography under an argon pressure of 50 kPa, on a column of silica gel (particle size 40–60 μm; diameter 2.5 cm), eluting with a cyclohexane/ethyl acetate mixture (80/20 by volume). The fractions containing the expected product are combined, evaporated under reduced pressure (2 kPa; 50° C.) and then dried (90 Pa; 45° C.) to give 1.4 g of N-[5,6-diphenyl-1-[[2-(trimethylsilyl)ethoxy]methyl]-1H-indazol-3-yl] butanamide in the form of a yellow oil.

$^1$H NMR spectrum (300 MHz, $(CD_3)_2SO$-d6, δ in ppm): –0.06 (s: 9H); 0.86 (t, J=8 Hz: 2H); 0.96 (t, J=7.5 Hz: 3H); 1.66 (mt: 2H); 2.42 (broad t, J=7 Hz: 2H); 3.59 (t, J=8 Hz: 2H); 5.74 (s: 2H); from 7.05 to 7.35 (mt: 10H); 7.71 (s: 1H); 7.89 (s: 1H); 10.57 (unresolved peak: 1H).

| EI | m/z = 485 | $M^{+\cdot}$ |
|----|-----------|--------------|
|    | m/z = 368 | $[M—OCH_2CH_2Si(CH_3)_3]^+$ |
|    | m/z = 357 | $[M—C_6H_{12}OSi]^{+\cdot}$ |

N-[5,6-diphenyl-1H-indazol-3-yl]butanamide 17.2 cm³ of tetrabutylammonium fluoride as a 1M solution in tetrahydrofuran are added to 1.5 g of N-[5,6-diphenyl-1-[[2-(trimethylsilyl)ethoxy]methyl]-1H-indazol-3-yl]butanamide, described previously, in 40 cm³ of tetrahydrofuran, and the mixture is refluxed for 18 hours; after cooling, 75 cm³ of ethyl acetate are added and the organic phase is washed with 75 cm³ of saturated sodium chloride solution. The organic phase is separated out after settling of the phases has taken place, dried over magnesium sulphate, filtered and concentrated to dryness under reduced pressure (2 kPa; 50° C.) to give 1.5 g of crude product, which is purified by chromatography under an argon pressure of 50 kPa, on a column of silica gel (particle size 40–60 μm; diameter 3.5 cm), eluting with a cyclohexane/ethyl acetate mixture (60/40 by volume). The fractions containing the expected product are combined and evaporated under reduced pressure (2 kPa; 50° C.); the product, which is still impure, is purified by HPLC (Hypersil column; $C_{18}$, 5 μm; length 250 mm, diameter 21 mm, eluent: methanol/water (70/30 by volume) containing 0.1% trifluoroacetic acid; flow rate 10 cm³/min); after concentrating to dryness the fractions containing the expected product, the residue is taken up in 10 cm³ of diisopropyl ether, filtered off, washed with 2×5 cm³ of diisopropyl ether and dried (90 Pa; 45° C.) to give 100 mg of N-[5,6-diphenyl-1H-indazol-3-yl]butanamide in the form of white crystals melting at 210° C.

$^1$H NMR spectrum (300 MHz, $(CD_3)_2SO$-d6, δ in ppm): 0.95 (t, J=7.5 Hz: 3H); 1.65 (mt: 2H); 2.40 (t, J=7 Hz: 2H); from 7.00 to 7.30 (mt: 10H); 7.40 (s: 1H); 7.82 (s: 1H); 10.43 (broad s: 1H); 12.75 (unresolved peak: 1H).

EXAMPLE 90

N-[6-chloro-5-(4-methylphenyl)-1-[[2-(trimethylsilyl)ethoxy]methyl]-1H-indazol-3-yl] butanamide The process is performed as in Example 62, starting with 1 g of N-[5-bromo-6-chloro-1-[[2-(trimethylsilyl)ethoxy]) methyl]-1H-indazol-3-yl]butanamide, described in Example 58, in 50 cm³ of dioxane, 456 mg of 4-methylphenylboronic acid, 560 mg of sodium carbonate, 20 cm³ of distilled water and 155 mg of tetrakis(triphenylphosphine)palladium. The mixture is refluxed for 90 minutes and is then allowed to return to 20° C., the reaction medium is filtered through a sinter funnel packed with Celite and 60 μm³ of ethyl acetate are then added to the filtrate. The organic phase separated out after settling of the phases has taken place, washed with 30 cm³ of saturated aqueous sodium chloride solution and then dried over magnesium sulphate. After filtration, the filtrate is concentrated to dryness under reduced pressure (2 kPa; 50° C.) and the residue is purified by chromatography under an argon pressure of 50 kPa, on a column of silica gel (particle size 40–60 μm; diameter 2.5 cm), eluting with a cyclohexane/ethyl acetate mixture (80/20 by volume). The fractions containing the expected product are combined and evaporated under reduced pressure (2 kPa; 50° C.). After drying (90 Pa; 45° C.), 880 mg of N-[6-chloro-5-(4-methylphenyl)-1-[[2-(trimethylsilyl)ethoxy]methyl]-1H-indazol-3-yl]butanamide are obtained in the form of an off-white powder.

¹H NMR spectrum (300 MHz, (CD₃)₂SO-d6, δ in ppm): –0.05 (s: 9H); 0.85 (t, J=8 Hz: 2H); 0.93 (t, J=7.5 Hz: 3H); 1.64 (mt: 2H); 2.39 (s: 3H); 2.39 (t, J=7 Hz: 2H); 3.56 (t, J=8 Hz: 2H); 5.70 (s: 2H); 7.30 (mt: 4H); 7.87 (s: 1H); 7.99 (s: 1H); 10.59 (unresolved peak: 1H)

| EI | m/z = 457 | M⁺· |
| --- | --- | --- |
|  | m/z = 340 | [M—OCH₂CH₂Si(CH₃)₃]⁺ |
|  | m/z = 329 | [M—C₆H₁₂OSi]⁺· |

N-[6-chloro-5-(4-methylphenyl)-1H-indazol-3-yl]butanamide 11.4 cm³ of tetrabutylammonium fluoride as a 1M solution in tetrahydrofuran are added to 870 mg of N-[6-chloro-5-(4-methylphenyl)-1-[[2-(trimethylsilyl)ethoxy]-methyl]-1H-indazol-3-yl]butanamide, described previously, in 20 cm³ of tetrahydrofuran. The medium is then refluxed for 20 hours and the mixture is then allowed to return to room temperature and 20 cm³ of ethyl acetate are added; the organic phase is washed with 2×20 cm³ of saturated aqueous sodium hydrogen carbonate solution and then with 2×20 cm³ of saturated aqueous sodium chloride solution. The organic phase is separated out after settling of the phases has taken place, dried over magnesium sulphate, filtered and evaporated to dryness under reduced pressure (2 kPa; 45° C.). The residue is taken up in 10 cm³ of diethyl ether, filtered off on a sinter funnel and then dried under reduced pressure (90 Pa; 50° C.) to give 195 mg of N-[6-chloro-5-(4-methylphenyl)-1H-indazol-3-yl]butanamide in the form of a beige-coloured powder.

¹H NMR spectrum (400 MHz, (CD₃)₂SO-d6, δ in ppm): 0.93 (t, J=7.5 Hz: 3H); 1.63 (mt: 2H); from 2.30 to 2.50 (mt: 2H); 2.38 (s: 3H); 7.28 (mt: 4H); 7.64 (s: 1H); 7.81 (s: 1H); 10.45 (unresolved peak: 1H).

| EI | m/z = 327 | M⁺· |
| --- | --- | --- |
|  | m/z = 257 | [M—C₄CH₆O]⁺· |

EXAMPLE 91

N-[6-[4-(Phenylmethoxy)phenyl-]-5-phenyl-1-[[2-(trimethylsilyl)ethoxy]methyl]-1H-indazol-3-yl]butanamide 306 mg of phenylboronic acid, 427 mg of sodium carbonate in 30 cm³ of water, and 248 mg of tetrakis(triphenylphosphine)palladium are added to 1 g of N-[5-bromo-6-[4-(phenylmethoxy)phenyl]-1-[[2-(trimethylsilyl) ethoxy]methyl]-1H-indazol-3-yl]butanamide, prepared in Example 63, in 100 cm³ of dioxane, and the mixture is refluxed for 18 hours. 100 cm³ of ethyl acetate and 100 cm³ of water are added and the reaction medium is filtered through a sinter funnel packed with Celite. The organic phase is separated out after settling of the phases has taken place, washed successively with 100 cm³ of water and with 100 cm³ of saturated sodium chloride solution, dried over magnesium sulphate, filtered and concentrated under reduced pressure (2 kPa-50° C.) to give 2.5 g of an oil, which is purified by chromatography under an argon pressure of 50 kPa, on a column of silica gel (particle size 40–60 μm; diameter 3.5 cm), eluting with a cyclohexane/ethyl acetate mixture (80/20 by volume). The fractions containing the expected product are combined and evaporated under reduced pressure (2 kPa; 50° C.) to give 1 g of N-[6-[4-(phenylmethoxy)phenyl]-5-phenyl-1-[[2-(trimethylsilyl)ethoxy]methyl]-1H-indazol-3-yl]butanamide in the form of a yellow oil.

¹H NMR spectrum (300 MHz, (CD₃)₂SO-d6, δ in ppm): –0.06 (s: 9H); 0.84 (t, J=8 Hz: 2H); 0.94 (t, J=7.5 Hz: 3H); 1.65 (mt: 2H); 2.40 (broad t, J=7 Hz: 2H); 3.57 (t, J=8 Hz: 2H); 5.09 (s: 2H); 5.71 (s: 2H); 6.92 (d, J=8.5 Hz: 2H); from 7.00 to 7.55 (mt: 10H); 7.08 (d, J=8.5 Hz: 2H); 7.66 (s: 1H); 7.85 (s: 1H); 10.54 (unresolved peak: 1H).

| EI | m/z = 591 | M⁺· |
| --- | --- | --- |
|  | m/z = 474 | [M—OCH₂CH₂Si(CH₃)₃]⁺ |

N-[5-phenyl-6-[4-(phenylmethoxy)phenyl]-1H-indazol-3-yl]butanamide 10.1 cm³ of tetrabutylammonium fluoride as a 1M solution in tetrahydrofuran are added to 1 g of N-[6-[4-(phenylmethoxy)phenyl]-5-phenyl-1-[[2-(trimethylsilyl)-ethoxy]methyl]-1H-indazol-3-yl]butanamide, described previously, in 40 cm³ of tetrahydrofuran, and the mixture is refluxed for 18 hours; after cooling, 75 cm³ of ethyl acetate are added and the organic phase is washed successively with 100 cm³ of saturated sodium hydrogen carbonate solution and with 75 cm³ of saturated sodium chloride solution. The organic phase is separated out after settling of the phases has taken place, dried over magnesium sulphate, filtered and concentrated to dryness under reduced pressure (2 kPa; 50° C.) to give 2 g of crude product, which is purified by chromatography under an argon pressure of 50 kPa, on a column of silica gel (particle size 40–60 μm; diameter 3.5 cm), eluting with a cyclohexane/ethyl acetate mixture (80/20 by volume). The fractions containing the expected product are combined and evaporated under reduced pressure (2 kPa; 50° C.); the residue is dried (90 Pa; 45° C.) to give 650 mg of N-[5-phenyl-6-[4-(phenylmethoxy)phenyl]-1H-indazol-3-yl]butanamide in the form of a yellow oil.

¹H NMR spectrum (300 MHz, (CD₃)₂SO-d6, δ in ppm): 0.96 (t, J=7.5 Hz: 3H); 1.66 (mt: 2H); 2.40 (t, J=7 Hz: 2H); 5.08 (s: 2H); 6.91 (d, J=8.5 Hz: 2H); from 7.05 to 7.55 (mt: 10H); 7.09 (d, J=8.5 Hz: 2H); 7.36 (s: 1H); 7.80 (s: 1H); 10.42 (broad s: 1H); 12.70 (broad s: 1H).

| EI | m/z = 461 | M+· |
| --- | --- | --- |
| | m/z = 391 | [M—C₄CH₆O]+· |
| | m/z = 300 | [391 – C₆H₅CH₂]+ |

N-[5-phenyl-6-(4-hydroxyphenyl)-1H-indazol-3-yl]butanamide 10 cm³ of trimethylsilyl iodide are added to 650 mg of N-[5-phenyl-6-[4-(phenylmethoxy)phenyl])-1H-indazol-3-yl]butanamide, prepared previously, and the mixture is refluxed for 3 hours. 3 cm³ of methanol are added and the reaction medium is refluxed for 15 minutes and then concentrated to dryness under reduced pressure (2 kPa; 50° C.). The residue is taken up in 75 cm³ of ethyl acetate and washed with 2×50 cm³ of 10% sodium thiosulphate solution and then with 50 cm³ of water and with 50 cm³ of saturated sodium chloride solution. The organic phase is separated out after settling of the phases has taken place, dried over magnesium sulphate, filtered and concentrated to dryness under reduced pressure to give 0.6 g of crude product, which is purified by chromatography under an argon pressure of 50 kPa, on a column of silica gel (particle size 40–60 μm; diameter 3 cm), eluting with a cyclohexane/ethyl acetate mixture (70/30 by volume). The fractions containing the expected product are combined and evaporated under reduced pressure (2 kPa; 50° C.); the residue is taken up in 10 cm³ of diisopropyl ether, filtered off, washed with 5 cm³ of ethyl acetate and with 5 cm³ of diethyl ether, and then dried (90 Pa; 45° C.) to give 200 mg of N-[5-phenyl-6-(4-hydroxyphenyl)-1H-indazol-3-yl]butanamide melting at 220° C.

¹H NMR spectrum (300 MHz, (CD₃)₂SO-d6, δ in ppm): 0.95 (t, J=7.5 Hz: 3H); 1.65 (mt: 2H); 2.38 (t, J=7 Hz: 2H); 6.63 (d, J=8 Hz: 2H); 6.94 (d, J=8 Hz: 2H); 7.09 (broad d, J=7.5 Hz: 2H); from 7.15 to 7.30 (mt: 3H); 7.33 (s: 1H); 7.77 (s: 1H); 9.40 (unresolved peak: 1H); 10.40 (broad s: 1H); 12.67 (unresolved peak: 1H).

EXAMPLE 92

N-[6-chloro-5-(4,4,5,5-tetramethyl[1,3,2]dioxaborolan-2-yl)-1-[2-(trimethylsilyl)ethoxy]methyl]-1H-indazol-3-yl]butanamide 5.11 g of bis(pinacolato)diborane, 277 mg of bis(dibenzylideneacetone)palladium, then 2.48 g of potassium acetate and finally 330 mg of tricyclohexylphosphine are added to 7.5 g of N-[5-bromo-6-chloro-1-[[2-(trimethylsilyl)ethoxy]methyl]-1H-indazol-3-yl]butanamide, described in Example 58, in 225 cm³ of dioxane. The medium is refluxed for 18 hours and the resulting mixture is then allowed to return to room temperature and 100 cm³ of ethyl acetate and 100 cm³ of water are added. The organic phase is separated out after settling of the phases has taken place, washed with 100 cm³ of water, with 100 cm³ of saturated sodium chloride solution, dried over magnesium sulphate, filtered and then concentrated to dryness under reduced pressure (2 kPa; 45° C.) to give 11.2 g of crude product, which is purified by chromatography under an argon pressure of 50 kPa, on a column of silica gel (particle size 40–60 μm; diameter 3 cm), eluting with a cyclohexane/ethyl acetate mixture (80/20 by volume). The fractions containing the expected product are combined and evaporated under reduced pressure (2 kPa; 50° C.); 6.16 g of N-[6-chloro-5-(4,4,5,5-tetramethyl[1,3,2]dioxaborolan-2-yl)-1-[[2-(trimethylsilyl)ethoxy]methyl]-1H-indazol-3-yl]butanamide are obtained in the form of an orange-coloured oil. The product is used directly.

N-[6-chloro-5-(4-nitrophenyl)-1-[[2-(trimethylsilyl)ethoxy]methyl]-1H-indazol-3-yl]butanamide 246 mg of 4-bromonitrobenzene, 1.2 g of sodium carbonate in 20 cm³ of water and 365 mg of tetrakis(triphenylphosphine)palladium are added to 2 g of N-[6-chloro-5-(4,4,5,5-tetramethyl[1,3,2]dioxaborolan-2-yl)-1-[[2-(trimethylsilyl)ethoxy]methyl]-1H-indazol-3-yl]butanamide, described previously, in 100 cm³ of dioxane. The medium is then refluxed for 20 hours and the resulting mixture is then allowed to return to room temperature and 100 cm³ of ethyl acetate and 100 cm³ of water are added. The reaction medium is filtered through a sinter funnel packed with Celite and the organic phase is separated out after settling of the phases has taken place, washed with 100 cm³ of water, with 100 cm³ of saturated aqueous sodium chloride solution, dried over magnesium sulphate, filtered and concentrated to dryness under reduced pressure (2 kPa; 45° C.). The crude product is purified by chromatography under an argon pressure of 50 kPa, on a column of silica gel (particle size 40–60/μm; diameter 4 cm), eluting with a cyclohexane/ethyl acetate mixture (85/15 by volume). The fractions containing the expected product are combined and evaporated under reduced pressure (2 kPa; 50° C.). 690 mg of N-[6-chloro-5-(4-nitrophenyl)-1-[[2-(trimethylsilyl)ethoxy]methyl]-1H-indazol-3-yl]butanamide are obtained in the form of yellow crystals.

¹H NMR spectrum (300 MHz, (CD₃)₂SO-d6, δ in ppm): –0.05 (s: 9H); 0.85 (t, J=8 Hz: 2H); 0.92 (t, J=7.5 Hz: 3H); 1.62 (mt: 2H); 2.39 (t, J=7 Hz: 2H); 3.56 (t, J=8 Hz: 2H); 5.72 (s: 2H); 7.74 (d, J=8.5 Hz: 2H); 8.01 (s: 1H); 8.09 (s: 1H); 8.35 (d, J=8.5 Hz: 2H); 10.70 (unresolved peak: 1H).

| EI | m/z = 488 | M+· |
| --- | --- | --- |
| | m/z = 371 | [M—OCH₂CH₂Si(CH₃)₃]+ |
| | m/z = 360 | [M—C₆H₁₂OSi]+· |
| | m/z = 73 | [Si(CH₃)₃]+ |

N-[6-chloro-5-(4-pyridyl)-1H-indazol-3-yl]butanamide 36.8 cm³ of tetrabutylammonium fluoride as a 1M solution in tetrahydrofuran are added to 3 g of N-[6-chloro-5-(4-nitrophenyl)-1-[[2-(trimethylsilyl)ethoxy]methyl]-1H-indazol-3-yl]butanamide, described previously, in 135 cm³ of tetrahydrofuran. The medium is then refluxed for 18 hours and is then allowed to return to room temperature to add 100 cm³ of ethyl acetate and 75 cm³ of saturated aqueous sodium hydrogen carbonate solution. The organic phase is separated out after settling of the phases has taken place, washed with 100 cm³ of saturated aqueous sodium hydrogen carbonate solution and then with 100 cm³ of saturated sodium chloride solution, dried over magnesium sulphate, filtered and concentrated to dryness under reduced pressure (2 kPa; 45° C.). The residue is purified by chromatography under an argon pressure of 50 kPa, on a column of silica gel (particle size 40–60 μm; diameter 2 cm), eluting with a cyclohexane/ethyl acetate mixture (80/20 by volume). The fractions containing the expected product are combined and concentrated to dryness under reduced pressure (2 kPa; 50° C.); the residue is taken up in 35 cm³ of diisopropyl ether, filtered off on a sinter funnel and then washed with 2×20 cm³ of diisopropyl ether. After drying (90 Pa; 50° C.), 88 mg of N-[6-chloro-5-(4-nitrophenyl)-1H-indazol-3-yl]butanamide are obtained in the form of yellow crystals melting at 260° C.

$^1$H NMR spectrum (300 MHz, $(CD_3)_2SO$-d6, δ in ppm): 0.92 (t, J=7.5 Hz: 3H); 1.62 (mt: 2H); 2.37 (t, J=7 Hz: 2H); 7.73 (d, J=8 Hz: 2H); 7.72 (s: 1H); 7.96 (s: 1H); 8.34 (d, J=8 Hz: 2H); 10.58 (broad s: 1H); from 12.50 to 13.20 (very broad unresolved peak: 1H).

EXAMPLE 93

N-[5-(4-aminophenyl)-6-chloro-1H-indazol-3-yl]butanamide 845 mg of zinc powder are added to 0.93 g of N-[6-chloro-5-(4-nitrophenyl)-1H-indazol-3-yl]butanamide, described previously, in 50 cm³ of acetic acid, followed, 1 hour later, by addition of a further 845 mg of zinc; the reaction medium is filtered through a sinter funnel packed with Celite and the filtrate is concentrated to dryness under reduced pressure (2 kPa; 50° C.). The residue is taken up in 100 cm³ of ethyl acetate and 75 cm³ of water and the organic phase is separated out after settling of the phases has taken place, washed successively with 75 cm³ of water and with 50 cm³ of saturated sodium hydrogen carbonate solution, dried over magnesium sulphate, filtered and concentrated to dryness to give 480 mg of crude product, which is purified by chromatography under an argon pressure of 50 kPa, on a column of silica gel (particle size 40–60 μm; diameter 4.5 cm), eluting with a cyclohexane/ethyl acetate mixture (60/40 by volume). The fractions containing the expected product are combined and the solid is triturated in 10 cm³ of diethyl ether, filtered off, washed with 2×5 cm³ of diethyl ether and then dried (90 Pa; 45° C.) to give 110 mg of N-[5-(4-aminophenyl)-6-chloro-1H-indazol-3-yl]butanamide in the form of an ochre-coloured solid.

$^1$H NMR spectrum (300 MHz, $(CD_3)_2SO$-d6, δ in ppm): 0.92 (t, J=7.5 Hz: 3H); 1.63 (mt: 2H); 2.36 (t, J=7 Hz: 2H); 5.21 (unresolved peak: 2H); 6.63 (d, J=8 Hz: 2H); 7.06 (d, J=8 Hz: 2H); 7.58 (s: 1H); 7.72 (s: 1H); 10.42 (broad s: 1H); 12.71 (unresolved peak: 1H).

| EI | m/z = 328 | M$^{+\cdot}$ |
|---|---|---|
|  | m/z = 284 | [M—$C_3H_6$]$^{+\cdot}$ |
|  | m/z = 258 | [M—$C_4CH_6O$]$^{+\cdot}$ |

EXAMPLE 94

N-[6-chloro-5-(4-ethylphenyl)-1-[[2-(trimethylsilyl)ethoxy]methyl]-1H-indazol-3-yl]butanamide 504 mg of 4-ethylphenylboronic acid, 664 mg of sodium carbonate in 20 cm³ of distilled water and 202 mg of tetrakis(triphenylphosphine)palladium are added to 1 g of N-[5-bromo-6-chloro-1-[[2-(trimethylsilyl)ethoxy]methyl]-1H-indazol-3-yl]butanamide, described in Example 58, in 75 cm³ of dioxane. The mixture is refluxed for 18 hours and then the temperature is allowed to return to room temperature to add 75 cm³ of ethyl acetate and 50 cm³ of water, and the reaction medium is filtered through a sinter funnel packed with Celite. The filtrate is separated by settling and the organic phase is washed successively with 50 cm³ of water, with 50 cm³ of saturated aqueous sodium chloride solution, separated out after settling of the phases has taken place, dried over magnesium sulphate, filtered and then concentrated to dryness under reduced pressure (2 kPa; 50° C.). The residue is purified by chromatography under an argon pressure of 50 kPa, on a column of silica gel (particle size 40–60 μm; diameter 4.5 cm), eluting with a cyclohexane/ethyl acetate mixture (80/20 by volume). The fractions containing the expected product are combined and evaporated under reduced pressure (2 kPa; 50° C.), and then dried (90 Pa; 50° C.) to give 1.1 g of N-[6-chloro-5-(4-ethylphenyl)-1-[[2-(trimethylsilyl)ethoxy]methyl]-1H-indazol-3-yl]butanamide in the form of a yellow oil.

$^1$H NMR spectrum (300 MHz, $(CD_3)_2SO$-d6, δ in ppm): −0.05 (s: 9H); 0.85 (t, J=8 Hz: 2H); 0.93 (t, J=7.5 Hz: 3H); 1.26 (t, J=7.5 Hz: 3H); 1.64 (mt: 2H); 2.39 (t, J=7 Hz: 2H); 2.69 (q, J=7.5 Hz: 2H); 3.55 (t, J=8 Hz: 2H); 5.70 (s: 2H); 7.33 (mt: 4H); 7.89 (s: 1H); 8.00 (s: 1H); 10.64 (unresolved peak: 1H).

| EI | m/z = 471 | M$^{+\cdot}$ |
|---|---|---|
|  | m/z = 354 | [M—$OCH_2CH_2Si(CH_3)_3$]$^{+\cdot}$ |
|  | m/z = 343 | [M—$C_6H_{12}OSi$]$^{+\cdot}$ |

N-[6-chloro-5-(4-ethylphenyl)-1H-indazol-3-yl]butanamide 14 cm³ of tetrabutylammonium fluoride as a 1M solution in tetrahydrofuran are added to 1.1 g of N-[6-chloro-5-(4-ethylphenyl)-1-[[2-(trimethylsilyl)ethoxy]methyl]-1H-indazol-3-yl]butanamide, described previously, in 50 cm³ of tetrahydrofuran. The medium is then refluxed for 18 hours and the mixture is then allowed to return to room temperature and 75 cm³ of ethyl acetate are added; the organic phase is washed with 2×100 cm³ of saturated aqueous sodium hydrogen carbonate solution and then with 75 cm³ of saturated aqueous sodium chloride solution. The organic phase is separated out after settling of the phases has taken place, dried over magnesium sulphate, filtered and evaporated to dryness under reduced pressure (2 kPa; 45° C.). The residue is purified by chromatography under an argon pressure of 50 kPa, on a column of silica gel (particle size 40–60 μm; diameter 3 cm), eluting with a cyclohexane/ethyl acetate mixture (70/30 by volume). The fractions containing the expected product are combined and evaporated under reduced pressure (2 kPa; 50° C.); the residue is taken up in 20 cm³ of diisopropyl ether, filtered off on a sinter funnel and washed with 2×10 cm³ of diisopropyl ether. After drying under reduced pressure (90 Pa; 50° C.), 440 mg of N-(6-chloro-5-phenyl-1H-indazol-3-yl)butanamide are obtained in the form of white crystals melting at 240° C.

$^1$H NMR spectrum (300 MHz, $(CD_3)_2SO$-d6, δ in ppm): 0.92 (t, J=7.5 Hz: 3H); 1.24 (t, J=7.5 Hz: 3H); 1.62 (mt: 2H); 2.37 (t, J=7 Hz: 2H); 2.67 (q, J=7.5 Hz: 2H); 7.31 (mt: 4H); 7.64 (s: 1H); 7.82 (s: 1H); 10.48 (unresolved peak: 1H); 12.80 (unresolved peak: 1H).

EXAMPLE 95

N-[6-chloro-5-[4-(phenylmethoxy)phenyl]-1-[[2-(trimethylsilyl)ethoxy]methyl]-1H-indazol-3-yl]butanamide 1.54 g of 4-benzyloxyphenylboronic acid, 1.32 g of sodium carbonate in 20 cm³ of water and 404 mg of tetrakis(triphenylphosphine)palladium are added to 2 g of N-[5-bromo-6-chloro-1-[[2-(trimethylsilyl)ethoxy]methyl]-1H-indazol-3-yl]butanamide, described in Example 58, in 100 cm³ of dioxane. The mixture is refluxed for 18 hours, the temperature is then allowed to return to room temperature to add 75 cm³ of ethyl acetate and 50 cm³ of water, and the reaction medium is filtered through a sinter funnel packed with Celite. The filtrate is separated by settling and the organic phase is washed successively with 100 cm³ of water and then with 75 cm³ of saturated aqueous sodium chloride solution, separated out after settling of the phases has taken place, dried over magnesium sulphate, filtered and concentrated to dryness under reduced pressure (2 kPa; 50° C.). The residue is purified by chromatography under an argon pressure of 50 kPa, on a column of silica gel (particle size 40–60/μm; diameter 4.5 cm), eluting with a cyclohexane/ethyl acetate mixture (80/20 by volume). The fractions containing the expected product are combined and evaporated under reduced pressure (2 kPa; 50° C.); the residue is taken up in 50 cm³ of cyclohexane, filtered off, washed with 2×25 cm³ of cyclohexane and dried under reduced pressure (90 Pa; 50° C.) to give 2.35 g of N-[6-chloro-5-[4-(phenylmethoxy)phenyl]-1-[[2-(trimethylsilyl)ethoxy]methyl]-1H-indazol-3-yl]butanamide in the form of white crystals melting at 130° C.

¹H NMR spectrum (300 MHz, (CD₃)₂SO-d6, δ in ppm): –0.06 (s: 9H); 0.84 (t, J=8 Hz: 2H); 0.92 (t, J=7.5 Hz: 3H); 1.63 (mt: 2H); 2.38 (t, J=7 Hz: 2H); 3.54 (t, J=8 Hz: 2H); 5.18 (s: 2H); 5.69 (s: 2H); 7.11 (d, J=8.5 Hz: 2H); from 7.30 to 7.55 (mt: 5H); 7.35 (d, J=8.5 Hz: 2H); 7.86 (s: 1H); 7.98 (s: 1H); 10.61 (unresolved peak: 1H).

N-[6-chloro-5-[4-(Phenylmethoxy)phenyl]-1H-indazol-3-yl]butanamide 25.1 cm³ of tetrabutylammonium fluoride as a 1M solution in tetrahydrofuran are added to 1.1 g of N-[6-chloro-5-[4-(phenylmethoxy)phenyl]-1-[[2-(trimethylsilyl)-ethoxy]methyl]-1H-indazol-3-yl]butanamide, described previously, in 50 cm³ of tetrahydrofuran. The medium is then refluxed for 18 hours and the resulting mixture is allowed to return to room temperature and 100 cm³ of ethyl acetate are added; the organic phase is washed with 2×100 cm³ of saturated aqueous sodium hydrogen carbonate solution and then with 100 cm³ of saturated aqueous sodium chloride solution. The organic phase is separated out after settling of the phases has taken place, dried over magnesium sulphate, filtered and evaporated to dryness under reduced pressure (2 kPa; 45° C.). The residue is purified by chromatography under an argon pressure of 50 kPa, on a column of silica gel (particle size 40–60 μm; diameter 4 cm), eluting with a cyclohexane/ethyl acetate mixture (70/30 by volume). The fractions containing the expected product are combined and evaporated under reduced pressure (2 kPa; 50° C.); the residue is taken up in 30 cm³ of diisopropyl ether, filtered off on a sinter funnel and washed with 2×20 cm³ of diisopropyl ether. After drying under reduced pressure (90 Pa; 50° C.), 1.3 g of N-[6-chloro-5-[4-(phenylmethoxy)phenyl]-1H-indazol-3-yl]butanamide are obtained in the form of white crystals melting at 230° C.

¹H NMR spectrum (300 MHz, (CD₃)₂SO-d6, δ in ppm): 0.93 (t, J=7.5 Hz: 3H); 1.63 (mt: 2H); 2.37 (t, J=7 Hz: 2H); 5.18 (s: 2H); 7.11 (d, J=8.5 Hz: 2H); 7.35 (d, J=8.5 Hz: 2H); 7.37 (mt: 1H); 7.44 (broad t, J=7.5 Hz: 2H); 7.51 (broad d, J=7.5 Hz: 2H); 7.64 (s: 1H); 7.81 (s: 1H); 10.48 (broad s: 1H); 12.80 (unresolved peak: 1H).

EXAMPLE 96

N-[6-chloro-5-(4-hydroxyphenyl)-1H-indazol-3-yl]butanamide 20 cm³ of trimethylsilyl iodide are added to 1.1 g of N-[6-chloro-5-[4-(phenylmethoxy)phenyl]-1H-indazol-3-yl]butanamide, prepared in Example 95, and the mixture is refluxed for 18 hours. 30 cm³ of methanol are added and the reaction medium is refluxed for 30 minutes and then concentrated to dryness under reduced pressure (2 kPa; 50° C.). The residue is taken up in 100 cm³ of ethyl acetate and 100 cm³ of water and the organic phase is washed with 2×75 cm³ of 10% sodium thiosulphate solution and then with 70 cm³ of water and 75 cm³ of saturated sodium chloride solution. The organic phase is separated out after settling of the phases has taken place, dried over magnesium sulphate, filtered and then concentrated to dryness under reduced pressure to give 1.44 g of crude product, which is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.); the residue is taken up in 20 cm³ of diisopropyl ether, filtered off, washed with 3×10 cm³ of diisopropyl ether and then dried (90 Pa; 45° C.) to give 210 mg of N-[6-chloro-5-(4-hydroxyphenyl)-1H-indazol-3-yl]butanamide in the form of a white powder.

¹H NMR spectrum (300 MHz, (CD₃)₂SO-d6, δ in ppm): 0.92 (t, J=7.5 Hz: 3H); 1.62 (mt: 2H); 2.37 (t, J=7 Hz: 2H); 6.84 (d, J=8.5 Hz: 2H); 7.21 (d, J=8.5 Hz: 2H); 7.61 (s: 1H); 7.77 (s: 1H); 9.57 (unresolved peak: 1H); 10.45 (broad s: 1H); 12.76 (unresolved peak: 1H).

| EI | m/z = 329 | M⁺· |
| --- | --- | --- |
|  | m/z = 259 | [M—C₄CH₆O]⁺· |

EXAMPLE 97

N-[5,6-bis 4-[(phenylmethoxy)phenyl]-1-F[2-(trimethylsilyl)ethoxy]methyl]-1H-indazol-3-yl]butanamide 1.9 g of 4-benzyloxyphenylboronic acid, 1.63 g of sodium carbonate in 20 cm³ of distilled water and 500 mg of tetrakis(triphenylphosphine)palladium are added to 1.35 g of N-[5,6-dibromo-1-[[2-(trimethylsilyl)ethoxy]methyl]-1H-indazol-3-yl]butanamide, described in Example 70, in 100 cm³ of dioxane. The mixture is refluxed for 18 hours, the temperature is then allowed to return to room temperature to add 100 cm³ of ethyl acetate and 100 cm³ of water, and the reaction medium is filtered through a sinter funnel packed with Celite. The organic phase is separated out after settling of the phases has taken place, washed with 100 cm of saturated aqueous sodium chloride solution, separated out after settling of the phases has taken place, dried over magnesium sulphate, filtered and concentrated to dryness under reduced pressure (2 kPa; 50° C.). The residue is purified by chromatography under an argon pressure of 50 kPa, on a column of silica gel (particle size 40–60 μm; diameter 4.5 cm), eluting with a cyclohexane/ethyl acetate mixture (70/30 by volume). The fractions containing the expected product are combined, evaporated under reduced pressure (2 kPa; 50° C.) and dried (90 Pa; 50° C.) to give 1.96 g of N-[5,6-bis[4-(phenylmethoxy)phenyl]-1-[[2-(trimethylsilyl)ethoxy]methyl]-1H-indazol-3-yl]butanamide in the form of an orange-coloured oil in a purity of 70%, which product is used without further modification in the following step.

¹H NMR spectrum (300 MHz, (CD₃)₂SO-d6, δ in ppm): –0.06 (s: 9H); 0.85 (t, J=8 Hz: 2H); 0.96 (t, J=7.5 Hz: 3H);

1.66 (mt: 2H); 2.41 (broad t, J=7 Hz: 2H); 3.57 (t, J=8 Hz: 2H); 5.10 (mt: 4H); 5.71 (broad s: 2H); from 6.90 to 7.00 (mt: 4H); 7.04 (d, J=8.5 Hz: 2H); 7.11 (d, J=8.5 Hz: 2H); from 7.30 to 7.55 (mt: 10H); 7.64 (s: 1H); 7.81 (s: 1H); 10.55 (unresolved peak: 1H).

| EI | m/z = 697 | M+· |
|---|---|---|
|    | m/z = 580 | [M—OCH$_2$CH$_2$Si(CH$_3$)$_3$]+ |
|    | m/z = 91  | [C$_6$H$_5$CH$_2$]+ |

N-[5,6-bis[4-(phenylmethoxy)phenyl]-1H-indazol-3-yl]butanamide 16.3 cm$^3$ of tetrabutylammonium fluoride as a 1M solution in tetrahydrofuran are added to 1.9 g of N-[5,6-bis[4-(phenylmethoxy)phenyl]-1-[[2-(trimethylsilyl)ethoxy]methyl]-1H-indazol-3-yl]butanamide, described previously, in 100 cm$^3$ of tetrahydrofuran. The medium is then refluxed for 18 hours and is then allowed to return to room temperature and 100 cm$^3$ of ethyl acetate are added; the organic phase is washed with 2×100 cm$^3$ of saturated aqueous sodium hydrogen carbonate solution and then with 100 cm$^3$ of saturated aqueous sodium chloride solution. The organic phase is separated out after settling of the phases has taken place, dried over magnesium sulphate, filtered and evaporated to dryness under reduced pressure (2 kPa; 50° C.). The residue is purified by chromatography under an argon pressure of 50 kPa, on a column of silica gel (particle size 40–60 µm; diameter 4.5 cm), eluting with a cyclohexane/ethyl acetate mixture (70/30 by volume). The fractions containing the expected product are combined and evaporated under reduced pressure (2 kPa; 50° C.); the residue is taken up in 25 cm$^3$ of diisopropyl ether, filtered off on a sinter funnel and washed with 2×20 cm$^3$ of diisopropyl ether. After drying under reduced pressure (90 Pa; 50° C.), 700 mg of N-[5,6-bis[4-(phenylmethoxy)phenyl]-1H-indazol-3-yl]butanamide are obtained in the form of white crystals melting at 140° C.

$^1$H NMR spectrum (300 MHz, (CD$_3$)$_2$SO-d6, δ in ppm): 0.95 (t, J=7.5 Hz: 3H); 1.65 (mt: 2H); 2.39 (t, J=7 Hz: 2H); 5.08 (broad s: 4H); from 6.85 to 7.00 (mt: 4H); 7.01 (d, J=9 Hz: 2H); 7.09 (d, J=9 Hz: 2H); from 7.30 to 7.55 (mt: 10H); 7.33 (s: 1H); 7.74 (s: 1H); 10.39 (broad s: 1H); 12.67 (broad s: 1H).

EXAMPLE 98

N-[5,6-bis(4-hydroxyphenyl)-1H-indazol-3-yl]butanamide 10 cm$^3$ of trimethylsilyl iodide are added to 700 mg of N-[5,6-bis[4-(phenylmethoxy)phenyl]-1H-indazol-3-yl]butanamide, prepared in Example 97, and the mixture is refluxed for 18 hours. 30 cm$^3$ of methanol are added and the reaction medium is refluxed for 15 minutes and is then concentrated to dryness under reduced pressure (2 kPa; 50° C.). The residue is taken up in 75 cm$^3$ of ethyl acetate and the organic phase is washed with 2×75 cm$^3$ of 10% sodium thiosulphate solution and then with 75 cm$^3$ of saturated sodium chloride solution. The organic phase is separated out after settling of the phases has taken place, dried over magnesium sulphate, filtered and then concentrated to dryness under reduced pressure (2 kPa; 50° C.) to give 900 mg of crude product, which is purified by chromatography under an argon pressure of 50 kPa, on a column of silica gel (particle size 40–60 µm; diameter 3 cm), eluting with a cyclohexane/ethyl acetate mixture (60/40 by volume). The fractions containing the expected product are combined and evaporated under reduced pressure (2 kPa; 50° C.) and the residue is taken up in 20 cm$^3$ of diisopropyl ether, filtered off, washed with 3 cm$^3$ of ethyl acetate, then with 2×10 cm$^3$ of diisopropyl ether and dried (90 Pa; 45° C.) to give 220 mg of N-[5,6-bis(4-hydroxyphenyl)-1H-indazol-3-yl]butanamide in the form of a white powder melting at 180° C.

$^1$H NMR spectrum (300 MHz, (CD$_3$)$_2$SO-d6, δ in ppm): 0.95 (t, J=7.5 Hz: 3H); 1.65 (mt: 2H); 2.38 (t, J=7 Hz: 2H); from 6.55 to 6.70 (mt: 4H); 6.86 (d, J=9 Hz: 2H); 6.94 (d, J=9 Hz: 2H); 7.28 (s: 1H); 7.68 (s: 1H); 9.34 (unresolved peak: 2H); 10.36 (broad s: 1H); 12.60 (unresolved peak: 1H).

EXAMPLE 99

N-[5-(3-furyl)-6-[4-(Phenylmethoxy)phenyl]-1-[[2-(trimethylsilyl)ethoxy]methyl]-1H-indazol-3-yl]butanamide 353 mg of 3-furylboronic acid, 624 mg of sodium carbonate in 25 cm$^3$ of water, and 311 mg of tetrakis(triphenylphosphine)palladium are added to 1.25 g of N-[5-bromo-6-[4-(phenylmethoxy)phenyl]-1-[[2-(trimethylsilyl)ethoxy]methyl]-1H-indazol-3-yl]butanamide, prepared in Example 63, in 125 cm$^3$ of dioxane, and the mixture is refluxed for 18 hours. 100 cm$^3$ of ethyl acetate and 75 cm$^3$ of water are added and the reaction medium is filtered through a sinter funnel packed with Celite. The organic phase is separated out after settling of the phases has taken place, washed successively with 75 cm$^3$ of water and with 75 cm$^3$ of saturated sodium chloride solution, dried over magnesium sulphate, filtered and concentrated under reduced pressure (2 kPa; 50° C.) to give 2.6 g of an oil, which is purified by chromatography under an argon pressure of 50 kPa, on a column of silica gel (particle size 40–60 µm; diameter 4 cm), eluting with a cyclohexane/ethyl acetate mixture (80/20 by volume). The fractions containing the expected product are combined and evaporated under reduced pressure (2 kPa; 50° C.) to give 1 g of N-[5-(3-furyl)-6-[4-(phenylmethoxy)phenyl]1-[[2-(trimethylsilyl)ethoxy]methyl]-1H-indazol-3-yl]butanamide in the form of cream-coloured crystals.

$^1$H NMR spectrum (300 MHz, (CD$_3$)$_2$SO-d6, δ in ppm): −0.07 (s: 9H); 0.83 (t, J=8 Hz: 2H); 0.97 (t, J=7.5 Hz: 3H); 1.68 (mt: 2H); 2.42 (t, J=7 Hz: 2H); 3.55 (t, J=8 Hz: 2H); 5.15 (s: 2H); 5.68 (s: 2H); 6.07 (mt: 1H); 7.04 (d, J=8.5 Hz: 2H); 7.19 (d, J=8.5 Hz: 2H); from 7.30 to 7.55 (mt: 6H); 7.55 (t, J=2 Hz: 1H); 7.61 (s: 1H); 7.91 (s: 1H); 10.53 (unresolved peak: 1H).

| EI | m/z = 581 | M+· |
|---|---|---|
|    | m/z = 464 | [M—OCH$_2$CH$_2$Si(CH$_3$)$_3$]+ |

N-[5-(3-furyl)-6-[4-(phenylmethoxy)phenyl]-1H-indazol-3-yl]butanamide 10.3 cm$^3$ of tetrabutylammonium fluoride as a 1M solution in tetrahydrofuran are added to 1 g of N-[5-(3-furyl)-6-[4-(phenylmethoxy)phenyl]-1-[[2-(trimethylsilyl)ethoxy]methyl]-1H-indazol-3-yl]butanamide, described previously, in 75 cm$^3$ of tetrahydrofuran, and the mixture is refluxed for 18 hours; after cooling, 75 cm$^3$ of ethyl acetate are added and the organic phase is washed successively with 100 cm³ of saturated sodium hydrogen carbonate solution and with 75 cm³ of saturated sodium chloride solution. The organic phase is separated out after settling of the phases has taken place, dried over magnesium sulphate, filtered and concentrated to dryness under reduced pressure (2 kPa; 50° C.) to give 1.4 g of crude product, which is purified by chromatography under an argon pressure of 50 kPa, on a column of silica gel (particle size 40–60 μm; diameter 4 cm), eluting with a cyclohexane/ethyl acetate mixture (70/30 by volume). The fractions containing the expected product are combined and evaporated under reduced pressure (2 kPa; 50° C.); the residue is dried (90 Pa; 45° C.) to give 530 mg of N-[5-(3-furyl)-6-[4-(phenylmethoxy)phenyl]-1H-indazol-3-yl]butanamide in the form of a yellow oil.

¹H NMR spectrum (300 MHz, (CD₃)₂SO-d6, δ in ppm): 0.98 (t, J=7.5 Hz: 3H); 1.68 (mt: 2H); 2.41 (t, J=7 Hz: 2H); 5.15 (s: 2H); 6.07 (broad s: 1H); 7.02 (d, J=8.5 Hz: 2H); 7.20 (d, J=8.5 Hz: 2H); from 7.30 to 7.60 (mt: 6H); 7.31 (s: 2H); 7.86 (s: 1H); 10.36 (unresolved peak: 1H); 12.66 (unresolved peak: 1H).

| EI | m/z = 451 | M⁺· |
|----|-----------|-----|
|    | m/z =381  | [M—C₄H₆O]⁺· |

N-[5-(3-furyl)-6-([4-hydroxyphenyl)-1H-indazol-3-yl]butanamide 10 cm³ of trimethylsilyl iodide are added to 500 mg of N-[5-(3-furyl)-6-[4-(phenylmethoxy)phenyl]-1H-indazol-3-yl)]butanamide, described previously, and the mixture is refluxed for 18 hours. 25 cm³ of methanol are added and the reaction medium is refluxed for 10 minutes and is then concentrated to dryness under reduced pressure (2 kPa; 50° C.). The residue is taken up in 75 cm³ of ethyl acetate and 50 cm³ of tetrahydrofuran and the organic phase is then washed with 2×100 cm³ of 10% sodium thiosulphate solution and then with 75 cm³ of saturated sodium chloride solution. The organic phase is separated out after settling of the phases has taken place, dried over magnesium sulphate, filtered and then concentrated to dryness under reduced pressure to give 950 mg of crude product, which is purified by chromatography under an argon pressure of 50 kPa, on a column of silica gel (particle size 40–60 μm; diameter 3.5 cm), eluting with a cyclohexane/ethyl acetate mixture (60/40 by volume). The fractions containing the expected product are combined and evaporated under reduced pressure (2 kPa; 50° C.); the residue is taken up in 5 cm³ of ethyl acetate, filtered off, washed with 1 cm³ of ethyl acetate and then with 20 cm³ of diethyl ether and dried (90 Pa; 45° C.) to give 10 mg of N-[5-(3-furyl)-6-(4-hydroxyphenyl)-1H-indazol-3-yl]butanamide in the form of a white powder melting at 185° C.

¹H NMR spectrum (300 MHz, (CD₃)₂SO-d6, δ in ppm): 0.97 (t, J=7.5 Hz: 3H); 1.67 (mt: 2H); 2.40 (t, J=7 Hz: 2H); 6.07 (broad s: 1H); 6.75 (d, J=8.5 Hz: 2H); 7.06 (d, J=8.5 Hz: 2H); 7.27 (broad s: 2H); 7.52 (mt: 1H); 7.83 (s: 1H); from 9.40 to 9.65 (unresolved peak: 1H); 10.33 (unresolved peak: 1H); from 12.50 to 12.75 (unresolved peak: 1H).

| DCI | m/z = 362 | [M + H]⁺ |
|-----|-----------|----------|

EXAMPLE 100

N-[5-(4-ethylphenyl)-6-[4-(Phenylmethoxy)phenyl]-1-[[2-(trimethylsilyl)ethoxy]-methyl]-1H-indazol-3-yl]butanamide 379 mg of 4-ethylphenylboronic acid, 428 mg of sodium carbonate in 30 cm³ of water, and 259 mg of tetrakis(triphenylphosphine)palladium are added to 1 g of N-[5-bromo-6-[4-(phenylmethoxy)phenyl]-1-[[2-(trimethylsilyl)ethoxy]methyl]-1H-indazol-3-yl]butanamide, prepared in Example 63, in 100 cm³ of dioxane, and the mixture is refluxed for 18 hours. 100 cm³ of ethyl acetate and 100 cm³ of water are added and the reaction medium is filtered through a sinter funnel packed with Celite. The organic phase is separated out after settling of the phases has taken place, washed successively with 75 cm³ of water and with 75 cm³ of saturated sodium chloride solution, dried over magnesium sulphate, filtered and concentrated under reduced pressure (2 kPa; 50° C.) to give 1.7 g of an oil, which is purified by chromatography under an argon pressure of 50 kPa, on a column of silica gel (particle size 40–60 μm; diameter 3.5 cm), eluting with a cyclohexane/ethyl acetate mixture (80/20 by volume). The fractions containing the expected product are combined and evaporated under reduced pressure (2 kPa; 50° C.) to give 850 mg of N-[5-(4-ethylphenyl)-6-[4-(phenylmethoxy)phenyl]-1-[[2-(trimethylsilyl)ethoxy]methyl]-1H-indazol-3-yl]butanamide in the form of grey crystals.

¹H NMR spectrum (300 MHz, (CD₃)₂SO-d6, δ in ppm): −0.07 (s: 9H); 0.84 (t, J=8 Hz: 2H); 0.94 (t, J=7.5 Hz: 3H); 1.18 (t, J=7.5 Hz: 3H); 1.65 (mt: 2H); 2.40 (t, J=7 Hz: 2H); 2.58 (q, J=7.5 Hz: 2H); 3.57 (t, J=8 Hz: 2H); 5.10 (s: 2H); 5.70 (s: 2H); 6.93 (d, J=8.5 Hz: 2H); 7.02 (d, J=8.5 Hz: 2H); 7.09 (d, J=8.5 Hz: 2H); 7.11 (d, J=8.5 Hz: 2H); from 7.30 to 7.50 (mt: 5H); 7.63 (s: 1H); 7.82 (s: 1H); 10.50 (unresolved peak: 1H).

| EI | m/z = 619 | M⁺· |
|----|-----------|-----|
|    | m/z = 502 | [M—OCH₂CH₂Si(CH₃)₃]⁺ |
|    | m/z = 91  | [C₆H₅CH₂]⁺ |

N-[5-(4-ethylphenyl)-6-[4-(phenylmethoxy)phenyl]-1H-indazol-3-yl]butanamide 8.3 cm³ of tetrabutylammonium fluoride as a 1M solution in tetrahydrofuran are added to 850 mg of N-[5-(4-ethylphenyl)-6-[4-(phenylmethoxy)phenyl]-1-[[2-(trimethylsilyl)ethoxy]methyl]-1H-indazol-3-yl]butanamide, described previously, in 50 cm³ of tetrahydrofuran, and the mixture is refluxed for 18 hours; after cooling, 75 cm³ of ethyl acetate are added and the organic phase is washed successively with 2×100 cm³ of saturated sodium hydrogen carbonate solution and with 75 cm³ of saturated sodium chloride solution. The organic phase is separated out after settling of the phases has taken place, dried over magnesium sulphate, filtered and concentrated to dryness under reduced pressure (2 kPa; 50° C.) to give 1.5 g of crude product, which is purified by chromatography under an argon pressure of 50 kPa, on a column of silica gel (particle size 40–60 μm; diameter 3 cm), eluting with a cyclohexane/ethyl acetate mixture (70/30 by volume). The fractions containing the expected product are combined and evaporated under reduced pressure (2 kPa; 50° C.); the residue is dried (90 Pa; 45° C.) to give 660 mg of N-[5-(4-ethylphenyl)-6-[4-(phenylmethoxy)phenyl]-1H-indazol-3-yl]butanamide in the form of grey crystals.

$^1$H NMR spectrum (300 MHz, $(CD_3)_2SO$-d6, δ in ppm): 0.95 (t, J=7.5 Hz: 3H); 1.17 (t, J=7.5 Hz: 3H); 1.65 (mt: 2H); 2.39 (t, J=7 Hz: 2H); 2.58 (q, J=7.5 Hz: 2H); 5.08 (s: 2H); 6.90 (d, J=8.5 Hz: 2H); 7.00 (d, J=8.5 Hz: 2H); 7.08 (d, J=8.5 Hz: 4H); from 7.30 to 7.50 (mt: 5H); 7.34 (s: 1H); 7.76 (s: 1H); 10.36 (unresolved peak: 1H); 12.66 (unresolved peak: 1H).

| EI | m/z = 489 | M$^{+\cdot}$ |
|---|---|---|
|   | m/z = 419 | [M—$C_4H_6O$]$^+$ |

N-[5-(4-ethylphenyl)-6-(4-hydroxyphenyl)-1H-indazol-3-yl]butanamide 10 cm$^3$ of trimethylsilyl iodide are added to 600 mg of N-[5-(4-ethylphenyl)-6-[4-(phenylmethoxy)phenyl]-1H-indazol-3-yl]butanamide, described previously, and the mixture is refluxed for 18 hours. 30 cm$^3$ of methanol are added and the reaction medium is refluxed for 5 minutes and then concentrated to dryness under reduced pressure (2 kPa; 50° C.). The residue is taken up in 100 cm$^3$ of ethyl acetate and the organic phase is washed with 2×100 cm$^3$ of 10% sodium thiosulphate solution and then with 75 cm$^3$ of saturated sodium chloride solution. The organic phase is separated out after settling of the phases has taken place, dried over magnesium sulphate, filtered and then concentrated to dryness under reduced pressure to give 650 mg of crude product, which is purified by chromatography under an argon pressure of 50 kPa, on a column of silica gel (particle size 40–60 μm; diameter 3 cm), eluting with a cyclohexane/ethyl acetate mixture (50/50 by volume). The fractions containing the expected product are combined and evaporated under reduced pressure (2 kPa; 50° C.); the residue is taken up in 15 cm$^3$ of diisopropyl ether, filtered off, washed with 5 cm$^3$ of ethyl acetate and then with 10 cm$^3$ of diisopropyl ether, and dried (90 Pa; 45° C.) to give 180 mg of N-[5-(4-ethylphenyl)-6-(4-hydroxyphenyl)-1H-indazol-3-yl]-butanamide in the form of cream-coloured crystals melting at 225° C.

$^1$H NMR spectrum (300 MHz, $(CD_3)_2SO$-d6, δ in ppm): 0.95 (t, J=7.5 Hz: 3H); 1.17 (t, J=7.5 Hz: 3H); 1.65 (mt: 2H); 2.39 (t, J=7 Hz: 2H); 2.58 (q, J=7.5 Hz: 2H); 6.63 (d, J=8.5 Hz: 2H); 6.95 (d, J=8.5 Hz: 2H); 7.00 (d, J=8.5 Hz: 2H); 7.08 (d, J=8.5 Hz: 2H); 7.31 (s: 1H); 7.74 (s: 1H); 9.36 (unresolved peak: 1H); 10.35 (broad s: 1H); 12.61 (unresolved peak: 1H).

EXAMPLE 101

N-[5-(3-pyridyl)-6-[4-(phenylmethoxy)phenyl]-1-[[2-(trimethylsilyl)ethoxy]-methyl]-1H-indazol-3-yl]butanamide 371 mg of 3-pyridyldiethylborane, 428 mg of sodium carbonate in 30 cm$^3$ of water, and 258 mg of tetrakis(triphenylphosphine)palladium are added to 1 g of N-[5-bromo-6-[4-(phenylmethoxy)phenyl]-1-[[2-(trimethylsilyl)ethoxy]methyl]-1H-indazol-3-yl]butanamide, prepared in Example 63, in 100 cm$^3$ of dioxane, and the mixture is refluxed for 18 hours. 100 cm$^3$ of ethyl acetate and 100 cm$^3$ of water are added and the reaction medium is filtered through a sinter funnel packed with Celite. The organic phase is separated out after settling of the phases has taken place, washed successively with 75 cm$^3$ of water and with 75 cm$^3$ of saturated sodium chloride solution, dried over magnesium sulphate, filtered and concentrated under reduced pressure (2 kPa; 50° C.) to give 1.6 g of an oil, which is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined and evaporated under reduced pressure (2 kPa; 50° C.) to give 700 mg of N-[5-(3-pyridyl)-6-[4-(phenylmethoxy)phenyl]-1-[[2-(trimethylsilyl)ethoxy]methyl])-1H-indazol-3-yl]butanamide in the form of a yellow oil.

$^1$H NMR spectrum (300 MHz, $(CD_3)_2SO$-d6, δ in ppm): −0.05 (s: 9H); 0.85 (t, J=8 Hz: 2H); 0.96 (t, J=7.5 Hz: 3H); 1.66 (mt: 2H); 2.42 (t, J=7 Hz: 2H); 3.58 (t, J=8 Hz: 2H); 5.11 (s: 2H); 5.73 (s: 2H); 6.96 (d, J=8.5 Hz: 2H); 7.10 (d, J=8.5 Hz: 2H); from 7.30 to 7.55 (mt: 5H); 7.31 (broad dd, J=7.5 and 5 Hz: 1H); 7.50 (ddd, J=7.5–2.5 and 2 Hz: 1H); 7.72 (s: 1H); 7.92 (s: 1H); 8.31 (broad d, J=2.5 Hz: 1H); 8.43 (dd, J=5 and 2 Hz: 1H); 10.57 (unresolved peak: 1H).

| EI | m/z = 592 | M$^{+\cdot}$ |
|---|---|---|
|   | m/z = 475 | [M—$OCH_2CH_2Si(CH_3)_3$]$^+$ |
|   | m/z = 91 | [$C_6H_5CH_2$]$^+$ |

N-[5-(3-pyridyl)-6-[4-(phenylmethoxy)phenyl]-1H-indazol-3-yl]butanamide 7.1 cm$^3$ of tetrabutylammonium fluoride as a 1M solution in tetrahydrofuran are added to 700 mg of N-[5-(3-pyridyl)-6-[4-(phenylmethoxy)phenyl]-1-[[2-(trimethylsilyl)ethoxy]methyl]-1H-indazol-3-yl]butanamide, described previously, in 50 cm$^3$ of tetrahydrofuran, and the mixture is refluxed for 18 hours; after cooling, 75 cm$^3$ of ethyl acetate are added and the organic phase is washed successively with 2×75 cm$^3$ of saturated sodium hydrogen carbonate solution and then with 50 cm$^3$ of saturated sodium chloride solution. The organic phase is separated out after settling of the phases has taken place, dried over magnesium sulphate, filtered and concentrated to dryness under reduced pressure (2 kPa; 50° C.) to give 850 mg of crude product, which is purified by chromatography under an argon pressure of 50 kPa, on a column of silica gel (particle size 40–60 μm; diameter 3 cm), eluting with a cyclohexane/ethyl acetate mixture (70/30 by volume). The fractions containing the expected product are combined and evaporated under reduced pressure (2 kPa; 50° C.); the residue is dried (90 Pa; 45° C.) to give 460 mg of N-[5-(3-pyridyl)-6-[4-(phenylmethoxy)phenyl]-1H-indazol-3-yl]butanamide in the form of cream-coloured crystals.

$^1$H NMR spectrum (300 MHz, $(CD_3)_2SO$-d6, δ in ppm): 0.95 (t, J=7.5 Hz: 3H); 1.66 (mt: 2H); 2.40 (t, J=7 Hz: 2H); 5.08 (s: 2H); 6.93 (d, J=8.5 Hz: 2H); 7.09 (d, J=8.5 Hz: 2H); 7.29 (broad dd, J=7.5 and 4.5 Hz: 1H); from 7.30 to 7.55 (mt: 6H); 7.40 (s: 1H); 7.86 (s: 1H); 8.28 (broad d, J=2 Hz: 1H); 8.41 (dd, J=4.5 and 2 Hz: 1H); 10.42 (unresolved peak: 1H); 12.76 (unresolved peak: 1H).

| EI | m/z = 462 | M+· |
|----|-----------|-----|
|    | m/z = 392 | [M—C₄CH₆O]⁺ |

N-[5-(3-pyridyl)-6-(4-hydroxyphenyl)-1H-indazol-3-yl]butanamide 10 cm³ of trimethylsilyl iodide are added to 460 mg of N-[5-(3-pyridyl)-6-[4-(phenylmethoxy)phenyl]-1H-indazol-3-yl]butanamide, described previously, and the mixture is refluxed for 18 hours. The insoluble material is filtered off, washed with 2×20 cm³ of diethyl ether and taken up in 50 cm³ of tetrahydrofuran and 25 cm³ of ethyl acetate, and the organic phase is washed with 2×100 cm³ of 10% sodium thiosulphate solution, dried over magnesium sulphate, filtered and then concentrated to dryness under reduced pressure to give 330 mg of crude product, which is purified by chromatography under an argon pressure of 50 kPa, on a column of silica gel (particle size 40–60 μm; diameter 2.5 cm), eluting with a cyclohexane/ethyl acetate mixture (50/50 by volume). The fractions containing the expected product are combined and evaporated under reduced pressure (2 kPa; 50° C.) and the residue is taken up in 10 cm³ of diisopropyl ether, filtered off, washed with 3×5 cm³ of diisopropyl ether, with 5 cm³ of ethyl acetate and then with 10 cm³ of diisopropyl ether and dried (90 Pa; 45° C.) to give 90 mg of N-[5-(3-pyridyl)-6-(4-hydroxyphenyl)-1H-indazol-3-yl]butanamide in the form of cream-coloured crystals melting at 165° C.

¹H NMR spectrum (300 MHz, (CD₃)₂SO-d6, δ in ppm): 0.96 (t, J=7.5 Hz: 3H); 1.66 (mt: 2H); 2.40 (t, J=7 Hz: 2H); 6.66 (d, J=8.5 Hz: 2H); 6.96 (d, J=8.5 Hz: 2H); 7.30 (dd, J=7.5 and 4.5 Hz: 1H); 7.38 (s: 1H); 7.49 (dt, J=7.5 and 2 Hz: 1H); 7.85 (s: 1H); 8.28 (d, J=2 Hz: 1H); 8.41 (dd, J=4.5 and 2 Hz: 1H); 9.46 (unresolved peak: 1H); 10.45 (unresolved peak: 1H); 12.74 (unresolved peak: 1H).

EXAMPLE 102

N-[5-(2-furyl)-6-[4-(Phenylmethoxy)phenyl]-1-[[2-(trimethylsilyl)ethoxy]methyl]-1H-indazol-3-yl]butanamide 353 mg of 2-furylboronic acid, 624 mg of sodium carbonate in 25 cm³ of water, and 311 mg of tetrakis(triphenylphosphine)palladium are added to 1.25 g of N-[5-bromo-6-[4-(phenylmethoxy)phenyl]-1-[[2-(trimethylsilyl)ethoxy]methyl]-1H-indazol-3-yl]butanamide, prepared in Example 63, in 125 cm³ of dioxane, and the mixture is refluxed for 18 hours, 611 mg of 2-furan-2-yl-4,4,5,5-tetramethyl[1,3,2]dioxaborolane are then added and heating is continued for 4 hours at reflux. 75 cm³ of ethyl acetate and 75 cm³ of water are added and the reaction medium is filtered through a sinter funnel packed with Celite. The organic phase is separated out after settling of the phases has taken place, washed with 75 cm³ of water, dried over magnesium sulphate, filtered and concentrated to dryness under reduced pressure (2 kPa; 50° C.) to give 2 g of an oil, which is purified by chromatography under an argon pressure of 50 kPa, on a column of silica gel (particle size 40–60 μm; diameter 3.5 cm), eluting with a cyclohexane/ethyl acetate mixture (75/25 by volume). The fractions containing the expected product are combined and evaporated under reduced pressure (2 kPa; 50° C.) to give 1.20 g of N-[5-(2-furyl)-6-[4-(phenylmethoxy)phenyl]-1-[[2-(trimethylsilyl)ethoxy]methyl]-1H-indazol-3-yl]butanamide in the form of a beige-coloured solid.

¹H NMR spectrum (300 MHz, (CD₃)₂SO-d6, δ in ppm): −0.09 (s: 9H); 0.82 (t, J=8 Hz: 2H); 0.97 (t, J=7.5 Hz: 3H); 1.68 (mt: 2H); 2.43 (t, J=7 Hz: 2H); 3.55 (t, J=8 Hz: 2H); 5.17 (s: 2H); 5.61 (d, J=3.5 Hz: 1H); 5.68 (broad s: 2H); 6.38 (dd, J=3.5 and 1.5 Hz: 1H); 7.07 (d, J=8.5 Hz: 2H); 7.19 (d, J=8.5 Hz: 2H); 7.36 (broad t, J=7.5 Hz: 1H); 7.43 (broad t, J=7.5 Hz: 2H); 7.50 (broad d, J=7.5 Hz: 2H); 7.59 (s: 1H); 7.61 (d, J=1.5 Hz: 1H); 8.20 (s: 1H); 10.58 (unresolved peak: 1H).

| EI | m/z = 581 | M+· |
|----|-----------|-----|
|    | m/z = 464 | [M—OCH₂CH₂Si(CH₃)₃]⁺ |
|    | m/z = 91  | [C₆H₅CH₂]⁺ |

N-[5-(2-furyl)-6-[4-(phenylmethoxy)phenyl]-1H-indazol-3-yl]butanamide 12.4 cm³ of tetrabutylammonium fluoride as a 1M solution in tetrahydrofuran are added to 1.20 g of N-[5-(2-furyl)-6-[4-(phenylmethoxy)phenyl]-1-[[2-(trimethylsilyl)ethoxy]methyl]-1H-indazol-3-yl]butanamide, described previously, in 50 cm³ of tetrahydrofuran, and the mixture is refluxed for 18 hours; after cooling, 75 cm³ of ethyl acetate are added and the organic phase is washed successively with 2×50 cm³ of saturated sodium hydrogen carbonate solution and with 50 cm³ of saturated sodium chloride solution. The organic phase is separated out after settling of the phases has taken place, dried over magnesium sulphate, filtered and concentrated to dryness under reduced pressure (2 kPa; 50° C.) to give 1.5 g of crude product, which is purified by chromatography under an argon pressure of 50 kPa, on a column of silica gel (particle size 40–60 μm; diameter 3.5 cm), eluting with a cyclohexane/ethyl acetate mixture (60/40 by volume). The fractions containing the expected product are combined and evaporated under reduced pressure (2 kPa; 50° C.); the residue is dried (90 Pa; 45° C.) to give 750 mg of N-[5-(2-furyl)-6-[4-(phenylmethoxy)phenyl]-1H-indazol-3-yl]butanamide in the form of a yellow oil.

¹H NMR spectrum (300 MHz, (CD₃)₂SO-d6, δ in ppm): 0.98 (t, J=7.5 Hz: 3H); 1.68 (mt: 2H); 2.42 (t, J=7 Hz: 2H); 5.16 (s: 2H); 5.60 (d, J=3.5 Hz: 1H); 6.37 (dd, J=3.5 and 1.5 Hz: 1H); 7.06 (d, J=8.5 Hz: 2H); 7.20 (d, J=8.5 Hz: 2H); 7.28 (s: 1H); 7.36 (broad t, J=7.5 Hz: 1H); 7.43 (broad t, J=7.5 Hz: 2H); 7.51 (broad d, J=7.5 Hz: 2H); 7.59 (broad s: 1H); 8.15 (s: 1H); 10.44 (unresolved peak: 1H); 12.73 (unresolved peak: 1H).

| EI | m/z = 451 | M+· |
|----|-----------|-----|
|    | m/z = 381 | [M—C₄CH₆O]⁺· |

N-[5-(2-furyl)-6-(4-hydroxyphenyl)-1H-indazol-3-yl]butanamide 10 cm³ of trimethylsilyl iodide are added to 750 mg of N-[(5-(2-furyl)-6-[4-(phenylmethoxy)phenyl]-1H-indazol-3-yl)]butanamide, described previously, and the mixture is refluxed for 18 hours. 40 cm³ of methanol are added and the reaction medium and the mixture is refluxed for 10 minutes and then concentrated to dryness under reduced pressure (2 kPa; 50° C.). The residue is taken up in 75 cm³ of ethyl acetate and 50 cm³ of tetrahydrofuran and the organic phase is washed with 2×75 cm³ of 10% sodium thiosulphate solution and then with 75 cm³ of saturated sodium chloride solution. The organic phase is separated out after settling of the phases has taken place, dried over magnesium sulphate, filtered and then concentrated to dryness under reduced pressure to give 700 mg of crude product, which is purified by chromatography under an argon pressure of 50 kPa, on a column of silica gel (particle size 40–60 µm; diameter 2.5 cm), eluting with a cyclohexane/ethyl acetate mixture (50/50 by volume). The fractions containing the expected product are combined and evaporated under reduced pressure (2 kPa; 50° C.); the residue is taken up in 3 cm$^3$ of ethyl acetate, filtered off, washed with 2 cm$^3$ of ethyl acetate, then with 15 cm$^3$ of diisopropyl ether and dried (90 Pa; 45° C.) to give 10 mg of N-[5-(2-furyl)-6-(4-hydroxyphenyl)-1H-indazol-3-yl] butanamide in the form of white crystals melting at 190° C.

$^1$H NMR spectrum (300 MHz, (CD$_3$)$_2$SO-d6, δ in ppm): 0.98 (t, J=7.5 Hz: 3H); 1.69 (mt: 2H); 2.43 (t, J=7 Hz: 2H); 5.58 (d, J=3.5 Hz: 1H); 6.38 (dd, J=3.5 and 1.5 Hz: 1H); 6.80 (d, J=8.5 Hz: 2H); 7.08 (d, J=8.5 Hz: 2H); 7.26 (s: 1H); 7.59 (broad s: 1H); 8.14 (s: 1H); 9.54 (unresolved peak: 1H); 10.44 (unresolved peak: 1H); 12.70 (unresolved peak: 1H).

EXAMPLE 103

N-(5-bromo-6-chloro-7-nitro-1H-indazol-3-yl) butanamide 418 mg of nitronium tetrafluoroborate are added to 4 g of N-(5-bromo-6-chloro-1H-indazol-3-yl)butanamide, described in Example 58, in 50 cm$^3$ of acetonitrile at 0° C., and the mixture is stirred for 4 hours. 200 cm$^3$ of ethyl acetate and 100 cm$^3$ of saturated sodium hydrogen carbonate solution are added to the reaction medium. The organic phase is washed with 2×40 cm$^3$ of saturated sodium hydrogen carbonate solution and then with 40 cm$^3$ of saturated sodium chloride solution. The organic phase is separated out after settling of the phases has taken place, dried over magnesium sulphate, filtered and concentrated to dryness under reduced pressure (2 kPa; 50° C.) to give 840 mg of crude product, which is purified by chromatography under an argon pressure of 50 kPa, on a column of silica gel (particle size 40–60 µm; diameter 3.5 cm), eluting with a cyclohexane/ethyl acetate mixture (80/20 by volume). The fractions containing the expected product are combined and evaporated under reduced pressure (2 kPa; 50° C.) and then dried (90 Pa; 45° C.) to give 20 mg of N-(5-bromo-6-chloro-7-nitro-1H-indazol-3-yl)butanamide in the form of a yellow solid melting above 260° C.

$^1$H NMR spectrum (300 MHz, (CD$_3$)$_2$SO-d6, δ in ppm): 0.97 (t, J=7.5 Hz: 3H); 1.68 (mt: 2H); 2.44 (t, J=7 Hz: 2H); 8.70 (s: 1H); 10.80 (unresolved peak: 1H); 13.63 (unresolved peak: 1H).

| EI | m/z = 360 | M$^{+\cdot}$ |
|---|---|---|
|  | m/z = 290 | [M—C$_4$CH$_6$O]$^{+\cdot}$ |

EXAMPLE 104

N-(6,7-difluoro-1-[[2-(trimethylsilyl)ethoxy] methyl]-1H-indazol-3-yl)butanamide A solution of 1.1 g of N-(6,7-difluoro-1H-indazol-3-yl) butanamide, prepared in Example 40, in 180 cm$^3$ of dimethylformamide is added dropwise over 3 hours to 1.65 g of sodium hydride at 60% in oil, in 50 cm$^3$ of dimethylformamide. The reaction medium is concentrated to dryness under reduced pressure and taken up in 250 cm$^3$ of ethyl acetate and 200 cm$^3$ of water; the organic phase is separated out after settling of the phases has taken place, washed with 150 cm$^3$ of water, dried over magnesium sulphate, filtered and concentrated to dryness under reduced pressure (2 kPa; 50° C.). The crude product is purified by chromatography under an argon pressure of 50 kPa, on a column of silica gel (particle size 40–60 µm; diameter 6 cm), eluting with a cyclohexane/ethyl acetate mixture (80/20 by volume). The fractions containing the expected product are combined and evaporated under reduced pressure (2 kPa; 50° C.) to give 7.3 g of N-[6,7-difluoro-1-[[2-(trimethylsilyl)ethoxy] methyl]-1H-indazol-3-yl]butanamide in the form of a yellow oil.

$^1$H NMR spectrum (300 MHz, (CD$_3$)$_2$SO-d6, δ in ppm): −0.09 (s: 9H); 0.82 (t, J=8 Hz: 2H); 0.96 (t, J=7.5 Hz: 3H); 1.67 (mt: 2H); 2.41 (t, J=7 Hz: 2H); 3.56 (t, J=8 Hz: 2H); 5.66 (s: 2H); 7.22 (ddd, J=11–9 and 7 Hz: 1H); 7.69 (broad dd, J=9 and 4.5 Hz: 1H); 10.60 (unresolved peak: 1H).

| EI | m/z = 369 | M$^{+\cdot}$ |
|---|---|---|
|  | m/z = 252 | [M—OCH$_2$CH$_2$Si(CH$_3$)$_3$]$^+$ |
|  | m/z = 241 | [M—C$_6$H$_{12}$OSi]$^{+\cdot}$ |

N-(5-bromo-6,7-difluoro-1-[[2-(trimethylsilyl) ethoxy]methyl]-1H-indazol-3-yl)butanamide 0.87 cm$^3$ of pyridine is added to 1 g of N-[6,7-difluoro-1-[[2-(trimethylsilyl)ethoxy]methyl]-1H-indazol-3-yl] butanamide, described previously, in 30 cm$^3$ of chloroform, followed by addition of 0.56 cm$^3$ of bromine, and the mixture is refluxed overnight. 50 cm$^3$ of dichloromethane and 50 cm$^3$ of aqueous 10% sodium thiosulphate solution are added to the reaction medium. After stirring for 10 minutes, the insoluble material is removed by filtration on a sinter funnel and the organic phase is washed with 50 cm$^3$ of water and with 50 cm$^3$ of saturated sodium chloride solution. The organic phase is separated out after settling of the phases has taken place, dried over magnesium sulphate, filtered and concentrated to dryness under reduced pressure (2 kPa; 45° C.). The crude product, 1.1 g, is purified by chromatography under an argon pressure of 50 kPa, on a column of silica gel (particle size 40–60 µm; diameter 3 cm), eluting with a cyclohexane/ethyl acetate mixture (90/10 by volume). The fractions containing the expected product are combined and evaporated under reduced pressure (2 kPa; 50° C.). After drying (90 Pa; 45° C.), 230 mg of N-(5-bromo-6,7-difluoro-1-[[2-(trimethylsilyl)ethoxy]methyl]-1H-indazol-3-yl)butanamide are obtained in the form of a colourless oil.

$^1$H NMR spectrum (300 MHz, (CD$_3$)$_2$SO-d6, δ in ppm): −0.05 (s: 9H); 0.84 (t, J=8 Hz: 2H); 0.95 (t, J=7.5 Hz: 3H); 1.66 (mt: 2H); 2.43 (t, J=7 Hz: 2H); 3.59 (t, J=8 Hz: 2H); 5.69 (s: 2H); from 7.40 to 7.65 (mt: 5H); 7.82 (broad d, J=7 Hz: 1H); 10.64 (unresolved peak: 1H).

| EI | m/z = 447 | M$^{+\cdot}$ |
|---|---|---|
|  | m/z = 330 | [M—OCH$_2$CH$_2$Si(CH$_3$)$_3$]$^+$ |
|  | m/z = 319 | [M—C$_6$H$_{12}$OSi]$^{+\cdot}$ |

N-(5-bromo-6,7-difluoro-1H-indazol-3-yl) butanamide 9.4 cm$^3$ of tetrabutylammonium fluoride as a 1M solution in tetrahydrofuran are added to 700 mg of N-[5-bromo-6,7- difluoro-1-[[2-(trimethylsilyl)ethoxy]methyl]-1H-indazol-3-yl]butanamide, described previously, in 30 cm³ of tetrahydrofuran, and the mixture is refluxed for 18 hours; after cooling, 100 cm³ of ethyl acetate and 75 cm³ of saturated sodium hydrogen carbonate solution are added and the organic phase is then washed successively with 75 cm³ of saturated sodium hydrogen carbonate solution and with 75 cm³ of saturated sodium chloride solution. The organic phase is separated out after settling of the phases has taken place, dried over magnesium sulphate and concentrated to dryness under reduced pressure (2 kPa; 50° C.) to give 850 mg of crude product, which is purified by chromatography under an argon pressure of 50 kPa, on a column of silica gel (particle size 40–60 μm; diameter 3 cm), eluting with a cyclohexane/ethyl acetate mixture (80/20 by volume). The fractions containing the expected product are combined and evaporated under reduced pressure (2 kPa; 50° C.); the residue is taken up in 8 cm³ of diisopropyl ether, filtered off, washed with 3 cm³ of diisopropyl ether, dried under reduced pressure (90 Pa; 45° C.) to give 200 mg of N-(5-bromo-6,7-difluoro-1H-indazol-3-yl)butanamide in the form of white crystals melting at 220° C.

$^1$H NMR spectrum (300 MHz, $(CD_3)_2$SO-d6, δ in ppm): 0.95 (t, J=7.5 Hz: 3H); 1.66 (mt: 2H); 2.41 (t, J=7 Hz: 2H); 8.03 (dd, J=6 and 2 Hz: 1H); 10.58 (broad s: 1H); 13.56 (unresolved peak: 1H).

EXAMPLE 105

N-[6-(4-cyanophenyl)-1-[[2-(trimethylsilyl)ethoxy]methyl]-1H-indazol-3-yl]butanamide 853 mg of 4-cyanophenylboronic acid, 15 cm³ of water, 1.0 g of sodium carbonate and 314 mg of tetrakis(triphenylphosphine)palladium are added to 500 mg of N-[6-bromo-1-[[2-(trimethylsilyl)ethoxy]methyl]-1H-indazol-3-yl]butanamide, prepared as described in Example 51, in 100 cm³ of dioxane. The reaction medium is then refluxed for 4 hours and diluted with 70 cm³ of ethyl acetate and 75 cm³ of water. The organic phase is separated out after settling of the phases has taken place and washed with 50 cm³ of distilled water and then with 2×50 cm³ of saturated aqueous sodium chloride solution. The organic phase is separated out after settling of the phases has taken place, dried over magnesium sulphate, filtered and concentrated to dryness under reduced pressure (2 kPa; 45° C.). The residue obtained, 2.0 g, is purified by chromatography under an argon pressure of 50 kPa, on a column of silica gel (particle size 40–60 μm; diameter 4 cm), eluting with a cyclohexane/ethyl acetate mixture (70/30 by volume). The fractions containing the expected product are combined and evaporated under reduced pressure (2 kPa; 50° C.); 1.0 g of N-[6-(4-cyanophenyl)-1-[[2-(trimethylsilyl)ethoxy]methyl]-1H-indazol-3-yl]butanamide is obtained in the form of a yellow solid melting at 136° C.

$^1$H NMR spectrum (300 MHz, $(CD_3)_2$SO-d6, δ in ppm): −0.09 (s: 9H); 0.83 (t, J=8 Hz: 2H); 0.98 (t, J=7.5 Hz: 3H); 1.69 (mt: 2H); 2.43 (t, J=7 Hz: 2H); 3.58 (t, J=8 Hz: 2H); 5.76 (s: 2H); 7.53 (broad d, J=8.5 Hz: 1H); from 7.95 to 8.05 (mt: 4H); 7.97 (d, J=8.5 Hz: 1H); 8.11 (s: 1H); 10.55 (unresolved peak: 1H).

N-[6-(4-cyanophenyl)-1H-indazol-3-yl]butanamide 3.0 cm³ of tetrabutylammonium fluoride as a 1M solution in tetrahydrofuran are added to 400 mg of N-[6-(4-cyanophenyl)-1-[[2-(trimethylsilyl)ethoxy]methyl]-1H-indazol-3-yl]butanamide, described previously, in 10 cm³ of tetrahydrofuran, and the mixture is refluxed for 18 hours. The reaction medium is diluted with 20 cm³ of ethyl acetate and the organic phase is washed successively with 20 cm³ of saturated sodium hydrogen carbonate solution, with 2×20 cm³ of water and with 20 cm³ of saturated sodium chloride solution. The organic phase is separated out after settling of the phases has taken place, dried over magnesium sulphate, filtered and then concentrated under reduced pressure (2 kPa; 50° C.). The crude product obtained is purified by chromatography under an argon pressure of 50 kPa, on a column of silica gel (particle size 40–60 μm; diameter 3 cm), eluting with a methylene chloride/methanol gradient (100/0 to 98/2 by volume). The fractions containing the expected product are combined and evaporated under reduced pressure (2 kPa; 50° C.); 120 mg of N-[6-(4-cyanophenyl)-1H-indazol-3-yl]butanamide are obtained in the form of a solid melting at 242° C.

$^1$H NMR spectrum (300 MHz, $(CD_3)_2$SO-d6, δ in ppm): 0.98 (t, J=7 Hz: 3H); 1.68 (mt: 2H); 2.40 (t, J=7 Hz: 2H); 7.42 (broad d, J=9 Hz: 1H); 7.74 (broad s: 1H); 7.92 (d, J=9 Hz: 1H); 7.96 (s: 4H); 10.37 (unresolved peak: 1H); 12.81 (unresolved peak: 1H).

EXAMPLE 106

N-(6,7-difluoro-5-nitro-1H-indazol-3-yl)butanamide 555 mg of nitronium tetrafluoroborate are added to a suspension of 500 mg of N-(6,7-difluoro-1H-indazol-3-yl)butanamide, prepared in Example 40, in 30 cm³ of acetonitrile and cooled to 0° C. After reaction for 30 minutes, 50 cm³ of ethyl acetate and 50 cm³ of saturated sodium hydrogen carbonate solution are added to the reaction medium. The organic phase is separated out after settling of the phases has taken place, washed with 50 cm³ of water and 50 cm³ of saturated sodium chloride solution, dried over magnesium sulphate, filtered and then concentrated to dryness under reduced pressure (2 kPa; 50° C.) to give 630 mg of a brown oil. The crude product is purified by chromatography under an argon pressure of 50 kPa, on a column of silica gel (particle size 40–60 μm; diameter 3.5 cm), eluting with a cyclohexane/ethyl acetate mixture (70/30 by volume). The fractions containing the expected product are combined, evaporated under reduced pressure (2 kPa; 50° C.) and dried (90 Pa, 45° C.); to give 300 mg of N-(6,7-difluoro-5-nitro-1H-indazol-3-yl)butanamide in the form of yellow crystals melting at 255° C.

$^1$H NMR spectrum (300 MHz, $(CD_3)_2$SO-d6, δ in ppm): 0.96 (t, J=7.5 Hz: 3H); 1.68 (mt: 2H); 2.45 (t, J=7 Hz: 2H); 8.89 (dd, J=6.5 and 2 Hz: 1H); 10.94 (unresolved peak: 1H); 14.05 (broad unresolved peak: 1H).

| EI | m/z = 284 | M$^{+\cdot}$ |
|---|---|---|
| | m/z = 214 | [M—C$_4$CH$_6$O]$^{+\cdot}$ |

EXAMPLE 107

N-[6,7-difluoro-5-phenyl-1-[[2-(trimethylsilyl)ethoxy]methyl]-1H-indazol-3-yl]butanamide 469 mg of phenylboronic acid, 760 mg of sodium carbonate in 30 cm³ of water and 379 mg of tetrakis(triphenylphosphine)palladium are added to 1.15 g of N-(5-bromo-6,7-difluoro-1-[[2-(trimethylsilyl)ethoxy]methyl]-1H-indazol-3-yl)butanamide, prepared in Example 104, in 150 cm³ of dioxane, and the mixture is refluxed for 4 hours. The reaction medium is diluted with 100 cm³ of ethyl acetate and 75 cm³ of water and filtered through a sinter funnel packed with Celite. The organic phase is separated out after settling of the phases has taken place, washed with 75 cm³ of water and with 75 cm³ of saturated sodium chloride solution, dried over magnesium sulphate, filtered and concentrated to dryness under reduced pressure (2 kPa; 50° C.) to give 2 g of crude product in the form of a black oil. The crude product is purified by chromatography under an argon pressure of 50 kPa, on a column of silica gel (particle size 40–60 µm; diameter 3.5 cm), eluting with a cyclohexane/ethyl acetate mixture (85/15 by volume). The fractions containing the expected product are combined, evaporated under reduced pressure (2 kPa; 50° C.) and dried (90 Pa, 45° C.); to give 1.1 g of N-[6,7-difluoro-5-phenyl-1-[[2-(trimethylsilyl)ethoxy]methyl]-1H-indazol-3-yl]butanamide in the form of a yellow oil.

¹H NMR spectrum (300 MHz, (CD₃)₂SO-d6, δ in ppm): −0.05 (s: 9H); 0.84 (t, J=8 Hz: 2H); 0.95 (t, J=7.5 Hz: 3H); 1.66 (mt: 2H); 2.43 (t, J=7 Hz: 2H); 3.59 (t, J=8 Hz: 2H); 5.69 (s: 2H); from 7.40 to 7.65 (mt: 5H); 7.82 (broad d, J=7 Hz: 1H); 10.64 (unresolved peak: 1H).

| EI | m/z = 445 | M⁺· |
| | m/z = 328 | [M—OCH₂CH₂Si(CH₃)₃]⁺ |
| | m/z = 317 | [M—C₆H₁₂OSi]⁺· |

N-(6,7-difluoro-5-phenyl-1H-indazol-3-yl) butanamide 14.8 cm³ of tetrabutylammonium fluoride as a 1M solution in tetrahydrofuran are added to 1.1 g of N-[6,7-difluoro-5-phenyl-1-[[2-(trimethylsilyl)ethoxy]methyl]-1H-indazol-3-yl]butanamide, described previously, in 50 cm³ of tetrahydrofuran, and the mixture is refluxed for 18 hours; as the reaction is incomplete, a further 9.9 cm³ of tetrabutylammonium fluoride solution are added and refluxing is continued for 18 hours. After cooling, 100 cm³ of ethyl acetate and 75 cm³ of saturated sodium hydrogen carbonate solution are added; the organic phase is separated out after settling of the phases has taken place and washed with 50 cm³ of saturated sodium chloride solution, dried over magnesium sulphate, filtered and concentrated to dryness under reduced pressure (2.7 kPa; 50° C.) to give 1.3 g of crude product, which is purified by chromatography under an argon pressure of 50 kPa, on a column of silica gel (particle size 40–60 µm; diameter 3.5 cm), eluting with a cyclohexane/ethyl acetate mixture (70/30 by volume). The fractions containing the expected product are combined and evaporated under reduced pressure (2 kPa; 50° C.); the solid obtained is taken up in 20 cm³ of diisopropyl ether, filtered off on a sinter funnel and washed with 5 cm³ of ethyl acetate and 20 cm³ of diisopropyl ether, and then dried (90 Pa; 45° C.) to give 340 mg of N-(6,7-difluoro-5-phenyl)-1H-indazol-3-yl)butanamide in the form of a white cottony solid melting at 224° C.

¹H NMR spectrum (300 MHz, (CD₃)₂SO-d6, δ in ppm): 0.95 (t, J=7.5 Hz: 3H); 1.66 (mt: 2H); 2.41 (t, J=7 Hz: 2H); from 7.40 to 7.60 (mt: 5H); 7.76 (broad d, J=6 Hz: 1H); 10.53 (unresolved peak: 1H); from 13.00 to 13.90 (broad unresolved peak: 1H).

| EI | m/z = 284 | M⁺· |
| | m/z = 245 | [M—C₄CH₆O]⁺· |

EXAMPLE 108

5-Bromo-2-[[2-(trimethylsilyl)ethoxy]methoxy] pyridine

A solution of 2.6 g of 5-bromo-2-hydroxypyridine in 80 cm³ of dimethylformamide is added over 30 minutes to 717 mg of sodium hydride at 60% in oil, in 50 cm³ of dimethylformamide, and the mixture is stirred for 1 hour at room temperature. The dimethylformamide is removed under reduced pressure and the residue is taken up in 75 cm³ of ethyl acetate and 50 cm³ of water; the organic phase is separated out after settling of the phases has taken place, washed with 2×50 cm³ of water and 50 cm³ of saturated sodium chloride solution, dried over magnesium sulphate, filtered and concentrated to dryness under reduced pressure (2 kPa; 50° C.) to give a yellow oil. The crude product is purified by chromatography under an argon pressure of 50 kPa, on a column of silica gel (particle size 40–60 µm; diameter 3.5 cm), eluting with a cyclohexane/ethyl acetate mixture (60/40 by volume). The fractions containing the expected product are combined and evaporated under reduced pressure (2 kPa; 50° C.) to give 2.64 g of 5-bromo-2-[[2-(trimethylsilyl)ethoxy]methyl]pyridine in the form of a yellow oil, which is used without further purification for the following test.

¹H NMR spectrum (300 MHz, (CD₃)₂SO-d6, δ in ppm): −0.02 (s: 9H); 0.89 (t, J=8 Hz: 2H); 3.73 (t, J=8 Hz: 2H); 5.49 (s: 2H); 6.89 (broad d, J=8.5 Hz: 1H); 7.96 (dd, J=8.5 and 2.5 Hz: 1H); 8.31 (broad d, J=2.5 Hz: 1H). DCI m/z=304 [M+H]⁺

N-[6-[6-[[2-(trimethylsilyl)ethoxy]methoxy]pyridyl-3-yl]-1-[[2-(trimethylsilyl)ethoxy]methyl]-1H-indazol-3-yl]butanamide 1.19 g of 5-bromo-2-[[2-(trimethylsilyl)ethoxy]methoxy] pyridine, prepared previously, are added to 1 g of N-[6-(4,4,5,5-tetramethyl[1,3,2]dioxaborolan-2-yl)-1-[[2-(trimethylsilyl)ethoxy]methyl]-1H-indazol-3-yl] butanamide, prepared in Example 56, in 70 cm³ of dioxane, and 201 mg of tetrakis(triphenylphosphine)palladium and 646 mg of sodium carbonate in 10 cm³ of water are added to the pale yellow solution, and the mixture is refluxed for 3 hours. The reaction medium is diluted with 75 cm³ of ethyl acetate and 50 cm³ of water and is filtered through a sinter funnel packed with Celite. The organic phase is separated out after settling of the phases has taken place, washed with 50 cm³ of water, with 50 cm³ of saturated sodium chloride solution, dried over magnesium sulphate, filtered and concentrated under reduced pressure (2 kPa; 50° C.). The crude product obtained is purified by chromatography under an argon pressure of 50 kPa, on a column of silica gel (particle size 40–60 µm; diameter 4.5 cm), eluting with a cyclohexane/ethyl acetate mixture (70/30 by volume). The fractions containing the expected product are combined and evaporated under reduced pressure (2 kPa; 50° C.) to give 0.45 g of N-[6-[6-[[2-(trimethylsilyl)-ethoxy]methoxy] pyridyl-3-yl]-[[2(trimethylsilyl)ethoxy]methyl]-1H-indazol-3-yl]butanamide in the form of an orange-coloured lacquer.

¹H NMR spectrum (300 MHz, (CD₃)₂SO-d6, δ in ppm): −0.09 (s: 9H); 0.00 (s: 9H); 0.83 (t, J=8 Hz: 2H); 0.93 (t, J=8

Hz: 2H); 0.98 (t, J=7.5 Hz: 3H); 1.69 (mt: 2H); 2.41 (t, J=7 Hz: 2H); 3.56 (t, J=8 Hz: 2H); 3.79 (t, J=8 Hz: 2H); 5.59 (s: 2H); 5.74 (broad s: 2H); 7.02 (d, J=8.5 Hz: 1H); 7.47 (broad d, J=8.5 Hz: 1H); 7.92 (d, J=8.5 Hz: 1H); 8.00 (broad s: 1H); 8.18 (dd, J=8.5 and 2.5 Hz: 1H); 8.61 (d, J=2.5 Hz: 1H); 10.53 (unresolved peak: 1H).

| EI | m/z = 556 | M+· |
|---|---|---|
|  | m/z = 439 | [M—OCH$_2$CH$_2$Si(CH$_3$)$_3$]+ |
|  | m/z = 73 | [Si(CH$_3$)$_3$]+ |

N-[6-(6-hydroxypyrid-3-yl)-1H-indazol-3-yl]butanamide 15.7 cm$^3$ of tetrabutylammonium fluoride as a 1M solution in tetrahydrofuran are added to 0.73 g of N-[6-[6-[[2-(trimethylsilyl)ethoxy]methoxy]pyridyl-3-yl]-1[[2-(trimethylsilyl)ethoxy]methyl]-1H-indazol-3-yl] butanamide, described previously, in 15 cm$^3$ of tetrahydrofuran, and the mixture is refluxed for 18 hours; as the reaction is incomplete, refluxing is continued for 18 hours. After cooling, 60 cm$^3$ of ethyl acetate are added and the organic phase is washed with 30 cm$^3$ of saturated sodium hydrogen carbonate solution and then with 2×30 cm$^3$ of water and with 30 cm$^3$ of saturated sodium chloride solution. The organic phase is separated out after settling of the phases has taken place, dried over magnesium sulphate, filtered and concentrated to dryness under reduced pressure (2 kPa; 50° C.) to give 1.3 g of crude product, which is purified by chromatography under an argon pressure of 50 kPa, on a column of silica gel (particle size 40–60 μm; diameter 3 cm), eluting with a methylene chloride/methanol gradient (95/5 to 90/10 by volume). The fractions containing the expected product are combined and evaporated under reduced pressure (2 kPa; 50° C.) to give 270 mg of product which is still impure, which is repurified by HPLC (X Terra column; C$_{18,}$ 5 μm; length 100 mm, diameter 30 mm, eluent: methanol/water (70/30 by volume) containing 0.05% trifluoroacetic acid; flow rate 20 cm$^3$/min). After concentrating the fractions containing the expected product and drying (90 Pa; 45° C.), 40 mg of N-[6-(6-hydroxypyrid-3-yl)-1H-indazol-3-yl]butanamide are obtained in the form of a solid melting above 260° C.

$^1$H NMR spectrum (300 MHz, (CD$_3$)$_2$SO-d6, δ in ppm): 0.98 (t, J=7.5 Hz: 3H); 1.68 (mt: 2H); 2.39 (t, J=7 Hz: 2H); 6.47 (d, J=9.5 Hz: 1H); 7.25 (broad d, J=9 Hz: 1H); 7.52 (broad s: 1H); 7.77 (d, J=2.5 Hz: 1H); 7.81 (d, J=9 Hz: 1H); 7.90 (dd, J=9.5 and 2.5 Hz: 1H); 10.30 (broad s: 1H); 11.83 (unresolved peak: 1H); 12.62 (unresolved peak: 1H).

| EI | m/z = 296 | M+· |
|---|---|---|
|  | m/z = 226 | [M—C$_4$CH$_6$O]+· |

EXAMPLE 109

N-[6-(2,2-diphenyl-benzo[1,3]dioxol-5-yl)-1-[[2-(trimethylsilyl)ethoxy]methoxy]-1H-indazol-3-yl]butanamide 1.38 g of 5-bromo-2,2-diphenyl-1,3-benzodioxole, prepared according to European patent application EP 303 172 A2, are added to 1.2 g of N-[6-(4,4,5,5-tetramethyl[1,3,2]dioxaborolan-2-yl)-1-[[2-(trimethylsilyl)ethoxy]methyl]-1H-indazol-3-yl]butanamide, prepared in Example 56, in 80 cm$^3$ of dioxane, and 242 mg of tetrakis(triphenylphosphine) palladium and 688 mg of sodium carbonate in 10 cm$^3$ of water are added to the pale yellow solution, and the mixture is refluxed for 4 hours. The reaction medium is diluted with 50 cm$^3$ of ethyl acetate and 50 cm$^3$ of water, and then filtered through a sinter funnel packed with Celite. The filtrate is separated by settling and the organic phase is washed with 50 cm$^3$ of water and with 50 cm$^3$ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 4.5 cm), eluting with a cyclohexane/ethyl acetate mixture (70/30 by volume). The fractions containing the expected product are combined and evaporated under reduced pressure (2 kPa; 50° C.); 840 mg of N-[6-(2,2-diphenyl-1,3-benzodioxole-5-yl)-1-[[2-(trimethylsilyl)ethoxy]-methoxy]-1H-indazol-3-yl] butanamide are obtained in the form of a sticky orange-coloured solid.

| EI | m/z = 605 | M+· |
|---|---|---|
|  | m/z = 488 | [M—OCH$_2$CH$_2$Si(CH$_3$)$_3$]+ |

N-[6-(3,4-dihydroxy-phenyl)-1H-indazol-3-yl]butanamide trifluoroacetate 10 cm$^3$ of trimethylsilyl iodide are added to 0.8 g of N-[6-(2,2-diphenyl-1,3-benzodioxole-5-yl)-1-[[2-(trimethylsilyl)ethoxy]methoxy]-1H-indazol-3-yl] butanamide, prepared previously, and the mixture is refluxed for 3 hours. 50 cm$^3$ of methanol are then added cautiously and refluxing is continued for 15 minutes. The reaction medium is concentrated to dryness under reduced pressure (2 kPa; 50° C.) and taken up in 50 cm$^3$ of ethyl acetate and 100 cm$^3$ of 10% sodium thiosulphate solution; the insoluble material formed is removed by filtration and the filtrate is separated by settling. The organic phase is dried over magnesium sulphate, filtered and concentrated to dryness under reduced pressure. The crude product is purified by chromatography under an argon pressure of 50 kPa, on a column of silica gel (particle size 40–60 μm; diameter 3 cm), eluting with a methylene chloride/methanol/7N aqueous ammonia gradient (97/3 by volume). The fractions containing the expected product are combined and evaporated under reduced pressure (2 kPa; 50° C.) to give 150 mg of product which is still impure, which is repurified by HPLC (X Terra column; C$_{18}$, 5 μm; length 100 mm, diameter 30 mm, eluent: acetonitrile/water gradient (15/85 to 45/55 by volume) containing 0.05% trifluoroacetic acid; flow rate 20 cm$^3$/min). After concentrating the fractions containing the expected product and drying (90 Pa; 45° C.), 30 mg of N-[6-(3,4-dihydroxy-phenyl)-1H-indazol-3-yl]butanamide trifluoroacetate are obtained in the form of a brown powder melting at 236° C.

$^1$H NMR spectrum (300 MHz, (CD$_3$)$_2$SO-d6, δ in ppm): 0.98 (t, J=7.5 Hz: 3H); 1.69 (mt: 2H); 2.40 (t, J=7 Hz: 2H); 6.85 (d, J=8 Hz: 1H); 7.01 (dd, J=8 and 2 Hz: 1H); 7.10 (d, J=2 Hz: 1H); 7.26 (broad d, J=9 Hz: 1H); 7.46 (broad s: 1H); 7.79 (d, J=9 Hz: 1H); from 8.80 to 9.30 (broad unresolved peak: 2H); 10.29 (broad s: 1H); 12.57 (unresolved peak: 1H).

| EI | m/z = 311 | M+· |
| | m/z = 241 | [M—C$_4$CH$_6$O]+· |

EXAMPLE 110

N-[6-(1,3-benzodioxol-5-yl)-1-[[2-(trimethylsilyl)ethoxy]methoxy]-1H-indazol-3-yl)butanamide 677 g of 1,3-benzodioxol-5-yl-boronic acid, 1.24 g of caesium fluoride, then 13.5 mg of palladium acetate and finally 31 mg of 2-dicyclohexylphosphine-2-(N,N-dimethylamino)biphenyl are added to 1 g of N-[6-chloro-1-[[2-(trimethylsilyl)ethoxy]methyl]-1H-indazol-3-yl]butanamide, described previously, in 30 cm³ of dioxane. The reaction mixture is then heated at about 94° C. for 15 hours and is then allowed to return to 19° C. and filtered through a sinter funnel packed with Celite. The product is rinsed with ethyl acetate and the organic phase is then dried over magnesium sulphate and filtered, and the filtrate is evaporated under reduced pressure (2 kPa; 45° C.). The residue is purified by chromatography under an argon pressure of 50 kPa, on a column of silica gel (particle size 15–40 μm; diameter 3 cm), eluting with a cyclohexane/ethyl acetate mixture (80/20 by volume); the fractions containing the expected product are combined and evaporated under reduced pressure (2 kPa; 50° C.). 620 mg of N-[6-(1,3-benzodioxol-5-yl)-1-[[2-(trimethylsilyl)ethoxy]methoxy]-1H-indazol-3-yl]butanamide are obtained in the form of a sticky pale yellow solid.

¹H NMR spectrum (300 MHz, (CD$_3$)$_2$SO-d6, δ in ppm): −0.09 (s: 9H); 0.83 (t, J=8 Hz: 2H); 0.98 (t, J=7.5 Hz: 3H); 1.68 (mt: 2H); 2.41 (t, J=7 Hz: 2H); 3.56 (t, J=8 Hz: 2H); 5.74 (broad s: 2H); 6.10 (s: 2H); 7.05 (d, J=8 Hz: 1H); 7.27 (dd, J=8 and 2 Hz: 1H); 7.37 (d, J=2 Hz: 1H); 7.42 (broad dd, J=9 and 1.5 Hz: 1H); 7.86 (d, J=9 Hz: 1H); 7.89 (broad s: 1H); 10.45 (unresolved peak: 1H).

| EI | m/z = 493 | M+· |
| | m/z = 336 | [M—OCH$_2$CH$_2$Si(CH$_3$)$_3$]+ |
| | m/z = 325 | [M—C$_6$H$_{12}$OSi]+· |

N-[6-(1,3-benzodioxol-5-yl)-1H-indazol-3-yl]butanamide 2 cm³ of tetrabutylammonium fluoride as a 1M solution in tetrahydrofuran are added to 600 mg of N-[6-(benzodioxol-5-yl)-1-[[2-(trimethylsilyl)ethoxy]methoxy]-1H-indazol-3-yl]butanamide, described previously, in 12 cm³ of tetrahydrofuran. The medium is then maintained at 67° C. for 16 hours. The mixture is then allowed to return to 19° C. and 60 μm³ of ethyl acetate are added, after which it is washed with 30 cm³ of saturated aqueous sodium hydrogen carbonate solution and then with 2×30 cm³ of distilled water and finally with 30 cm³ of saturated aqueous sodium chloride solution. The organic phase is dried over magnesium sulphate, filtered through a sinter funnel and evaporated under reduced pressure (2 kPa; 45° C.). The residue obtained is purified by chromatography under an argon pressure of 50 kPa, on a column of silica gel (particle size 15–40 μm; diameter 3 cm), eluting with a cyclohexane/ethyl acetate mixture (60/40 by volume) and collecting 15 cm³ fractions. The fractions containing the expected product are combined and evaporated under reduced pressure (2 kPa; 50° C.). After drying (90 Pa; 50° C.), 260 mg of N-[6-(1,3-benzodioxol-5-yl)-1H-indazol-3-yl]butanamide are obtained in the form of a white solid melting at 240° C.

¹H NMR spectrum (300 MHz, (CD$_3$)$_2$SO-d6, δ in ppm): 0.98 (t, J=7.5 Hz: 3H); 1.68 (mt: 2H); 2.40 (t, J=7 Hz: 2H); 6.09 (s: 2H); 7.03 (d, J=8 Hz: 1H); 7.21 (dd, J=8 and 2 Hz: 1H); 7.30 (broad dd, J=9 and 1.5 Hz: 1H); 7.31 (d, J=2 Hz: 1H); 7.55 (broad s: 1H); 7.82 (d, J=9 Hz: 1H); 10.31 (broad s: 1H); 12.63 (broad s: 1H).

| EI | m/z = 323 | M+· |
| | m/z = 253 | [M—C$_4$CH$_6$O]+· |

EXAMPLE 111

N-[7-fluoro-5-nitro-6-[2-(phenylethyl)amino]-1H-indazol-3-yl]butanamide 1.11 cm³ of phenethylamine are added to a solution of 500 mg of N-(6,7-difluoro-5-nitro-1H-indazol-3-yl)butanamide, prepared in Example 106, in 10 cm³ of dimethylsulphoxide, and the mixture is refluxed for 1 hour. The reaction medium is taken up in 50 cm³ of ethyl acetate and the organic phase is washed with 4×35 cm³ of saturated sodium chloride solution. The organic phase is separated out after settling of the phases has taken place, dried over magnesium sulphate, filtered and concentrated to dryness under reduced pressure to give 1.5 g of oil. The crude product is purified by chromatography under an argon pressure of 50 kPa, on a column of silica gel (particle size 15–40 μm; diameter 3 cm), eluting with a cyclohexane/ethyl acetate mixture (70/30 by volume). The fractions containing the expected product are combined and evaporated under reduced pressure (2 kPa; 50° C.) and the residue is taken up in 30 cm³ of diethyl ether, filtered off on a sinter funnel and washed with 2×20 cm³ of diethyl ether, and then dried (90 Pa; 50° C.) to give 360 mg of N-[7-fluoro-5-nitro-6-[(phenylethyl)amino]-1H-indazol-3-yl]butanamide in the form of brown crystals melting at 212° C.

¹H NMR spectrum (300 MHz, (CD$_3$)$_2$SO-d6, δ in ppm): 0.96 (t, J=7.5 Hz: 3H); 1.67 (mt: 2H); 2.42 (t, J=7 Hz: 2H); 2.93 (t, J=7 Hz: 2H); 3.76 (mt: 2H); 7.03 (mt: 1H); from 7.15 to 7.40 (mt: 5H); 8.85 (s: 1H); 10.73 (broad s: 1H); 13.10 (unresolved peak: 1H).

| EI | m/z = 385 | M+· |
| | m/z = 294 | [M—CH$_2$C$_6$H$_5$]+ |
| | m/z = 224 | [294 − C$_4$CH$_6$O]+ |

EXAMPLE 112

N-(7-fluoro-5-nitro-6-morpholino-1H-indazol-3-yl)butanamide

The process is performed as in Example 110, starting with 500 mg of N-(6,7-difluoro-5-nitro-1H-indazol-3-yl)butanamide, prepared in Example 106, 10 cm³ of dimethylsulphoxide and 0.77 cm³ of morpholine, and the mixture is refluxed for 1 hour. The reaction medium is taken up in 75 cm³ of ethyl acetate and the organic phase is washed with 2×75 cm³ of water and 50 cm³ of saturated sodium chloride solution. The organic phase is separated out after settling of the phases has taken place, dried over magnesium sulphate, filtered and concentrated to dryness under reduced pressure to give 1 g of a brown solid. The crude product is purified by chromatography under an argon pressure of 50 kPa, on a column of silica gel (particle size 15–40 μm; diameter 3 cm), eluting with a cyclohexane/ethyl acetate mixture (60/40 by volume). The fractions containing the expected product are combined and evaporated under reduced pressure (2 kPa; 50° C.) and the residue is taken up in 30 cm$^3$ of diethyl ether, filtered off on a sinter funnel and washed with 2×20 cm$^3$ of diethyl ether, and then dried (90 Pa; 50° C.) to give 280 mg of N-(7-fluoro-5-nitro-6-morpholino-1H-indazol-3-yl) butanamide in the form of brown crystals melting at 250° C.

$^1$H NMR spectrum (300 MHz, (CD$_3$)$_2$SO-d6, δ in ppm): 0.96 (t, J=7.5 Hz: 3H); 1.67 (mt: 2H); 2.42 (t, J=7 Hz: 2H); 3.16 (mt: 4H); 3.69 (t, J=4 Hz: 4H); 8.30 (broad s: 1H); 10.75 (unresolved peak: 1H); 13.68 (unresolved peak: 1H).

| EI | m/z = 351 | M$^{+\cdot}$ |
|---|---|---|
|    | m/z = 334 | [M—OH]$^+$ |

EXAMPLE 113

N-(7-fluoro-5-amino-6-morpholino-1H-indazol-3-yl) butanamide 200 mg of 3% palladium-on-charcoal and 1 g of ammonium formate are added to a solution of 1.1 g of N-(7-fluoro-5-nitro-1H-indazol-3-yl)butanamide, prepared in Example 112, in 50 cm$^3$ of methanol, and the mixture is stirred at room temperature for 18 hours. The reaction medium is filtered through a sinter funnel packed with Celite and concentrated to dryness under reduced pressure (2 kPa; 50° C.), then purified by chromatography under an argon pressure of 50 kPa, on a column of silica gel (particle size 15–40 μm; diameter 3 cm), eluting with a methylene chloride/methanol mixture (97.5/2.5 by volume). The fractions containing the expected product are combined and evaporated under reduced pressure (2 kPa; 50° C.) and the residue is taken up in 20 cm$^3$ of ethyl acetate, filtered off on a sinter funnel and washed with 2×5 cm$^3$ of ethyl acetate and with 10 cm$^3$ of diethyl ether, then dried (90 Pa; 50° C.) to give 306 mg of N-(7-fluoro-5-amino-6-morpholino-1H-indazol-3-yl)butanamide in the form of white crystals melting at 180° C.

$^1$H NMR spectrum (300 MHz, (CD$_3$)$_2$SO-d6, δ in ppm): 0.97 (t, J=7.5 Hz: 3H); 1.67 (mt: 2H); 2.34 (broad t, J=7 Hz: 2H); 3.04 (broad unresolved peak: 4H); 3.77 (unresolved peak: 4H); 4.95 (broad s: 2H); 6.55 (s: 1H); 10.03 (unresolved peak: 1H); 13.57 (unresolved peak: 1H).

| EI | m/z = 321 | M$^{+\cdot}$ |
|---|---|---|
|    | m/z = 306 | [M—CH$_3$]$^+$ |

EXAMPLE 114

N-(5-bromo-7-fluoro-6-morpholino-1H-indazol-3-yl)butanamide

A solution of 213 mg of sodium nitrite in 9 cm$^3$ of water is added dropwise to a suspension, cooled to 5° C., of 900 mg of N-(5-amino-7-fluoro-6-morpholino-1H-indazol-3-yl) butanamide, prepared as previously, in 9 cm$^3$ of water and 0.94 cm$^3$ of 48% hydrobromic acid, and the mixture is stirred at 0° C. This suspension is added portionwise to a refluxing solution of 482 mg of cuprous bromide, 4.5 cm$^3$ of water and 4.5 cm$^3$ of 48% hydrobromic acid. Refluxing is continued for 45 minutes and the reaction medium is then filtered through a sinter funnel, dissolved in 75 cm$^3$ of tetrahydrofuran and purified by chromatography under an argon pressure of 50 kPa, on a column of silica gel (particle size 15–40 μm; diameter 3 cm), eluting with a cyclohexane/ethyl acetate mixture (80/20 by volume). The fractions containing the expected product are combined and evaporated under reduced pressure (2 kPa; 50° C.) and the residue is taken up in 10 cm$^3$ of ethyl acetate, filtered off and washed with 2×5 cm$^3$ of ethyl acetate and with 20 cm$^3$ of diisopropyl ether. After filtration and drying (90 Pa; 45° C.), 60 mg of N-(5-bromo-7-fluoro-6-morpholino-1H-indazol-3-yl) butanamide are obtained in the form of white crystals melting at 240° C.

$^1$H NMR spectrum (300 MHz, (CD$_3$)$_2$SO-d6, δ in ppm): 0.96 (t, J=7.5 Hz: 3H); 1.66 (mt: 2H); 2.38 (t, J=7 Hz: 2H); 3.16 (unresolved peak: 4H); 3.76 (unresolved peak: 4H); 7.96 (s: 1H); 10.48 (unresolved peak: 1H); 13.20 (unresolved peak: 1H).

| EI | m/z = 384 | M$^{+\cdot}$ |
|---|---|---|
|    | m/z = 314 | [M—C$_4$CH$_6$O]$^{+\cdot}$ |

EXAMPLE 115

N-[7-fluoro-6-(trifluoromethyl)-1H-indazol-3-yl] butanamide 1.0 cm$^3$ of butyryl chloride is added to 2.1 g of 7-fluoro-6-(trifluoromethyl)-1H-indazole-3-amine, prepared as in patent application WO 02/22608, in 20 cm$^3$ of pyridine, after cooling to about 3° C., and the mixture is then left at room temperature for 76 hours. The reaction medium is concentrated under reduced pressure (2 kPa; 40° C.) and the residue is taken up in 50 cm$^3$ of ethyl acetate and 20 cm$^3$ of water. The organic phase is washed with 2×20 cm$^3$ of distilled water and then with 20 cm$^3$ of saturated aqueous sodium chloride solution. After drying over magnesium sulphate, filtration and concentration under reduced pressure (2 kPa; 40° C.), the residue obtained is purified by chromatography under an argon pressure of 50 kPa, on a column of silica gel (particle size 40–60 μm; diameter 4 cm), eluting with a cyclohexane/ethyl acetate mixture (60/40 by volume). The fractions containing the expected product are combined and then evaporated under reduced pressure (2 kPa; 40° C.); after drying (90 Pa; 40° C.), 875 mg of N-[7-fluoro-6-(trifluoromethyl)-1H-indazol-3-yl)butanamide are obtained in the form of a pink solid melting at 220°–222° C.

$^1$H NMR spectrum (300 MHz, (CD$_3$)$_2$SO-d6, δ in ppm): 0.98 (t, J=7.5 Hz: 3H); 1.69 (mt: 2H); 2.42 (t, J=7 Hz: 2H); 7.31 (dd, J=8.5 and 6 Hz: 1H); 7.82 (broad d, J=8.5 Hz: 1H); 10.59 (unresolved peak: 1H); from 13.50 to 14.20 (broad unresolved peak: 1H).

| EI | m/z = 289 | M+· |
|---|---|---|
|  | m/z = 270 | [M—F]+ |
|  | m/z = 219 | [M—C$_4$CH$_6$O]+· |

EXAMPLE 116

6-bromo-4,5,7-trifluoro-1H-indazole-3-amine 1.14 cm$^3$ of hydrazine monohydrate are added to 2.0 g of 4-bromo-2,3,5,6-tetrafluorobenzonitrile in 40 cm$^3$ of absolute ethanol. The mixture is refluxed for 18 hours, 30 cm$^3$ of distilled water are then added and the reaction medium is concentrated under reduced pressure (2 kPa; 50° C.). The residue is taken up in 100 cm$^3$ of ethyl acetate and 10 cm$^3$ of water, and the organic phase is separated out after settling of the phases has taken place, dried over magnesium sulphate, filtered and concentrated to dryness under reduced pressure (2 kPa; 50° C.); after drying (90 Pa; 40° C.), 2.1 g of 6-bromo-4,5,7-trifluoro-1H-indazole-3-amine are obtained in the form of a beige-coloured solid.

$^1$H NMR spectrum (300 MHz, (CD$_3$)$_2$SO-d6, δ in ppm): 5.52 (s: 2H); from 12.10 to 12.90 (broad unresolved peak: 1H).

| EI | m/z = 265 | M+· |
|---|---|---|
|  | m/z = 236 | [M—HN$_2$]+ |
|  | m/z = 186 | [M—Br]+ |

N-(6-bromo-4,5,7-trifluoro-1H-indazol-3-yl)butanamide 0.82 cm$^3$ of butyryl chloride is added to 2.1 g of 6-bromo-4,5,7-trifluoro-1H-indazole-3-amine, prepared previously, in 20 cm$^3$ of pyridine, after cooling to about 3° C., and the mixture is then left at room temperature for 76 hours. The reaction medium is concentrated under reduced pressure (2 kPa; 40° C.) and the residue is taken up in 100 cm$^3$ of ethyl acetate, 100 cm$^3$ of tetrahydrofuran and 40 cm$^3$ of water. The organic phase is washed with 2×40 cm$^3$ of distilled water and then with 40 cm$^3$ of saturated aqueous sodium chloride solution. After drying over magnesium sulphate, filtration and concentration under reduced pressure (2 kPa; 40° C.), the residue obtained is purified by chromatography under an argon pressure of 50 kPa, on a column of silica gel (particle size 40–60 μm; diameter 4 cm), eluting with a cyclohexane/ethyl acetate mixture (80/20 by volume). The fractions containing the expected product are combined and then evaporated under reduced pressure (2 kPa; 40° C.); after drying (90 Pa; 40° C.), 0.53 g of N-(6-bromo-4,5,7-trifluoro-1H-indazol-3-yl)butanamide is obtained in the form of a pink solid melting at 255°–257° C.

$^1$H NMR spectrum (300 MHz, (CD$_3$)$_2$SO-d6, δ in ppm): 0.97 (t, J=7.5 Hz: 3H); 1.66 (mt: 2H); 2.36 (t, J=7 Hz: 2H); 10.26 (unresolved peak: 1H); from 13.50 to 14.40 (broad unresolved peak: 1H).

| EI | m/z = 335 | M+· |
|---|---|---|
|  | m/z = 265 | [M—C$_4$CH$_6$O]+· |

EXAMPLE 117

N-[6-(6-aminopyrid-3-yl)-1-[[2-(trimethylsilyl)ethoxy]methyl]-1H-indazol-3-yl]butanamide 0.45 g of 2-amino-5-bromopyridine is added to 1.0 g of N-[6-(4,4,5,5-tetramethyl[1,3,2]dioxaborolan-2-yl)-1-[[2-(trimethylsilyl)ethoxy]methyl]-1H-indazol-3-yl]butanamide, prepared in Example 56, in 50 cm$^3$ of dioxane, 142 mg of dichloro[1,1'-bis(diphenylphosphino)ferrocene] palladium, dichloromethane and 646 mg of sodium carbonate in 10 cm$^3$ of water are added to the pale yellow solution, and the mixture is refluxed for 2 hours. The reaction medium is diluted with 50 cm$^3$ of ethyl acetate and 50 cm$^3$ of water, and then filtered through a sinter funnel packed with Celite. The filtrate is separated by settling and the aqueous phase is washed with 2×50 cm$^3$ of saturated sodium chloride solution, dried over magnesium sulphate, filtered and concentrated to dryness under reduced pressure (2 kPa; 50° C.). The crude product obtained is purified by chromatography under an argon pressure of 50 kPa, on a column of silica gel (particle size 40–60 μm; diameter 3 cm), eluting with a cyclohexane/ethyl acetate gradient mixture (70/30 to 50/50 by volume). The fractions containing the expected product are combined and evaporated under reduced pressure (2 kPa; 50° C.) to give 0.53 mg of N-[6-(6-amino-pyrid-3-yl)-1-[[2-(trimethylsilyl)ethoxy]methyl]-1H-indazol-3-yl]butanamide in the form of a solid melting at 138° C.

$^1$H NMR spectrum (300 MHz, (CD$_3$)$_2$SO-d6, δ in ppm): −0.09 (s: 9H); 0.83 (t, J=8 Hz: 2H); 0.97 (t, J=7.5 Hz: 3H); 1.67 (mt: 2H); 2.39 (t, J=7 Hz: 2H); 3.55 (t, J=8 Hz: 2H); 5.70 (s: 2H); 6.12 (s: 2H); 6.57 (d, J=9 Hz: 1H); 7.37 (dd, J=8.5 and 1.5 Hz: 1H); from 7.80 to 7.90 (mt: 3H); 8.37 (d, J=2 Hz: 1H); 10.43 (unresolved peak: 1H).

| EI | m/z = 425 | M+· |
|---|---|---|
|  | m/z = 308 | M—OCH$_2$CH$_2$Si(CH$_3$)$_3$]+ |
|  | m/z = 297 | M—C$_6$H$_{12}$OSi]+· |

N-[6-(6-aminopyrid-3-yl)-1H-indazol-3-yl]butanamide difluoroacetate 3.8 cm$^3$ of tetrabutylamonium fluoride as a 1M solution in tetrahydrofuran are added to 0.8 g of N-[6-(6-aminopyrid-3-yl)-1-[[2-(trimethylsilyl)ethoxy]methyl]-1H-indazol-3-yl]butanamide, prepared previously, in 13 cm$^3$ of tetrahydrofuran, and the mixture is refluxed for 6 hours, followed by addition of 50 cm$^3$ of ethyl acetate and 25 cm$^3$ of saturated sodium hydrogen carbonate solution. The organic phase is separated out after settling of the phases has taken place, washed with 25 cm$^3$ of water, dried over magnesium sulphate, filtered and concentrated to dryness under reduced pressure. The crude product is purified by HPLC (X Terra column; C$_{18}$, 5 μm; length 50 mm, diameter 21 mm, eluent: acetonitrile/water gradient (5/95 to 95/5 by volume) containing 0.05% trifluoroacetic acid; flow rate 20 cm$^3$/min). After concentrating the fractions containing the expected product, a solid is obtained, which is taken up in 10 cm$^3$ of diisopropyl ether and 2 cm$^3$ of acetonitrile, filtered off, washed with 5 cm$^3$ of diisopropyl ether and dried (90 Pa; 45° C.) to give 18 mg of N-[6-(6-amino-pyrid-3-yl)-1H-indazol-3-yl]butanamide difluoroacetate in the form of white crystals melting at 230–235° C.

$^1$H NMR spectrum (300 MHz, (CD$_3$)$_2$SO-d6, δ in ppm): 0.99 (t, J=7.5 Hz: 3H); 1.69 (mt: 2H); 2.40 (t, J=7 Hz: 2H); 7.05 (d, J=9.5 Hz: 1H); 7.33 (dd, J=8.5 and 1.5 Hz: 1H); 7.65 (broad s: 1H); 7.79 (unresolved peak: 2H); 7.90 (d, J=8.5 Hz: 1H); 8.31 (dd, J=9.5 and 1.5 Hz: 1H); 8.36 (d, J=1.5 Hz: 1H); 10.37 (broad s: 1H); 12.79 (unresolved peak: 1H).

| EI | m/z = 295 | M$^{+\cdot}$ |
|---|---|---|
|  | m/z = 225 | [M—C$_4$CH$_6$O]$^{+\cdot}$ |
|  | m/z = 43 | [C$_3$H$_7$]$^+$ |

EXAMPLE 118

2-chloro-N-(6,7-difluoro-1H-indazol-3-yl)acetamide 5.0 g of chloracetic anhydride are added to 5 g of 6,7-difluoro-1H-indazole-3-amine, prepared in Example 40, in 300 cm$^3$ of toluene, and the mixture is refluxed for 18 hours. The precipitate formed is concentrated to dryness under reduced pressure (2 kPa; 50° C.), and the residue is then purified by chromatography under an argon pressure of 50 kPa, on a column of silica gel (particle size 40–60 µm; diameter 4.5 cm), eluting with a dichloromethane/methanol mixture (98/2 by volume). The fractions containing the expected product are combined and evaporated under reduced pressure (2 kPa; 50° C.) and then dried (90 Pa; 45° C.) to give 8.5 g of 2-chloro-N-(6,7-difluoro-1H-indazol-3-yl)acetamide in the form of a cream-coloured crystalline mass.

$^1$H NMR spectrum (400 MHz, (CD$_3$)$_2$SO-d6, at a temperature of 353 K, δ in ppm): 4.37 (s: 2H); 7.11 (ddd, J=8.5–7.5 and 5 Hz: 1H); 7.67 (broad dd, J=7.5 and 3 Hz: 1H); 10.65 (broad s: 1H); 13.30 (unresolved peak: 1H).

| EI | m/z = 245 | M$^{+\cdot}$ |
|---|---|---|
|  | m/z = 169 | [M—C$_2$HOCl]$^{+\cdot}$ |
|  | m/z = 140 | [169 − HN$_2$]$^+$ |

N-(6,7-difluoro-1H-indazol-3-yl)-1-piperidineacetamide

The process is performed as in Example 75, starting with 8.5 g of 2-chloro-N-(6,7-difluoro-1H-indazol-3-yl)acetamide, 200 cm$^3$ of acetonitrile and 8.8 cm$^3$ of piperidine. The reaction medium is refluxed for 1 hour, the precipitate formed is then filtered off on a sinter funnel and the crystals are taken up in 200 cm$^3$ of ethyl acetate and 100 cm$^3$ of water. The organic phase is separated out after settling of the phases has taken place, dried over magnesium sulphate, filtered and concentrated to dryness under reduced pressure (2 kPa; 50° C.). The crude product is purified by chromatography under an argon pressure of 50 kPa, on a column of silica gel (particle size 40–60 µm; diameter 3.5 cm), eluting with ethyl acetate. The fractions containing the expected product are combined and evaporated under reduced pressure (2 kPa; 50° C.); the residue is recristallized from a mixture of 50 cm$^3$ of cyclohexane and 16 cm$^3$ of ethyl acetate, filtered off and dried (90 Pa; 45° C.) to give 3.2 g of N-(6,7-difluoro-1H-indazol-3-yl)-1-piperidineacetamide in the form of white crystals melting at 158° C.

$^1$H NMR spectrum (300 MHz, (CD$_3$)$_2$SO-d6, δ in ppm): 1.42 (mt: 2H); 1.59 (mt: 4H); 2.52 (mt: 4H); 3.19 (s: 2H); 7.13 (ddd, J=10.5–9 and 7 Hz: 1H); 7.66 (broad dd, J=9 and 4.5 Hz: 1H); 10.14 (unresolved peak: 1H); 13.42 (unresolved peak: 1H).

| DCI | m/z = 295 | [M + H]$^+$ |
|---|---|---|

The pharmaceutical compositions according to the invention consist of a compound of formula (I) or a salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration that may be used include tablets, pills, powders (gelatin capsules or cachets) or granules. In these compositions, the active principle according to the invention is mixed with one or more inert diluents, such as starch, cellulose, sucrose, lactose or silica, under a stream of argon. These compositions may also comprise substances other than diluents, for example one or more lubricants such as magnesium stearate or talc, a colorant, a coating agent (for sugar coated tablets) or a varnish.

Liquid compositions for oral administration that may be used include pharmaceutically acceptable solutions, suspensions, emulsions, syrups and elixirs containing inert diluents such as water, ethanol, glycerol, plant oils or liquid paraffin.

These compositions may comprise substances other than diluents, for example wetting agents, sweeteners, thickeners, flavorings or stabilizers.

The sterile compositions for parenteral administration may preferably be aqueous or nonaqueous solutions, suspensions or emulsions. Solvents or vehicles that may be used include water, propylene glycol, a polyethylene glycol, plant oils, in particular olive oil, injectable organic esters, for example ethyl oleate, or other suitable organic solvents. These compositions may also contain adjuvants, in particular wetting agents, tonicity agents, emulsifiers, dispersants and stabilizers. Sterilization may be performed in several ways, for example by aseptic filtration, by incorporating sterilizing agents into the composition, by irradiation or by heating. They may also be prepared in the form of sterile solid compositions that may be dissolved at the time of use in sterile water or any other injectable sterile medium.

The compositions for rectal administration are suppositories or rectal capsules that contain, besides the active product, excipients such as cocoa butter, semisynthetic glycerides or polyethylene glycols.

The compositions for topical administration may be, for example, creams, lotions, eyedrops, mouthwashes, nasal drops or aerosols.

One subject of the invention is the aminoindazole compounds of formula (I), and the use thereof, and the pharmaceutically acceptable salts thereof, for the preparation of pharmaceutical compositions intended for preventing and treating diseases that may result from an abnormal activity of kinases, such as, for example, those involved in neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovary syndrome, syndrome X, immunodeficiency and cancer.

Examples of abnormal kinase activity that may be mentioned include that of PI3K, AkT, GSK3beta, CDKs, etc.

In human therapy, the compounds according to the invention are particularly useful for treating and/or preventing neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovary syndrome, syndrome X, immunodeficiency and cancer.

The doses depend on the desired effect, the duration of the treatment and the administration route used; they are generally between 5 mg and 1000 mg per day orally for an adult, with unit doses ranging from 1 mg to 250 mg of active substance.

In general, the doctor will determine the appropriate dosage depending on the age and weight and all the other personal factors of the individual to be treated.

The examples that follow illustrate compositions according to the invention:

EXAMPLE A

Gel capsules containing a 50 mg dose of active product and having the composition below are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing a 50 mg dose of active product and having the composition below are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) qs 1 finished film-coated tablet weighing 245 mg | |

EXAMPLE C

An injectable solution containing 10 mg of active product and having the composition below is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |

-continued

| | |
|---|---|
| Propylene glycol | 1.6 ml |
| Water qs | 4 ml |

The present invention also relates to the method for preventing and treating diseases in which phosphorylation of the Tau protein is involved, by administering a compound of formula (I) and pharmaceutically acceptable salts thereof.

What is claimed is:

1. A compound of formula (I)

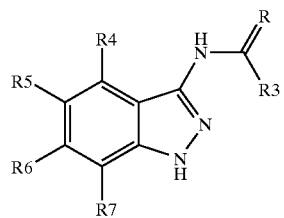

(I)

wherein

R is O, S or NH

R3 is (1–6C)alkyl, aryl, aryl(1–6C)alkyl, heteroaryl, heteroaryl(1–6C)alkyl, aryl or heteroaryl fused to a cycloalkyl (1–10C), heterocycle, cycloalkyl, adamantyl, polycycloalkyls, alkenyl, or alkynyl radical; these radicals being optionally substituted with one or more substituents selected from the group consisting of halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;

R4, R5, R6 and R7 are, independently of each other, selected from the group consisting of hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, and polycycloalkyls; these radicals being optionally substituted with one or more substituents selected from the group consisting of halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;

R8, R9, R10, R11 are, independently of each other, selected from the group consisting of hydrogen, (1–6C) alkyl, aryl, alkenyl, alkynyl or heteroaryl, themselves optionally being substituted with one or more substituents chosen from halogen, (1–6C)alkyl, (1–6C)alkoxy, CN, $NO_2$, $NH_2$, OH, COOH, COOalkyl, $CONH_2$, formyl, trifluoromethyl and trifluoromethoxy;

or a racemic mixture, an enantiomer, a diastereoisomer or mixtures thereof, or a tautomer thereof, or a pharmaceutically acceptable salt thereof, and with the exception of following compounds:

3-(2-nitrobenzamido)indazole, 3-(2-aminobenzamido) indazole,
3-(4-chloro-2-nitrobenzamido)indazole,
3-(5-chloro-2-nitrobenzamido)indazole,
3-(2-amino-4-chlorobenzamido)indazole,
3-(2-amino-5-chlorobenzamido)indazole, 3-(benzamido) indazole,
3-(4-methylbenzamido)indazole, 3-(4-chlorobenzamido) indazole,
3-(4-nitrobenzamido)indazole, 3-acetamidoindazole,
N-(1H-indazol-3-yl)butanamide, N-(1H-indazol-3-yl) phenylacetamide,
N-(1H-indazol-3-yl)benzhydrylacetamide,
5-amino-3-acetamidoindazole, 3-(2-hydroxybenzamido) indazole,
N-(6-chloro-1H-indazol-3-yl)-2,2,2-trifluoroacetamide,
N-(6-chloro-1H-indazol-3-yl)-2-furancarboxamide,
N-(6-chloro-1H-indazol-3-yl)-2-thiophenecarboxamide,
N-(6-chloro-1H-indazol-3-yl)-4-(hexyloxy)benzamide,
3-chloro-N-(6-chloro-1H-indazol-3-yl)benzamide,
4-chloro-N-(6-chloro-1H-indazol-3-yl)benzamide, and
N-(5-nitro-1H-indazol-3-yl)acetamide.

2. The compound of claim 1 wherein:
R is O, S or NH
R3 is (1–6C)alkyl, aryl, aryl(1–6C)alkyl, heteroaryl, heteroaryl(1–6C)alkyl, cycloalkyl, alkenyl or alkynyl radical; these radicals being optionally substituted with one or more substituents selected from the group consisting of halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;
R4 and R7 are hydrogen;
R5 and R6 are, independently of each other, selected from the group consisting of hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl (1–6C)alkyl, heteroaryl, heteroaryl(1–6C)alkyl, cycloalkyl, heterocycle, alkenyl, alkynyl, adamantyl, polycycloalkyl; these radicals being optionally substituted with one or more substituents selected from the group consisting of halogen, CN, $NO_2$, $NH_2$, OH, OR10, COOH, C(O)OR10, —O—C(O)R10, NR10R11, NHC(O)R10, C(O)NR10R11, NHC(S)R10, C(S)NR10R11, SR10, S(O)R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;
R8, R9, R10, R11 are, independently of each other, a hydrogen, (1–6C)alkyl, aryl, alkenyl, alkynyl or heteroaryl, themselves being optionally substituted with one or more substituents selected from the group consisting of halogen, (1–6C)alkyl, (1–6C)alkoxy, CN, $NO_2$, $NH_2$, OH, COOH, COOalkyl, $CONH_2$, formyl, trifluoromethyl and trifluoromethoxy;
or a racemic mixture, an enantiomer, a diastereoisomer or a mixture thereof, or a tautomer thereof or a pharmaceutically acceptable salt thereof.

3. The compound of claim 1 wherein:
R is O
R4 and R7 are H
R3 is (1–6C)alkyl, aryl, aryl(1–6C)alkyl, heteroaryl, heteroaryl(1–6C)alkyl, heterocycle, cycloalkyl or alkenyl radical; these radicals being optionally substituted with one or more substituents selected from the group consisting of halogen, CN, $NO_2$, $NH_2$, OH, OR8, COOH, C(O)OR8, —O—C(O)R8, NR8R9, NHC(O)R8, C(O)NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;
R5 and R6 are, independently of each other, selected from the group consisting of hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, and alkenyl; these radicals being optionally substituted with one or more substituents selected from the group consisting of halogen, CN, $NO_2$, $NH_2$, OH, OR10, COOH, C(O) OR10, —O—C(O)R10, NR10R11, NHC(O)R10, C(O) NR10R11, NHC(S)R10, C(S)NR10R11, SR10, S(O) R10, $SO_2$R10, $NHSO_2$R10, $SO_2$NR10R11, —O—$SO_2$R10, —$SO_2$—O—R10, aryl, heteroaryl, formyl, trifluoromethyl and trifluoromethoxy;
R8, R9, R10, R11 are, independently of each other, selected from the group consisting of a hydrogen, (1–6C)alkyl, aryl, alkenyl, alkynyl and heteroaryl, themselves being optionally substituted with one or more substituents selected from the group consisting of halogen, (1–6C)alkyl, (1–6C)alkoxy, CN, $NO_2$, $NH_2$, OH, COOH, COOalkyl, $CONH_2$, formyl, trifluoromethyl and trifluoromethoxy;
or a racemic mixture, an enantiomer, a diastereoisomer or a mixture thereof, or a tautomer thereof or a pharmaceutically acceptable salt thereof.

4. The compound of claim 1 wherein
R is O, S or NH
R3 is (1–6C)alkyl, aryl, aryl(1–6C)alkyl, heteroaryl, heteroaryl(1–6C)alkyl, aryl or heteroaryl fused to a cycloalkyl (1–10C), heterocycle, cycloalkyl, adamantyl, polycycloalkyls, alkenyl, or alkynyl radical; these radicals being optionally substituted with one or more substituents selected from the group consisting of halogen, CN, $NO_2$, $NH_2$, OH, OR8, COOH, C(O) OR8, —O—C(O)R8, NR8R9, NHC(O)R8, C(O) NR8R9, SR8, S(O)R8, $SO_2$R8, $NHSO_2$R8, $SO_2$NR8R9, C(S)NR8R9, NHC(S)R8, —O—$SO_2$R8, —$SO_2$—O—R8, aryl, heteroaryl, formyl, trifluoromethyl, trifluoromethylsulphanyl and trifluoromethoxy;
R4, R5, R6 and R7 are chosen, independently of each other, selected from the group consisting of hydrogen, halogen, CN, $NO_2$, $NH_2$, OH, COOH, C(O)OR8, —O—C(O)R8, NR8R9, NHC(O)R8, C(O)NR8R9, NHC(S)R8, C(S)NR8R9, SR8, S(O)R8, $SO_2$R8, $NHSO_2$R8, $SO_2$NR8R9, —O—$SO_2$R8, —$SO_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl, and polycycloalkyls; these radicals being optionally substituted with one or more substituents selected from the group consisting of halogen, CN, NO₂, NH₂, OH, OR10, COOH, C(O)OR10, —O—C(O)R10, NR10R11, NHC(O)R10, C(O)NR10R11, NHC(S)R10, C(S)NR10R11, SR10, S(O)R10, SO₂R10, NHSO₂R10, SO₂NR10R11, —O—SO₂R10, —SO₂—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents selected from the group consisting of halogen, (1–6C)alkyl, (1–6C)alkoxy, CN, NO₂, NH₂, OH, COOH, CQOalkyl, CONH₂, formyl, trifluoromethyl and trifluoromethoxy;

or a racemic mixture, an enantiomer, a diastereoisomer or a mixture thereof, or a tautomer thereof or a pharmaceutically acceptable salt thereof.

5. The compound of claim 1 wherein

R is O, S or NH

R3 is (1–6C)alkyl, aryl, aryl(1–6C)alkyl, heteroaryl, heteroaryl(1–6C)alkyl, cycloalkyl, alkenyl or alkynyl radical; these radicals being optionally substituted with one or more substituents selected from the group consisting of halogen, CN, NO₂, NH₂, OH, OR8, COOH, C(O)OR8, —O—C(O)R8, NR8R9, NHC(O)R8, C(O)NR8R9, SR8, S(O)R8, SO₂R8, NHSO₂R8, SO₂NR8R9, C(S)NR8R9, NHC(S)R8, —O—SO₂R8, —SO₂—O—R8, aryl, heteroaryl, formyl, trifluoromethyl, trifluoromethylsulphanyl and trifluoromethoxy;

R4 and R7 are hydrogen;

R5, R6 are independently of each other, selected from the group consisting of hydrogen, halogen, CN, NO₂, NH₂, OH, COOH, C(O)OR8, —O—C(O)R8, NR8R9, NHC(O)R8, C(O)NR8R9, NHC(S)R8, C(S)NR8R9, SR8, S(O)R8, SO₂R8, NHSO₂R8, SO₂NR8R9, —O—SO₂R8, —SO₂—O—R8, trifluoromethyl, trifluoromethoxy, (1–6C)alkyl, (1–6C)alkoxy, aryl, aryl (1–6C)alkyl, heteroaryl, heteroaryl(1–6C)alkyl, cycloalkyl, heterocycle, alkenyl, alkynyl, adamantyl, and polycycloalkyl; these radicals being optionally substituted with one or more substituents selected from the group consisting of halogen, CN, NO₂, NH₂, OH, OR10, COOH, C(O)OR10, —O—C(O)R10, NR10R11, NHC(O)R10, C(O)NR10R11, NHC(S)R10, C(S)NR10R11, SR10, S(O)R10, SO₂R10, NHSO₂R10, SO₂NR10R11, —O—SO₂R10, —SO₂—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents selected from the group consisting of halogen, (1–6C)alkyl, (1–6C)alkoxy, CN, NO₂, NH₂, OH, COOH, COOalkyl, CONH₂, formyl, trifluoromethyl and trifluoromethoxy;

or a racemic mixture, an enantiomer, a diastereoisomer or a mixture thereof, or a tautomer thereof or a pharmaceutically acceptable salt thereof.

6. The compounds of claim 1 wherein

R is O

R4 and R7 are H

R3 is (1–6C)alkyl, aryl, aryl(1–6C)alkyl, heteroaryl, heteroaryl(1–6C)alkyl, heterocycle, cycloalkyl or alkenyl radical; these radicals being optionally substituted with one or more substituents selected from the group consisting of halogen, CN, NO₂, NH₂, OH, OR8, COOH, C(O)OR8, —O—C(O)R8, NR8R9, NHC(O)R8, C(O)NR8R9, SR8, S(O)R8, SO₂R8, NHSO₂R8, SO₂NR8R9, C(S)NR8R9, NHC(S)R8, —O—SO₂R8, —SO₂—O—R8, aryl, heteroaryl, formyl, trifluoromethyl, trifluoromethylsulphanyl and trifluoromethoxy;

R5 and R6 are independently of each other, selected from the group consisting of hydrogen, halogen, CN, NO₂, NH₂, OH, COOH, C(O)OR8, —O—C(O)R8, NR8R9, NHC(O)R8, C(O)NR8R9, NHC(S)R8, C(S)NR8R9, SR8, S(O)R8, SO₂R8, NHSO₂R8, SO₂NR8R9, trifluoromethyl, trifluoromethoxy, (1–6C)alkyl, (1–6C)alkoxy, aryl, aryl(1–6C)alkyl, heteroaryl, heteroaryl (1–6C)alkyl, heterocycle, cycloalkyl, and alkenyl; these radicals being optionally substituted with one or more substituents selected from the group consisting of halogen, CN, NO₂, NH₂, OH, OR10, COOH, C(O)OR10, —O—C(O)R10, NR10R11, NHC(O)R10, C(O)NR10R11, NHC(S)R10, C(S)NR10R11, SR10, S(O)R10, SO₂R10, NHSO₂R10, SO₂NR10R11, —O—SO₂R10, —SO₂—O—R10, aryl, heteroaryl, formyl, trifluoromethyl and trifluoromethoxy;

R8, R9, R10, R11 are, independently of each other, a hydrogen, (1–6C)alkyl, aryl, alkenyl, alkynyl or heteroaryl, themselves being optionally substituted with one or more substituents selected from the group consisting of halogen, (1–6C)alkyl, (1–6C)alkoxy, CN, NO₂, NH₂, OH, COOH, COOalkyl, CONH₂, formyl, trifluoromethyl and trifluoromethoxy;

or a racemic mixture, an enantiomer, a diastereoisomer or a mixture thereof, or a tautomer thereof or a pharmaceutically acceptable salt thereof.

7. The compound according to claim 4, which is selected from the group consisting of:

(2Z) 4-[(6-chloro-1H-indazol-3-yl)amino]-4-oxo-2-butenoic acid, (2E) 4-[(6-chloro-1H-indazol-3-yl)amino]-4-oxo-2-butenoic acid, ethyl (2E) 4-[(6-chloro-1H-indazol-3-yl)amino]-4-oxo-2-butenoate, ethyl (2Z) 4-[(6-chloro-1H-indazol-3-yl)amino]-4-oxo-2-butenoate, 4-[(6-chloro-1H-indazol-3-yl)amino]-4-oxo-2-butanoic acid, (2Z) 4-[(5-bromo-1H-indazol-3-yl)amino]-4-oxo-2-butenoic acid, (2E) 4-[(6-chloro-1H-indazol-3-yl)amino]-4-oxo-2-butenoic acid, (2E) 4-[(5-bromo-1H-indazol-3-yl)amino]-4-oxo-2-butenoic acid, (2Z) 4-[(6-chloro-1H-indazol-3-yl)amino]-4-oxo-2-butenoic acid, 4-[(5-bromo-1H-indazol-3-yl)amino]-4-oxo-2-butanoic acid, (2E) N-(6-chloro-1H-indazol-3-yl)-2-butenamide, (2Z) N-(6-chloro-1H-indazol-3-yl)-2-butenamide, N-(6-chloro-1H-indazol-3-yl)-3-butenamide hydrochloride, methyl 4-[(6-chloro-1H-indazol-3-yl)amino]-4-oxo-2-butenoate, N-(6-chloro-1H-indazol-3-yl)acetamide, N-(6-chloro-1H-indazol-3-yl)butanamide,
(2E) N-(6-bromo-1H-indazol-3-yl)-2-butenamide,
(2E) N-(5-methyl-1H-indazol-3-yl)-2-butenamide,
(2Z) N-(6-bromo-1H-indazol-3-yl)-2-butenamide,
(2Z) N-(5-methyl-1H-indazol-3-yl)-2-butenamide,
N-(6-chloro-1H-indazol-3-yl)-2-propanamide,
(2E) N-[6-(trifluoromethyl)-1H-indazol-3-yl]-2-butenamide,
(2Z) N-[6-(trifluoromethyl)1-1H-indazol-3-yl]-2-butenamide,
ethyl 4-[[6-(trifluoromethyl)-1H-indazol-3-yl]amino]-4-oxobutanoate,
(2E) N-[5-(trifluoromethyl)-1H-indazol-3-yl]-2-butenamide,
(2Z) N-[5-(trifluoromethyl)-1H-indazol-3-yl]-2-butenamide,
N-[5-chloro-1H-indazol-3-yl]-2-butanamide,
N-[4-chloro-1H-indazol-3-yl]butanamide,
N-[6-(trifluoromethyl)-1H-indazol-3-yl]butanamide,
N-[6-chloro-1H-indazol-3-yl]propenamide,
N-[5-(trifluoromethyl)-1H-indazol-3-yl]butanamide,
N-[5-nitro-1H-indazol-3-yl]butanamide,
N-[6-bromo-1H-indazol-3-yl]butanamide,
N-[6-(3-pyridyl)-1H-indazol-3-yl]butanamide,
N-[4-iodo-1H-indazol-3-yl]butanamide,
N-[6-phenyl-1H-indazol-3-yl]butanamide,
N-[6-bromo-5,7-dinitro-1H-indazol-3-yl]butanamide,
N-[6-bromo-7-nitro-1H-indazol-3-yl]butanamide,
N-[6-bromo-5-nitro-1H-indazol-3-yl]butanamide,
N-[6-(3-furyl)-1H-indazol-3-yl]butanamide,
N-[6-[4-(benzyloxy)phenyl]-1H-indazol-3-yl]butanamide,
N-[6-(4-hydroxyphenyl)-1H-indazol-3-yl]butanamide,
N-[6-chloro-1H-indazol-3-yl]benzenamide,
N-[6-(3,5-difluorophenyl)-1H-indazol-3-yl]butanamide,
N-[6-(3-thienyl)-1H-indazol-3-yl]butanamide,
N-[6-chloro-1H-indazol-3-yl]-2-thiopheneacetamide,
N-[5-(3-fluorobenzenesulphonylamino)-1H-indazol-3-yl]benzamide,
N-[6-(2-chlorophenyl)-1H-indazol-3-yl]butanamide,
N-[6-(2-chloro-4-hydroxyphenyl)-1H-indazol-3-yl]butanamide,
N-[6-(4-ethylphenyl)-1H-indazol-3-yl]butanamide,
N-[6-(4-ethenylphenyl)-1H-indazol-3-yl]butanamide,
N-[6-(4-pyridyl)-1H-indazol-3-yl]butanamide,
N-[6-(phenylmethyl)-1H-indazol-3-yl]butanamide,
N-[6-(4-aminophenyl)-1H-indazol-3-yl]butanamide,
N-[6-(1-morpholino)-1H-indazol-3-yl]butanamide,
N-[6-[(4-phenylethynyl)phenyl]-1H-indazol-3-yl]butanamide,
N-[6-(2-propenyl)-1H-indazol-3-yl]butanamide,
N-[5-amino-1H-indazol-3-yl]butanamide,
N-[6-bromo-5-chloro-1H-indazol-3-yl]butanamide,
N-[6-chloro-5-bromo-1H-indazol-3-yl]butanamide,
N-[6-chloro-5-nitro-1H-indazol-3-yl]butanamide,
N-[6-(4-hydroxyphenyl)-5-bromo-1H-indazol-3-yl]butanamide,
N-[6-(4-hydroxyphenyl)-5-(phenylamino)-1H-indazol-3-yl]butanamide,
N-[6-(4-hydroxyphenyl)-5-(2-phenylethenyl)-1H-indazol-3-yl]butanamide,
N-[6-(4-hydroxyphenyl)-5-phenylcarbonyl-1H-indazol-3-yl]butanamide,
N-[6-(4-hydroxyphenyl)-5-[3-(dimethylamino)propynyl]-1H-indazol-3-yl]butanamide,
N-[6-chloro-1H-indazol-3-yl]-3-thiophenecarboxamide,
N-[6-chloro-1H-indazol-3-yl]-2-pyridineacetamide,
N-[6-chloro-1H-indazol-3-yl]-3-pyridinecarboxamide,
N-[6-chloro-1H-indazol-3-yl]benzeneacetamide,
N-[6-chloro-1H-indazol-3-yl]benzenepropanamide,
N-[6-chloro-1H-indazol-3-yl]-3-pyridineacetamide,
N-[6-chloro-1H-indazol-3-yl]-2-chloroacetamide,
N-[6-chloro-1H-indazol-3-yl]-4-morpholineacetamide,
N-[6-chloro-1H-indazol-3-yl]-1-piperazineacetamide,
N-[6-chloro-1H-indazol-3-yl]-4-[(2-methoxyethyl)amino]cyclohexanecarboxamide,
4-amino-N-[6-chloro-1H-indazol-3-yl]-1-piperidinecarboxamide, and
N-[6-chloro-1H-indazol-3-yl]-4-morpholinylcarboxamide;
or a racemic mixture, an enantiomer, a diastereoisomer or a mixture thereof, or a tautomer thereof or a pharmaceutically acceptable salt thereof.
8. The compound of claim 4 selected from the group consisting of:
(2Z) 4-[(6-chloro-1H-indazol-3-yl)amino]-4-oxo-2-butenoic acid,
ethyl (2E) 4-[(6-chloro-1H-indazol-3-yl)amino]-4-oxo-2-butenoate,
4-[(6-chloro-1H-indazol-3-yl)amino]-4-oxo-2-butanoic acid,
(2Z) 4-[(5-bromo-1H-indazol-3-yl)amino]-4-oxo-2-butenoic acid,
(2E) 4-[(6-chloro-1H-indazol-3-yl)amino]-4-oxo-2-butenoic acid,
4-[(5-bromo-1H-indazol-3-yl)amino]-4-oxo-2-butanoic acid,
(2E) N-(6-chloro-1H-indazol-3-yl)-2-butenamide,
N-(6-chloro-1H-indazol-3-yl)-3-butenamide hydrochloride,
methyl 4-[(6-chloro-1H-indazol-3-yl)amino]-4-oxo-2-butanoate,
N-(6-chloro-1H-indazol-3-yl)acetamide,
N-(6-chloro-1H-indazol-3-yl)butanamide,
(2E) N-(6-bromo-1H-indazol-3-yl)-2-butenamide,
(2E) N-(5-methyl-1H-indazol-3-yl)-2-butenamide,
N-(6-chloro-1H-indazol-3-yl)-2-propanamide,
(2E) N-[6-(trifluoromethyl)-1H-indazol-3-yl]-2-butenamide,
ethyl 4-[[6-(trifluoromethyl)-1H-indazol-3-yl]amino]-4-oxobutanoate,
(2E) N-[5-(trifluoromethyl)-1H-indazol-3-yl]-2-butenamide,
N-[5-chloro-1H-indazol-3-yl]-2-butanamide,
N-[4-chloro-1H-indazol-3-yl]butanamide,
N-[6-(trifluoromethyl)-1H-indazol-3-yl]butanamide,
N-[6-chloro-1H-indazol-3-yl]propenamide,
N-[5-(trifluoromethyl)-1H-indazol-3-yl]butanamide,
N-[5-nitro-1H-indazol-3-yl]butanamide, N-[6-bromo-1H-indazol-3-yl]butanamide,
N-[6-(3-pyridyl)-1H-indazol-3-yl]butanamide,
N-[4-iodo-1H-indazol-3-yl]butanamide,
N-[6-phenyl-1H-indazol-3-yl]butanamide,
N-[6-bromo-5,7-dinitro-1H-indazol-3-yl]butanamide,
N-[6-bromo-7-nitro-1H-indazol-3-yl]butanamide,
N-[6-bromo-5-nitro-1H-indazol-3-yl]butanamide,
N-[6-(3-furyl)-1H-indazol-3-yl]butanamide,
N-[6-[4-(benzyloxy)phenyl]-1H-indazol-3-yl]butanamide,
N-[6-(4-hydroxyphenyl)-1H-indazol-3-yl]butanamide,
N-[6-chloro-1H-indazol-3-yl]benzenamide,
N-[[6-(3,5-difluorophenyl)-1H-indazol-3-yl]]butanamide,
N-[6-(3-thienyl)-1H-indazol-3-yl]butanamide,
N-[6-chloro-1H-indazol-3-yl]-2-thiopheneacetamide,
N-[5-(3-fluorobenzenesulphonylamino)-1H-indazol-3-yl]benzamide,
N-[6-(2-phenylethyl)-1H-indazol-3-yl]butanamide,
N-(6,7-difluoro-1H-indazol-3-yl)butanamide,
N-[6-(4-methoxyphenyl)-1H-indazol-3-yl]butanamide,
N-[6-(4-methylthiophenyl)-1H-indazol-3-yl]butanamide,
N-[6-(4-trifluoromethoxyphenyl)-1H-indazol-3-yl]butanamide,
N-[(6-(1-propenyl))-1H-indazol-3-yl]butanamide,
N-[6-chloro-1H-indazol-3-yl]-2-pyridinecarboxamide,
N-[6-(4-fluorophenyl)-1H-indazol-3-yl]butanamide,
N-[6-[4-(1,1-dimethylethyl)phenyl]-1H-indazol-3-yl]butanamide,
N-[6-bromo-7-amino-1H-indazol-3-yl]butanamide,
N-[6-[4-(trifluoromethyl)phenyl]-1H-indazol-3-yl]butanamide,
N-[6-(4-methylphenyl)-1H-indazol-3-yl]butanamide,
N-[6-(3,5-dichlorophenyl)-1H-indazol-3-yl]butanamide,
N-[6-chloro-1H-indazol-3-yl]-3,5-dichlorobenzamide,
N-[6-(4-chlorophenyl)-1H-indazol-3-yl]butanamide,
N-[6-chloro-1H-indazol-3-yl]benzenepropanamide trifluoroacetate,
N-[6-chloro-1H-indazol-3-yl]benzenepropanamide,
N-[[6-(4-ethylphenyl)-1H-indazol-3-yl]]butanamide,
N-[6-(4-pyridyl)-1H-indazol-3-yl]butanamide,
N-(5-amino-1H-indazol-3-yl)butanamide,
N-(5-bromo-6-chloro-1H-indazol-3-yl)butanamide,
N-(6-chloro-1H-indazol-3-yl)-2-thiophenecarboxamide,
N-(6-chloro-1H-indazol-3-yl)-2-methylpropylamide,
4-chloro-N-(6-chloro-1H-indazol-3-yl)butanamide,
N-(5-phenyl-6-chloro-1H-indazol-3-yl)butanamide,
N-[5-bromo-6-[4-(phenylmethoxy)phenyl]-1H-indazol-3-yl]butanamide,
N-[5-bromo-6-(4-hydroxyphenyl)-1H-indazol-3-yl]butanamide,
N-[[5-(4-nitrophenyl)-1H-indazol-3-yl]]butanamide,
N-[6-(2-chlorophenyl)-1H-indazol-3-yl]butanamide,
N-[6-[3-(phenylmethoxy)phenyl]-1H-indazol-3-yl]butanamide,
N-[6-(3-hydroxyphenyl)-1H-indazol-3-yl]butanamide,
N-[6-chloro-5-(4-pyridyl)-1H-indazol-3-yl]butanamide,
N-[6-chloro-5-(3-furyl)-1H-indazol-3-yl]butanamide,
N-[6-[2-chloro-4-(phenylmethoxy)phenyl]-1H-indazol-3-yl]butanamide,
N-[6-(2-chloro-4-hydroxyphenyl)-1H-indazol-3-yl]butanamide,
N-[5,6-dibromo-1H-indazol-3-yl]butanamide,
N-[6-chloro-1H-indazol-3-yl]-2,2,3,3,4,4,4-heptafluorobutanamide,
N-[6-chloro-5-(4-fluorophenyl)-1H-indazol-3-yl]butanamide,
N-[[6-(4-aminophenyl)-1H-indazol-3-yl]]butanamide,
N-[6-[4-(dimethylamino)phenyl]-1H-indazol-3-yl]butanamide,
N-(6-chloro-1H-indazol-3-yl)-4-methyl-1-piperazineacetamide,
N-(6-chloro-1H-indazol-3-yl)-1-piperidineacetamide,
N-(6-chloro-1H-indazol-3-yl)-4-morpholineacetamide,
N-(6-chloro-1H-indazol-3-yl)-1H-1,2,4-triazole-1-acetamide,
N-(6-chloro-1H-indazol-3-yl)-2-(cyclohexylamino)acetamide,
2-[(phenylmethyl)amino]-N-(6-chloro-1H-indazol-3-yl)acetamide,
N-(6-chloro-1H-indazol-3-yl)-1H-azepine-1-acetamide,
N-(6-chloro-1H-indazol-3-yl)-1-piperazineacetamide,
N-(6-chloro-1H-indazol-3-yl)-2-[[3-(dimethylamino)propyl]amino]acetamide,
N-(6-chloro-1H-indazol-3-yl)thiomorpholine-4-acetamide,
N-(6-chloro-1H-indazol-3-yl)-1-pyrrolidineacetamide,
N-(6-chloro-1H-indazol-3-yl)-2-[[2-(dimethylamino)ethyl]amino]acetamide,
N-(6-chloro-1H-indazol-3-yl)-1-cyclopropylaminoacetamide trifluoroacetate,
N-(6-chloro-1H-indazol-3-yl)-1-cyclopropylaminoacetamide,
N-(6-chloro-1H-indazol-3-yl)-2-(2-diethylaminoethylamino)acetamide tris(trifluoroacetate),
N-(6-chloro-1H-indazol-3-yl)-2-(2-diethylaminoethylamino)acetamide,
N-[5,6-diphenyl-1H-indazol-3-yl]butanamide,
N-[6-chloro-5-(4-methylphenyl)-1H-indazol-3-yl]butanamide,
N-[5-phenyl-6-[4-(phenylmethoxy)phenyl]-1H-indazol-3-yl]butanamide,
N-[5-phenyl-6-(4-hydroxyphenyl)-1H-indazol-3-yl]butanamide,
N-[6-chloro-5-(4-pyridyl)-1H-indazol-3-yl]butanamide,
N-[5-(4-aminophenyl)-6-chloro-1H-indazol-3-yl]butanamide,
N-[6-chloro-5-(4-ethylphenyl)-1H-indazol-3-yl]butanamide, N-[6-chloro-5-[4-(phenylmethoxy)phenyl]-1H-indazol-3-yl]butanamide,
N-[6-chloro-5-(4-hydroxyphenyl)-1H-indazol-3-yl]butanamide,
N-[5,6-bis[4-(phenylmethoxy)phenyl]-1H-indazol-3-yl]butanamide,
N-[5,6-bis(4-hydroxyphenyl)-1H-indazol-3-yl]butanamide,
N-[5-(3-furyl)-6-[4-(phenylmethoxy)phenyl]-1H-indazol-3-yl]butanamide,
N-[5-(3-furyl)-6-([4-hydroxyphenyl)-1H-indazol-3-yl]butanamide,
N-[5-(4-ethylphenyl)-6-[4-(phenylmethoxy)phenyl]-1H-indazol-3-yl]butanamide,
N-[5-(4-ethylphenyl)-6-(4-hydroxyphenyl)-1H-indazol-3-yl]butanamide,
N-[5-(3-pyridyl)-6-[4-(phenylmethoxy)phenyl]-1H-indazol-3-yl]butanamide,
N-[5-(3-pyridyl)-6-(4-hydroxyphenyl)-1H-indazol-3-yl]butanamide,
N-[5-(2-furyl)-6-[4-(phenylmethoxy)phenyl]-1H-indazol-3-yl]butanamide,
N-[5-(2-furyl)-6-(4-hydroxyphenyl)-1H-indazol-3-yl]butanamide,
N-(5-bromo-6-chloro-7-nitro-1H-indazol-3-yl)butanamide,
N-(5-bromo-6,7-difluoro-1H-indazol-3-yl)butanamide,
N-[6-(4-cyanophenyl)-1H-indazol-3-yl]butanamide,
N-(6,7-difluoro-5-nitro-1H-indazol-3-yl)butanamide,
N-(6,7-difluoro-5-phenyl-1H-indazol-3-yl)butanamide,
N-[6-(6-hydroxypyrid-3-yl)-1H-indazol-3-yl]butanamide,
N-[6-(3,4-dihydroxyphenyl)-1H-indazol-3-yl]butanamide trifluoroacetate,
N-[6-(3,4-dihydroxyphenyl)-1H-indazol-3-yl]butanamide,
N-[7-fluoro-5-nitro-6-[2-(phenylethyl)amino]-1H-indazol-3-yl]butanamide,
N-(7-fluoro-5-nitro-6-morpholino-1H-indazol-3-yl)butanamide,
N-(7-fluoro-5-amino-6-morpholino-1H-indazol-3-yl)butanamide,
N-(5-bromo-7-fluoro-6-morpholino-1H-indazol-3-yl)butanamide,
N-[7-fluoro-6-(trifluoromethyl)-1H-indazol-3-yl]butanamide,
N-(6-bromo-4,5,7-trifluoro-1H-indazol-3-yl)butanamide,
N-[6-(6-aminopyrid-3-yl)-1H-indazol-3-yl]butanamide difluoroacetate,
N-[6-(6-aminopyrid-3-yl)-1H-indazol-3-yl]butanamide,
2-chloro-N-(6,7-difluoro-1H-indazol-3-yl)acetamide, and
N-(6,7-difluoro-1H-indazol-3-yl)-1-piperidineacetamide,
or a racemic mixture, an enantiomer, a diastereoisomer or a mixture thereof, or a tautomer thereof or a pharmaceutically acceptable salt thereof.

9. A pharmaceutical composition comprising at least one compound as defined in claim 1 in combination with at least one pharmaceutically acceptable carrier.

10. A method of treating a disease wherein phosphorylation of the Tau protein is observed which comprises administering to a patient an effective Tau protein phosphorylation inhibiting amount of a compound of claim 1, wherein said disease is selected from the group consisting of Alzheimer's diseases, Parkinson's diseases, frontoparietal dementia, corticobasal degenaration, Pick's disease stroke, cranial and spinal trauma and peripheral neuropathies, obesity, metabolic diseases, type II diabetes, essential hypertension, atherosclerotic cardiovascular diseases, polycystic ovarian syndrome, syndrome X and immunodeficiency.

11. The method of claim 10 wherein said disease is selected from the group consisting of Alzheimer's disease, Parkinson's disease, frontoparietal dementia, corticobasal degenaration Pick's disease, stroke, cranial and spinal trauma and peripheral neuropathies.

12. The method of claim 11 wherein said disease is selected from the group consisting of Alzheimer's disease, Parkinson's disease, frontoparietal dementia, corticobasal degenaration and Pick's disease.

13. A process for preparing the compounds of formula (I) as defined in claim 1 wherein R is oxygen, comprising:
a) acylating an amine of formula (II) to produce a compound of formula (I) wherein R is oxygen; and

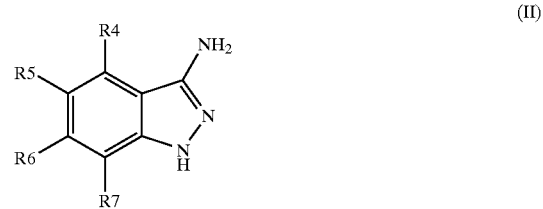

(II)

b) optionally converting the product of (a) into a pharmaceutically acceptable salt,
wherein R4, R5, R6 and R7 have the same meanings as in claim 1.

14. A process for preparing the compounds of formula (I) as defined in claim 1 and wherein R is sulfur, comprising:
a) thionating a compound of formula I, wherein R is oxygen to produce a compound of formula (I) wherein R is sulfur; and
b) optionally converting the product of (a) into a pharmaceutically acceptable salt.

15. A process for preparing the compounds of formula (I) as defined in claim 1 and wherein R is NH, comprising:
a) reacting an amine of formula (II) with a nitrile or optionally with a Meerwein salt to produce a compound of the formula (I) wherein R is NH; and

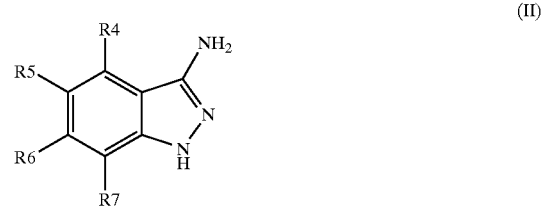

(II)

b) optionally converting the product of (a) into a pharmaceutically acceptable salt,
wherein R4, R5, R6 and R7 have the same meanings as in claim 1.

16. Tho process according to claim 15, for preparing a compound of formula (II), comprising:
a) reacting a compound of formula (III) with hydrazine to produce a compound of formula (II)

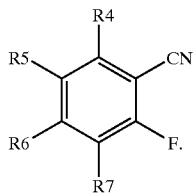 (III)

17. A compound selected from the group consisting of:
3-amino-6-chloro-1-[(2-trimethylsilylethoxy)methyl] indazole,
N-[[6-chloro-1-[(2-trimethylsilylethoxy)methyl]indazol-3-yl]]propenamide,
N-[[6-chloro-1-(2-trimethylsilylethoxy)methyl]indazol-3-yl]]butanamide,
N-[[6-(3-pyridyl)-1-[(2-trimethylsilylethoxy)methyl] indazol-3-yl]]butanamide,
N-[6-(3-pyridyl)-1H-indazol-3-yl]butanamide,
N-[[6-phenyl-1-[(2-trimethylsilylethoxy)methyl]indazol-3-yl]]butanamide,
N-[[(6-furan-3-yl)-1-[(2-trimethylsilylethoxy)methyl] indazol-3-yl]]butanamide,
N-[[[6-(4-benzyloxy)phenyl-1-[(2-trimethylsilylethoxy) methyl]indazol-3-yl]]butanamide,
N-[[6-(3,5-difluorophenyl)-1-[(2-trimethylsilylethoxy) methyl]indazol-3-yl]]butanamide,
N-[[6-(3-thienyl)-1-[(2-trimethylsilylethoxy)methyl] indazol-3-yl]]butanamide,
N-[6-(2-phenylethyl)-1-[[2-(trimethylsilyl)ethoxy] methyl]-1H-indazol-3-yl]butanamide,
N-[6-[4-(methylthio)phenyl]-1-[[2-(trimethylsilyl) ethoxy]methyl]-1H-indazol-3-yl]butanamide,
N-[6-(4-methoxyphenyl)-1-[[2-(trimethylsilyl)ethoxy] methyl]-1H-indazol-3-yl]butanamide,
N-[6-[4-(trifluoromethoxy)phenyl]-1-[[2-(trimethylsilyl) ethoxy]methyl]-1H-indazol-3-yl]butanamide,
N-[(6-(2-propenyl)-1-[[2-(trimethylsilyl)ethoxy]methyl]-1H-indazol-3-yl]butanamide,
N-[6-(4-fluorophenyl)-1-[[2-(trimethylsilyl)ethoxy] methyl]-1H-indazol-3-yl]butanamide,
N-[6-[(1,1-dimethylethyl)phenyl]-1-[[2-(trimethylsilyl) ethoxy]methyl]-1H-indazol-3-yl]butanamide,
N-[6-[4-(trifluoromethyl)phenyl]-1-[[2-(trimethylsilyl) ethoxy]methyl]-1H-indazol-3-yl]butanamide,
N-[6-(4-methylphenyl)-1-[[2-(trimethylsilyl)ethoxy] methyl]-1H-indazol-3-yl]butanamide,
N-[6-bromo-1-[[2-(trimethylsilyl)ethoxy]methyl]-1H-indazol-3-yl]butanamide,
N-[6-(3,5-dichlorophenyl)-1-[[2-(trimethylsilyl)ethoxy] methyl]-1H-indazol-3-yl]butanamide,
N-[6-(4-chlorophenyl)-1-[[2-(trimethylsilyl)ethoxy] methyl]-1H-indazol-3-yl]butanamide,
N-[6-(4-ethylphenyl)-1-[[2-(trimethylsilyl)ethoxy] methyl]-1H-indazol-3-yl]butanamide,
N-[6-(4,4,5,5-tetramethyl-[1,3,2]dioxaborolan-2-yl)-1-[[2-(trimethylsilyl)ethoxy]methyl]-1H-indazol-3-yl] butanamide,
N-[6-(4-pyridyl)-1-[[2-(trimethylsilyl)ethoxy]methyl]-1H-indazol-3-yl]butanamide,
N-[5-bromo-6-chloro-1-[[2-(trimethylsilyl)ethoxy] methyl]-1H-indazol-3-yl]butanamide,
N-[5-phenyl-6-chloro-1-[[2-(trimethylsilyl)ethoxy] methyl]-1H-indazol-3-yl]butanamide,
N-[5-bromo-6-[4-(phenylmethoxy)phenyl]-1-[[2-(trimethylsilyl)ethoxy]methyl]-1H-indazol-3-yl] butanamide,
N-[6-(4-nitrophenyl)-1-[[2-(trimethylsilyl)ethoxy] methyl]-1H-indazol-3-yl]butanamide,
N-[6-(2-chlorophenyl)-1-[(2-(trimethylsilyl)ethoxy] methyl]-1H-indazol-3-yl]butanamide,
N-[6-[3-(phenylmethoxy)phenyl]-1-[[2-(trimethylsilyl) ethoxy]methyl]-1H-indazol-3-yl]butanamide,
N-[6-chloro-5-(4-pyridyl)-1-[[2-(trimethylsilyl)ethoxy] methyl]-1H-indazol-3-yl]butanamide,
N-[6-chloro-5-(3-furyl)-1-[[2-(trimethylsilyl)ethoxy] methyl]-1H-indazol-3-yl]butanamide,
1-bromo-2-chloro-4-(phenylmethoxy)benzene,
N-[6-[2-chloro-4-(phenylmethoxy)phenyl]-1-[[2-(trimethylsilyl)ethoxy]methyl]-1H-indazol-3-yl] butanamide,
N-[5,6-dibromo-1-[[2-(trimethylsilyl)ethoxy]methyl]-1H-indazol-3-yl]butanamide,
N-[5-(4-fluorophenyl)-6-chloro-1-[[2-(trimethylsilyl) ethoxy]methyl]-1H-indazol-3-yl]butanamide,
N-[6-[4-(dimethylamino)phenyl]-1-[[2-(trimethylsilyl) ethoxy]methyl]-1H-indazol-3-yl]butanamide,
2-chloro-N-(6-chloro-1H-indazol-3-yl)acetamide,
N-[5,6-diphenyl-1-[[2-(trimethylsilyl)ethoxy]methyl]-1H-indazol-3-yl]butanamide,
N-[6-chloro-5-(4-methylphenyl)-1-[[2-(trimethylsilyl) ethoxy]methyl]-1H-indazol-3-yl]butanamide,
N-[6-[4-(phenylmethoxy)phenyl]-5-phenyl-1-[[2-(trimethylsilyl)ethoxy]methyl]-1H-indazol-3-yl] butanamide,
N-[6-chloro-5-(4,4,5,5-tetramethyl-[1,3,2]-dioxaborolan-2-yl)-1-[2-(trimethylsilyl)ethoxy]methyl]-1H-indazol-3-yl]butanamide,
N-[6-chloro-5-(4-nitrophenyl)-1-[[2-(trimethylsilyl) ethoxy]methyl]-1H-indazol-3-yl]butanamide,
N-[6-chloro-5-(4-ethylphenyl)-1-[[2-(trimethylsilyl) ethoxy]methyl]-1H-indazol-3-yl]butanamide,
N-[6-chloro-5-[4-(phenylmethoxy)phenyl]-1-[[2-(trimethylsilyl)ethoxy]methyl]-1H-indazol-3-yl] butanamide,
N-[5,6-bis[4-(phenylmethoxy)phenyl]-1-[[2-(trimethylsilyl)ethoxy]methyl]-1H-indazol-3-yl] butanamide,
N-[5-(3-furyl)-6-[4-(phenylmethoxy)phenyl]-1-[[2-(trimethylsilyl)ethoxy]methyl]-1H-indazol-3-yl] butanamide,
N-[5-(4-ethylphenyl)-6-[4-(phenylmethoxy)phenyl]-1-[[2-(trimethylsilyl)ethoxy]methyl]-1H-indazol-3-yl] butanamide,
N-[5-(3-pyridyl)-6-[4-(phenylmethoxy)phenyl]-1-[[2-(trimethylsilyl)ethoxy]methyl]-1H-indazol-3-yl] butanamide,
N-[5-(2-furyl)-6-[4-(phenylmethoxy)phenyl]-1-[[2-(trimethylsilyl)ethoxy]methyl]-1H-indazol-3-yl] butanamide,
N-(6,7-difluoro-1-[[2-(trimethylsilyl)ethoxy]methyl]-1H-indazol-3-yl)butanamide,
N-(5-bromo-6,7-difluoro-1-[[2-(trimethylsilyl)ethoxy] methyl]-1H-indazol-3-yl)butanamide, N-[6-(4-cyanophenyl)-1-[[2-(trimethylsilyl)ethoxy]
   methyl]-1H-indazol-3-yl]butanamide,
N-[6,7-difluoro-5-phenyl-1-[[2-(trimethylsilyl)ethoxy]
   methyl]-1H-indazol-3-yl]butanamide,
5-bromo-2-[[2-(trimethylsilyl)ethoxy]methoxy]pyridine,
N-[6-[6-[[2-(trimethylsilyl)ethoxy]methoxy]pyridyl-3-
   yl]-1-[[2-(trimethylsilyl)ethoxy]methyl]-1H-indazol-3-
   yl]butanamide,
N-[6-(2,2-diphenylbenzo[1,3]dioxol-5-yl)-1-[[2-
   (trimethylsilyl)ethoxy]methoxy]-1H-indazol-3-yl]
   butanamide,
N-[6-(1,3-benzodioxol-5-yl)-1-[[2-(trimethylsilyl)
   ethoxy]methoxy]-1H-indazol-3-yl)butanamide,
N-[6-(1,3-benzodioxol-5-yl)-1H-indazol-3-yl]
   butanamide,
6-chloro-4,5,7-trifluoro-1H-indazole-3-amine,
N-[6-(6-aminopyrid-3-yl)-1-[[2-(trimethylsilyl)ethoxy]
   methyl]-1H-indazol-3-yl]butanamide,
3-amino-6-(3-pyridyl)-1H-indazole,
3-amino-4-iodo-1H-indazole,
3-amino-6-bromo-5,7-dinitro-1H-indazole,
3-amino-6-bromo-7-nitro-1H-indazole,
3-amino-6-bromo-5-nitro-1H-indazole,
3-amino-6-(3-furyl)-1H-indazole,
3-amino-6-[4-(phenylmethoxy)phenyl]-1H-indazole,
3-amino-6-(4-hydroxyphenyl)-1H-indazole,
3-amino-6-(3,5-difluorophenyl)-1H-indazole,
3-amino-6-(3-thienyl)-1H-indazole,
3-amino-5-[[(3-fluorophenyl)sulfonyl]amino]-1H-
   indazole,
3-amino-6-(2-phenylethyl)-1H-indazole,
3-amino-6,7-difluoro-1H-indazole,
3-amino-6-(4-methoxyphenyl)-1H-indazole,
3-amino-6-(4-methylthiophenyl)-1H-indazole,
3-amino-6-(4-trifluoromethoxyphenyl)-1H-indazole,
3-amino-(6-(1-propenyl)-1H-indazole,
3-amino-6-(4-fluorophenyl)-1H-indazole,
3-amino-6-[4-(1,1-dimethylethyl)phenyl]-1H-indazole,
3-amino-6-bromo-7-amino-1H-indazole,
3-amino-6-(4-methylphenyl)-1H-indazole,
3-amino-6-(3,5-dichlorophenyl)-1H-indazole,
3-amino-6-(4-chlorophenyl)-1H-indazole,
3-amino-6-(4-ethylphenyl)-1H-indazole,
3-amino-6-(4-pyridyl)-1H-indazole,
3-amino-5-amino-1H-indazole,
3-amino-5-bromo-6-chloro-1H-indazole,
3-amino-5-phenyl-6-chloro-1H-indazole,
3-amino-5-bromo-6-[4-(phenylmethoxy)phenyl]-1H-
   indazole,
3-amino-5-bromo-6-(4-hydroxyphenyl)-1H-indazole,
3-amino-6-(4-nitrophenyl)-1H-indazole,
3-amino-6-(2-chlorophenyl)-1H-indazole,
3-amino-6-[3-(phenylmethoxy)phenyl]-1H-indazole,
3-amino-6-(3-hydroxyphenyl)-1H-indazole,
3-amino-6-chloro-5-(4-pyridyl)-1H-indazole,
3-amino-6-chloro-5-(3-furyl)-1H-indazole,
3-amino-6-[2-chloro-4-(phenylmethoxy)phenyl]-1H-
   indazole,
3-amino-6-(2-chloro-4-hydroxyphenyl)-1H-indazole,
3-amino-5,6-dibromo-1H-indazole,
3-amino-6-chloro-5-(4-fluorophenyl)-1H-indazole,
3-amino-6-(4-aminophenyl)-1H-indazole,
3-amino-6-[4-(dimethylamino)phenyl]-1H-indazole,
3-amino-5,6-diphenyl-1H-indazole,
3-amino-6-chloro-5-(4-methylphenyl)-1H-indazole,
3-amino-5-phenyl-6-[4-(phenylmethoxy)phenyl]-1H-
   indazole,
3-amino-5-phenyl-6-(4-hydroxyphenyl)-1H-indazole,
3-amino-5-(4-aminophenyl)-6-chloro-1H-indazole,
3-amino-6-chloro-5-(4-ethylphenyl)-1H-indazole,
3-amino-6-chloro-5-[4-(phenylmethoxy)phenyl]-1H-
   indazole,
3-amino-6-chloro-5-(4-hydroxyphenyl)-1H-indazole,
3-amino-5,6-bis[4-(phenylmethoxy)phenyl]-1H-
   indazole,
3-amino-5,6-bis(4-hydroxyphenyl)-1H-indazole,
3-amino-5-(3-furyl)-6-[4-(phenylmethoxy)phenyl]-1H-
   indazole,
3-amino-5-(3-furyl)-6-([4-hydroxyphenyl)-1H-indazole,
3-amino-5-(4-ethylphenyl)-6-[4-(phenylmethoxy)
   phenyl]-1H-indazole,
3-amino-5-(4-ethylphenyl)-6-(4-hydroxyphenyl)-1H-
   indazole,
3-amino-5-(3-pyridyl)-6-[4-(phenylmethoxy)phenyl]-
   1H-indazole,
3-amino-5-(3-pyridyl)-6-(4-hydroxyphenyl)-1H-
   indazole,
3-amino-5-(2-furyl)-6-[4-(phenylmethoxy)phenyl]-1H-
   indazole,
3-amino-5-(2-furyl)-6-(4-hydroxyphenyl)-1H-indazole,
3-amino-5-bromo-6-chloro-7-nitro-1H-indazole,
3-amino-5-bromo-6,7-difluoro-1H-indazole,
3-amino-6-(4-cyanophenyl)-1H-indazole,
3-amino-6,7-difluoro-5-nitro-1H-indazole,
3-amino-6,7-difluoro-5-phenyl-1H-indazole,
3-amino-6-(6-hydroxypyrid-3-yl)-1H-indazole,
3-amino-6-(3,4-dihydroxyphenyl)-1H-indazole,
3-amino-7-fluoro-5-nitro-6-[2-(phenylethyl)amino]-1H-
   indazole,
3-amino-7-fluoro-5-nitro-6-morpholino-1H-indazole,
3-amino-7-fluoro-5-amino-6-morpholino-1H-indazole,
3-amino-5-bromo-7-fluoro-6-morpholino-1H-indazole,
3-amino-7-fluoro-6-(trifluoromethyl)-1H-indazole,
3-amino-6-bromo-4,5,7-trifluoro-1H-indazole, and
3-amino-6-(6-aminopyrid-3-yl)-1H-indazole.

* * * * *